(12) United States Patent
Konradi et al.

(10) Patent No.: US 11,591,322 B2
(45) Date of Patent: Feb. 28, 2023

(54) CERTAIN CHEMICAL COMPOSITIONS AND METHODS OF USE THEREOF

(71) Applicant: Algen Biotechnologies, Inc., San Francisco, CA (US)

(72) Inventors: Andrei W. Konradi, Burlingame, CA (US); Chun-Hao Huang, San Francisco, CA (US); Ko-Chuan Lee, San Francisco, CA (US)

(73) Assignee: Algen Biotechnologies, Inc., San Francisco, CA (US)

( * ) Notice: Subject to any disclaimer, the term of this patent is extended or adjusted under 35 U.S.C. 154(b) by 0 days.

(21) Appl. No.: 17/731,943

(22) Filed: Apr. 28, 2022

(65) Prior Publication Data

US 2022/0289725 A1 Sep. 15, 2022

Related U.S. Application Data

(63) Continuation of application No. PCT/US2021/032495, filed on May 14, 2021.

(60) Provisional application No. 63/025,474, filed on May 15, 2020.

(51) Int. Cl.
C07D 405/14 (2006.01)

(52) U.S. Cl.
CPC ................. *C07D 405/14* (2013.01)

(58) Field of Classification Search
CPC .................................................. C07D 405/14
USPC ........................................................ 514/269
See application file for complete search history.

(56) References Cited

U.S. PATENT DOCUMENTS

| | | | |
|---|---|---|---|
| 4,932,412 A | 6/1990 | Goldenberg | |
| 7,635,698 B2 | 12/2009 | Rosse et al. | |
| 7,781,442 B2 | 8/2010 | Cheng et al. | |
| 7,799,808 B2 | 9/2010 | Cheng et al. | |
| 8,017,629 B2 | 9/2011 | Cheng et al. | |
| 8,119,680 B2 | 2/2012 | Cheng et al. | |
| 8,399,455 B2 | 3/2013 | Rosse et al. | |
| 8,415,381 B2 | 4/2013 | Barsanti et al. | |
| 8,778,951 B2 | 7/2014 | Barsanti et al. | |
| 10,208,017 B2 | 2/2019 | Hommes et al. | |
| 10,562,883 B2 | 2/2020 | Hommes et al. | |
| 10,597,364 B2 | 3/2020 | Long et al. | |
| 10,781,218 B2 | 9/2020 | Wu et al. | |
| 2013/0172354 A1 | 7/2013 | Barsanti et al. | |
| 2013/0303507 A1 | 11/2013 | Antonios-McCrea et al. | |
| 2014/0288076 A1 | 9/2014 | Barsanti et al. | |

FOREIGN PATENT DOCUMENTS

| | | | |
|---|---|---|---|
| WO | WO-0124684 A2 | 4/2001 | |
| WO | WO-2011012661 A1 | 2/2011 | |
| WO | WO-2012101062 A1 * | 8/2012 | ........... C07D 213/74 |
| WO | WO-2012101063 A1 | 8/2012 | |
| WO | WO-2012101065 A2 | 8/2012 | |
| WO | WO-2012101066 A1 | 8/2012 | |

OTHER PUBLICATIONS

International Search Report and Written Opinion dated Aug. 24, 2021 for International Application No. PCT/US2021/032495.
Robert, T. et al., "Development of a CDK10/CycM in vitro Kinase Screening Assay and Identification of First Small-Molecule Inhibitors", Frontiers in Chemistry, Feb. 27, 2020, vol. 8, Article 147, pp. 1-10.

* cited by examiner

*Primary Examiner* — Kahsay Habte
(74) *Attorney, Agent, or Firm* — Wilson Sonsini Goodrich & Rosati

(57) ABSTRACT

The present disclosure provides CDK9 inhibitors. Also provided are methods of treating a disease or a disorder comprising administering to a subject in need of treatment one of the CDK9 inhibitors disclosed herein. In some embodiments, the disease or disorder to be treated is cancer. In some embodiments, the disease or disorder is liver cancer.

29 Claims, 3 Drawing Sheets

CERTAIN CHEMICAL COMPOSITIONS AND METHODS OF USE THEREOF

CROSS-REFERENCE

This application is a continuation of International Application No. PCT/US2021/032495, filed May 14, 2021, which claims the benefit of U.S. Provisional Application No. 63/025,474, filed May 15, 2020, each of which is incorporated by reference herein in its entirety.

BACKGROUND OF THE INVENTION

Despite advances, treatment of cancer remains relatively difficult. Systemic treatments such as chemotherapies may be toxic and have negative side effects on patients. While CDK9 inhibitors have shown promise as small molecule cancer therapeutics, their potential utility has been limited by poor targeting to cancerous tissue and resulting peripheral exposure. Accordingly, there is a need for the development of CDK9 inhibitors as small molecule cancer therapeutics with improved targeting.

SUMMARY OF THE INVENTION

Provided herein, in one aspect, is a compound of Formula (I):

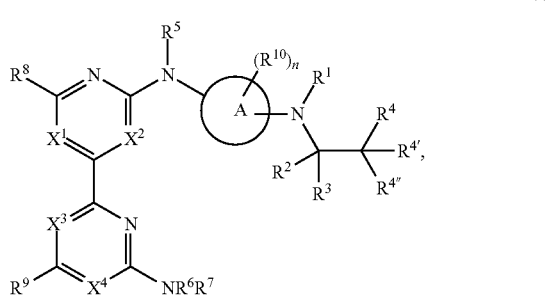

Formula (I)

or a pharmaceutically acceptable salt thereof, wherein:

Ring A is selected from $C_{3-6}$cycloalkyl, 3- to 10-membered heterocycloalkyl, $C_{6-10}$aryl, and 6- to 10-membered heteroaryl;

$X^1$ is selected from N and $CR^{11}$;
$X^2$ is selected from N and $CR^{12}$;
$X^3$ is selected from N and $CR^{13}$;
$X^4$ is selected from N and $CR^{14}$;

$R^1$ is selected from H, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, 6- to 10-membered heteroaryl; wherein each alkyl, cycloalkyl, heterocycloalkyl, aryl, and heteroaryl is independently optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$;

$R^2$ is selected from halo, —CN, —$OR^{18}$, —$SOR^{15}$, —$SO_2R^{15}$, —$NR^{16}R^{17}$, —$C(O)NR^{16}R^{17}$, —$SO_2NR^{16}R^{17}$, —$C(O)R^{18}$, —$C(O)OR^{18}$, —$NR^{19}C(O)R^{18}$, —$NR^{19}C(O)NR^{16}R^{17}$, —$NR^{19}SO_2R^{15}$, —$NR^{19}SO_2NR^{16}R^{17}$, $C_{1-6}$alkyl, $C_{2-6}$alkenyl, $C_{2-6}$alkynyl, $C_{1-6}$heteroalkyl, $C_{1-6}$haloalkyl, $C_{3-6}$cycloalkyl, 3- to 10-membered heterocycloalkyl, $C_{6-10}$aryl, and 6- to 10-membered heteroaryl; wherein each alkyl, alkenyl, alkynyl, cycloalkyl, heterocycloalkyl, aryl, and heteroaryl is independently optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$;

$R^3$ is selected from H, halo, —CN, —$OR^{18}$, —$SOR^{15}$, —$SO_2R^{15}$, —$NR^{16}R^{17}$, —$C(O)NR^{16}R^{17}$, —$SO_2NR^{16}R^{17}$, —$C(O)R^{18}$, —$C(O)OR^{18}$, —$NR^{19}C(O)R^{18}$, —$NR^{19}C(O)NR^{16}R^{17}$, —$NR^{19}SO_2R^{15}$, —$NR^{19}SO_2NR^{16}R^{17}$, $C_{1-6}$alkyl, $C_{2-6}$alkenyl, $C_{2-6}$alkynyl, $C_{1-6}$heteroalkyl, $C_{1-6}$haloalkyl, $C_{3-6}$cycloalkyl, 3- to 10-membered heterocycloalkyl, $C_{6-10}$aryl, and 6- to 10-membered heteroaryl; wherein each alkyl, alkenyl, alkynyl, cycloalkyl, heterocycloalkyl, aryl, and heteroaryl is independently optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$;

$R^4$ is selected from $C_{1-6}$alkyl, $C_{2-6}$heteroalkyl, $C_{1-6}$haloalkyl, $C_{3-6}$cycloalkyl, 3- to 10-membered heterocycloalkyl, $C_{6-10}$aryl, 6- to 10-membered heteroaryl, —$O(C_{0-4}$alkyl)$C_{3-6}$ cycloalkyl, —$O(C_{0-4}$alkyl)(3- to 10-membered heterocycloalkyl), —$O(C_{0-4}$alkyl)$C_{6-10}$aryl, —$O(C_{0-4}$alkyl)(6- to 10-membered heteroaryl), —$O(C_{0-4}$alkyl)$C(O)OR^{18}$, —$O(C_{0-4}$alkyl)$C(O)NR^{19}SO_2R^{15}$, —$O(C_{0-4}$alkyl)$SO_2NR^{19}C(O)R^{18}$, —$O(C_{3-6}$cycloalkyl)$C_{3-6}$cycloalkyl, —$O(C_{3-6}$cycloalkyl)(3- to 10-membered heterocycloalkyl), —$O(C_{3-6}$cycloalkyl)$C_{6-10}$aryl, —$O(C_{3-6}$cycloalkyl)(6- to 10-membered heteroaryl), —$O(C_{3-6}$cycloalkyl)$C(O)OR^{18}$, —$(C_{1-4}$alkyl)$C_{3-6}$cycloalkyl, —$(C_{1-4}$alkyl)(3- to 10-membered heterocycloalkyl), —$(C_{1-4}$alkyl)$C_{6-10}$aryl, —$(C_{1-4}$alkyl)(6- to 10-membered heteroaryl), and —$(C_{1-4}$alkyl)$C(O)OR^{18}$; wherein each alkyl, cycloalkyl, heterocycloalkyl, aryl, and heteroaryl is independently optionally substituted with one or more substituents selected from $C_{1-4}$alkyl, oxo, halo, —$OR^{18}$, —CN, —$NR^{16}R^{17}$, —$C(O)NR^{16}R^{17}$, —$SO_2NR^{16}R^{17}$, —$C(O)R^{18}$, —$C(O)OR^{18}$, —$(C_{1-4}$alkyl)$OC(O)(C_{1-4}$alkyl), —$(C_{1-4}$alkyl)$OC(O)OR^{18}$, —$NR^{19}C(O)R^{18}$, —$NR^{19}C(O)NR^{16}R^{17}$, —$NR^{19}SO_2R^{15}$, and —$NR^{19}SO_2NR^{16}R^{17}$; and $R^{4'}$ and $R^{4''}$ are each independently selected from H, $C_{1-6}$alkyl, $C_{2-6}$heteroalkyl, $C_{1-6}$haloalkyl, $C_{3-6}$cycloalkyl, 3- to 10-membered heterocycloalkyl, $C_{6-10}$aryl, 6- to 10-membered heteroaryl, —$O(C_{0-4}$alkyl)$C_{3-6}$cycloalkyl, —$O(C_{0-4}$alkyl)(3- to 10-membered heterocycloalkyl), —$O(C_{0-4}$alkyl)$C_{6-10}$aryl, —$O(C_{0-4}$alkyl)(6- to 10-membered heteroaryl), —$O(C_{0-4}$alkyl)$C(O)OR^{18}$, —$O(C_{0-4}$alkyl)$C(O)NR^{19}SO_2R^{15}$, —$O(C_{0-4}$alkyl)$SO_2 NR^{19}C(O)R^{18}$, —$O(C_{3-6}$cycloalkyl)$C_{3-6}$cycloalkyl, —$O(C_{3-6}$cycloalkyl)(3- to 10-membered heterocycloalkyl), —$O(C_{3-6}$cycloalkyl)$C_{6-10}$aryl, —$O(C_{3-6}$cycloalkyl)(6- to 10-membered heteroaryl), —$O(C_{3-6}$cycloalkyl)$C(O)OR^{18}$, —$(C_{1-4}$alkyl)$C_{3-6}$cycloalkyl, —$(C_{1-4}$alkyl)(3- to 10-membered heterocycloalkyl), —$(C_{1-4}$alkyl)$C_{6-10}$aryl, and —$(C_{1-4}$alkyl)(6- to 10-membered heteroaryl); wherein each alkyl, cycloalkyl, heterocycloalkyl, aryl, and heteroaryl is independently optionally substituted with one or more substituents selected from oxo, halo, —$OR^{18}$, —CN, —$NR^{16}R^{17}$, —$C(O)NR^{16}R^{17}$, —$SO_2NR^{16}R^{17}$, —$C(O)R^{18}$, —$C(O)OR^{18}$, —$(C_{1-4}$alkyl)$OC(O)(C_{1-4}$alkyl), —$(C_{1-4}$alkyl)$OC(O)OR^{18}$, —$NR^{19}C(O)R^{18}$, —$NR^{19}C(O)NR^{16}R^{17}$, —$NR^{19}SO_2R^{15}$, and —$NR^{19}SO_2NR^{16}R^{17}$; or $R^3$ is H; and
$R^4$, $R^{4'}$, and $R^{4''}$ are taken together, along with the carbon atom to which they are attached, to form —$C(O)R^{18}$ or 6- to 10-membered heteroaryl;

$R^5$ is selected from H, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 6- to 10-membered heteroaryl; wherein each alkyl, cycloalkyl, heterocycloalkyl, aryl, and heteroaryl is independently optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$;

$R^6$ and $R^7$ are each independently selected from H, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, 6- to 10-membered heteroaryl, —($C_{1-4}$alkyl)$C_{3-6}$cycloalkyl, —($C_{1-4}$alkyl) (3- to 10-membered heterocycloalkyl), —($C_{1-4}$alkyl)$C_{6-10}$aryl, and —($C_{1-4}$alkyl)(6- to 10-membered heteroaryl); wherein each alkyl, cycloalkyl, heterocycloalkyl, aryl, and heteroaryl is independently optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$; or $R^6$ and $R^7$, along with the nitrogen atom to which they are attached, are taken together to form a 3- to 10-membered heterocycloalkyl optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$;

$R^8$ and $R^9$ are each independently selected from H, halo, —CN, —$OR^{18}$, —$SOR^{15}$, —$SO_2R^{15}$, —$NR^{16}R^{17}$, —C(O)$NR^{16}R^{17}$, —$SO_2NR^{16}R^{17}$, —C(O)$R^{18}$, —C(O)O$R^{18}$, —$NR^{19}$C(O)$R^{18}$, —$NR^{19}$C(O)$NR^{16}R^{17}$, —$NR^{19}SO_2R^{15}$, —$NR^{19}SO_2NR^{16}R^{17}$, $C_{1-6}$alkyl, $C_{2-6}$alkenyl, $C_{2-6}$alkynyl, $C_{1-6}$heteroalkyl, and $C_{1-6}$haloalkyl; wherein each alkyl, alkenyl, and alkynyl is independently optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$;

each $R^{10}$ is independently selected from halo, —CN, —$OR^{18}$, —$NR^{16}R^{17}$, —C(O)$NR^{16}R^{17}$, —$SO_2NR^{16}R^{17}$, —C(O)$R^{18}$, —C(O)O$R^{18}$, —$NR^{19}$C(O)$R^{18}$, $C_{1-6}$alkyl, $C_{1-6}$heteroalkyl, $C_{1-6}$haloalkyl, $C_{3-6}$cycloalkyl, 3- to 10-membered heterocycloalkyl; wherein each alkyl, cycloalkyl, and heterocycloalkyl is independently optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$;

$R^{11}$, $R^{12}$, $R^{13}$, and $R^{14}$ are each independently selected from H, halo, —CN, —$OR^{18}$, —$NR^{16}R^{17}$, —C(O)$NR^{16}R^{17}$, —$SO_2NR^{16}R^{17}$, —C(O)$R^{18}$, —C(O)O$R^{18}$, —$NR^{19}$C(O) $R^{18}$, $C_{1-6}$alkyl, $C_{1-6}$heteroalkyl, $C_{1-6}$haloalkyl, $C_{3-6}$cycloalkyl, 3- to 10-membered heterocycloalkyl; wherein each alkyl, cycloalkyl, and heterocycloalkyl is independently optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$;

each $R^{15}$ is independently selected from $C_{1-4}$alkyl, $C_{1-4}$haloalkyl, $C_{3-6}$cycloalkyl, 3- to 10-membered heterocycloalkyl, $C_{6-10}$aryl, and 6- to 10-membered heteroaryl;

each $R^{16}$ and $R^{17}$ is independently selected from H, $C_{1-4}$alkyl, $C_{1-4}$heteroalkyl, $C_{1-4}$haloalkyl, $C_{3-6}$cycloalkyl, 3- to 10-membered heterocycloalkyl, $C_{6-10}$aryl, 6- to 10-membered heteroaryl; or an $R^{16}$ and an $R^{17}$ may be taken together along with the nitrogen atom to which they are attached to form a 3- to 10-membered heterocycloalkyl;

each $R^{18}$ is independently selected from H, $C_{1-4}$alkyl, $C_{1-4}$heteroalkyl, $C_{1-4}$haloalkyl, and $C_{3-6}$cycloalkyl;

each $R^{19}$ is independently selected from H, $C_{1-4}$alkyl, $C_{1-4}$heteroalkyl, $C_{1-4}$haloalkyl, and $C_{3-6}$cycloalkyl;

each $R^{20}$ and $R^{21}$ is independently selected from H, $C_{1-4}$alkyl, $C_{1-4}$heteroalkyl, $C_{1-4}$haloalkyl, $C_{3-6}$cycloalkyl, 3- to 10-membered heterocycloalkyl, $C_{6-10}$aryl, 6- to 10-membered heteroaryl; or an $R^{20}$ and an $R^{21}$ may be taken together along with the nitrogen atom to which they are attached to form a 3- to 10-membered heterocycloalkyl; and n is 0, 1, 2, 3, or 4.

In some embodiments, Ring A is selected from $C_{3-6}$cycloalkyl and 3- to 10-membered heterocycloalkyl. In some embodiments, Ring A is $C_{3-6}$cycloalkyl. In some embodiments, Ring A is selected from the group consisting of:

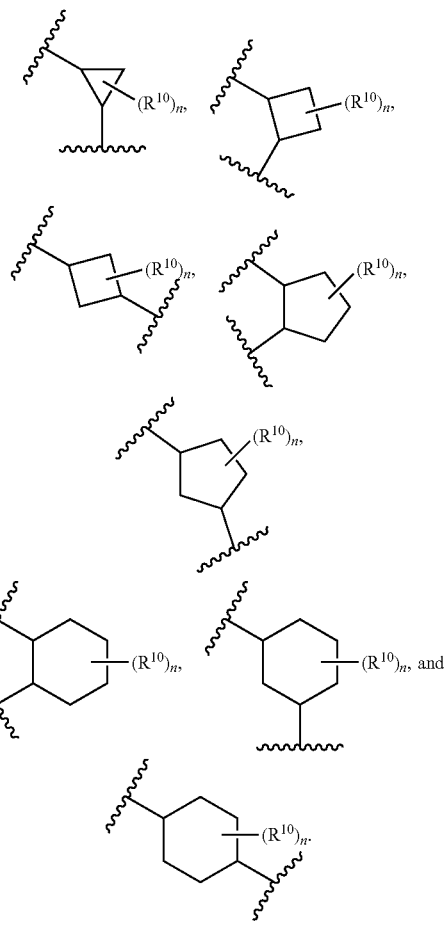

In some embodiments, Ring A is selected from the group consisting of:

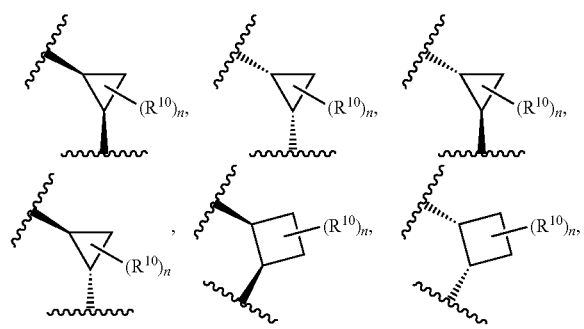

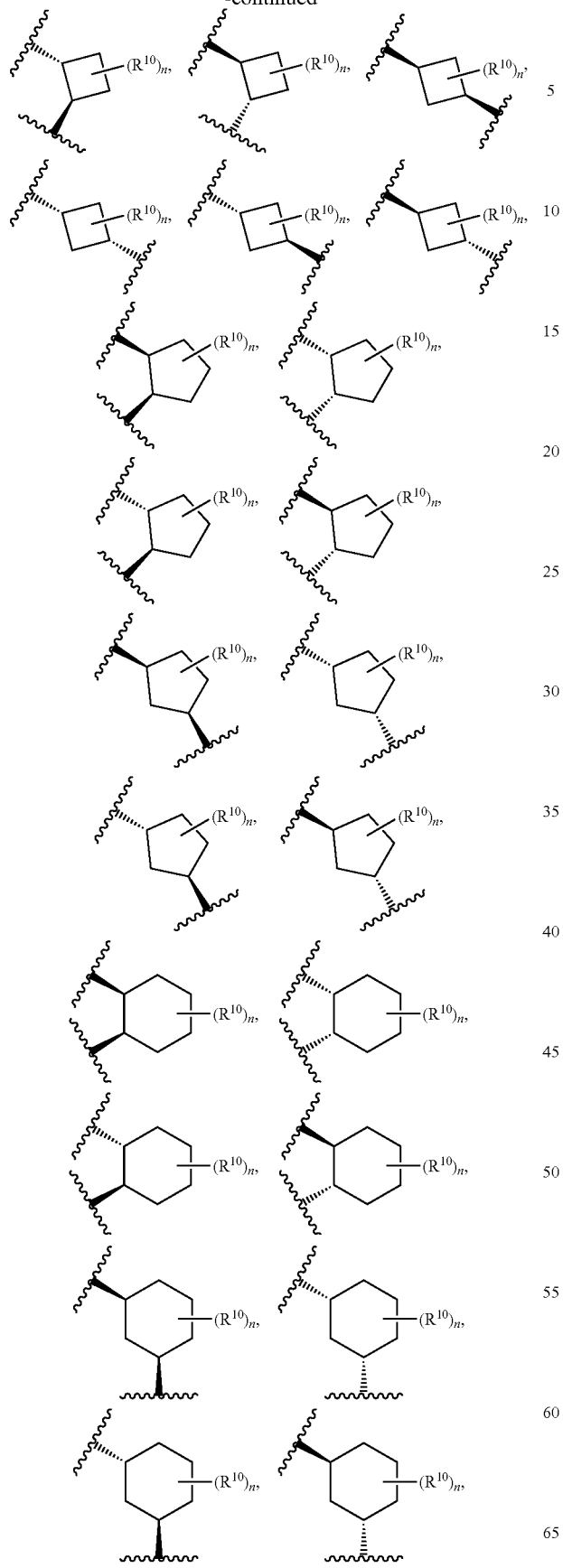

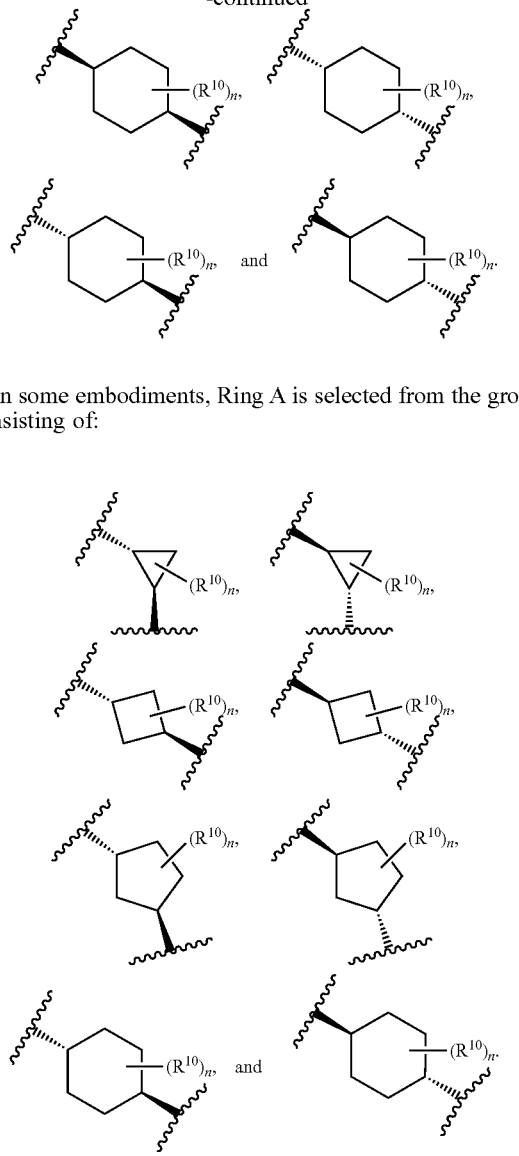

In some embodiments, Ring A is selected from the group consisting of:

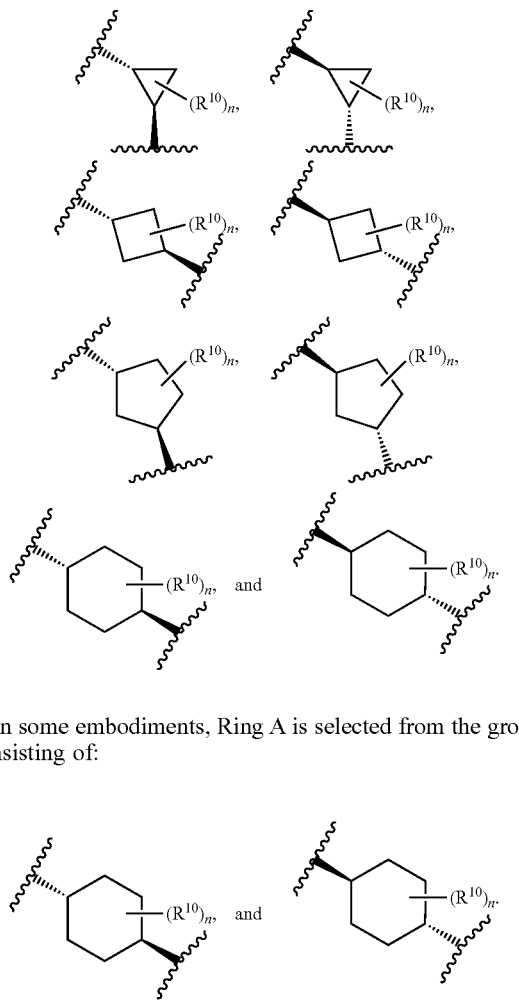

In some embodiments, Ring A is selected from the group consisting of:

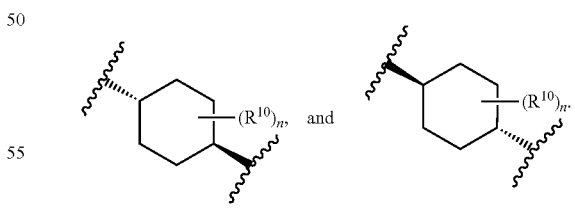

In some embodiments, one of $X^1$, $X^2$, $X^3$, and $X^4$ is N. In some embodiments, none of $X^1$, $X^2$, $X^3$, and $X^4$ is N.

In some embodiments, $R^{11}$, $R^{12}$, $R^{13}$, and $R^{14}$ are each independently selected from H, halo, —CN, —OR$^{18}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —NR$^{19}$C(O)R$^{18}$, $C_{1-6}$alkyl, and $C_{1-6}$haloalkyl. In some embodiments, $R^{11}$, $R^{12}$, $R^{13}$, and $R^{14}$ are each independently selected from H, halo, —CN, —OR$^{18}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, and —NR$^{19}$C(O)R$^{18}$. In some embodiments, R$^{11}$, R$^{12}$, R$^{13}$, and R$^{14}$ are each independently selected from H, halo, —CN, —OR$^{18}$, and —NR$^{16}$R$^{17}$. In some embodiments, R$^{11}$ is chloro, and R$^{12}$, R$^{13}$, and R$^{14}$ are each H.

In some embodiments, R$^1$ is selected from H, C$_{1-6}$alkyl, C$_{1-6}$haloalkyl, and C$_{3-6}$cycloalkyl. In some embodiments, R$^1$ is Me. In some embodiments, R$^1$ is H.

In some embodiments, R$^2$ is selected from halo, —CN, —OR$^{18}$, —SOR$^{15}$, —SO$_2$R$^{15}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —NR$^{19}$C(O)R$^{18}$, —NR$^{19}$C(O)NR$^{16}$R$^{17}$, —NR$^{19}$SO$_2$R$^{15}$, —NR$^{19}$SO$_2$NR$^{16}$R$^{17}$, C$_{1-6}$alkyl, C$_{1-6}$haloalkyl, and C$_{3-6}$cycloalkyl. In some embodiments, R$^2$ is selected from halo, —CN, —OH, —OMe, —OEt, —NH$_2$, —NHMe, —NMe$_2$, Me, Et, n-Pr, i-Pr, —CF$_3$, and cyclopropyl. In some embodiments, R$^2$ is Me.

In some embodiments, R$^3$ is selected from H, C$_{1-6}$alkyl, C$_{1-6}$haloalkyl, C$_{3-6}$cycloalkyl, and 3- to 10-membered heterocycloalkyl. In some embodiments, R$^3$ is selected from H, Me, Et, —CF$_3$, and cyclopropyl. In some embodiments, R$^3$ is H.

In some embodiments, R$^2$ is Me and R$^3$ is H.

In some embodiments,

R$^4$ is selected from C$_{6-10}$aryl, 6- to 10-membered heteroaryl, —O(C$_{0-4}$alkyl)C$_{3-6}$cycloalkyl, —O(C$_{0-4}$alkyl)(3- to 10-membered heterocycloalkyl), —O(C$_{0-4}$alkyl)C$_{6-10}$aryl, —O(C$_{0-4}$alkyl)(6- to 10-membered heteroaryl), —O(C$_{0-4}$alkyl)C(O)OR$^{18}$, —O(C$_{0-4}$alkyl)C(O)NR$^{19}$SO$_2$R$^{15}$, —O(C$_{0-4}$alkyl)SO$_2$ NR$^{19}$C(O)R$^{18}$, —O(C$_{3-6}$cycloalkyl)C$_{3-6}$cycloalkyl, —O(C$_{3-6}$cycloalkyl)(3- to 10-membered heterocycloalkyl), —O(C$_{3-6}$cycloalkyl)C$_{6-10}$aryl, —O(C$_{3-6}$cycloalkyl)(6- to 10-membered heteroaryl), —O(C$_{3-6}$cycloalkyl)C(O)OR$^{18}$, —(C$_{1-4}$alkyl)C$_{3-6}$cycloalkyl, —(C$_{1-4}$alkyl)(3- to 10-membered heterocycloalkyl), —(C$_{1-4}$alkyl)C$_{6-10}$aryl, —(C$_{1-4}$alkyl)(6- to 10-membered heteroaryl) and —(C$_{1-4}$alkyl)C(O)OR$^{18}$; wherein each alkyl, cycloalkyl, heterocycloalkyl, aryl, and heteroaryl is independently optionally substituted with one or more substituents selected from C$_{1-4}$alkyl, oxo, halo, —OR$^{18}$, —CN, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —(C$_{1-4}$alkyl)OC(O)(C$_{1-4}$alkyl), —(C$_{1-4}$alkyl)OC(O)OR$^{18}$, —NR$^{19}$C(O)R$^{18}$, —NR$^{19}$C(O)NR$^{16}$R$^{17}$, —NR$^{19}$SO$_2$R$^{15}$, and —NR$^{19}$SO$_2$NR$^{16}$R$^{17}$; and R$^{4'}$ and R$^{4''}$ are each independently selected from H, C$_{1-6}$alkyl, C$_{1-6}$haloalkyl, and C$_{3-6}$cycloalkyl; wherein each alkyl and cycloalkyl is independently optionally substituted with one or more substituents selected from halo, —OR$^{18}$, —CN, and —NR$^{16}$R$^{17}$; or R$^3$ is H; and R$^4$, R$^{4'}$, and R$^{4''}$ are taken together, along with the carbon atom to which they are attached, to form —C(O)R$^{18}$ or 6- to 10-membered heteroaryl.

In some embodiments,

R$^4$ is selected from 6- to 10-membered heteroaryl, —O(C$_{0-4}$alkyl)(3- to 10-membered heterocycloalkyl), —O(C$_{0-4}$alkyl)C$_{6-10}$aryl, —O(C$_{0-4}$alkyl)(6- to 10-membered heteroaryl), —O(C$_{0-4}$alkyl)C(O)OR$^{18}$, —O(C$_{0-4}$alkyl)C(O)NR$^{19}$SO$_2$R$^{15}$, —O(C$_{0-4}$alkyl)SO$_2$ NR$^{19}$C(O)R$^{18}$, —O(C$_{3-6}$cycloalkyl)(6- to 10-membered heteroaryl), —O(C$_{3-6}$cycloalkyl)C(O)OR$^{18}$, —(C$_{1-4}$alkyl)(6- to 10-membered heteroaryl) and —(C$_{1-4}$alkyl)C(O)OR$^{18}$; wherein each alkyl, cycloalkyl, heterocycloalkyl, aryl, and heteroaryl is independently optionally substituted with one or more substituents selected from C$_{1-4}$alkyl, oxo, halo, —OR$^{18}$, —CN, —NR$^{16}$R$^{17}$, —C(O)NR$^{16}$R$^{17}$, —SO$_2$NR$^{16}$R$^{17}$, —C(O)OR$^{18}$, —(C$_{1-4}$alkyl)OC(O)(C$_{1-4}$alkyl), —(C$_{1-4}$alkyl)OC(O)OR$^{18}$, —NR$^{19}$C(O)R$^{18}$, —NR$^{19}$C(O)NR$^{16}$R$^{17}$, —NR$^{19}$SO$_2$R$^{15}$, and —NR$^{19}$SO$_2$NR$^{16}$R$^{17}$; and R$^{4'}$ and R$^{4''}$ are both H; or R$^3$ is H; and R$^4$, R$^{4'}$, and R$^{4''}$ are taken together, along with the carbon atom to which they are attached, to form —C(O)R$^{18}$ or 6- to 10-membered heteroaryl.

In some embodiments,

R$^4$ is selected from 6- to 10-membered heteroaryl, —O(C$_{0-4}$alkyl)(3- to 10-membered heterocycloalkyl), —O(C$_{0-4}$alkyl)C$_{6-10}$aryl, —O(C$_{0-4}$alkyl)(6- to 10-membered heteroaryl), —O(C$_{0-4}$alkyl)C(O)OR$^{18}$, —O(C$_{0-4}$alkyl)C(O)NR$^{19}$SO$_2$R$^{15}$, —O(C$_{0-4}$alkyl)SO$_2$ NR$^{19}$C(O)R$^{18}$, —O(C$_{3-6}$cycloalkyl)(6- to 10-membered heteroaryl), —O(C$_{3-6}$cycloalkyl)C(O)OR$^{18}$, —(C$_{1-4}$alkyl)(6- to 10-membered heteroaryl) and —(C$_{1-4}$alkyl)C(O)OR$^{18}$; wherein each alkyl, cycloalkyl, heterocycloalkyl, aryl, and heteroaryl is independently optionally substituted with one or more substituents selected from C$_{1-4}$alkyl, oxo, halo, —OR$^{18}$, —CN, —NR$^{16}$R$^{17}$, —C(O)NR$^{16}$R$^{17}$, —SO$_2$NR$^{16}$R$^{17}$, —C(O)OR$^{18}$, —(C$_{1-4}$alkyl)OC(O)(C$_{1-4}$alkyl), —(C$_{1-4}$alkyl)OC(O)OR$^{18}$, —NR$^{19}$C(O)R$^{18}$, —NR$^{19}$C(O)NR$^{16}$R$^{17}$, —NR$^{19}$SO$_2$R$^{15}$, and —NR$^{19}$SO$_2$NR$^{16}$R$^{17}$; and R$^{4'}$ and R$^{4''}$ are both H.

In some embodiments,

R$^3$ is H; and

R$^4$, R$^{4'}$, and R$^{4''}$ are taken together, along with the carbon atom to which they are attached, to form —C(O)R$^{18}$ or 6- to 10-membered heteroaryl.

In some embodiments, R$^5$ is selected from H, C$_{1-6}$alkyl, C$_{1-6}$haloalkyl, and C$_{3-6}$cycloalkyl. In some embodiments, R$^5$ is Me. In some embodiments, R$^5$ is H.

In some embodiments,

R$^6$ and R$^7$ are each independently selected from H, —(C$_{1-4}$ alkyl)C$_{3-6}$cycloalkyl, —(C$_{1-4}$alkyl)(3- to 10-membered heterocycloalkyl), —(C$_{1-4}$alkyl)C$_{6-10}$aryl, and —(C$_{1-4}$ alkyl)(6- to 10-membered heteroaryl); wherein each alkyl, cycloalkyl, heterocycloalkyl, aryl, and heteroaryl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$; or R$^6$ and R$^7$, along with the nitrogen atom to which they are attached, are taken together to form a 3- to 10-membered heterocycloalkyl optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$.

In some embodiments, R$^6$ and R$^7$ are each independently selected from H and —(C$_{1-4}$alkyl)(3- to 10-membered heterocycloalkyl); wherein each alkyl and heterocycloalkyl is independently optionally substituted with one or more substituents selected from halo, —OR$^{18}$, —CN, and —NR$^{20}$R$^{21}$.

In some embodiments, one of R$^6$ and R$^7$ is H and the other is

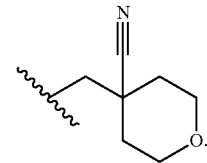 [SMILES: *CC1(C#N)CCOCC1]

In some embodiments, $R^8$ and $R^9$ are each independently selected from H, halo, —CN, —OR$^{18}$, —SO$_2$R$^{15}$, —NR$^{16}$R$^{17}$, —C(O)NR$^{16}$R$^{17}$, —SO$_2$NR$^{16}$R$^{17}$, —C(O)OR$^{18}$, —NR$^{19}$C(O)R$^{18}$, —NR$^{19}$SO$_2$R$^{15}$. In some embodiments, $R^8$ and $R^9$ are each independently selected from H, halo, —CN, —OR$^{18}$, and —NR$^{16}$R$^{17}$. In some embodiments, $R^8$ and $R^9$ are both H.

In some embodiments, n is 0, 1, or 2. In some embodiments, n is 0.

In some embodiments, the compound of Formula (I) is represented by Formula (I-A):

Formula (I-A)

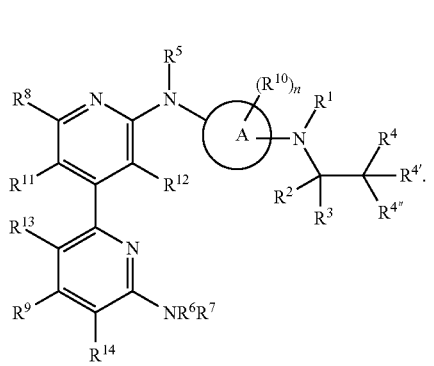

In some embodiments, the compound of Formula (I) is represented by Formula (I-B):

Formula (I-B)

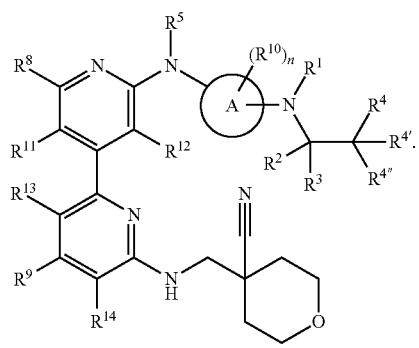

In some embodiments, the compound of Formula (I) is represented by Formula (I-C), Formula (I-D), Formula (I-E), or Formula (I-F):

Formula (I-C)

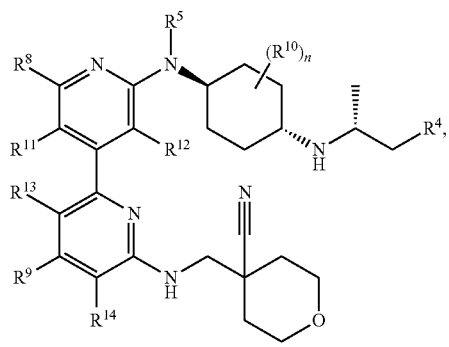

Formula (I-D)

Formula (I-E)

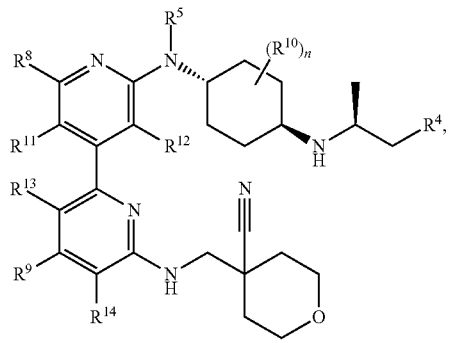

Formula (I-F)

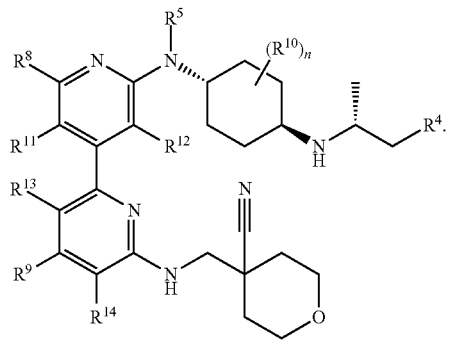

In some embodiments, the compound is selected from the group consisting of:

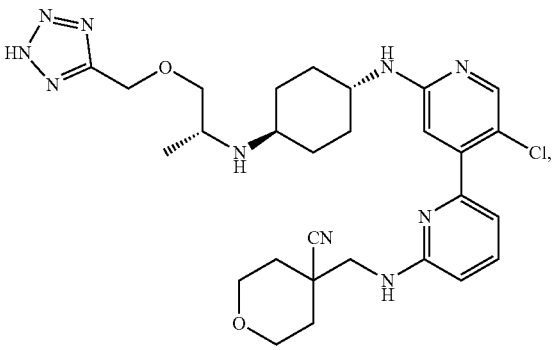

11
-continued
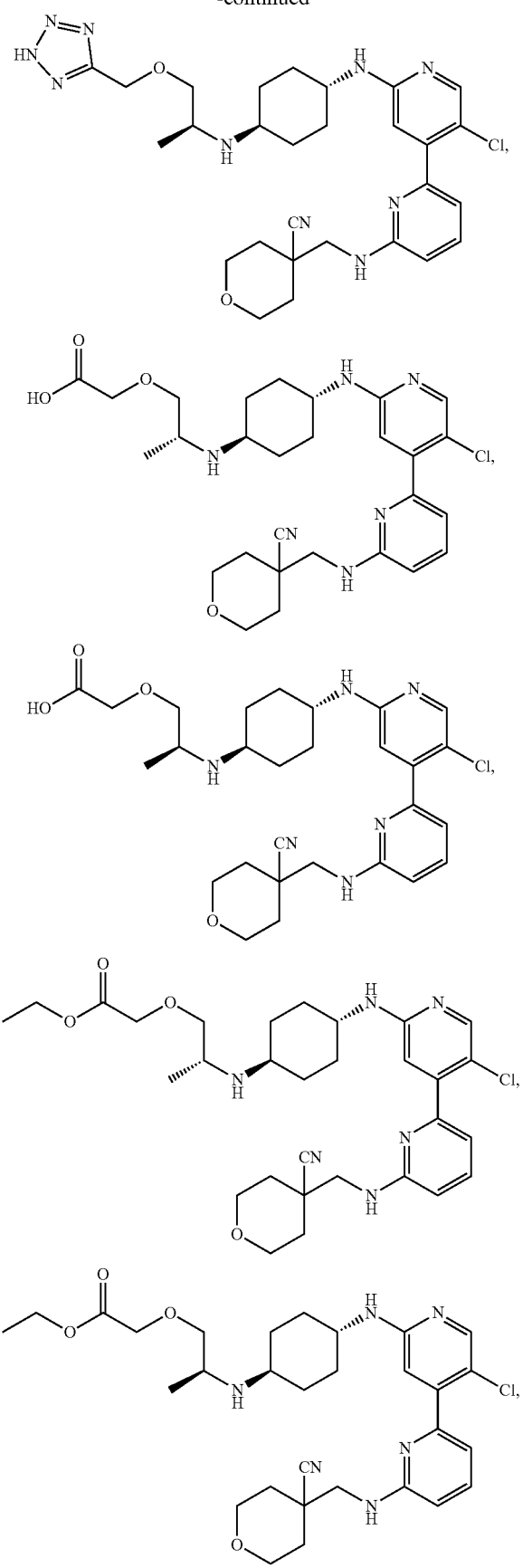
12
-continued
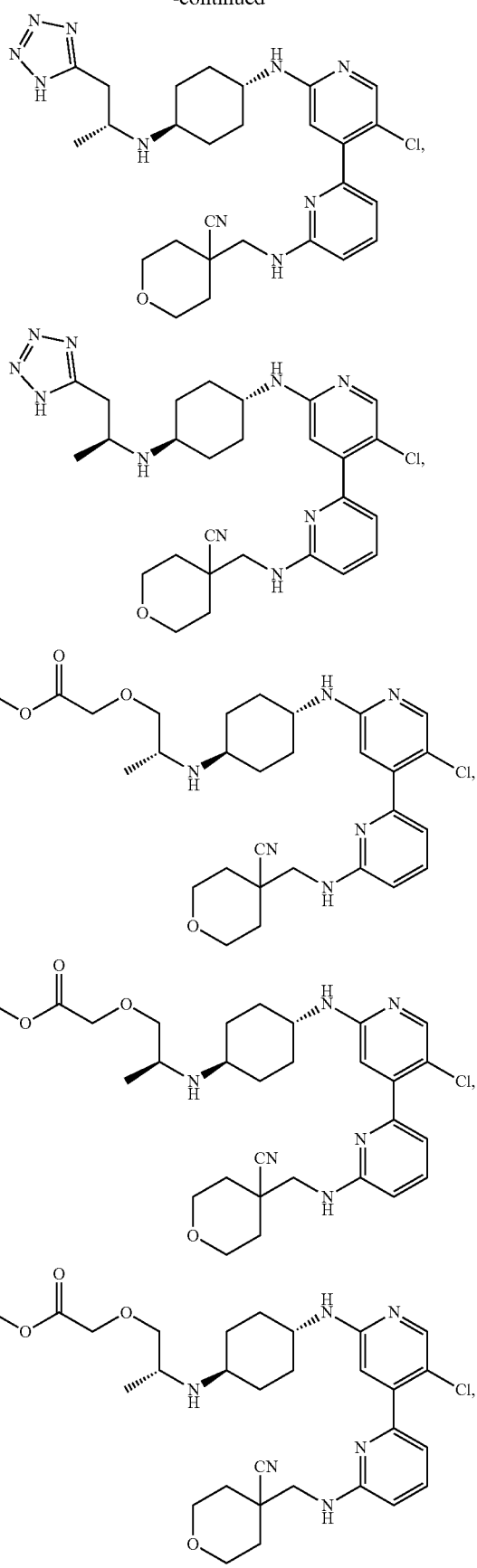

13
-continued
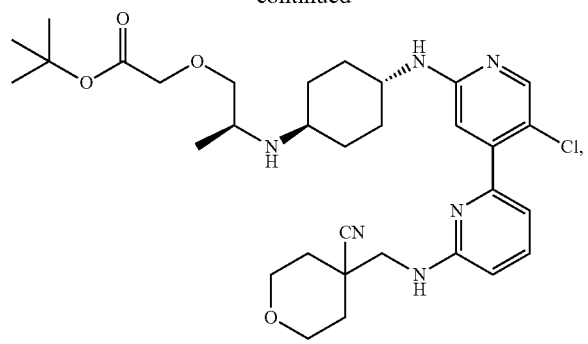
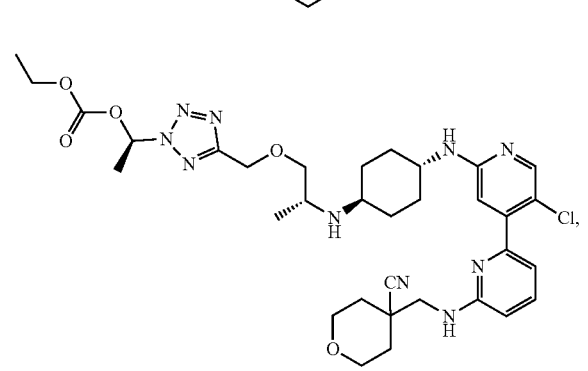
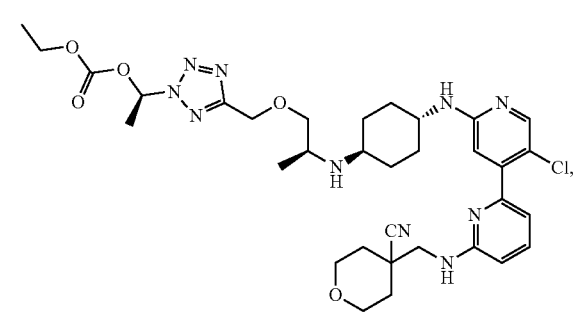
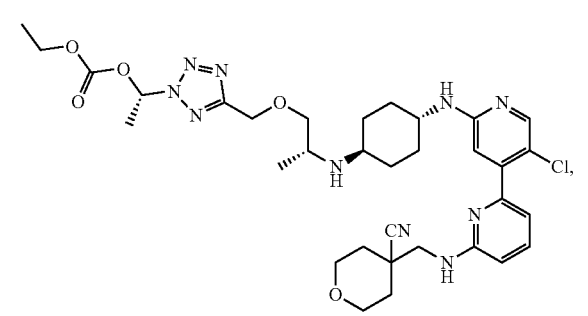
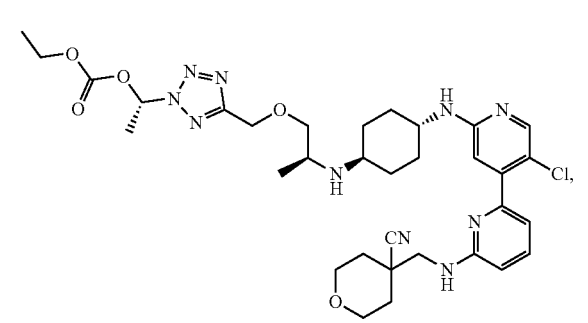
14
-continued
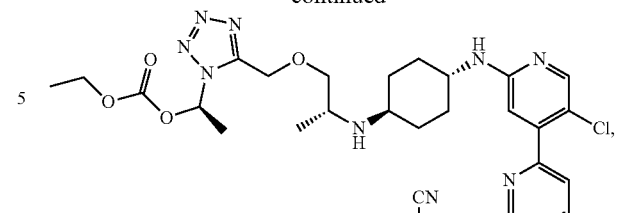
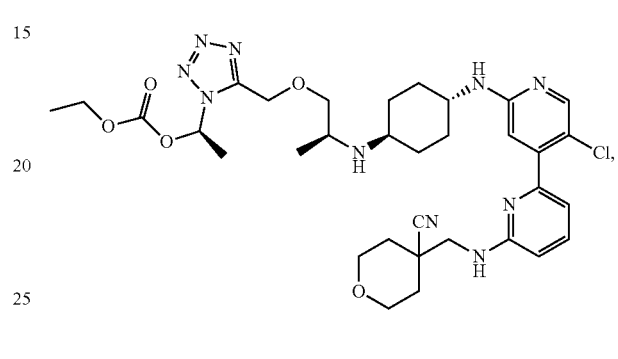
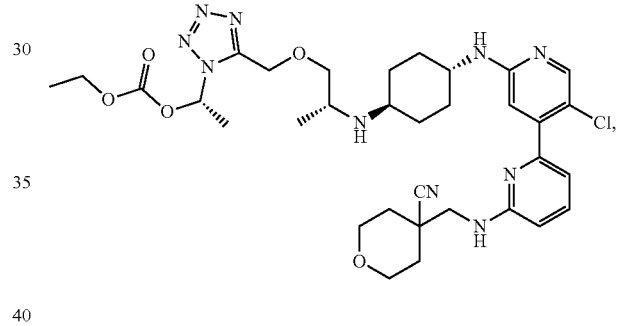
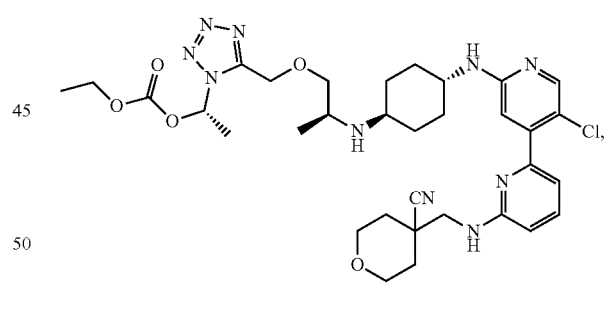
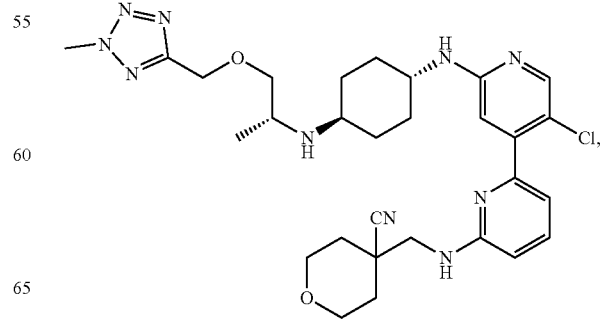

15
-continued
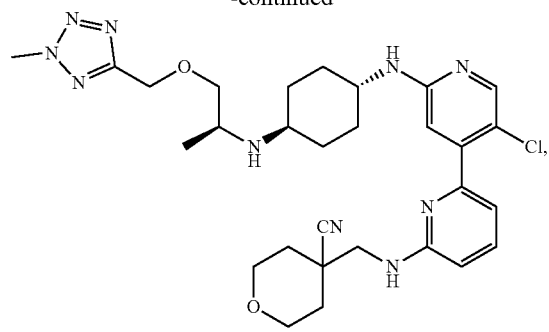
16
-continued
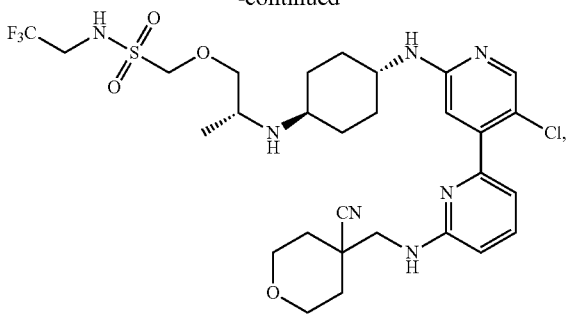
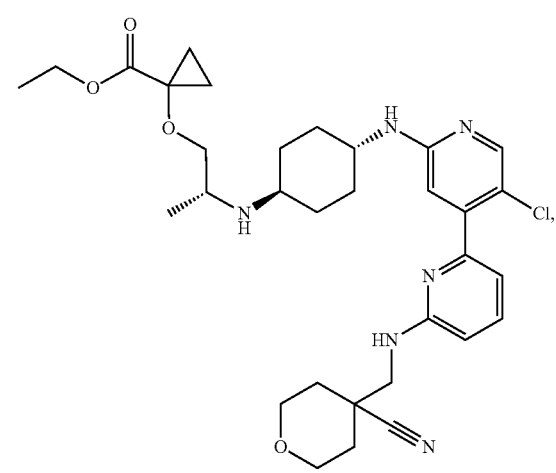

17
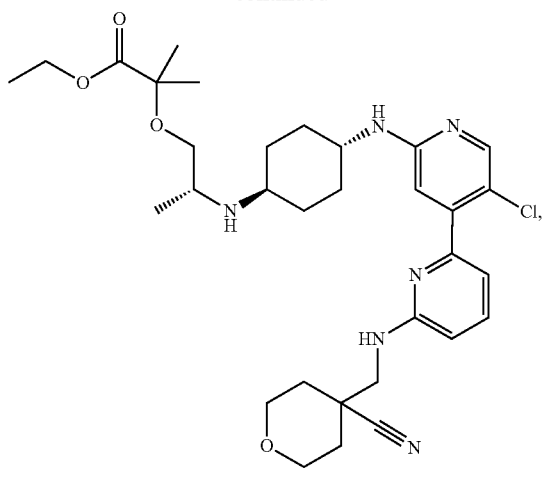
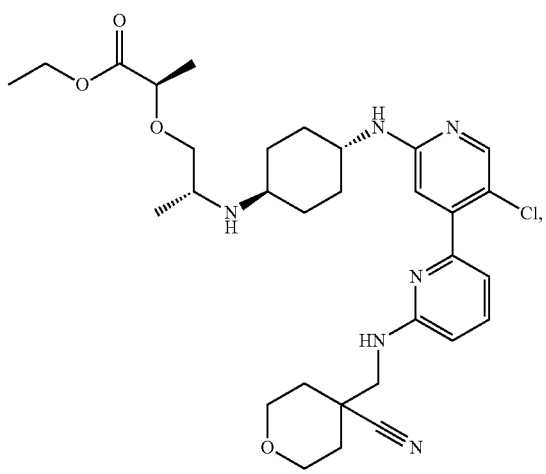
18
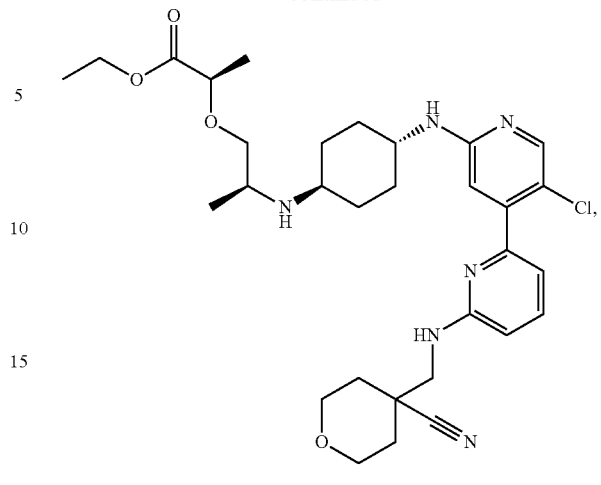
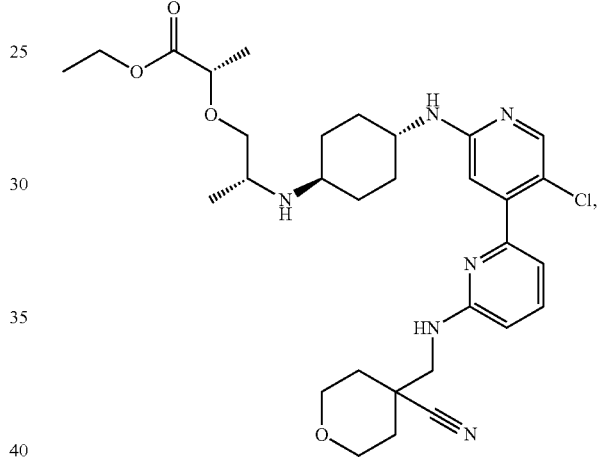
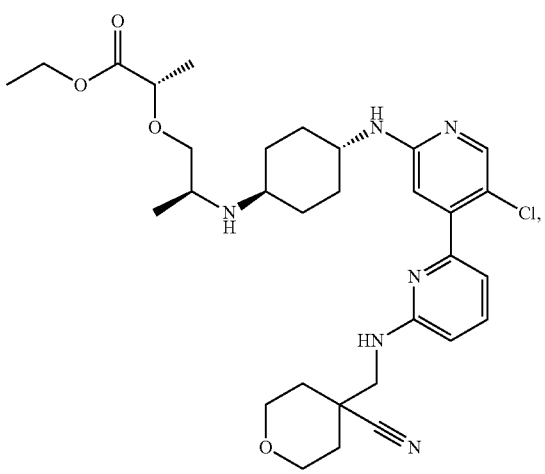

-continued
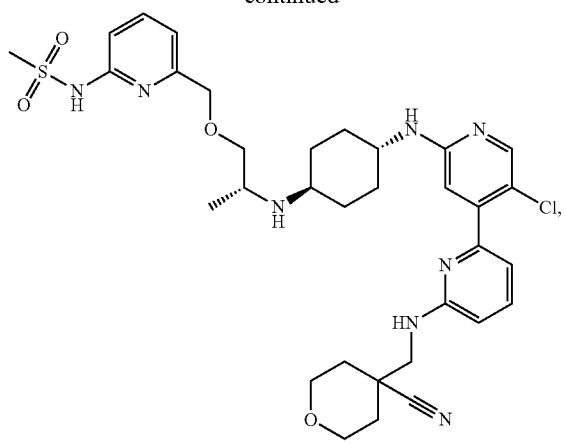
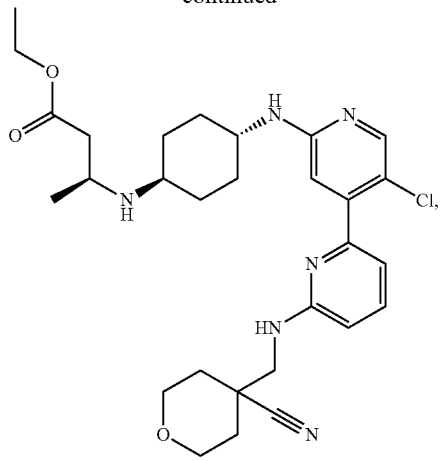
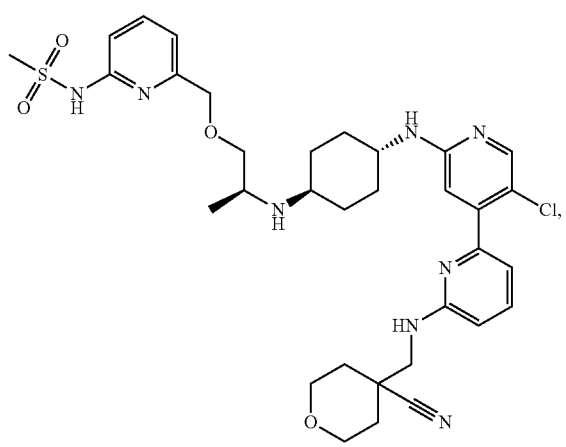
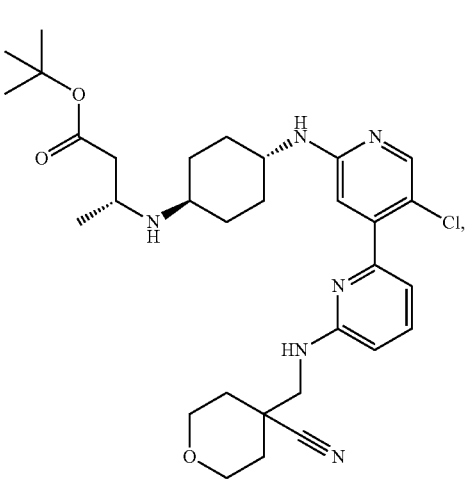
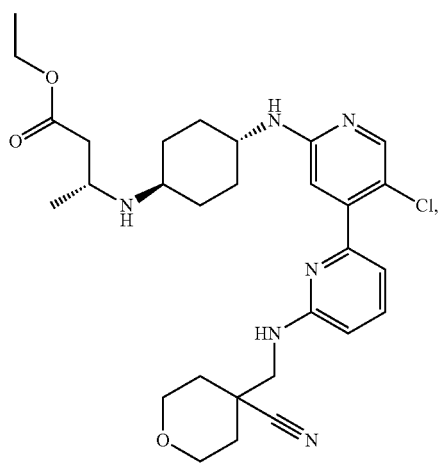
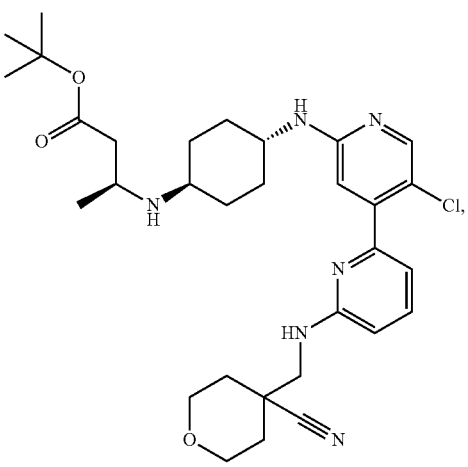

21
-continued
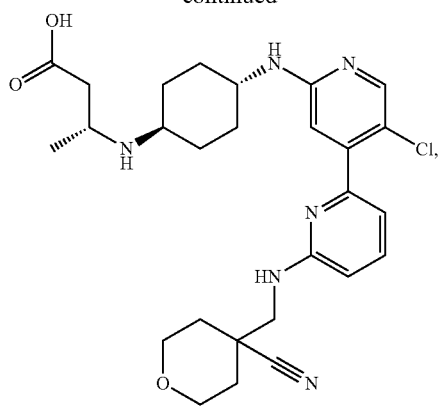
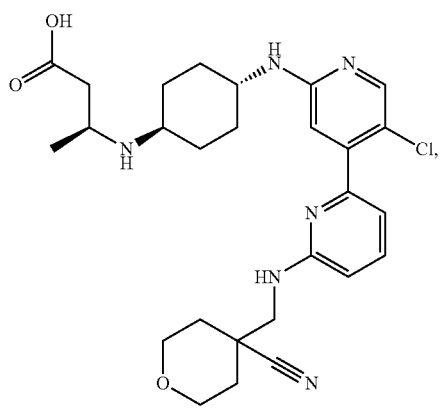
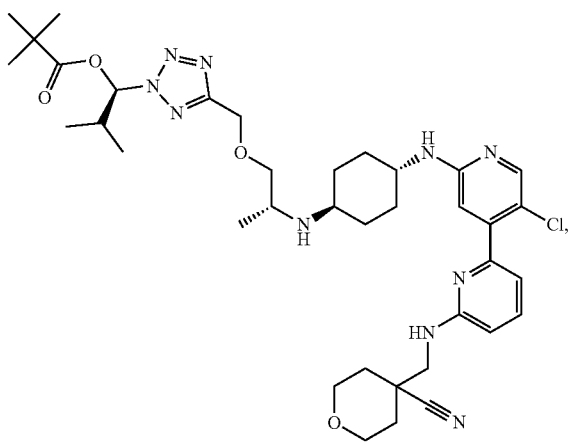
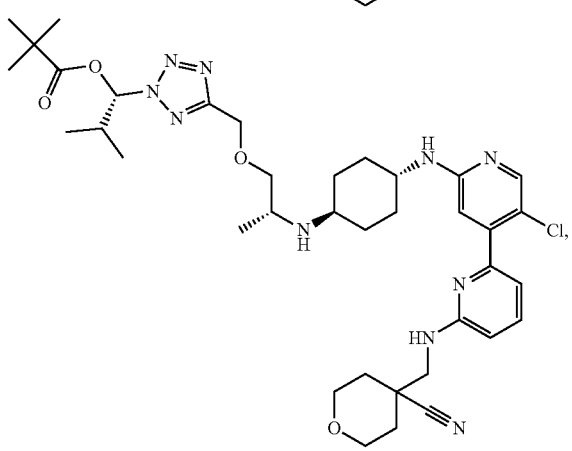
22
-continued
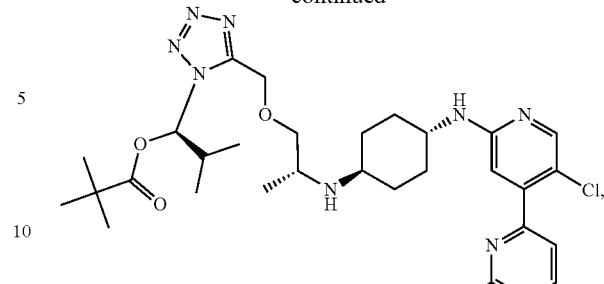
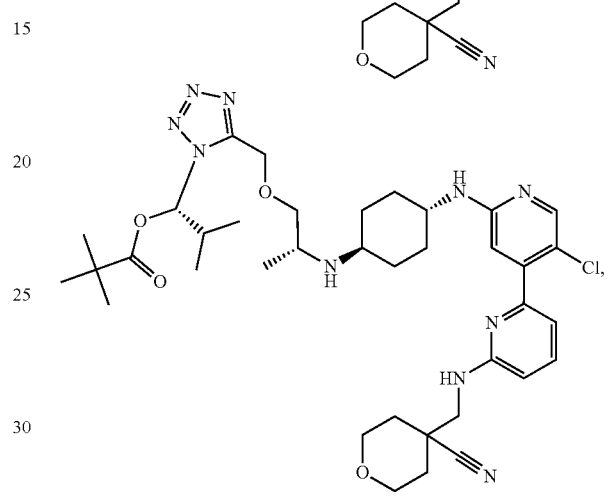
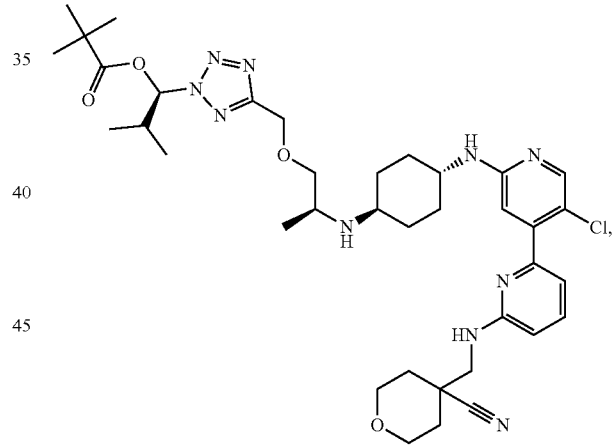
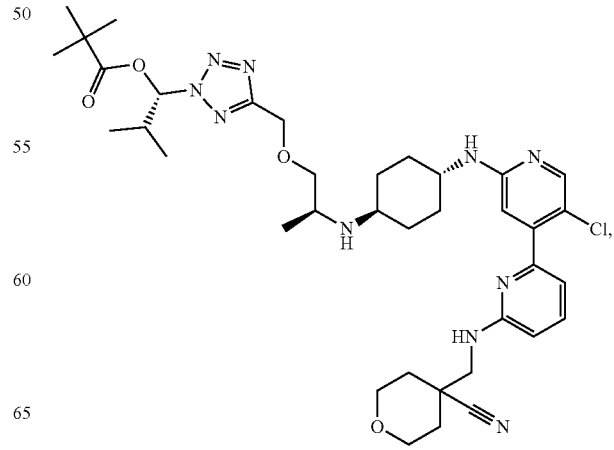

23
-continued
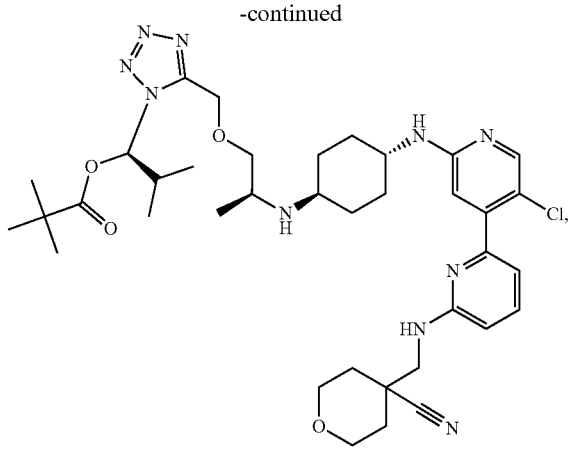
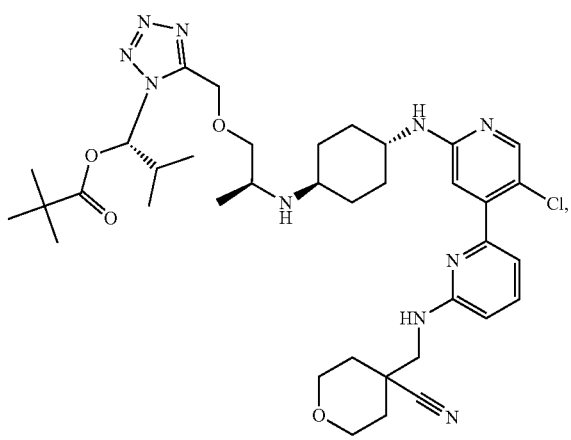
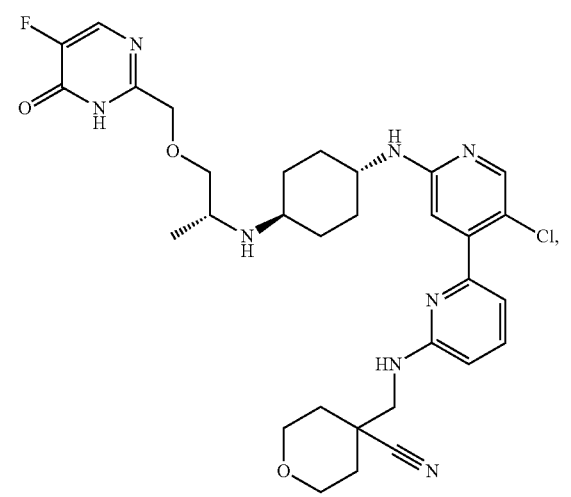
24
-continued
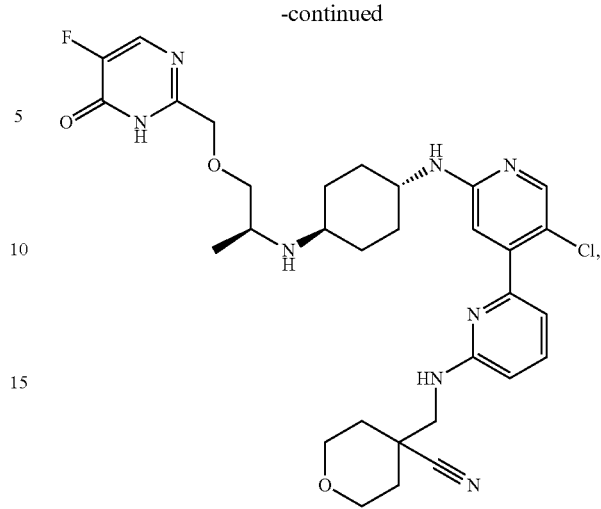
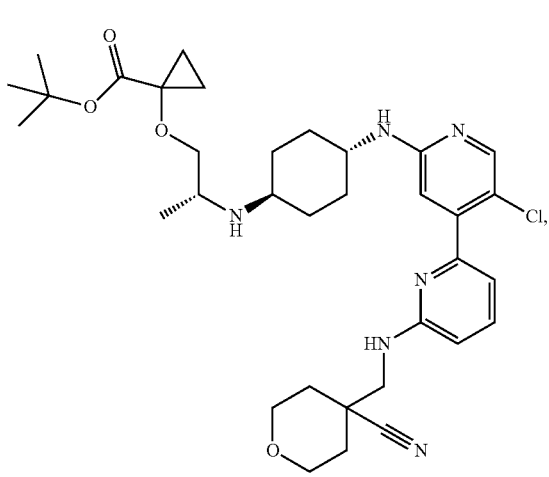
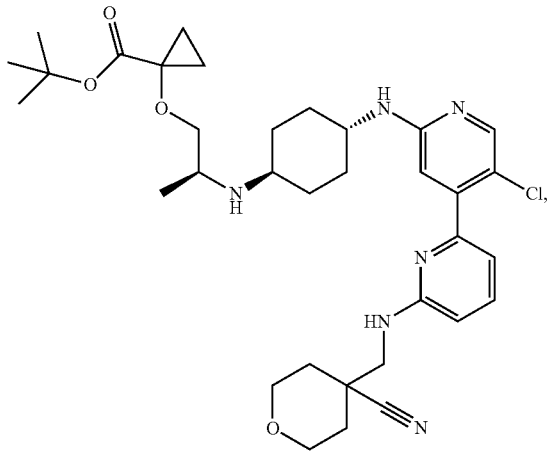

25
-continued
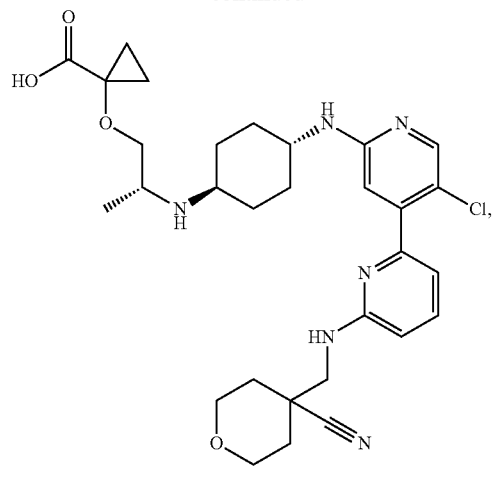
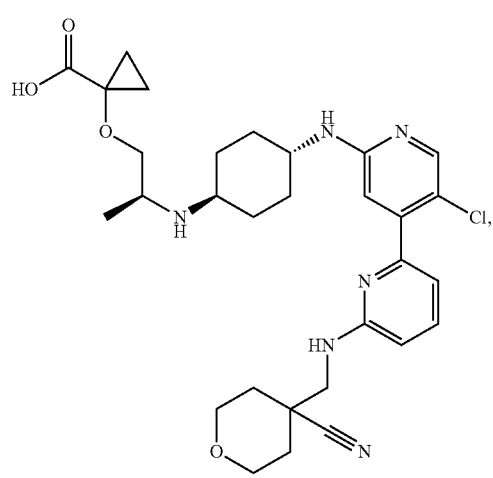
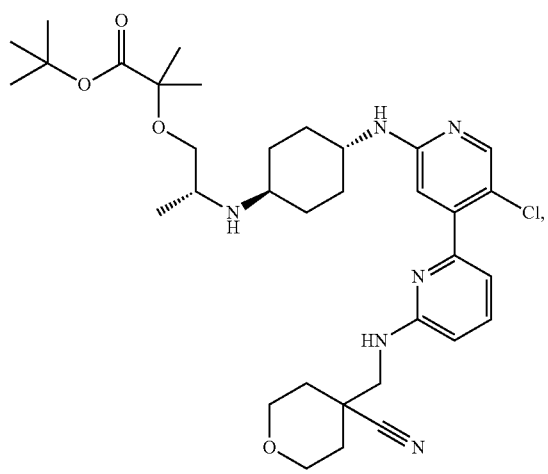
26
-continued
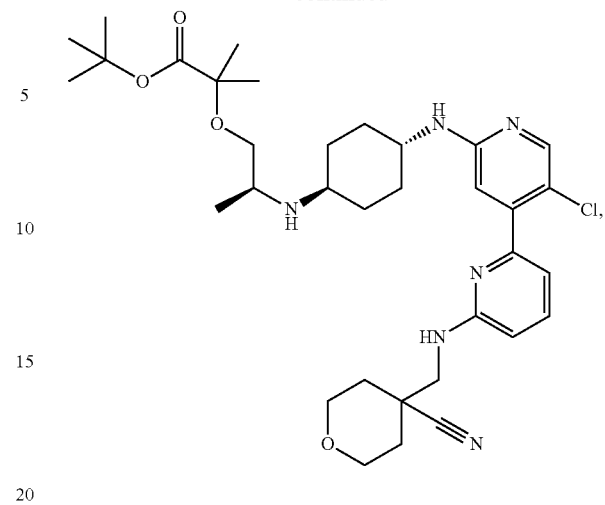
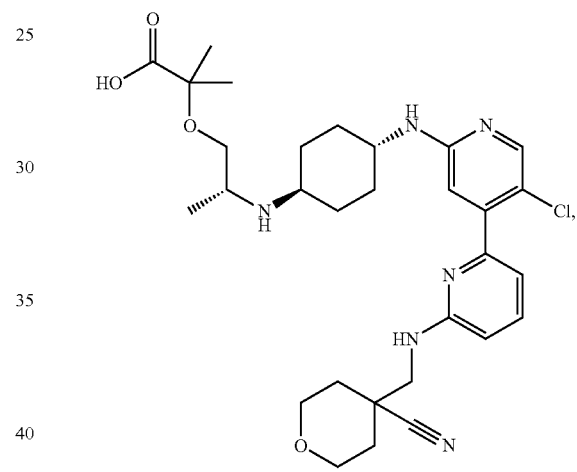
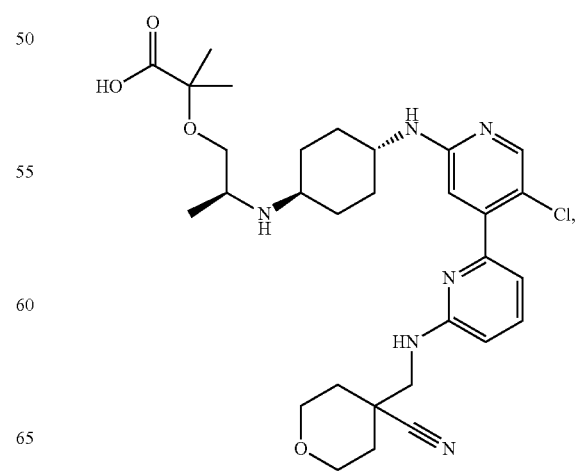

27
-continued
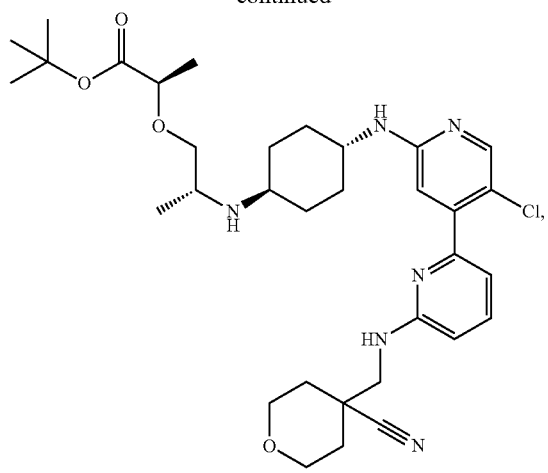
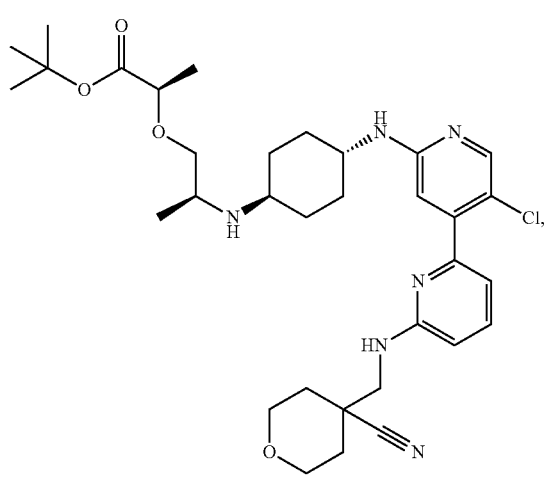
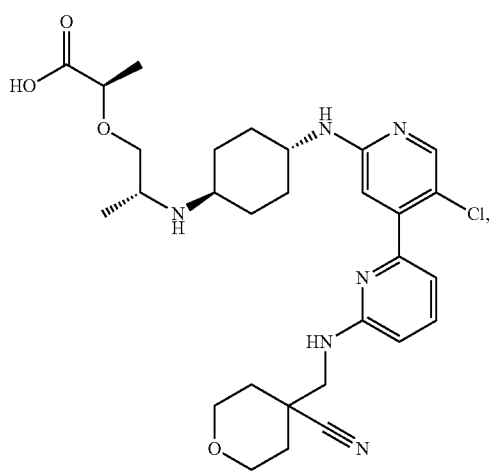
28
-continued
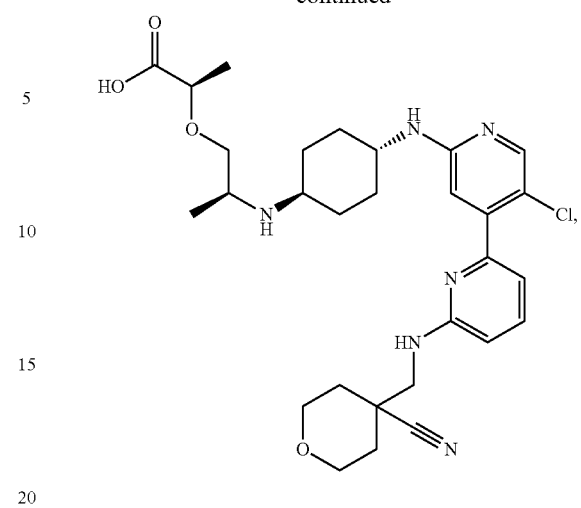
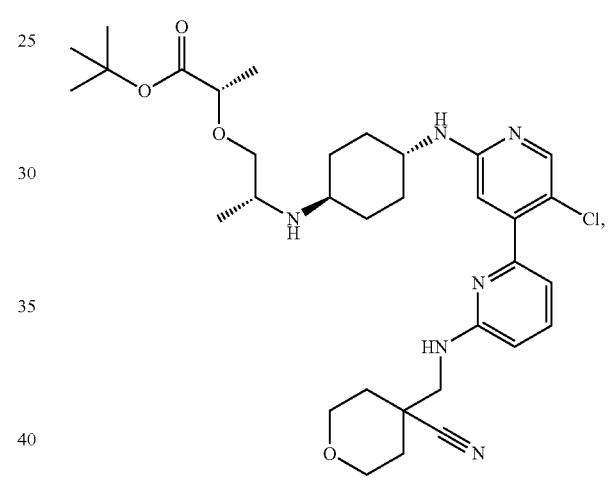
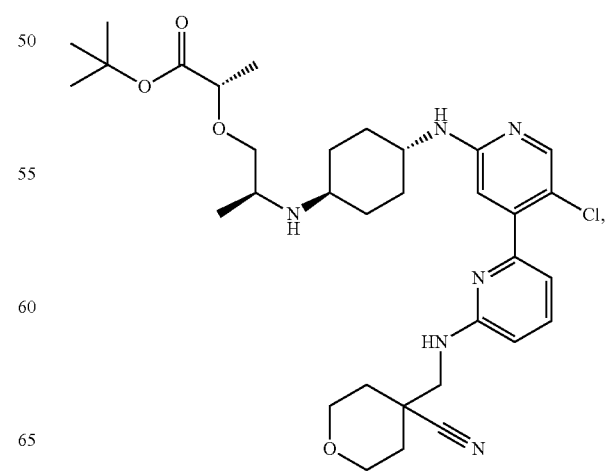

29
-continued
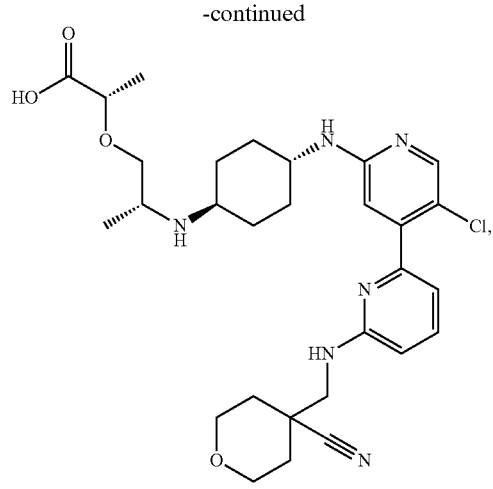
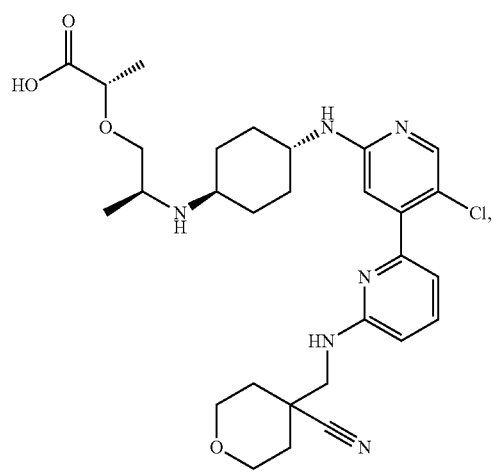
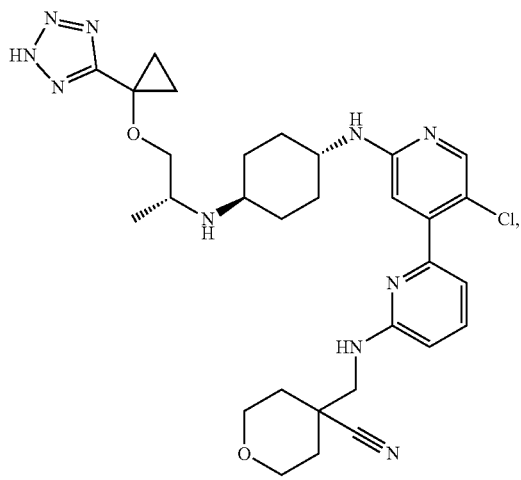
30
-continued
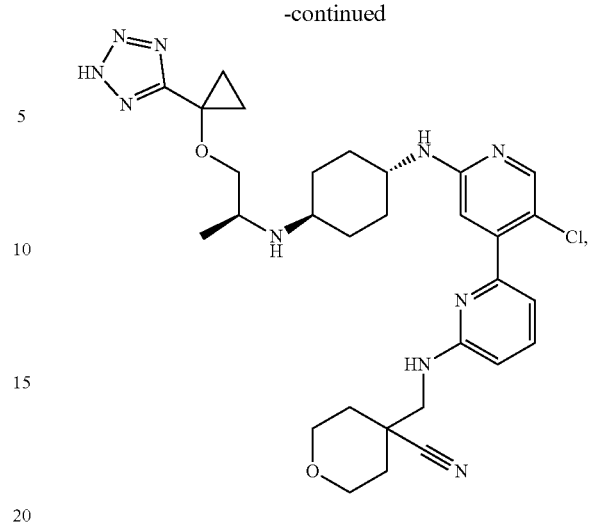
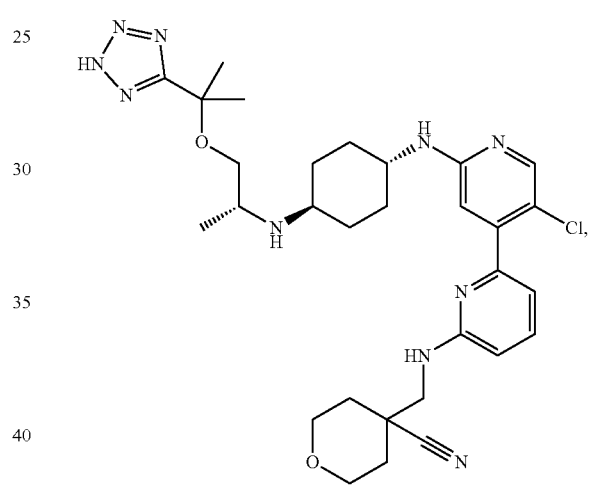
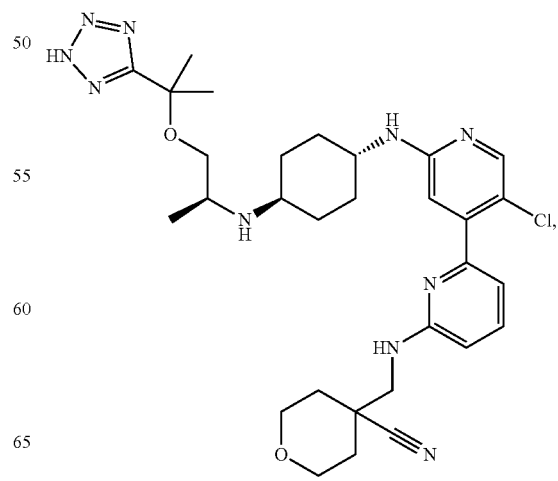

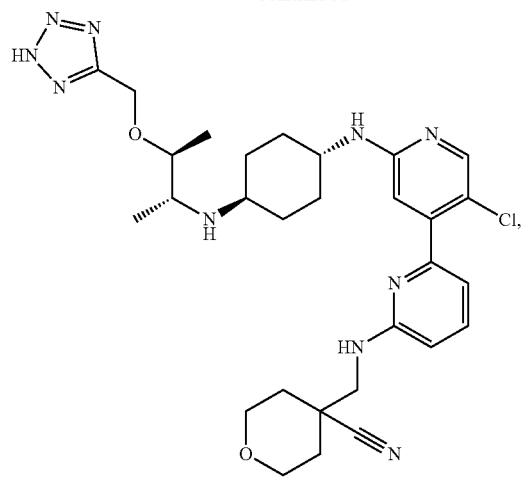
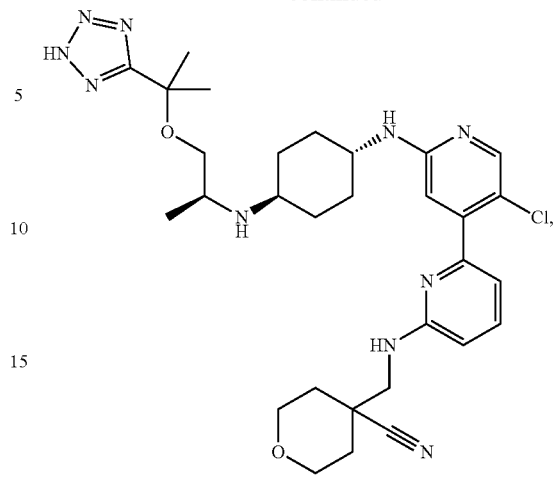

Provided herein, in another aspect, is a pharmaceutical composition comprising a compound described herein, or a pharmaceutically acceptable salt thereof, and a pharmaceutically acceptable excipient.

Provided herein, in another aspect, is a method of treating a disease or disorder in a patient in need thereof, comprising administering to the subject a therapeutically effective amount of a compound described herein, or a pharmaceutically acceptable salt thereof, or a pharmaceutical composition described herein.

In some embodiments, the disease or disorder is cancer. In some embodiments, the cancer is selected from leukemia, breast cancer, prostate cancer, ovarian cancer, colon cancer, cervical cancer, lung cancer, lymphoma, and liver cancer. In some embodiments, the cancer is liver cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
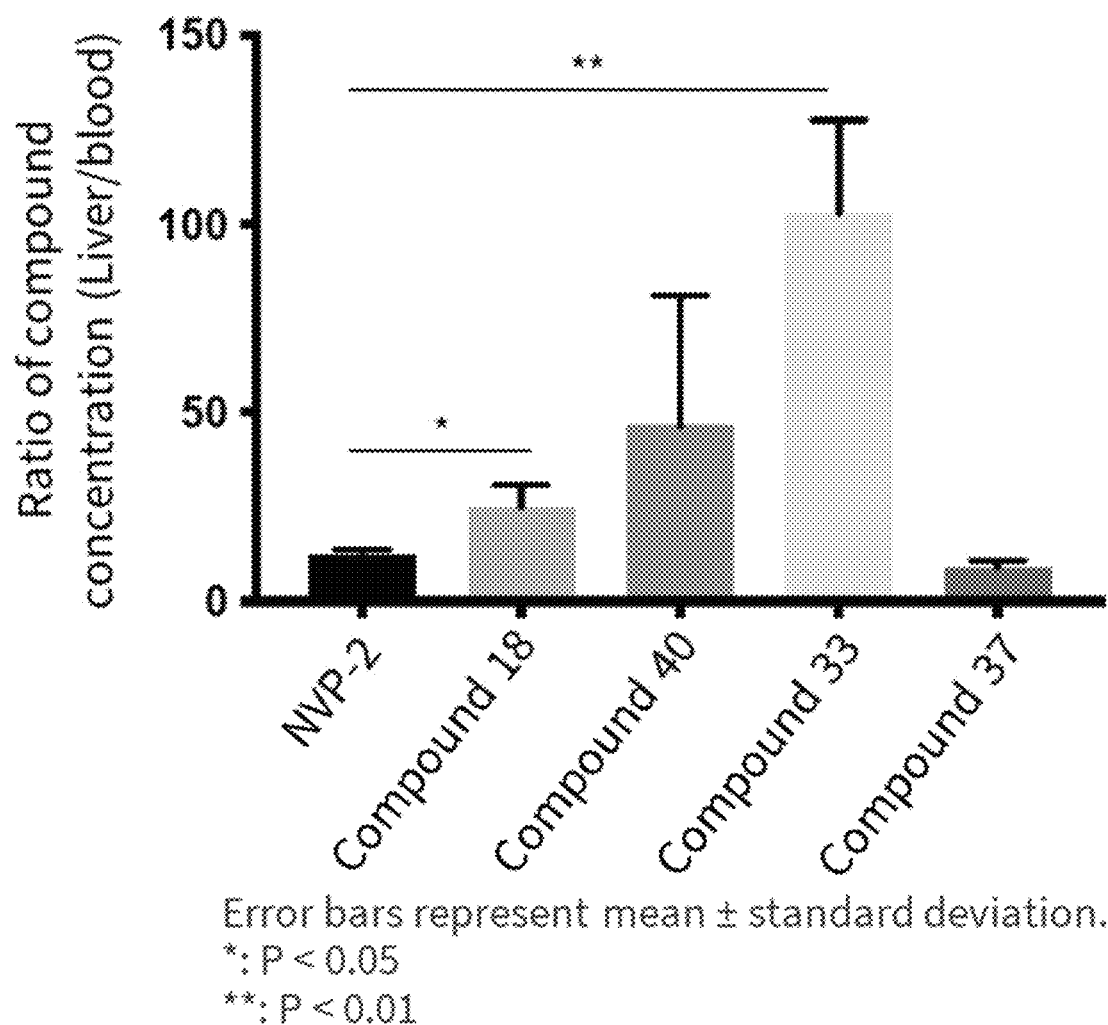
FIG. 1 shows ratios of compound concentrations in liver versus blood in CD-1 mice following a single oral administration dose of 5 mg/kg compound suspension.

Unless defined otherwise, all technical and scientific terms used herein have the same meaning as is commonly understood by one of skill in the art to which this disclosure belongs.

As used herein, the singular form "a", "an" and "the" includes plural references unless the context clearly dictates otherwise.

The term "$C_{x-y}$" when used in conjunction with a chemical moiety, such as alkyl, alkenyl, or alkynyl is meant to include groups that contain from x to y carbons in the chain. For example, the term "$C_{1-6}$alkyl" refers to substituted or unsubstituted saturated hydrocarbon groups, including straight-chain alkyl and branched-chain alkyl groups that contain from 1 to 6 carbons. The term —$C_{x-y}$alkylene-refers to a substituted or unsubstituted alkylene chain with from x to y carbons in the alkylene chain. For example —$C_{1-6}$ alkylene-may be selected from methylene, ethylene, propylene, butylene, pentylene, and hexylene, any one of which is optionally substituted.

"Alkyl" refers to substituted or unsubstituted saturated hydrocarbon groups, including straight-chain alkyl and branched-chain alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including straight-chain or branched-chain alkenyl groups containing at least one double bond. An alkenyl group may contain from two to twelve carbon atoms (e.g., $C_{2-12}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including straight-chain or branched-chain alkynyl groups containing at least one triple bond. An alkynyl group may contain from two to twelve carbon atoms (e.g., $C_{2-12}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Heteroalkyl", "heteroalkenyl" and "heteroalkynyl" refer to substituted or unsubstituted alkyl, alkenyl and alkynyl groups which respectively have one or more skeletal chain atoms selected from an atom other than carbon. Exemplary skeletal chain atoms selected from an atom other than carbon include, e.g., O, N, P, Si, S, or combinations thereof, wherein the nitrogen, phosphorus, and sulfur atoms may optionally be oxidized and the nitrogen heteroatom may optionally be quaternized. If given, a numerical range refers to the chain length in total. For example, a 3- to 8-membered heteroalkyl has a chain length of 3 to 8 atoms. Connection to the rest of the molecule may be through either a heteroatom or a carbon in the heteroalkyl, heteroalkenyl or heteroalkynyl chain. Unless stated otherwise specifically in the specification, a heteroalkyl, heteroalkenyl, or heteroalkynyl group is optionally substituted by one or more substituents such as those substituents described herein.

"Aryl" refers to an aromatic ring wherein each of the atoms forming the ring is a carbon atom. Aryl groups can be optionally substituted. Examples of aryl groups include, but are not limited to, phenyl and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Heteroaryl" refers to a 3- to 12-membered aromatic ring that comprises at least one heteroatom wherein each heteroatom may be independently selected from N, O, and S.

As used herein, the heteroaryl ring may be selected from monocyclic or bicyclic and fused or bridged ring systems wherein at least one of the rings in the ring system is aromatic, i.e., it contains a cyclic, delocalized (4n+2) π-electron system in accordance with the Hückel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl is optionally substituted by one or more substituents such as those substituents described herein.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted.

The term "heterocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical may be partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —$CH_2O$— is equivalent to —$OCH_2$—.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1H$ (protium), $^2H$ (deuterium), and $^3H$ (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When stereochemistry is not specified, certain small molecules described herein include, but are not limited to, when possible, their isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration. In addition, such certain small molecules include Z- and E-forms (or cis- and trans-forms) of certain small molecules with carbon-carbon double bonds or carbon-nitrogen double bonds. Where certain small molecules described herein exist in various tautomeric forms, the term "certain small molecule" is intended to include all tautomeric forms of the certain small molecule.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including but not limited to a therapeutic benefit and/or a prophylactic benefit. A therapeutic benefit can include, for example, the eradication or amelioration of the underlying disorder being treated. Also, a therapeutic benefit can include, for example, the eradication or amelioration of one or more of the physiological symptoms associated with the underlying disorder such that an improvement is observed in the subject, notwithstanding that the subject may still be afflicted with the underlying disorder. In certain embodiments, for pro-phylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function (e.g., activity, expression, binding, protein-protein interaction) of a target protein or enzyme. Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

Compounds

Provided herein, in one aspect, is a compound of Formula (I):

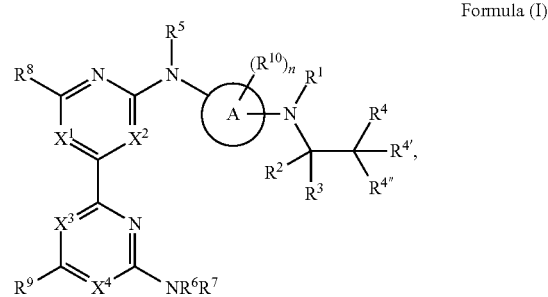

Formula (I)

or a pharmaceutically acceptable salt thereof, wherein:

Ring A is selected from $C_{3-6}$cycloalkyl, 3- to 10-membered heterocycloalkyl, $C_{6-10}$aryl, and 6- to 10-membered heteroaryl;

$X^1$ is selected from N and $CR^{11}$;
$X^2$ is selected from N and $CR^{12}$;
$X^3$ is selected from N and $CR^{13}$;
$X^4$ is selected from N and $CR^{14}$;
$R^1$ is selected from H, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, 6- to 10-membered heteroaryl; wherein each alkyl, cycloalkyl, heterocycloalkyl, aryl, and heteroaryl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

R$^2$ is selected from halo, —CN, —OR$^{18}$, —SOR$^{15}$, —SO$_2$R$^{15}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —NR$^{19}$C(O)R$^{18}$, —NR$^{19}$C(O)NR$^{16}$R$^{17}$, —NR$^{19}$SO$_2$R$^{15}$, —NR$^{19}$SO$_2$NR$^{16}$R$^{17}$, C$_{1-6}$alkyl, C$_{2-6}$alkenyl, C$_{2-6}$alkynyl, C$_{1-6}$heteroalkyl, C$_{1-6}$haloalkyl, C$_{3-6}$cycloalkyl, 3- to 10-membered heterocycloalkyl, C$_{6-10}$aryl, and 6- to 10-membered heteroaryl; wherein each alkyl, alkenyl, alkynyl, cycloalkyl, heterocycloalkyl, aryl, and heteroaryl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

R$^3$ is selected from H, halo, —CN, —OR$^{18}$, —SOR$^{15}$, —SO$_2$R$^{15}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —NR$^{19}$C(O)R$^{18}$, —NR$^{19}$C(O)NR$^{16}$R$^{17}$, —NR$^{19}$SO$_2$R$^{15}$, —NR$^{19}$SO$_2$NR$^{16}$R$^{17}$, C$_{1-6}$alkyl, C$_{2-6}$alkenyl, C$_{2-6}$alkynyl, C$_{1-6}$heteroalkyl, C$_{1-6}$haloalkyl, C$_{3-6}$cycloalkyl, 3- to 10-membered heterocycloalkyl, C$_{6-10}$aryl, and 6- to 10-membered heteroaryl; wherein each alkyl, alkenyl, alkynyl, cycloalkyl, heterocycloalkyl, aryl, and heteroaryl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

R$^4$ is selected from C$_{1-6}$alkyl, C$_{2-6}$heteroalkyl, C$_{1-6}$haloalkyl, C$_{3-6}$cycloalkyl, 3- to 10-membered heterocycloalkyl, C$_{6-10}$aryl, 6- to 10-membered heteroaryl, —O(C$_{0-4}$alkyl)C$_{3-6}$ cycloalkyl, —O(C$_{0-4}$alkyl)(3- to 10-membered heterocycloalkyl), —O(C$_{0-4}$alkyl)C$_{6-10}$aryl, —O(C$_{0-4}$alkyl)(6- to 10-membered heteroaryl), —O(C$_{0-4}$alkyl)C(O)OR$^{18}$, —O(C$_{0-4}$alkyl)C(O)NR$^{19}$SO$_2$R$^{15}$, —O(C$_{0-4}$alkyl)SO$_2$NR$^{19}$C(O)R$^{18}$, —O(C$_{3-6}$cycloalkyl)C$_{3-6}$cycloalkyl, —O(C$_{3-6}$cycloalkyl)(3- to 10-membered heterocycloalkyl), —O(C$_{3-6}$cycloalkyl)C$_{6-10}$aryl, —O(C$_{3-6}$cycloalkyl)(6- to 10-membered heteroaryl), —O(C$_{3-6}$cycloalkyl)C(O)OR$^{18}$, —(C$_{1-4}$alkyl)C$_{3-6}$cycloalkyl, —(C$_{1-4}$alkyl)(3- to 10-membered heterocycloalkyl), —(C$_{1-4}$alkyl)C$_{6-10}$aryl, —(C$_{1-4}$alkyl)(6- to 10-membered heteroaryl), and —(C$_{1-4}$alkyl)C(O)OR$^{18}$; wherein each alkyl, cycloalkyl, heterocycloalkyl, aryl, and heteroaryl is independently optionally substituted with one or more substituents selected from C$_{1-4}$alkyl, oxo, halo, —OR$^{18}$, —CN, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —(C$_{1-4}$alkyl)OC(O)(C$_{1-4}$alkyl), —(C$_{1-4}$alkyl)OC(O)OR$^{18}$, —NR$^{19}$C(O)R$^{18}$, —NR$^{19}$C(O)NR$^{16}$R$^{17}$, —NR$^{19}$SO$_2$R$^{15}$, and —NR$^{19}$SO$_2$NR$^{16}$R$^{17}$; and R$^{4'}$ and R$^{4''}$ are each independently selected from H, C$_{1-6}$alkyl, C$_{2-6}$heteroalkyl, C$_{1-6}$haloalkyl, C$_{3-6}$cycloalkyl, 3- to 10-membered heterocycloalkyl, C$_{6-10}$aryl, 6- to 10-membered heteroaryl, —O(C$_{0-4}$alkyl)C$_{3-6}$cycloalkyl, —O(C$_{0-4}$alkyl)(3- to 10-membered heterocycloalkyl), —O(C$_{0-4}$alkyl)C$_{6-10}$aryl, —O(C$_{0-4}$alkyl)(6- to 10-membered heteroaryl), —O(C$_{0-4}$alkyl)C(O)OR$^{18}$, —O(C$_{0-4}$alkyl)C(O)NR$^{19}$SO$_2$R$^{15}$, —O(C$_{0-4}$alkyl)SO$_2$ NR$^{19}$C(O)R$^{18}$, —O(C$_{3-6}$cycloalkyl)C$_{3-6}$cycloalkyl, —O(C$_{3-6}$cycloalkyl)(3- to 10-membered heterocycloalkyl), —O(C$_{3-6}$cycloalkyl)C$_{6-10}$aryl, —O(C$_{3-6}$cycloalkyl)(6- to 10-membered heteroaryl), —O(C$_{3-6}$cycloalkyl)C(O)OR$^{18}$, —(C$_{1-4}$alkyl)C$_{3-6}$cycloalkyl, —(C$_{1-4}$alkyl)(3- to 10-membered heterocycloalkyl), —(C$_{1-4}$alkyl)C$_{6-10}$aryl, and —(C$_{1-4}$alkyl)(6- to 10-membered heteroaryl); wherein each alkyl, cycloalkyl, heterocycloalkyl, aryl, and heteroaryl is independently optionally substituted with one or more substituents selected from oxo, halo, —OR$^{18}$, —CN, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —(C$_{1-4}$alkyl)OC(O)(C$_{1-4}$alkyl), —(C$_{1-4}$alkyl)OC(O)OR$^{18}$, —NR$^{19}$C(O)R$^{18}$, —NR$^{19}$C(O)NR$^{16}$R$^{17}$, —NR$^{19}$SO$_2$R$^{15}$, and —NR$^{19}$SO$_2$NR$^{16}$R$^{17}$; or R$^3$ is H; and R$^4$, R$^{4'}$, and R$^{4''}$ are taken together, along with the carbon atom to which they are attached, to form —C(O)R$^{18}$ or 6- to 10-membered heteroaryl;

R$^5$ is selected from H, C$_{1-6}$alkyl, C$_{1-6}$heteroalkyl, C$_{1-6}$haloalkyl, C$_{3-6}$cycloalkyl, 3- to 10-membered heterocycloalkyl, C$_{6-10}$aryl, and 6- to 10-membered heteroaryl; wherein each alkyl, cycloalkyl, heterocycloalkyl, aryl, and heteroaryl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

R$^6$ and R$^7$ are each independently selected from H, C$_{1-6}$alkyl, C$_{1-6}$heteroalkyl, C$_{1-6}$haloalkyl, C$_{3-6}$cycloalkyl, 3- to 10-membered heterocycloalkyl, C$_{6-10}$aryl, 6- to 10-membered heteroaryl, —(C$_{1-4}$alkyl)C$_{3-6}$cycloalkyl, —(C$_{1-4}$alkyl)(3- to 10-membered heterocycloalkyl), —(C$_{1-4}$alkyl)C$_{6-10}$aryl, and —(C$_{1-4}$alkyl)(6- to 10-membered heteroaryl); wherein each alkyl, cycloalkyl, heterocycloalkyl, aryl, and heteroaryl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$; or R$^6$ and R$^7$, along with the nitrogen atom to which they are attached, are taken together to form a 3- to 10-membered heterocycloalkyl optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

R$^8$ and R$^9$ are each independently selected from H, halo, —CN, —OR$^{18}$, —SOR$^{15}$, —SO$_2$R$^{15}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —NR$^{19}$C(O)R$^{18}$, —NR$^{19}$C(O)NR$^{16}$R$^{17}$, —NR$^{19}$SO$_2$R$^{15}$, —NR$^{19}$SO$_2$NR$^{16}$R$^{17}$, C$_{1-6}$alkyl, C$_{2-6}$alkenyl, C$_{2-6}$alkynyl, C$_{1-6}$heteroalkyl, and C$_{1-6}$haloalkyl; wherein each alkyl, alkenyl, and alkynyl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

each R$^{10}$ is independently selected from halo, —CN, —OR$^{18}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —NR$^{19}$C(O)R$^{18}$, C$_{1-6}$alkyl, C$_{1-6}$heteroalkyl, C$_{1-6}$haloalkyl, C$_{3-6}$cycloalkyl, 3- to 10-membered heterocycloalkyl; wherein each alkyl, cycloalkyl, and heterocycloalkyl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

R$^{11}$, R$^{12}$, R$^{13}$, and R$^{14}$ are each independently selected from H, halo, —CN, —OR$^{18}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —NR$^{19}$C(O)R$^{18}$, C$_{1-6}$alkyl, C$_{1-6}$heteroalkyl, C$_{1-6}$haloalkyl, C$_{3-6}$cycloalkyl, 3- to 10-membered heterocycloalkyl; wherein each alkyl, cycloalkyl, and heterocycloalkyl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

each R$^{15}$ is independently selected from C$_{1-4}$alkyl, C$_{1-4}$haloalkyl, C$_{3-6}$cycloalkyl, 3- to 10-membered heterocycloalkyl, C$_{6-10}$aryl, and 6- to 10-membered heteroaryl;

each $R^{16}$ and $R^{17}$ is independently selected from H, $C_{1-4}$alkyl, $C_{1-4}$heteroalkyl, $C_{1-4}$haloalkyl, $C_{3-6}$cycloalkyl, 3- to 10-membered heterocycloalkyl, $C_{6-10}$aryl, 6- to 10-membered heteroaryl; or an $R^{16}$ and an $R^{17}$ may be taken together along with the nitrogen atom to which they are attached to form a 3- to 10-membered heterocycloalkyl;

each $R^{18}$ is independently selected from H, $C_{1-4}$alkyl, $C_{1-4}$heteroalkyl, $C_{1-4}$haloalkyl, and $C_{3-6}$cycloalkyl;

each $R^{19}$ is independently selected from H, $C_{1-4}$alkyl, $C_{1-4}$heteroalkyl, $C_{1-4}$haloalkyl, and $C_{3-6}$cycloalkyl;

each $R^{20}$ and $R^{21}$ is independently selected from H, $C_{1-4}$alkyl, $C_{1-4}$heteroalkyl, $C_{1-4}$haloalkyl, $C_{3-6}$cycloalkyl, 3- to 10-membered heterocycloalkyl, $C_{6-10}$aryl, 6- to 10-membered heteroaryl; or an $R^{20}$ and an $R^{21}$ may be taken together along with the nitrogen atom to which they are attached to form a 3- to 10-membered heterocycloalkyl; and n is 0, 1, 2, 3, or 4.

In some embodiments, Ring A is selected from $C_{3-6}$cycloalkyl, 3- to 10-membered heterocycloalkyl, $C_{6-10}$aryl, and 6- to 10-membered heteroaryl. In some embodiments, Ring A is selected from $C_{3-6}$cycloalkyl, 3- to 10-membered heterocycloalkyl, and $C_{6-10}$aryl. In some embodiments, Ring A is selected from $C_{3-6}$cycloalkyl and 3- to 10-membered heterocycloalkyl. In some embodiments, Ring A is 3- to 10-membered heterocycloalkyl. In some embodiments, Ring A is $C_{6-10}$aryl. In some embodiments, Ring A is 6- to 10-membered heteroaryl. In some embodiments, Ring A is $C_{3-6}$cycloalkyl. In some embodiments, Ring A is selected from the group consisting of:

In some embodiments, Ring A is

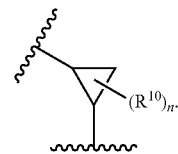

In some embodiments, Ring A is

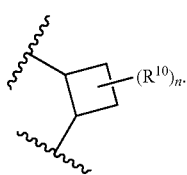

In some embodiments, Ring A is

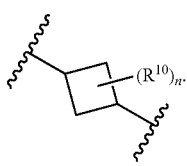

In some embodiments, Ring A is

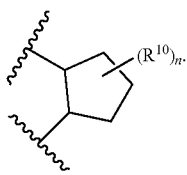

In some embodiments, Ring A is

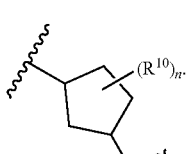

In some embodiments, Ring A is

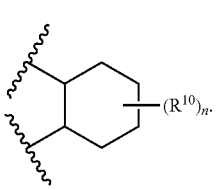

In some embodiments, Ring A is
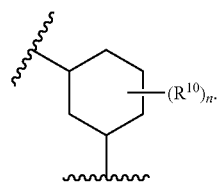
In some embodiments, Ring A is
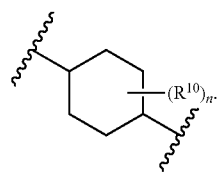
In some embodiments, Ring A is selected from the group consisting of
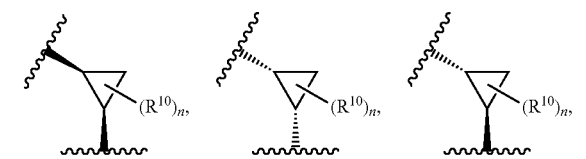
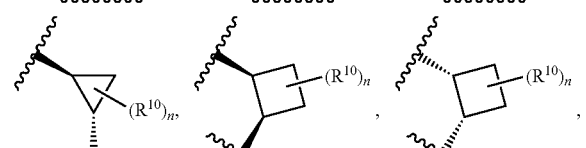
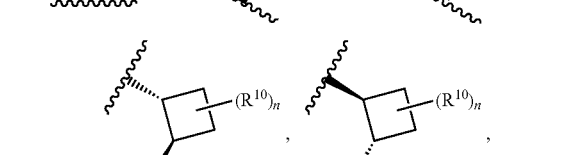
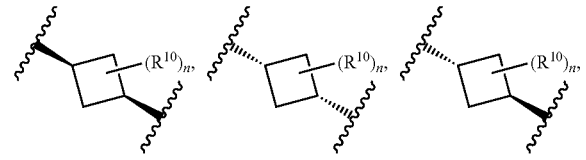
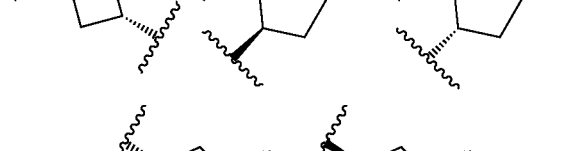
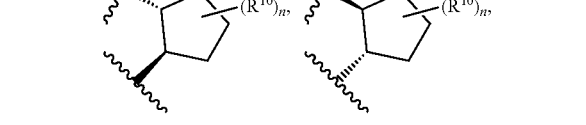
-continued
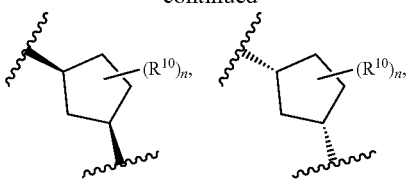
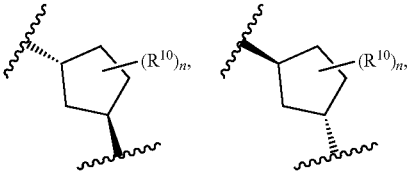
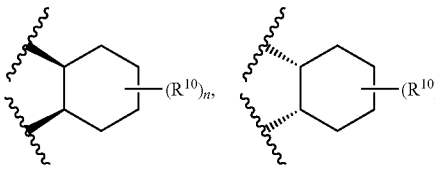
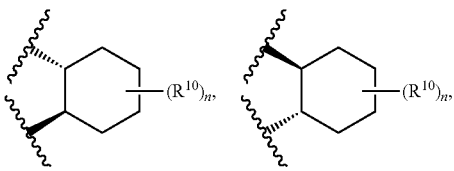
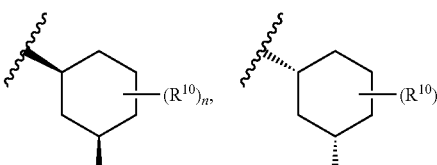
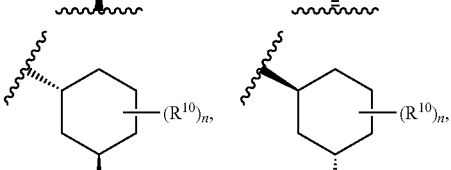
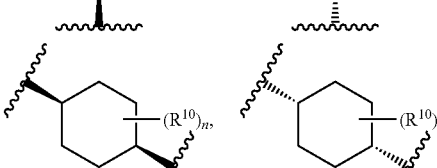
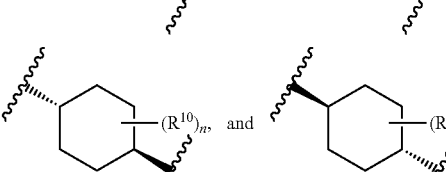
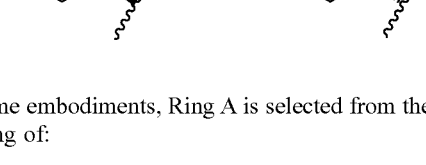
In some embodiments, Ring A is selected from the group consisting of:
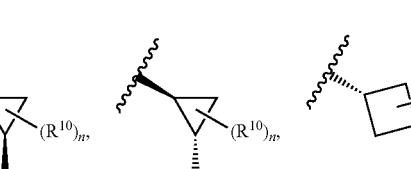

-continued
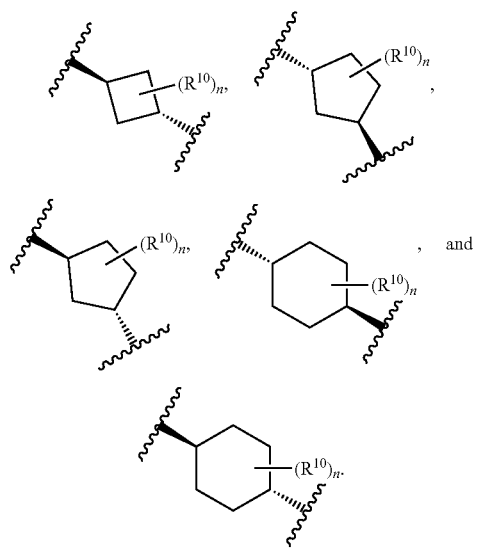
In some embodiments, Ring A is selected from the group consisting of
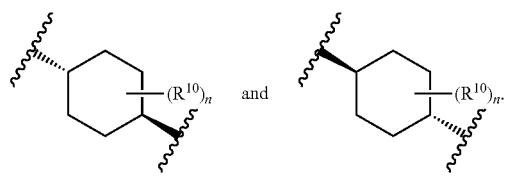
In some embodiments, Ring A is
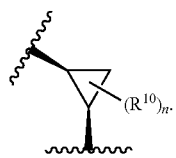
In some embodiments, Ring A is
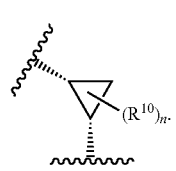
In some embodiments, Ring A is
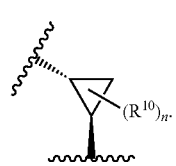
In some embodiments, Ring A is
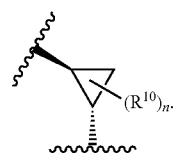
In some embodiments, Ring A is
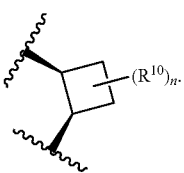
In some embodiments, Ring A is
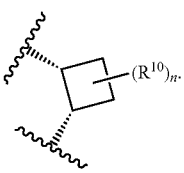
In some embodiments, Ring A is
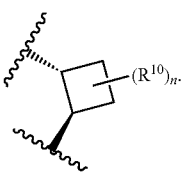
In some embodiments, Ring A is
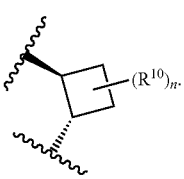
In some embodiments, Ring A is
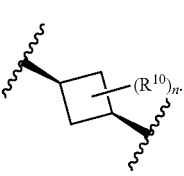

In some embodiments, Ring A is
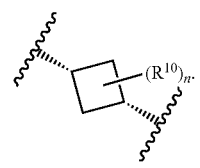
In some embodiments, Ring A is
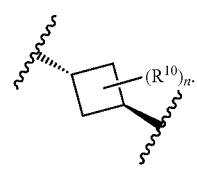
In some embodiments, Ring A is
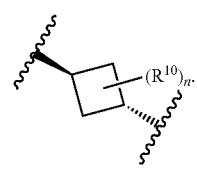
In some embodiments, Ring A is
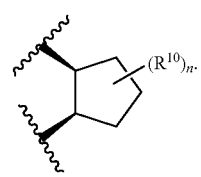
In some embodiments, Ring A is
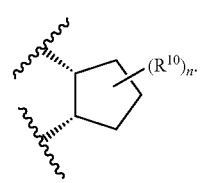
In some embodiments, Ring A is
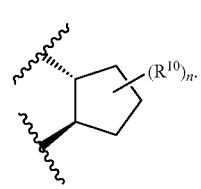
In some embodiments, Ring A is
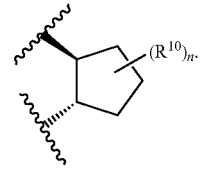
In some embodiments, Ring A is
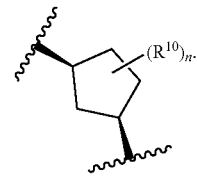
In some embodiments, Ring A is
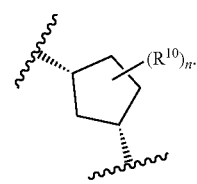
In some embodiments, Ring A is
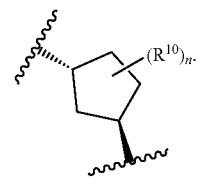
In some embodiments, Ring A is
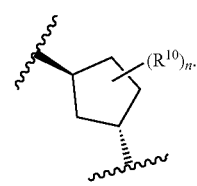
In some embodiments, Ring A is
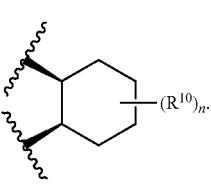

In some embodiments, Ring A is

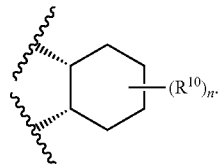

In some embodiments, Ring A is

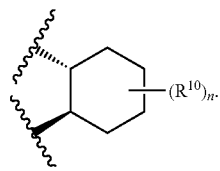

In some embodiments, Ring A is

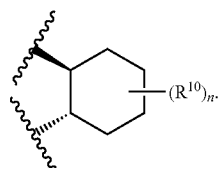

In some embodiments, Ring A is

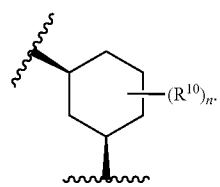

In some embodiments, Ring A is

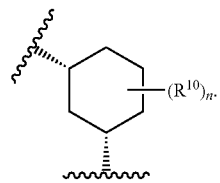

In some embodiments, Ring A is

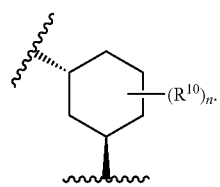

In some embodiments, Ring A is

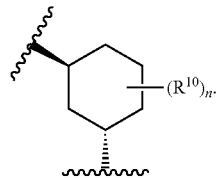

In some embodiments, Ring A is

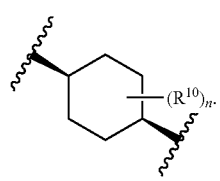

In some embodiments, Ring A is

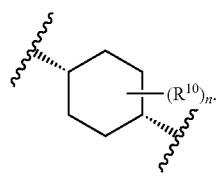

In some embodiments, Ring A is

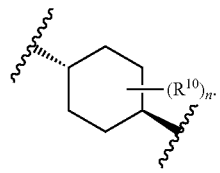

In some embodiments, Ring A is

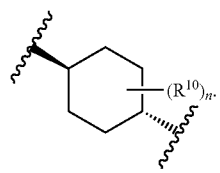

In some embodiments, none of $X^1$, $X^2$, $X^3$, and $X^4$ is N. In some embodiments, one of $X^1$, $X^2$, $X^3$, and $X^4$ is N. In some embodiments, two of $X^1$, $X^2$, $X^3$, and $X^4$ are N. In some embodiments, three of $X^1$, $X^2$, $X^3$, and $X^4$ are N. In some embodiments, $X^1$, $X^2$, $X^3$, and $X^4$ are all N. In some embodiments, $X^1$ is N. In some embodiments, $X^2$ is N. In some embodiments, $X^3$ is N. In some embodiments, $X^4$ is N. In some embodiments, $X^1$ and $X^2$ are N. In some embodiments, $X^1$ and $X^3$ are N. In some embodiments, $X^1$ and $X^4$ are N. In some embodiments, $X^2$ and $X^3$ are N. In some embodiments, $X^2$ and $X^4$ are N. In some embodiments, $X^3$ and $X^4$ are N. In some embodiments, $X^1$, $X^2$, and $X^3$ are N. In some embodiments, $X^1$, $X^2$, and $X^4$ are N. In some embodiments, $X^1$, $X^3$, and $X^4$ are N. In some embodiments, $X^2$, $X^3$, and $X^4$ are N. In some embodiments, $X^1$, $X^2$, $X^3$, and $X^4$ are N.

In some embodiments, $R^{11}$, $R^{12}$, $R^{13}$, and $R^{14}$ are each independently selected from H, halo, —CN, —$OR^{18}$, —$NR^{16}R^{17}$, —$C(O)NR^{16}R^{17}$, —$SO_2NR^{16}R^{17}$, —$C(O)R^{18}$, —$C(O)OR^{18}$, —$NR^{19}C(O)R^{18}$, $C_{1-6}$alkyl, and $C_{1-6}$haloalkyl. In some embodiments, $R^{11}$, $R^{12}$, $R^{13}$, and $R^{14}$ are each independently selected from H, halo, —CN, —$OR^{18}$, —$NR^{16}R^{17}$, —$C(O)NR^{16}R^{17}$, —$SO_2NR^{16}R^{17}$, —$C(O)R^{18}$, —$C(O)OR^{18}$, and —$NR^{19}C(O)R^{18}$. In some embodiments, $R^{11}$, $R^{12}$, $R^{13}$, and $R^{14}$ are each independently selected from H, halo, —CN, —$OR^{18}$, and —$NR^{16}R^{17}$. In some embodiments, one of $R^{11}$, $R^1$, $R^{13}$, and $R^{14}$ is halo and the others are H. In some embodiments, $R^{11}$ is chloro, and $R^{12}$, $R^{13}$, and $R^{14}$ are each H.

In some embodiments, $R^1$ is selected from H, $C_{1-6}$alkyl, $C_{1-6}$haloalkyl, and $C_{3-6}$cycloalkyl. In some embodiments, $R^1$ is $C_{1-6}$alkyl. In some embodiments, $R^1$ is $C_{1-6}$haloalkyl. In some embodiments, $R^1$ is $C_{3-6}$cycloalkyl. In some embodiments, $R^1$ is selected from H, Me, Et, n-Pr, i-Pr, —$CF_3$, cyclopropyl, cyclobutyl, cyclopentyl, and cyclohexyl. In some embodiments, $R^1$ is selected from H, cyclopropyl, cyclobutyl, cyclopentyl, and cyclohexyl. In some embodiments, $R^1$ is selected from Me, Et, n-Pr, and i-Pr. In some embodiments, $R^1$ is Me. In some embodiments, $R^1$ is H.

In some embodiments, $R^2$ is selected from halo, —CN, —$OR^{18}$, —$SOR^{15}$, —$SO_2R^{15}$, —$NR^{16}R^{17}$, —$C(O)NR^{16}R^{17}$, —$SO_2NR^{16}R^{17}$, —$C(O)R^{18}$, —$C(O)OR^{18}$, —$NR^{19}C(O)R^{18}$, —$NR^{19}C(O)NR^{16}R^{17}$, —$NR^{19}SO_2R^{15}$, —$NR^{19}SO_2NR^{16}R^{17}$, $C_{1-6}$alkyl, $C_{1-6}$haloalkyl, and $C_{3-6}$cycloalkyl. In some embodiments, $R^2$ is selected from halo, —CN, —OH, —OMe, —OEt, —$NH_2$, —NHMe, —$NMe_2$, Me, Et, n-Pr, i-Pr, —$CF_3$, and cyclopropyl. In some embodiments, $R^2$ is selected from Me, Et, n-Pr, and i-Pr. In some embodiments, $R^2$ is Me. In some embodiments, $R^2$ is —$CF_3$. In some embodiments, $R^2$ is cyclopropyl.

In some embodiments, $R^3$ is selected from H, $C_{1-6}$alkyl, $C_{1-6}$haloalkyl, $C_{3-6}$cycloalkyl, and 3- to 10-membered heterocycloalkyl. In some embodiments, $R^3$ is $C_{1-6}$alkyl. In some embodiments, $R^3$ is $C_{1-6}$haloalkyl. In some embodiments, $R^3$ is $C_{3-6}$cycloalkyl. In some embodiments, $R^3$ is 3- to 10-membered heterocycloalkyl. In some embodiments, $R^3$ is selected from H, Me, Et, —$CF_3$, and cyclopropyl. In some embodiments, $R^3$ is H. In some embodiments, $R^3$ is Me. In some embodiments, $R^3$ is —$CF_3$.

In some embodiments, $R^2$ is Me and $R^3$ is H.

In some embodiments, $R^4$ is selected from $C_{6-10}$aryl, 6- to 10-membered heteroaryl, —O($C_{0-4}$alkyl)$C_{3-6}$cycloalkyl, —O($C_{0-4}$alkyl)(3- to 10-membered heterocycloalkyl), —O($C_{0-4}$alkyl)$C_{6-10}$aryl, —O($C_{0-4}$alkyl)(6- to 10-membered heteroaryl), —O($C_{0-4}$alkyl)C(O)$OR^{18}$, —O($C_{0-4}$alkyl)C(O)$NR^{19}SO_2R^{15}$, —O($C_{0-4}$alkyl)$SO_2$ $NR^{19}C(O)R^{18}$, —O($C_{3-6}$cycloalkyl)$C_{3-6}$cycloalkyl, —O($C_{3-6}$cycloalkyl)(3- to 10-membered heterocycloalkyl), —O($C_{3-6}$cycloalkyl)$C_{6-10}$aryl, —O($C_{3-6}$cycloalkyl)(6- to 10-membered heteroaryl), —O($C_{3-6}$cycloalkyl)C(O)$OR^{18}$, —($C_{1-4}$alkyl)$C_{3-6}$cycloalkyl, —($C_{1-4}$alkyl)(3- to 10-membered heterocycloalkyl), —($C_{1-4}$alkyl)$C_{6-10}$aryl, —($C_{1-4}$alkyl)(6- to 10-membered heteroaryl) and —($C_{1-4}$alkyl)C(O)$OR^{18}$; wherein each alkyl, cycloalkyl, heterocycloalkyl, aryl, and heteroaryl is independently optionally substituted with one or more substituents selected from $C_{1-4}$alkyl, oxo, halo, —$OR^{18}$, —CN, —$NR^{16}R^{17}$, —C(O)$NR^{16}R^{17}$, —$SO_2NR^{16}R^{17}$, —C(O)$R^{18}$, —C(O)$OR^{18}$, —($C_{1-4}$alkyl)OC(O)($C_{1-4}$alkyl), —($C_{1-4}$alkyl)OC(O)$OR^{18}$, —$NR^{19}C(O)R^{18}$, —$NR^{19}C(O)NR^{16}R^{17}$, —$NR^{19}SO_2R^{15}$, and —$NR^{19}SO_2NR^{16}R^{17}$; and $R^{4'}$ and $R^{4''}$ are each independently selected from H, $C_{1-6}$alkyl, $C_{1-6}$haloalkyl, and $C_{3-6}$cycloalkyl; wherein each alkyl and cycloalkyl is independently optionally substituted with one or more substituents selected from halo, —$OR^{18}$, —CN, and —$NR^{16}R^{17}$; or $R^3$ is H; and $R^4$, $R^{4'}$, and $R^{4''}$ are taken together, along with the carbon atom to which they are attached, to form —C(O)$R^{18}$ or 6- to 10-membered heteroaryl.

In some embodiments, $R^4$ is selected from 6- to 10-membered heteroaryl, —O($C_{0-4}$alkyl)(3- to 10-membered heterocycloalkyl), —O($C_{0-4}$alkyl)$C_{6-10}$aryl, —O($C_{0-4}$alkyl)(6- to 10-membered heteroaryl), —O($C_{0-4}$alkyl)C(O)$OR^{18}$, —O($C_{0-4}$alkyl)C(O)$NR^{19}SO_2R^{15}$, —O($C_{0-4}$alkyl)$SO_2$ $NR^{19}C(O)R^{18}$, —O($C_{3-6}$cycloalkyl)(6- to 10-membered heteroaryl), —O($C_{3-6}$cycloalkyl)C(O)$OR^{18}$, —($C_{1-4}$alkyl)(6- to 10-membered heteroaryl) and —($C_{1-4}$alkyl)C(O)$OR^{18}$; wherein each alkyl, cycloalkyl, heterocycloalkyl, aryl, and heteroaryl is independently optionally substituted with one or more substituents selected from $C_{1-4}$alkyl, oxo, halo, —$OR^{18}$, —CN, —$NR^{16}R^{17}$, —C(O)$NR^{16}R^{17}$, —$SO_2NR^{16}R^{17}$, —C(O)$OR^{18}$, —($C_{1-4}$alkyl)OC(O)($C_{1-4}$alkyl), —($C_{1-4}$alkyl)OC(O)$OR^{18}$, —$NR^{19}C(O)R^{18}$, —$NR^{19}C(O)NR^{16}R^{17}$, —$NR^{19}SO_2R^{15}$, and —$NR^{19}SO_2NR^{16}R^{17}$; and $R^{4'}$ and $R^{4''}$ are both H; or $R^3$ is H; and $R^4$, $R^{4'}$, and $R^{4''}$ are taken together, along with the carbon atom to which they are attached, to form —C(O)$R^{18}$ or 6- to 10-membered heteroaryl.

In some embodiments, $R^4$ is selected from 6- to 10-membered heteroaryl, —O($C_{0-4}$alkyl)(3- to 10-membered heterocycloalkyl), —O($C_{0-4}$alkyl)$C_{6-10}$aryl, —O($C_{0-4}$alkyl)(6- to 10-membered heteroaryl), —O($C_{0-4}$alkyl)C(O)$OR^{18}$, —O($C_{0-4}$alkyl)C(O)$NR^{19}SO_2R^{15}$, —O($C_{0-4}$alkyl)$SO_2$ $NR^{19}C(O)R^{18}$, —O($C_{3-6}$cycloalkyl)(6- to 10-membered heteroaryl), —O($C_{3-6}$cycloalkyl)C(O)$OR^{18}$, —($C_{1-4}$alkyl)(6- to 10-membered heteroaryl) and —($C_{1-4}$alkyl)C(O)$OR^{18}$; wherein each alkyl, cycloalkyl, heterocycloalkyl, aryl, and heteroaryl is independently optionally substituted with one or more substituents selected from $C_{1-4}$alkyl, oxo, halo, —$OR^{18}$, —CN, —$NR^{16}R^{17}$, —C(O)$NR^{16}R^{17}$, —$SO_2NR^{16}R^{17}$, —C(O)$OR^{18}$, —($C_{1-4}$alkyl)OC(O)($C_{1-4}$alkyl), —($C_{1-4}$alkyl)OC(O)$OR^{18}$, —$NR^{19}C(O)R^{18}$, —$NR^{19}C(O)NR^{16}R^{17}$, —$NR^{19}SO_2R^{15}$, and —$NR^{19}SO_2NR^{16}R^{17}$; and $R^{4'}$ and $R^{4''}$ are both H.

In some embodiments, $R^3$ is H; and $R^4$, $R^{4'}$, and $R^{4''}$ are taken together, along with the carbon atom to which they are attached, to form —C(O)$R^{18}$ or 6- to 10-membered heteroaryl.

In some embodiments, $R^3$ is H; and $R^4$, $R^{4'}$, and $R^{4''}$ are taken together, along with the carbon atom to which they are attached, to form —C(O)$R^{18}$ or 6- to 10-membered heteroaryl.

In some embodiments, $R^3$ is H; and $R^4$, $R^{4'}$, and $R^{4''}$ are taken together, along with the carbon atom to which they are attached, to form 6- to 10-membered heteroaryl.

In some embodiments, $R^5$ is selected from H, $C_{1-6}$alkyl, $C_{1-6}$haloalkyl, and $C_{3-6}$cycloalkyl. In some embodiments, $R^5$ is $C_{1-6}$haloalkyl. In some embodiments, $R^5$ is $C_{3-6}$cycloalkyl. In some embodiments, $R^5$ is $C_{1-6}$alkyl. In some embodiments, $R^5$ is Me, Et, n-Pr, or i-Pr. In some embodiments, $R^5$ is Me. In some embodiments, $R^5$ is H.

In some embodiments, $R^6$ and $R^7$ are each independently selected from H, —$(C_{1-4}$alkyl$)C_{3-6}$cycloalkyl, —$(C_{1-4}$alkyl$)$(3- to 10-membered heterocycloalkyl), —$(C_{1-4}$alkyl$)C_{6-10}$aryl, and —$(C_{1-4}$alkyl$)$(6- to 10-membered heteroaryl); wherein each alkyl, cycloalkyl, heterocycloalkyl, aryl, and heteroaryl is independently optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$; or $R^6$ and $R^7$, along with the nitrogen atom to which they are attached, are taken together to form a 3- to 10-membered heterocycloalkyl optionally substituted with one or more substituents selected from oxo, halo, —$OR^{18}$, $C_{1-4}$alkyl, $C_{1-4}$alkoxy, $C_{1-4}$heteroalkyl, $C_{1-4}$haloalkyl, —CN, and —$NR^{20}R^{21}$.

In some embodiments, $R^6$ and $R^7$ are each independently selected from H and —$(C_{1-4}$alkyl$)$(3- to 10-membered heterocycloalkyl); wherein each alkyl and heterocycloalkyl is independently optionally substituted with one or more substituents selected from halo, —$OR^{18}$, —CN, and —$NR^{20}R^{21}$.

In some embodiments, one of $R^6$ and $R^7$ is H and the other is

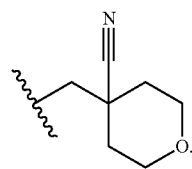

In some embodiments, $R^6$ is H and $R^7$ is

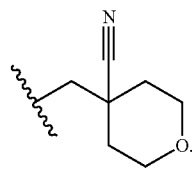

In some embodiments, $R^7$ is H and $R^6$ is

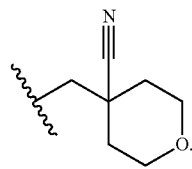

In some embodiments, $R^8$ and $R^9$ are each independently selected from H, halo, —CN, —$OR^{18}$, —$SO_2R^{15}$, —$NR^{16}R^{17}$, —$C(O)NR^{16}R^{17}$, —$SO_2NR^{16}R^{17}$, —$C(O)OR^{18}$, —$NR^{19}C(O)R^{18}$, —$NR^{19}SO_2R^{15}$. In some embodiments, $R^8$ and $R^9$ are each independently selected from H, halo, —CN, —$OR^{18}$, and —$NR^{16}R^{17}$. In some embodiments, $R^8$ and $R^9$ are both H.

In some embodiments, n is 0, 1, 2, 3, or 4. In some embodiments, n is 0, 1, 2, or 3. In some embodiments, n is 0, 1, or 2. In some embodiments, n is 0 or 1. In some embodiments, n is 0. In some embodiments, n is 1. In some embodiments, n is 2. In some embodiments, n is 3. In some embodiments, n is 4.

In some embodiments, the compound of Formula (I) is represented by Formula (I-A):

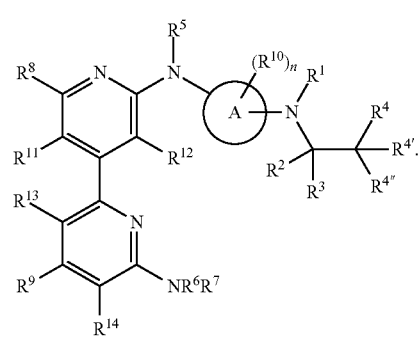

Formula (I-A)

In some embodiments, the compound of Formula (I) is represented by Formula (I-B):

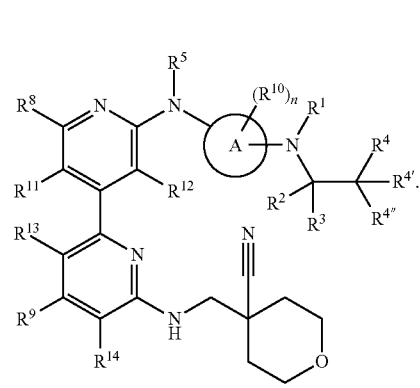

Formula (I-B)

In some embodiments, the compound of Formula (I) is represented by Formula (I-C), Formula (I-D), Formula (I-E), or Formula (I-F):

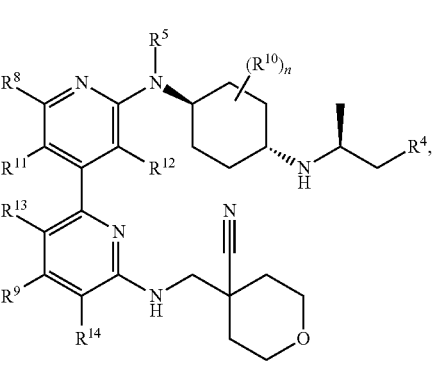

Formula (I-C)

In some embodiments, the compound of Formula (I) is represented by Formula (I-C):

Formula (I-C)

In some embodiments, the compound of Formula (I) is represented by Formula (I-D):

Formula (I-D)

In some embodiments, the compound of Formula (I) is represented by Formula (I-E):

Formula (I-E)

In some embodiments, the compound of Formula (I) is represented by Formula (I-F):

Formula (I-F)

In some embodiments, the compound is selected from the group consisting of:

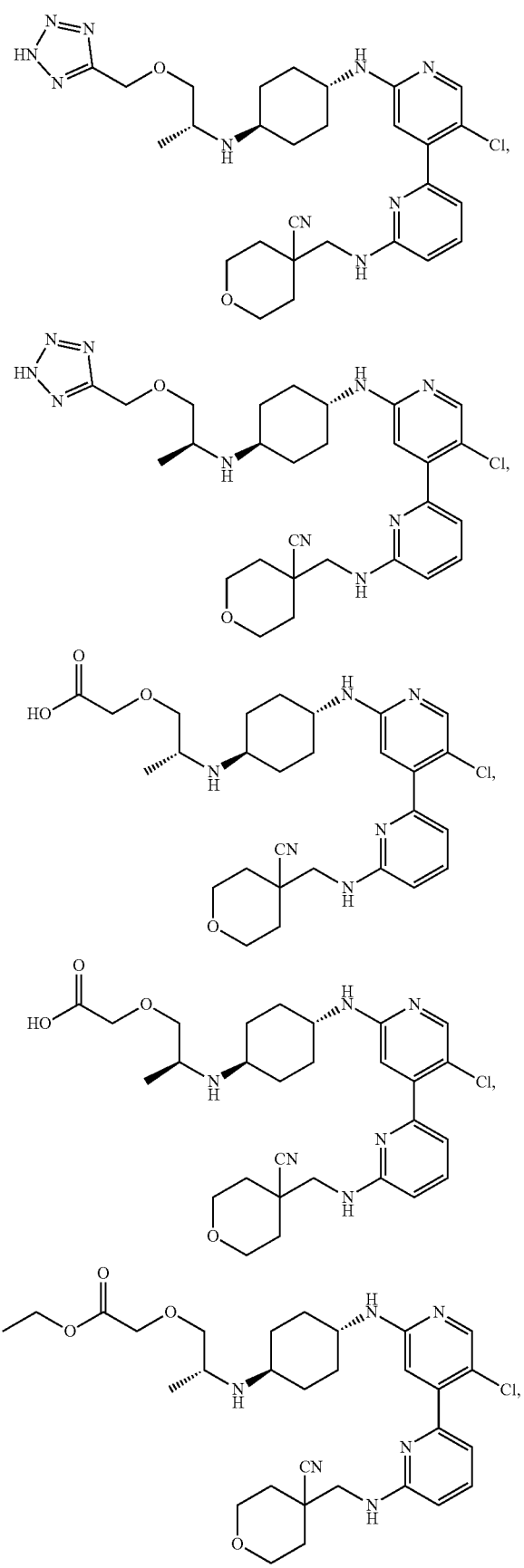 [SMILES: C[C@H](COCc1nn[nH]n1)N[C@H]1CC[C@H](Nc2cc(-c3cccc(NCC4(C#N)CCOCC4)n3)c(Cl)cn2)CC1 ; C[C@@H](COCc1nn[nH]n1)N[C@H]1CC[C@H](Nc2cc(-c3cccc(NCC4(C#N)CCOCC4)n3)c(Cl)cn2)CC1 ; C[C@H](COCC(=O)O)N[C@H]1CC[C@H](Nc2cc(-c3cccc(NCC4(C#N)CCOCC4)n3)c(Cl)cn2)CC1 ; C[C@@H](COCC(=O)O)N[C@H]1CC[C@H](Nc2cc(-c3cccc(NCC4(C#N)CCOCC4)n3)c(Cl)cn2)CC1 ; CCOC(=O)COC[C@@H](C)N[C@H]1CC[C@H](Nc2cc(-c3cccc(NCC4(C#N)CCOCC4)n3)c(Cl)cn2)CC1]

61
-continued
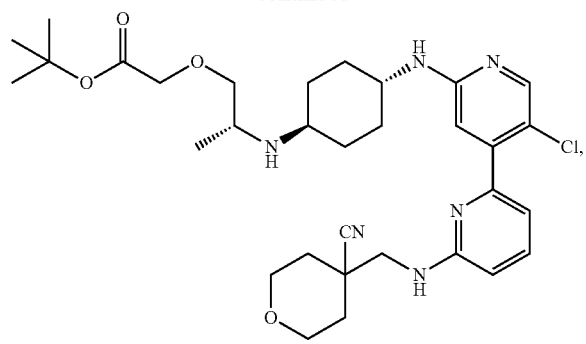
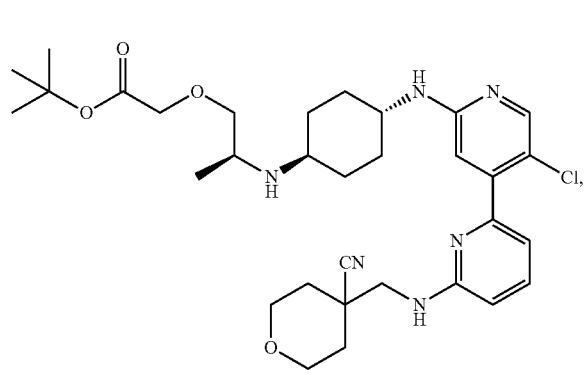
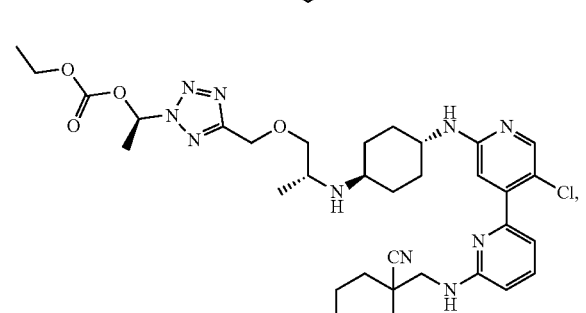
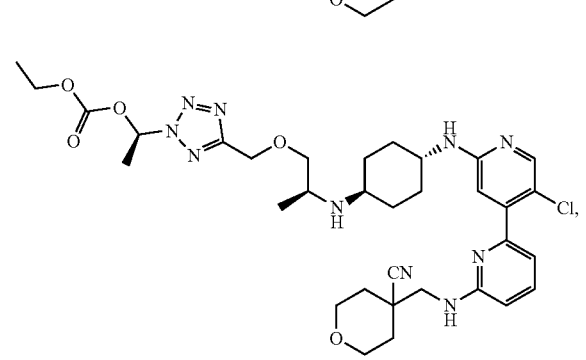
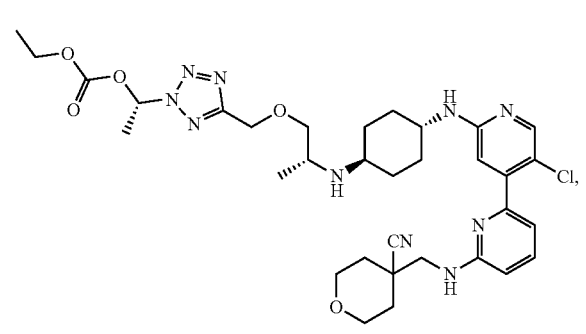
62
-continued
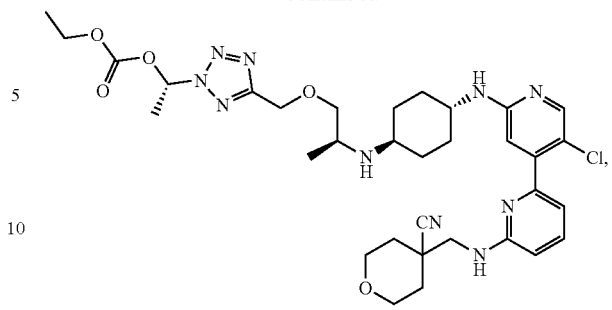
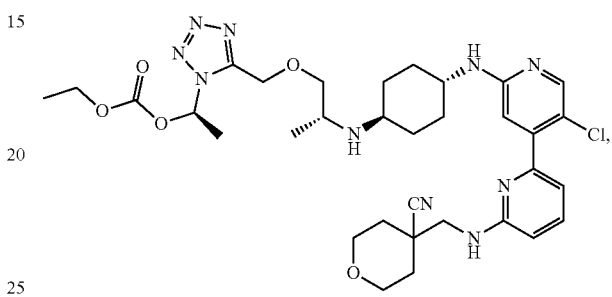
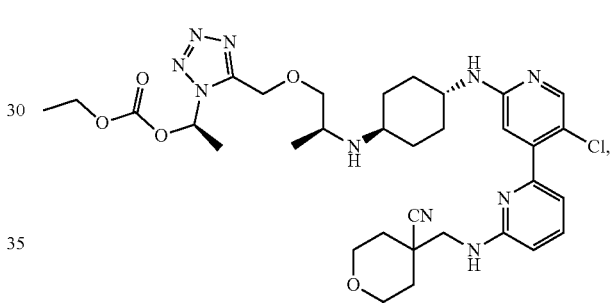
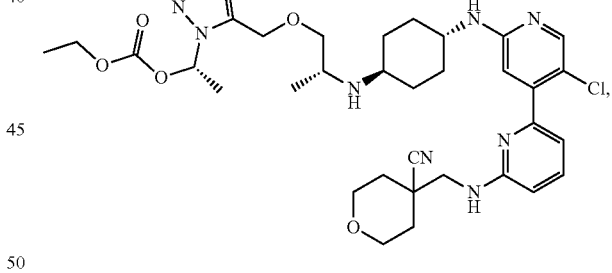
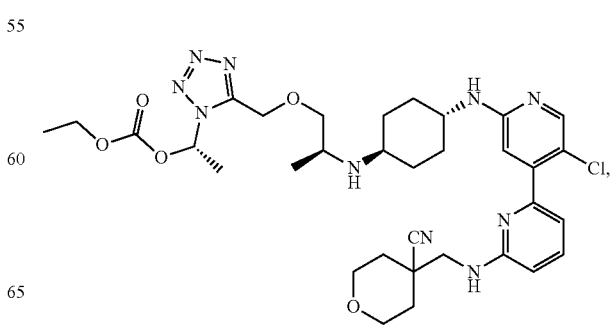

-continued
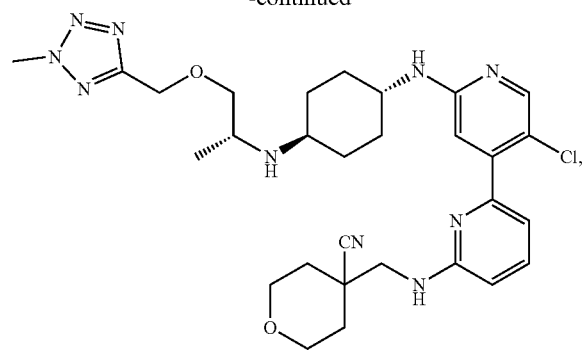
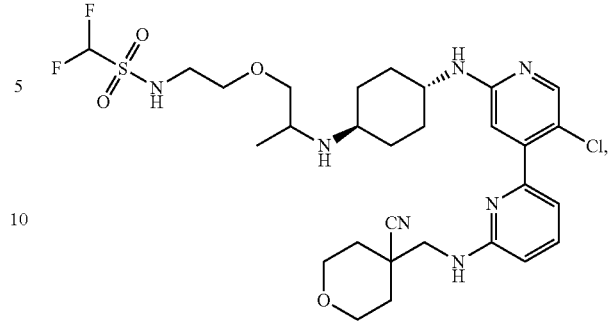
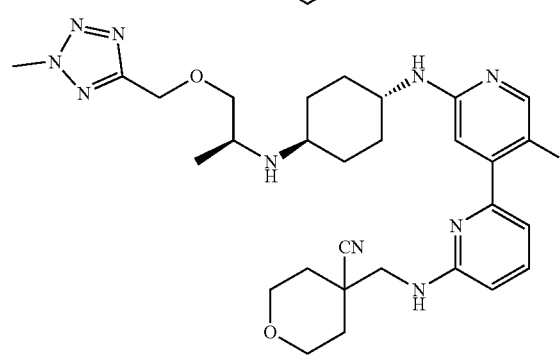
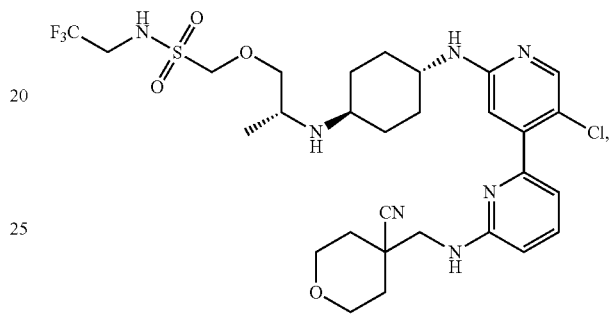
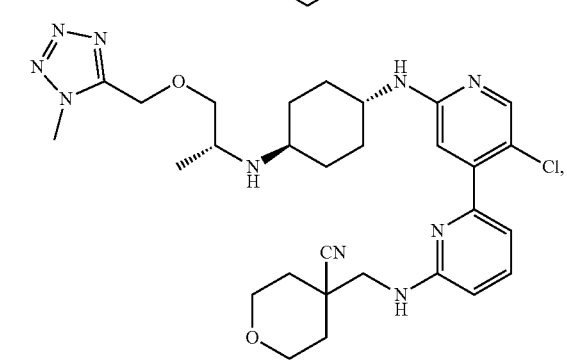
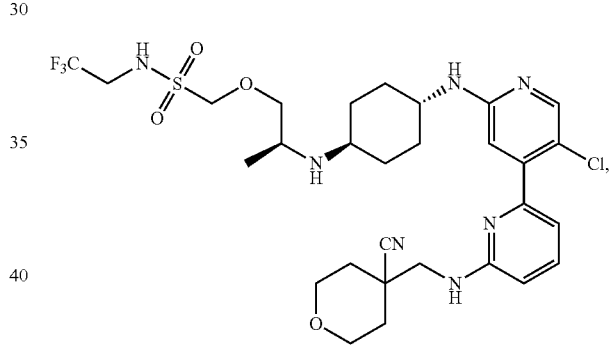
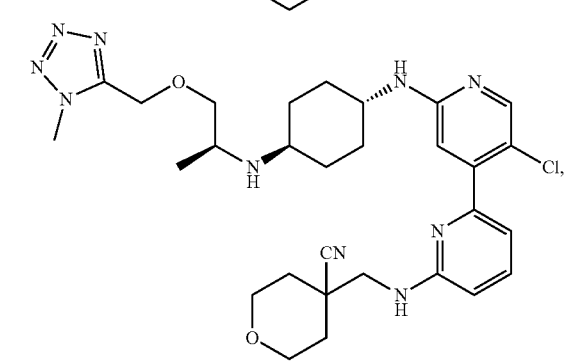
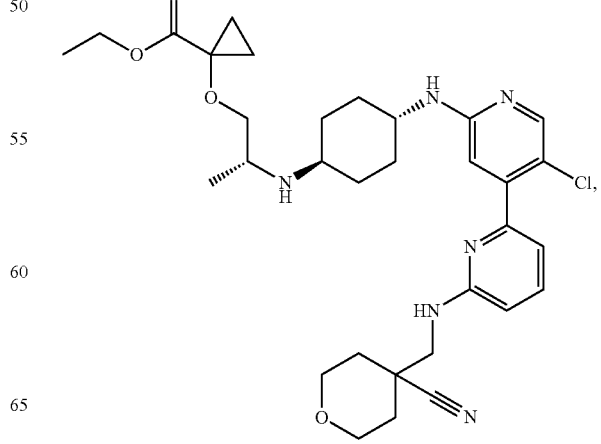

65
-continued
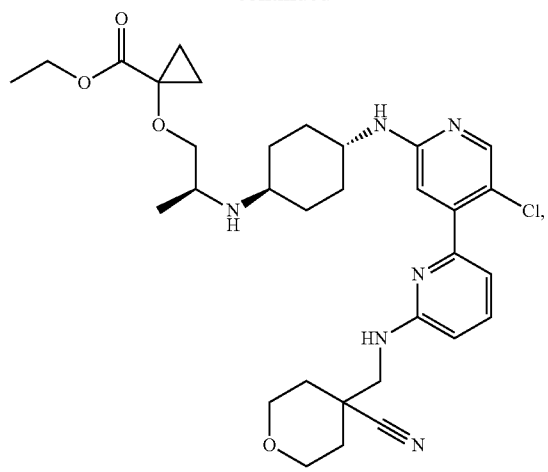
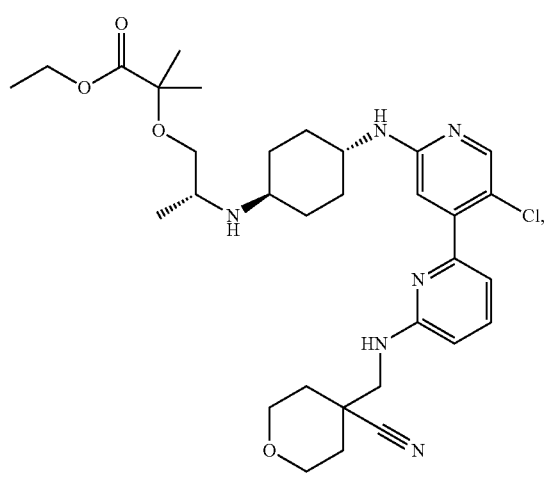
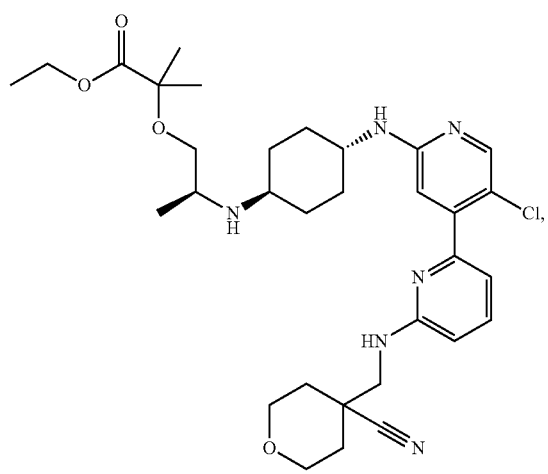
66
-continued
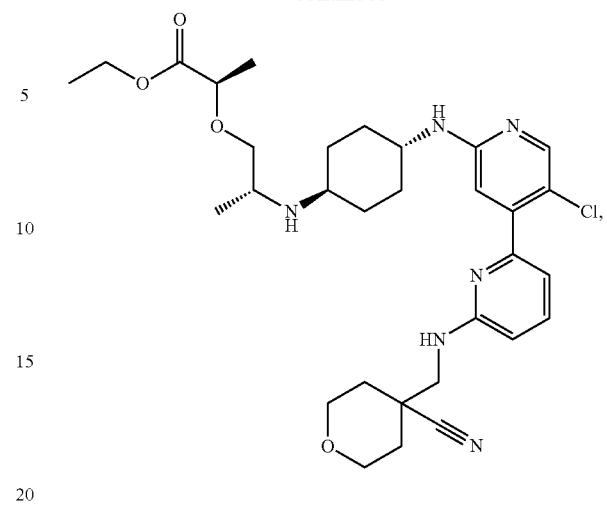
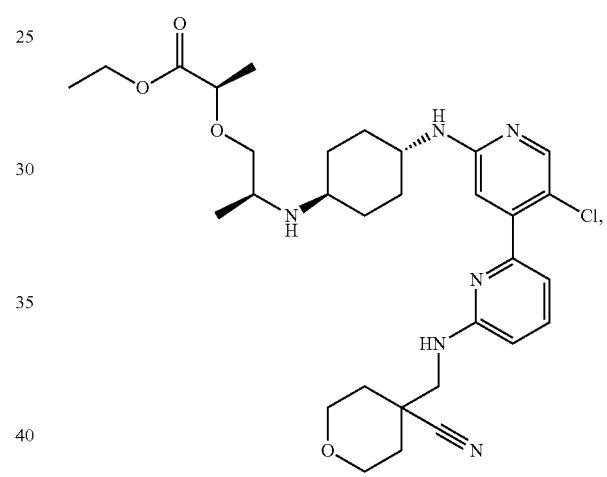
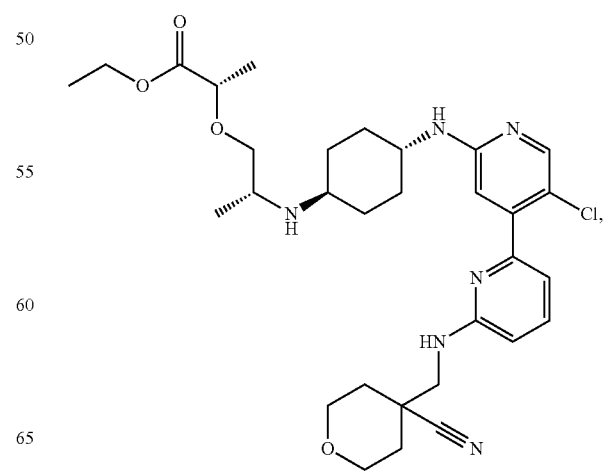

67
-continued
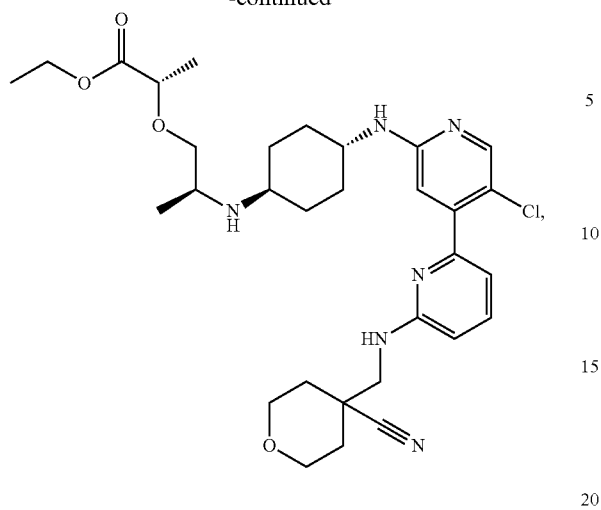
68
-continued
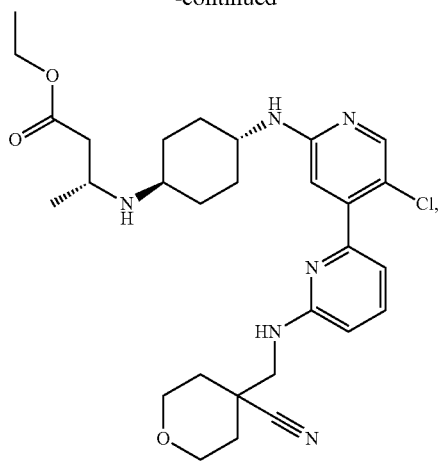
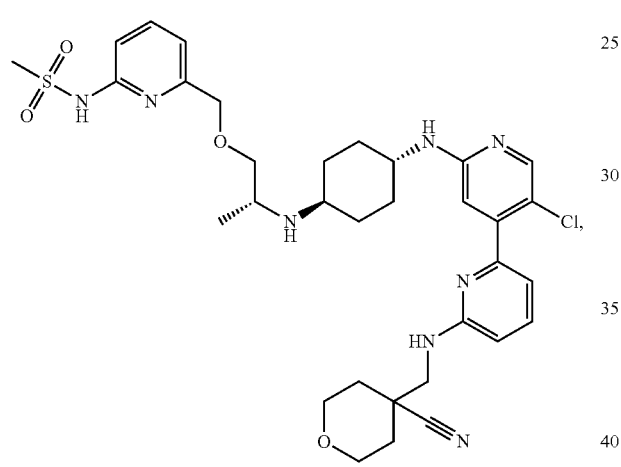
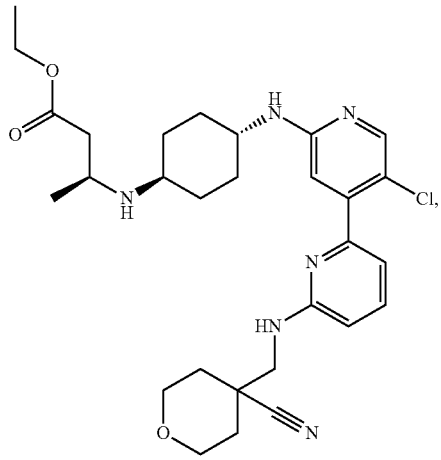
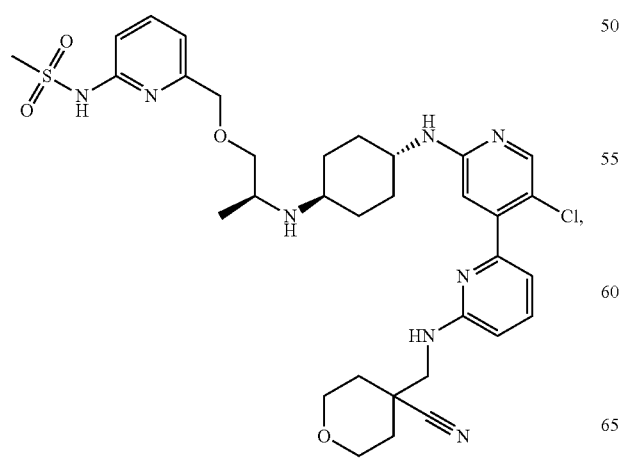
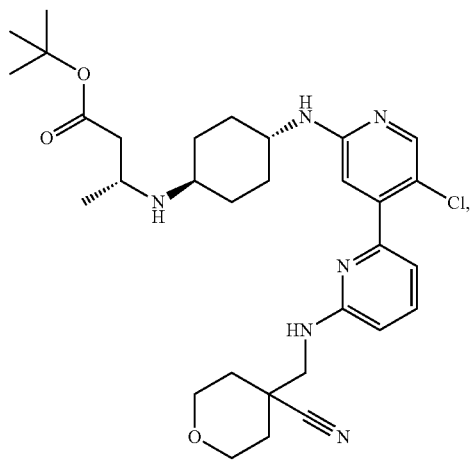

69
-continued
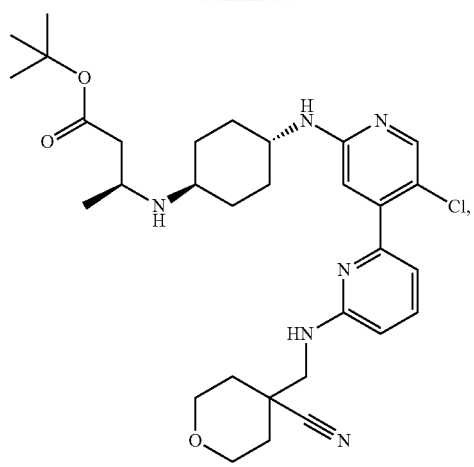
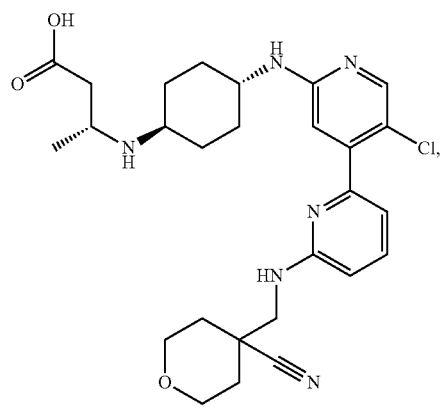
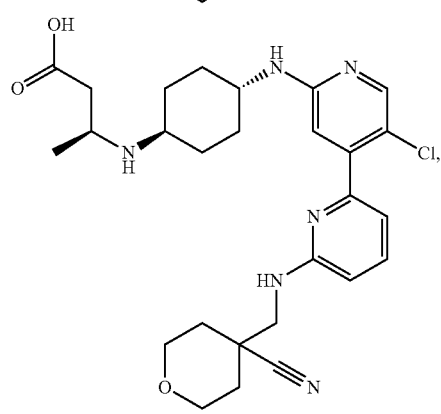
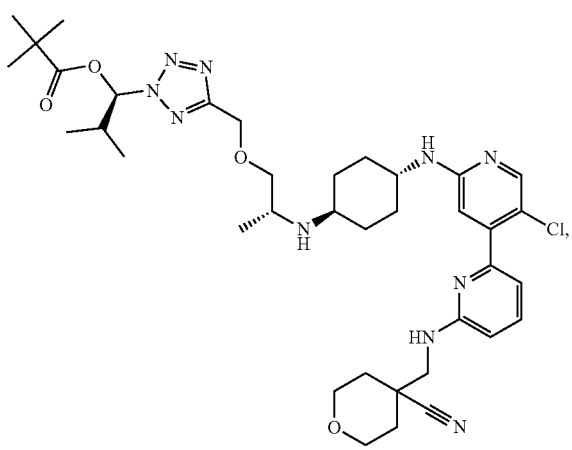
70
-continued
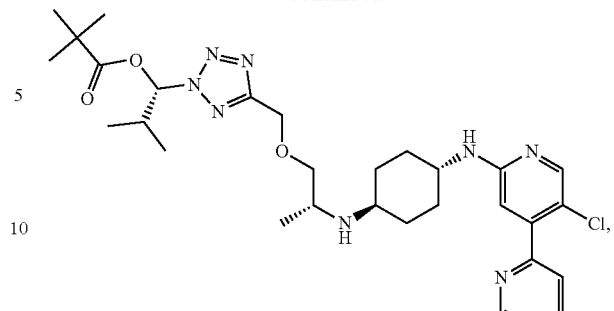
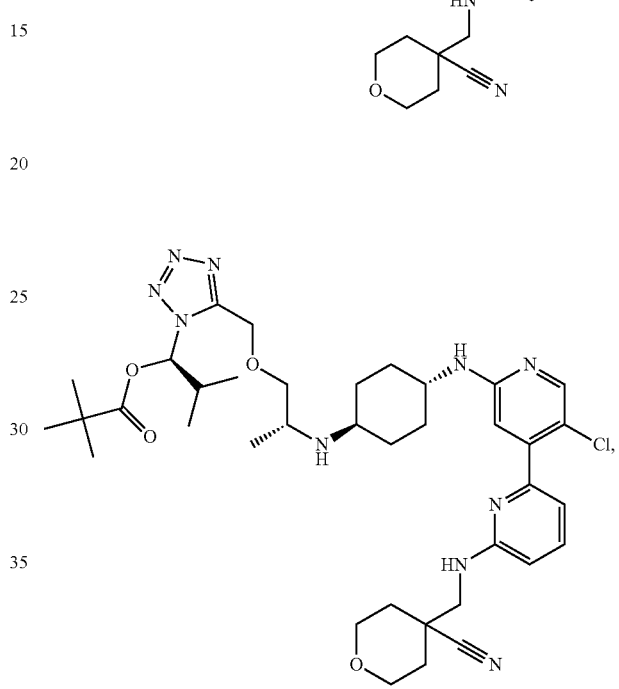
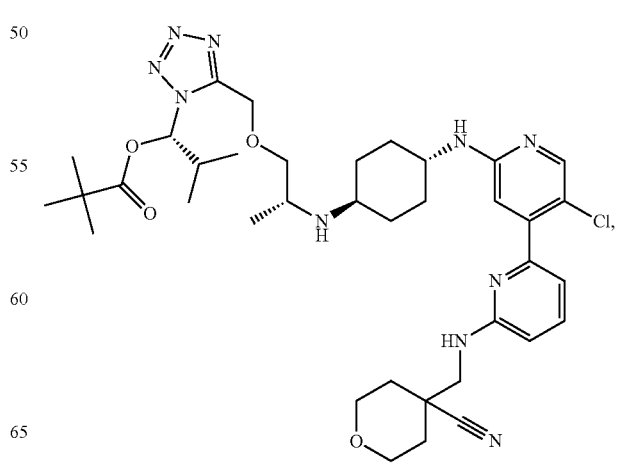

71
-continued
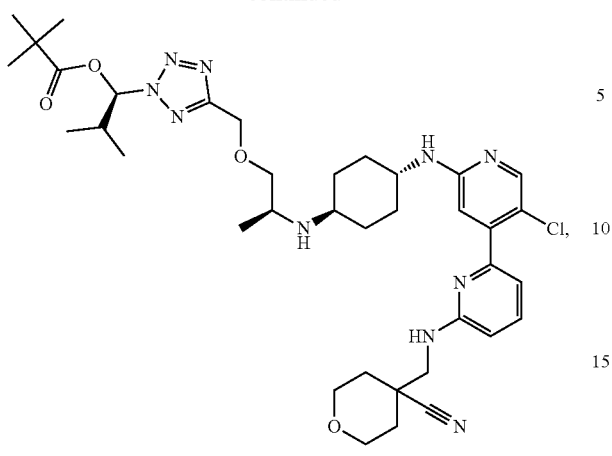
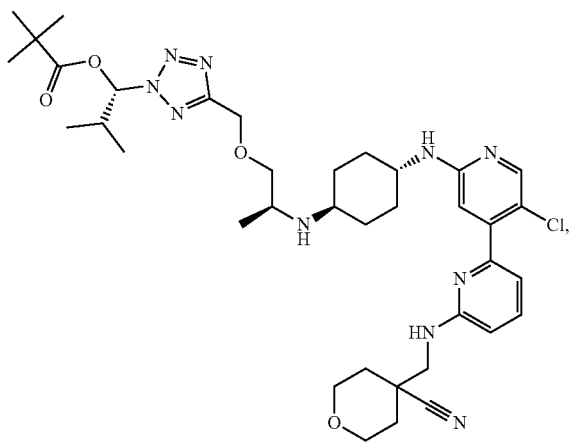
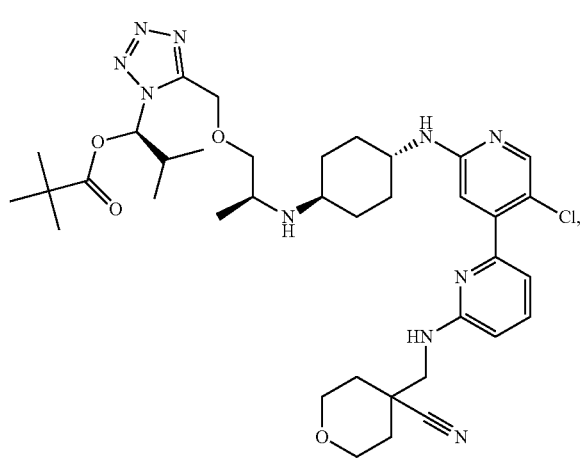
72
-continued
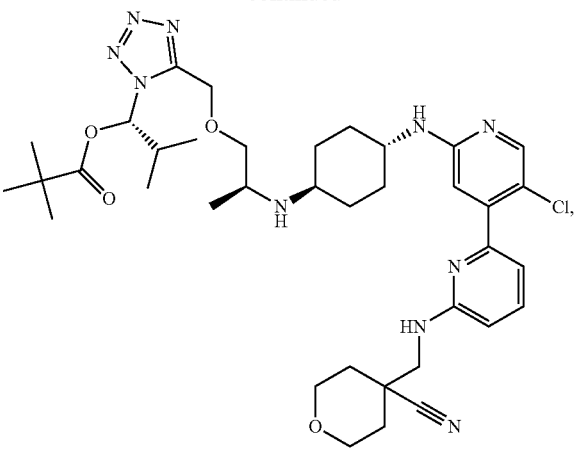
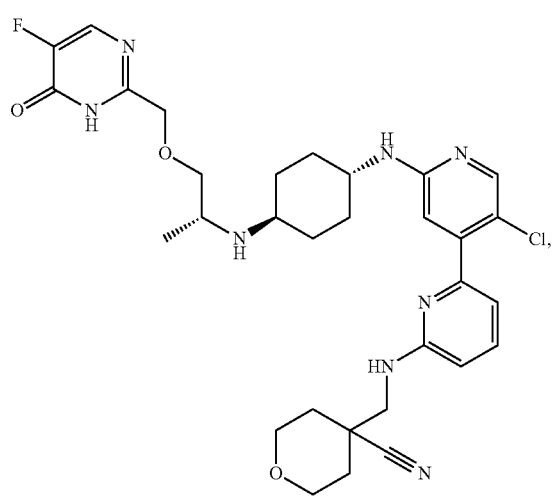
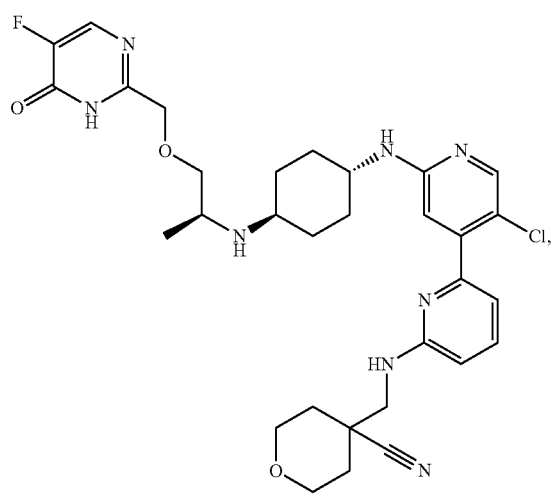

73
-continued
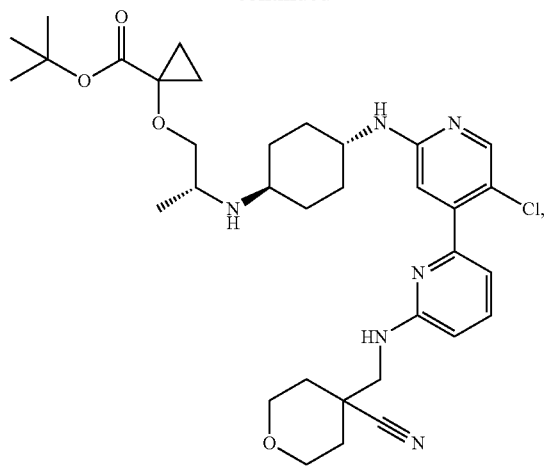
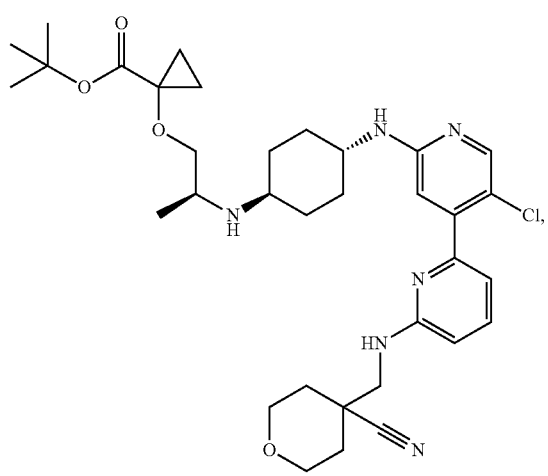
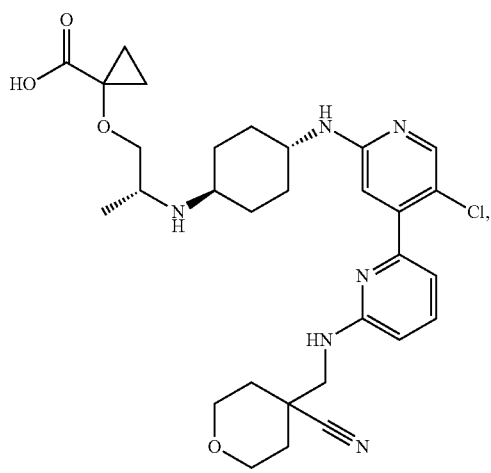
74
-continued
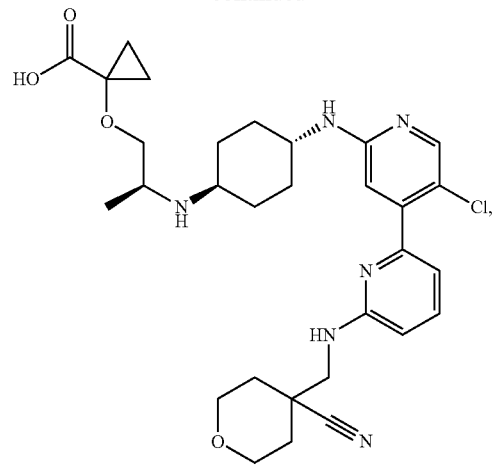
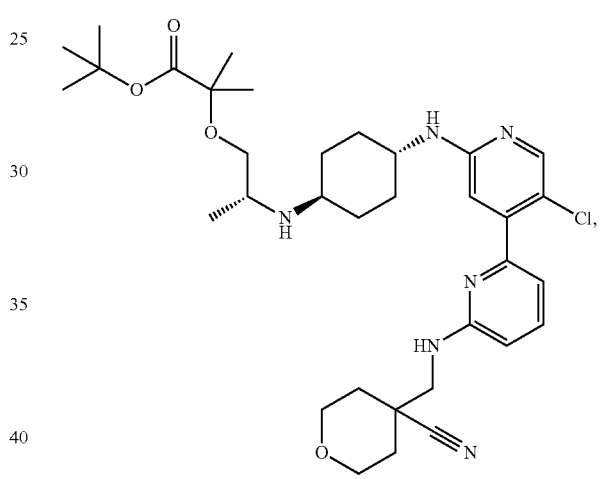
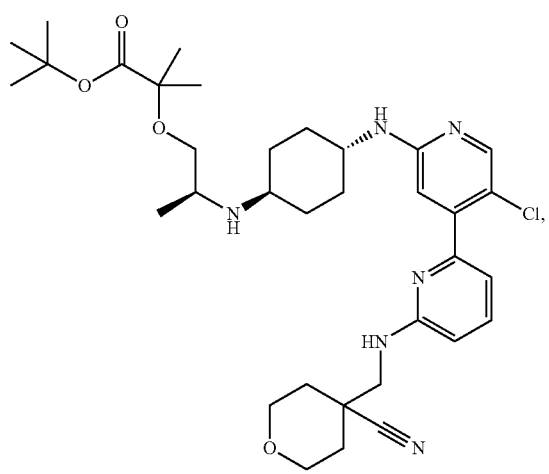

75
-continued
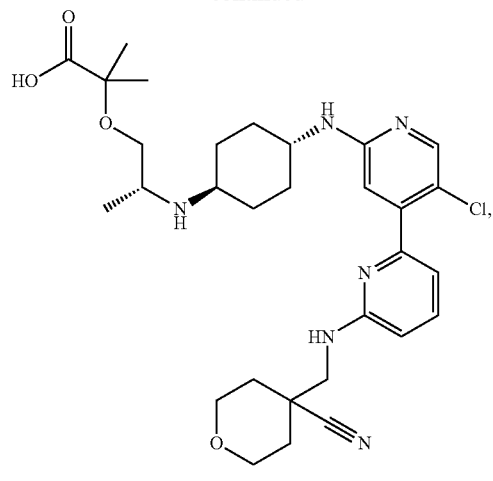
76
-continued
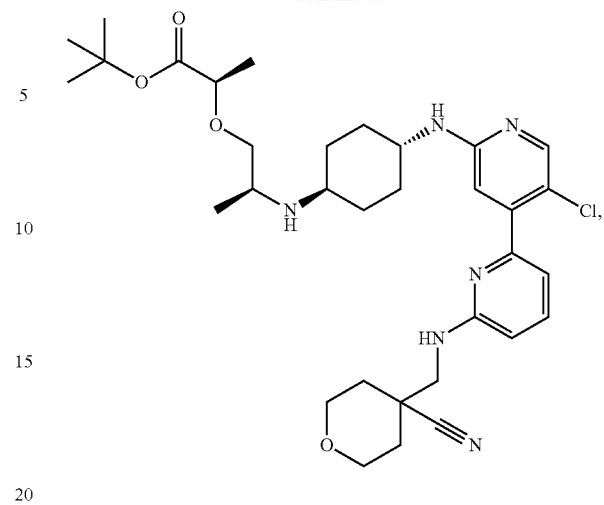
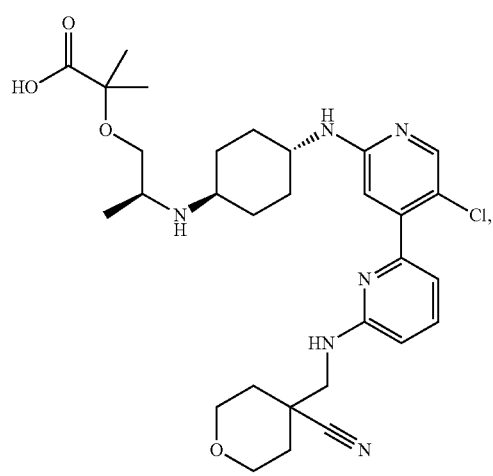
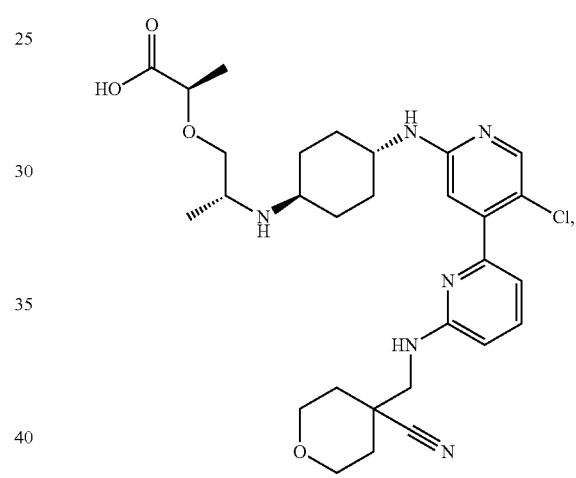
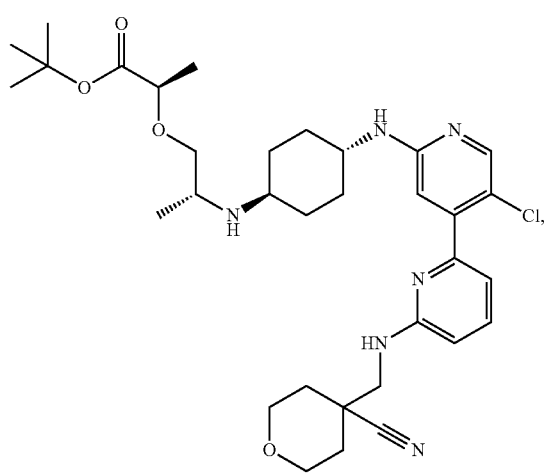
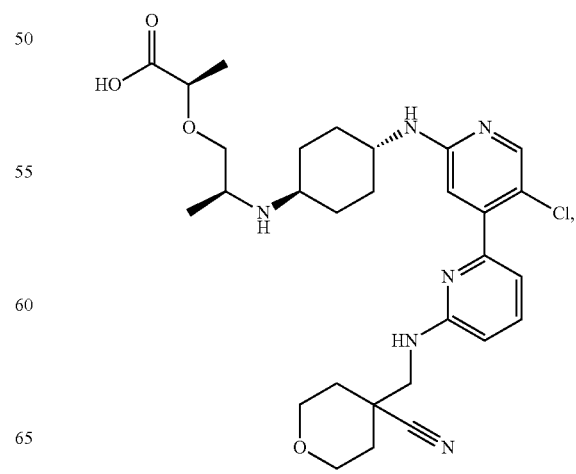

77
-continued
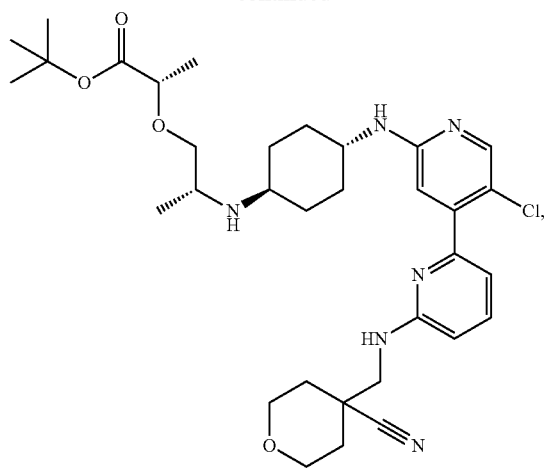
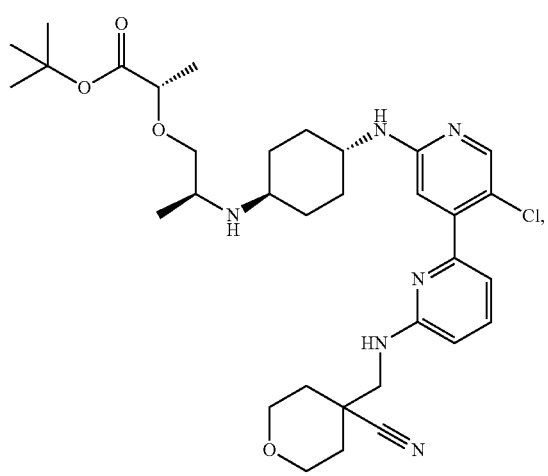
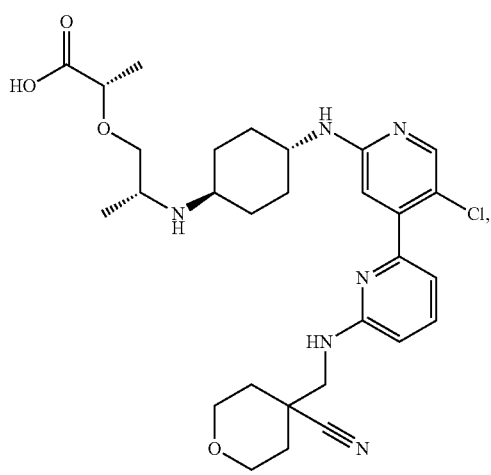
78
-continued
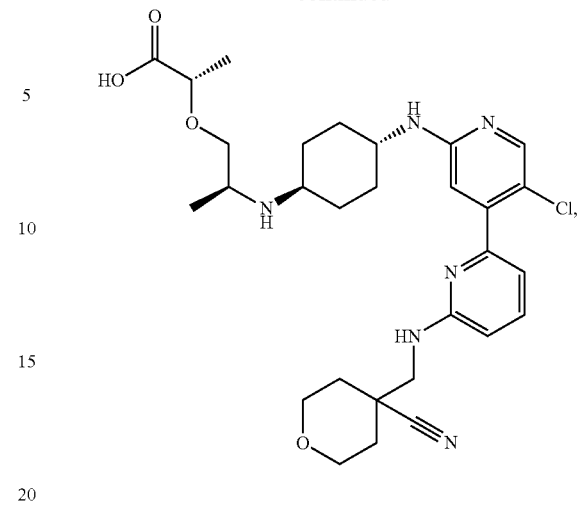
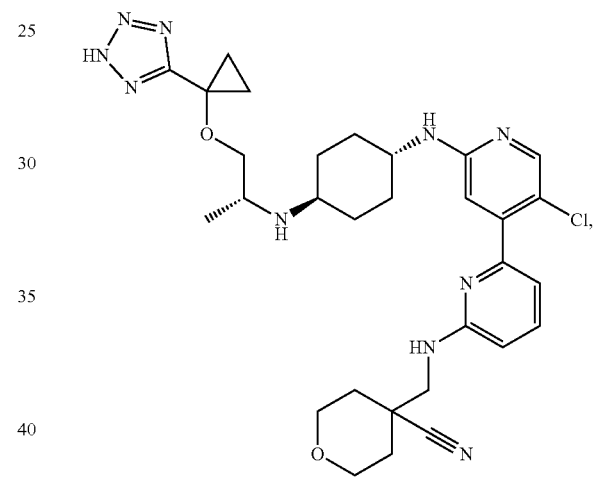
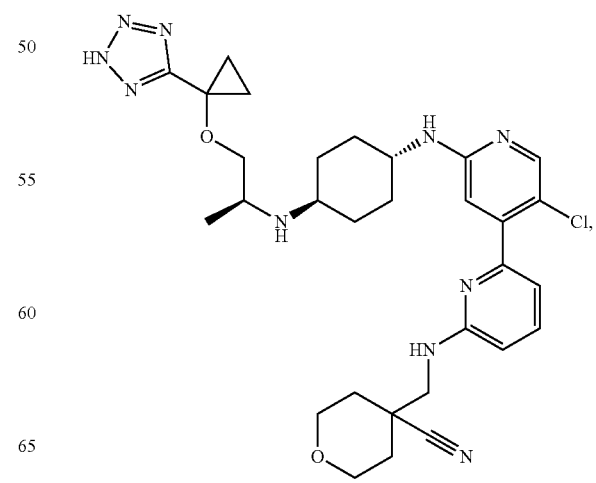

79
-continued
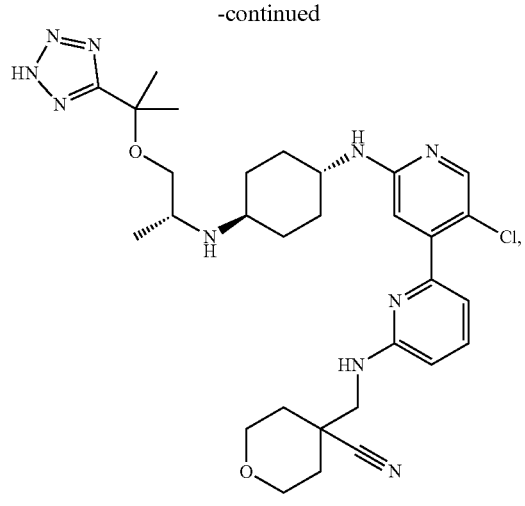
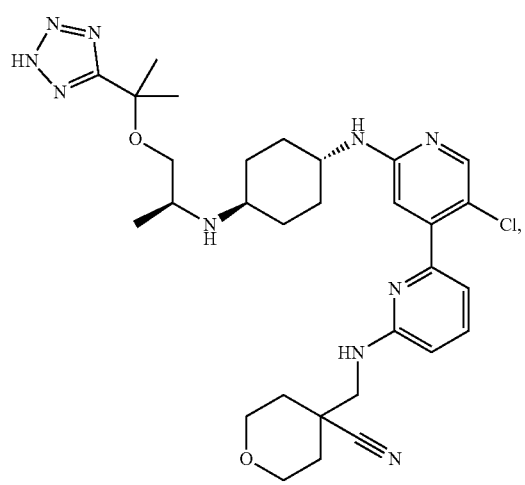
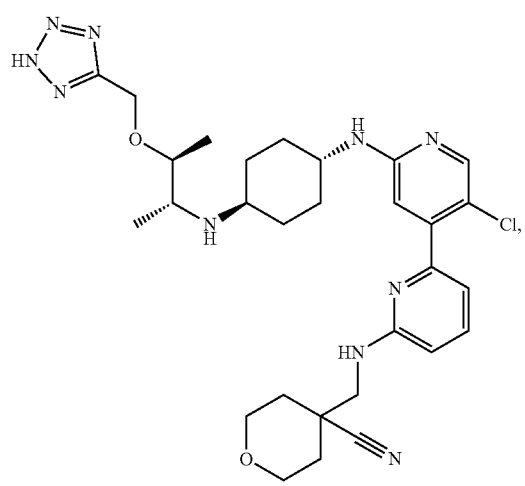
80
-continued
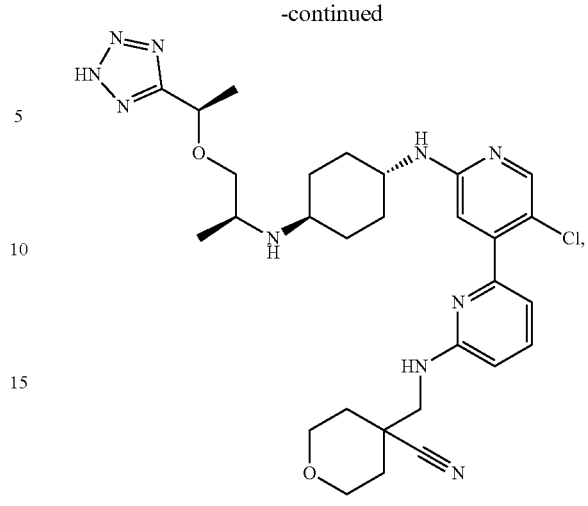
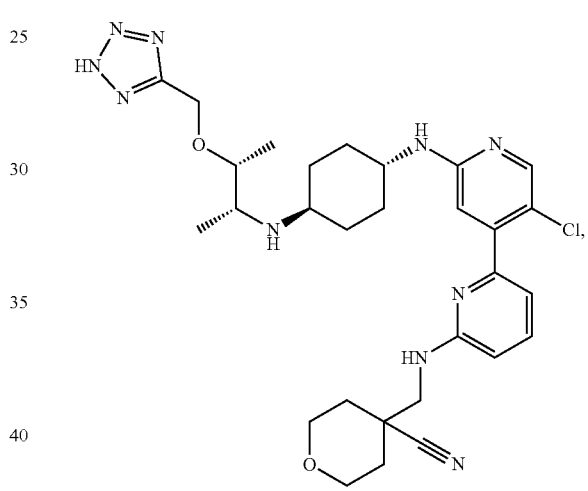
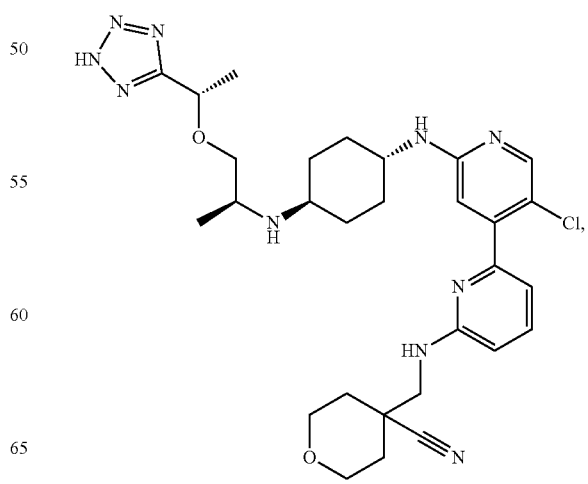

-continued
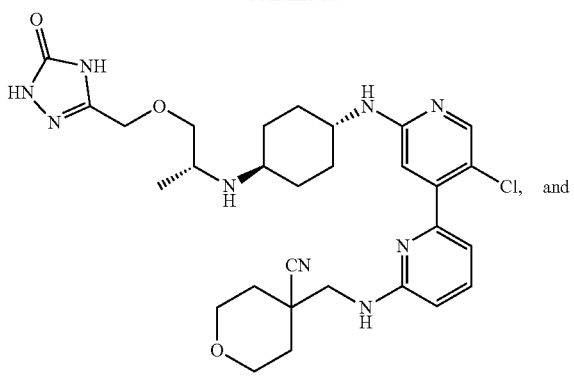
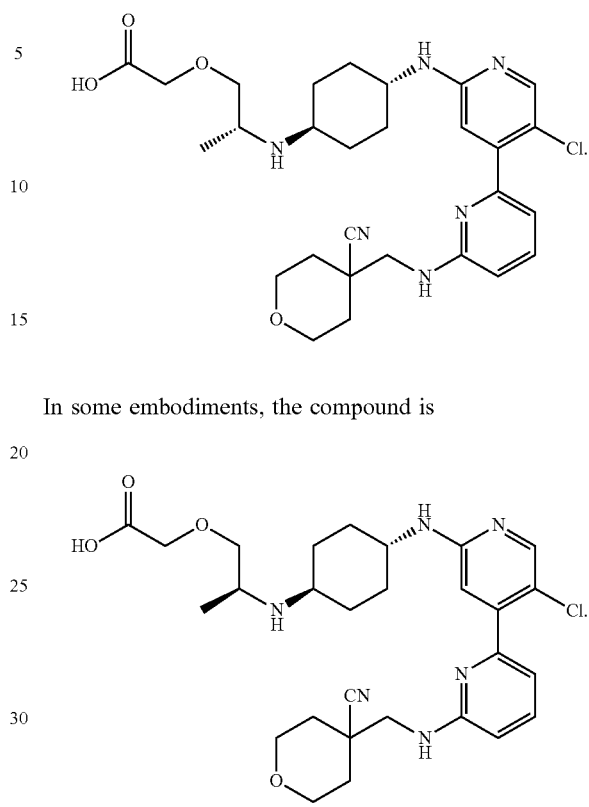
In some embodiments, the compound is
In some embodiments, the compound is
In some embodiments, the compound is
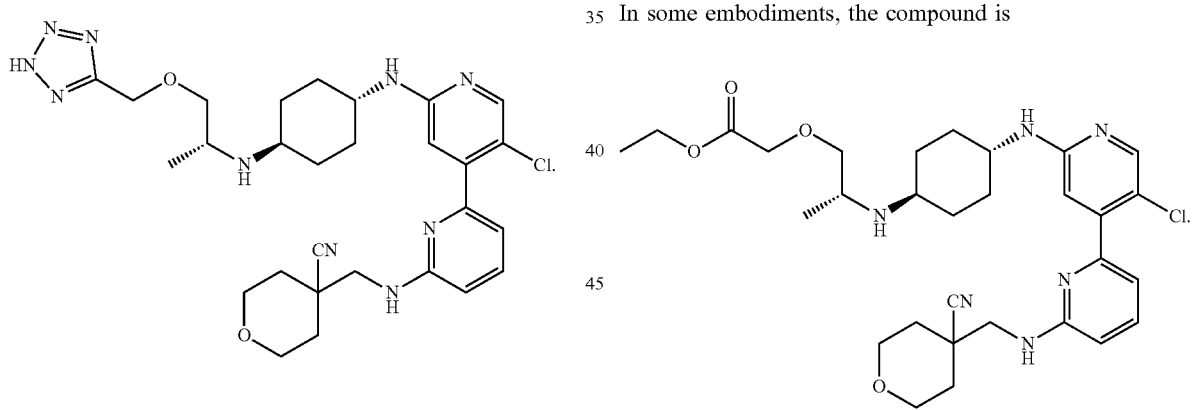
In some embodiments, the compound is
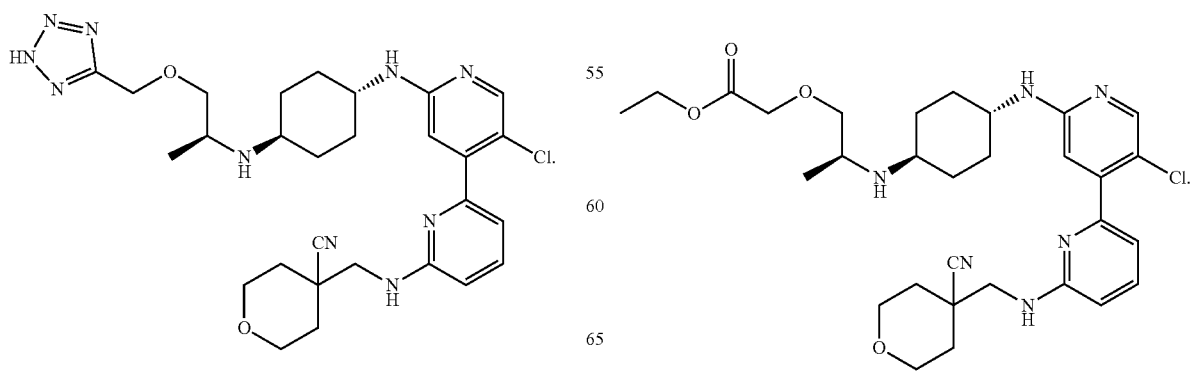
In some embodiments, the compound is In some embodiments, the compound is
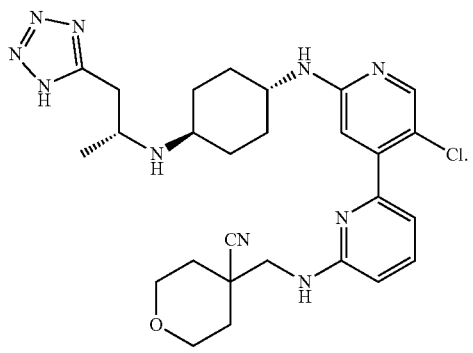 [SMILES: C[C@H](Cc1nnn[nH]1)N[C@H]1CC[C@H](Nc2cc(-c3cccc(NCC4(C#N)CCOCC4)n3)c(Cl)cn2)CC1]
In some embodiments, the compound is
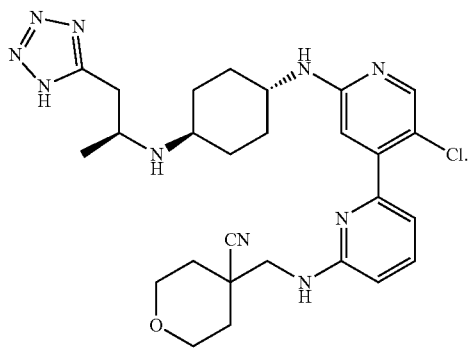 [SMILES: C[C@@H](Cc1nnn[nH]1)N[C@H]1CC[C@H](Nc2cc(-c3cccc(NCC4(C#N)CCOCC4)n3)c(Cl)cn2)CC1]
In some embodiments, the compound is
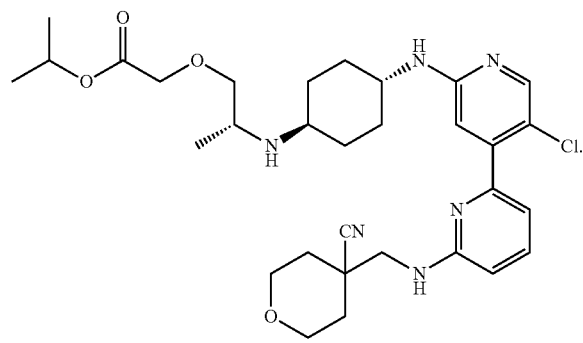 [SMILES: CC(C)OC(=O)COC[C@@H](C)N[C@H]1CC[C@H](Nc2cc(-c3cccc(NCC4(C#N)CCOCC4)n3)c(Cl)cn2)CC1]
In some embodiments, the compound is
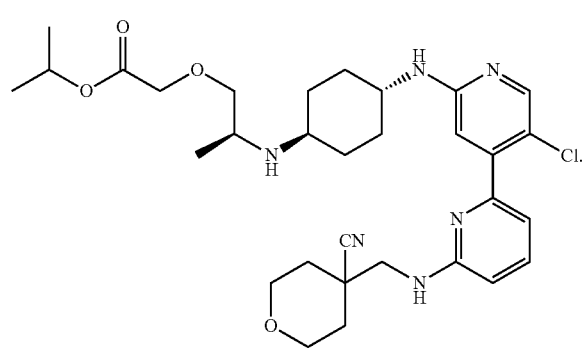 [SMILES: CC(C)OC(=O)COC[C@H](C)N[C@H]1CC[C@H](Nc2cc(-c3cccc(NCC4(C#N)CCOCC4)n3)c(Cl)cn2)CC1]
In some embodiments, the compound is
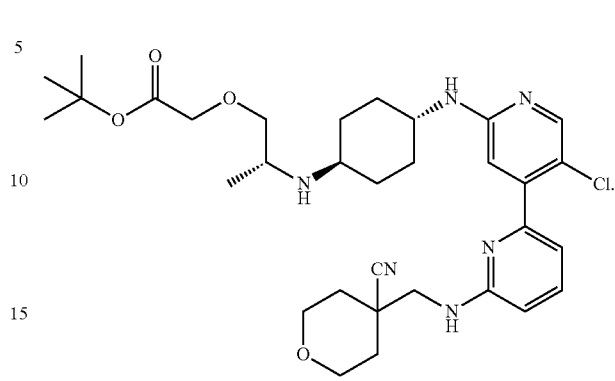
In some embodiments, the compound is
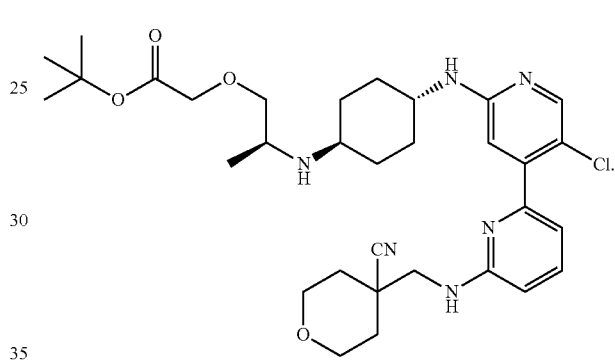
In some embodiments, the compound is
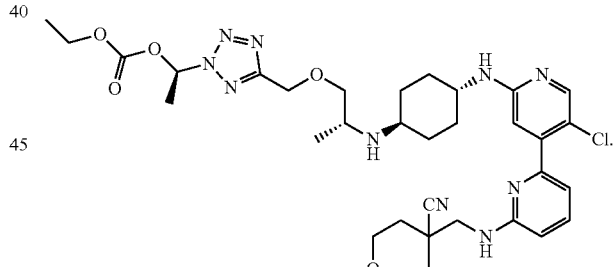
In some embodiments, the compound is
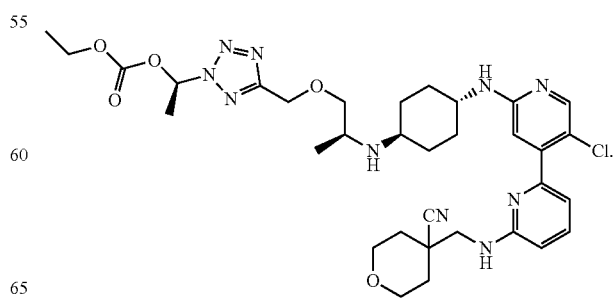

In some embodiments, the compound is
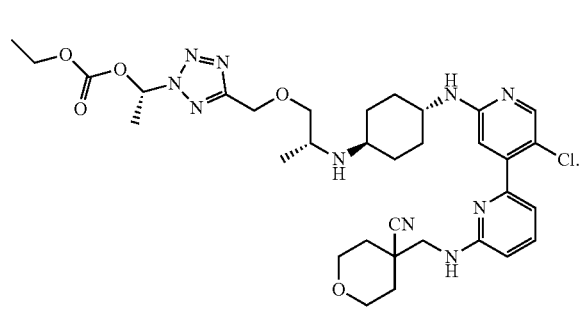 [SMILES: CCOC(=O)O[C@@H](C)n1nnc(COC[C@@H](C)N[C@H]2CC[C@H](Nc3cc(-c4cccc(NCC5(C#N)CCOCC5)n4)c(Cl)cn3)CC2)n1]
In some embodiments, the compound is
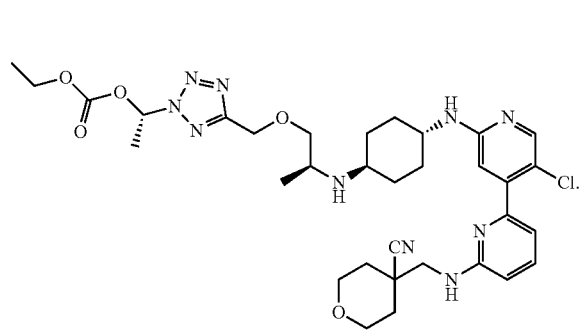 [SMILES: CCOC(=O)O[C@@H](C)n1nnc(COC[C@H](C)N[C@H]2CC[C@H](Nc3cc(-c4cccc(NCC5(C#N)CCOCC5)n4)c(Cl)cn3)CC2)n1]
In some embodiments, the compound is
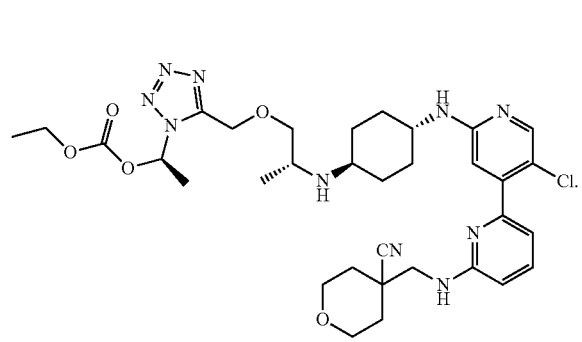 [SMILES: CCOC(=O)O[C@H](C)n1nnnc1COC[C@@H](C)N[C@H]1CC[C@H](Nc2cc(-c3cccc(NCC4(C#N)CCOCC4)n3)c(Cl)cn2)CC1]
In some embodiments, the compound is
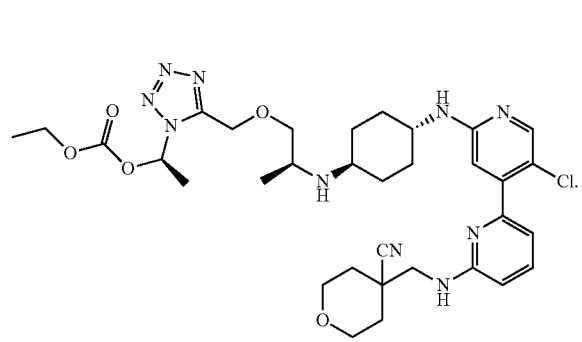 [SMILES: CCOC(=O)O[C@H](C)n1nnnc1COC[C@H](C)N[C@H]1CC[C@H](Nc2cc(-c3cccc(NCC4(C#N)CCOCC4)n3)c(Cl)cn2)CC1]
In some embodiments, the compound is
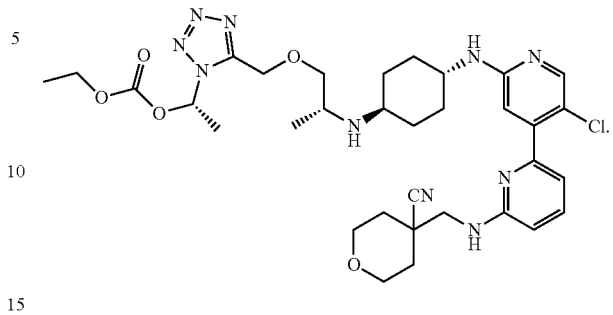
In some embodiments, the compound is
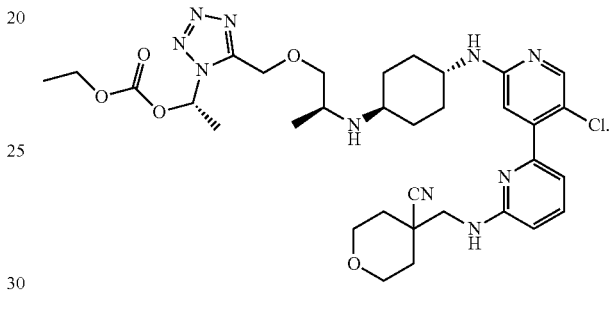
In some embodiments, the compound is
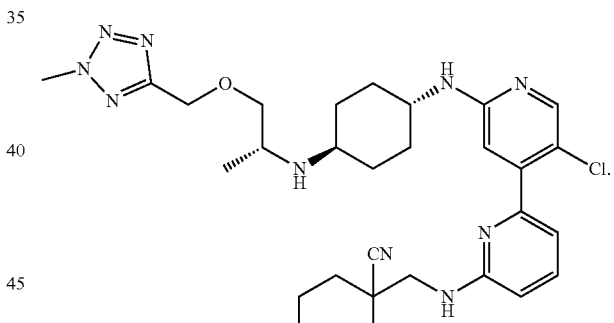
In some embodiments, the compound is
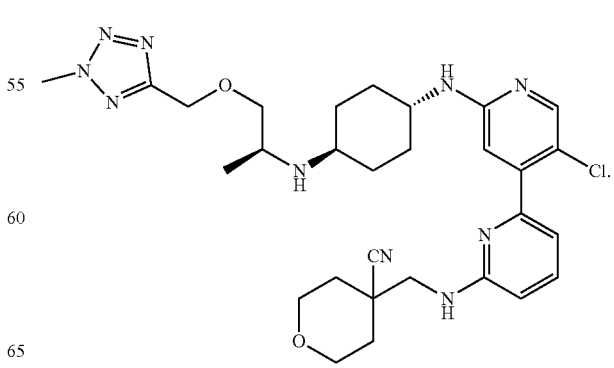

In some embodiments, the compound is
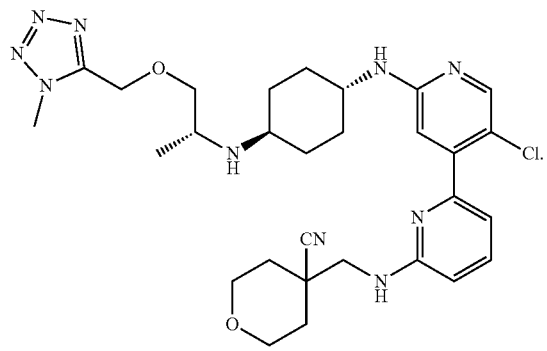 [SMILES: C[C@H](COCc1nnnn1C)N[C@H]1CC[C@H](Nc2cc(-c3cccc(NCC4(C#N)CCOCC4)n3)c(Cl)cn2)CC1]
In some embodiments, the compound is
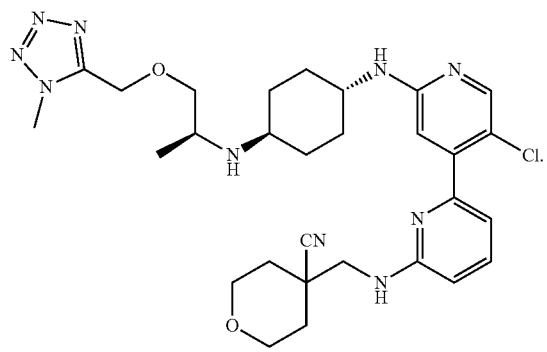 [SMILES: C[C@@H](COCc1nnnn1C)N[C@H]1CC[C@H](Nc2cc(-c3cccc(NCC4(C#N)CCOCC4)n3)c(Cl)cn2)CC1]
In some embodiments, the compound is
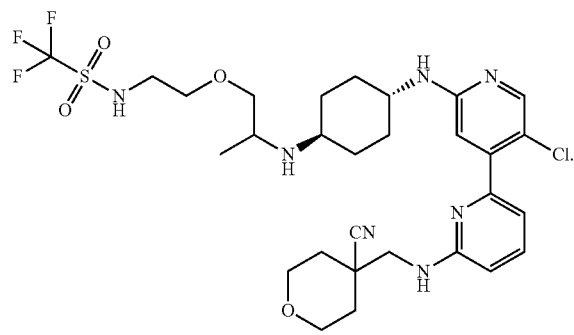 [SMILES: CC(COCCNS(=O)(=O)C(F)(F)F)N[C@H]1CC[C@H](Nc2cc(-c3cccc(NCC4(C#N)CCOCC4)n3)c(Cl)cn2)CC1]
In some embodiments, the compound is
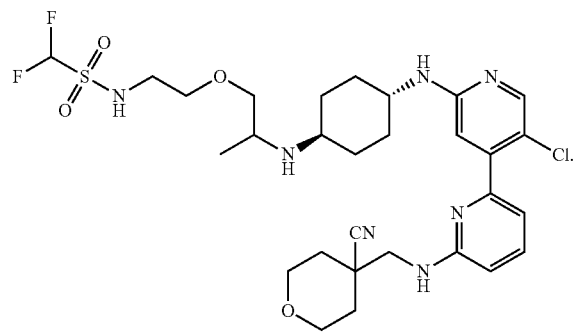 [SMILES: CC(COCCNS(=O)(=O)C(F)F)N[C@H]1CC[C@H](Nc2cc(-c3cccc(NCC4(C#N)CCOCC4)n3)c(Cl)cn2)CC1]
In some embodiments, the compound is
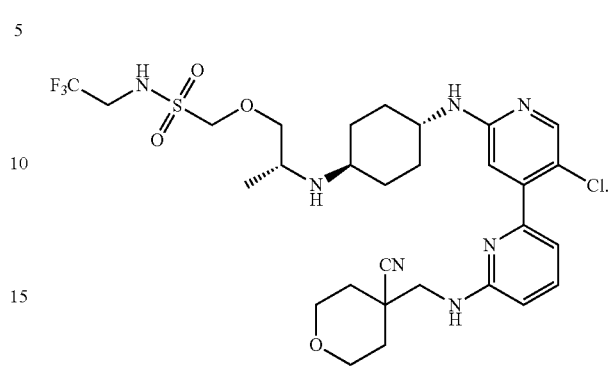
In some embodiments, the compound is
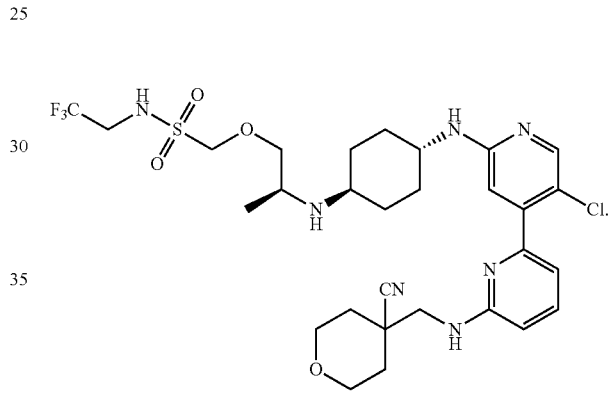
In some embodiments, the compound is
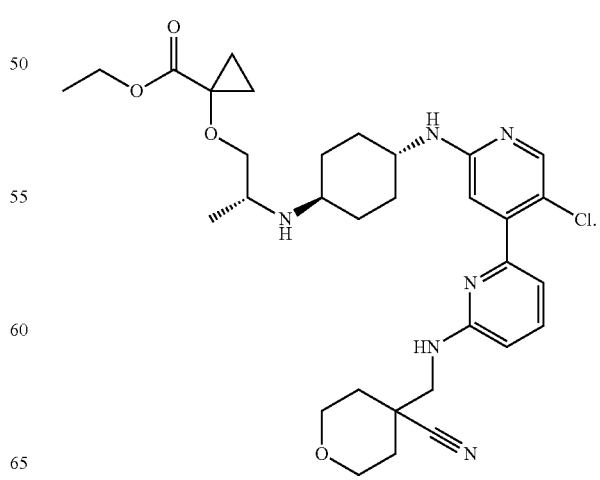

In some embodiments, the compound is
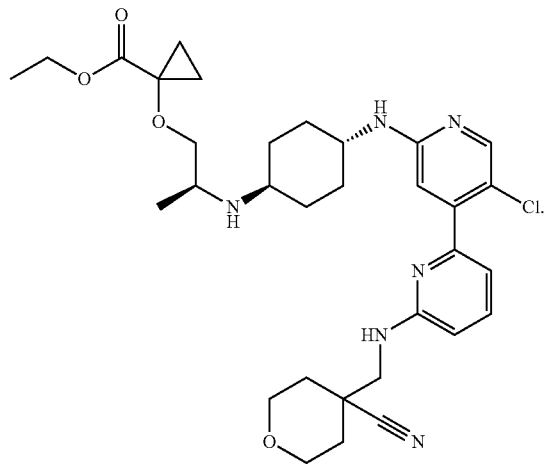 [SMILES: CCOC(=O)C1(OC[C@H](C)N[C@H]2CC[C@H](Nc3cc(-c4cccc(NCC5(C#N)CCOCC5)n4)c(Cl)cn3)CC2)CC1]
In some embodiments, the compound is
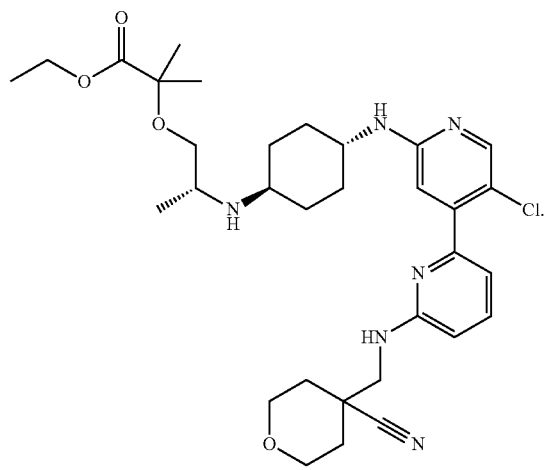 [SMILES: CCOC(=O)C(C)(C)OC[C@@H](C)N[C@H]1CC[C@H](Nc2cc(-c3cccc(NCC4(C#N)CCOCC4)n3)c(Cl)cn2)CC1]
In some embodiments, the compound is
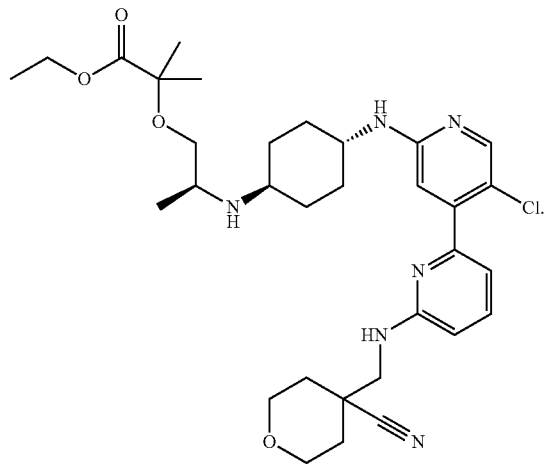 [SMILES: CCOC(=O)C(C)(C)OC[C@H](C)N[C@H]1CC[C@H](Nc2cc(-c3cccc(NCC4(C#N)CCOCC4)n3)c(Cl)cn2)CC1]
In some embodiments, the compound is
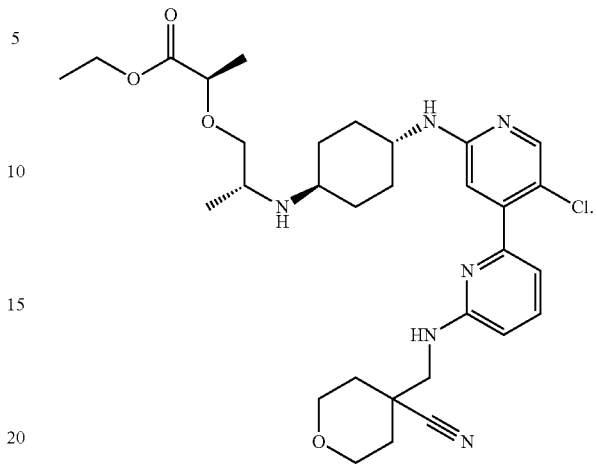
In some embodiments, the compound is
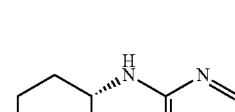
In some embodiments, the compound is
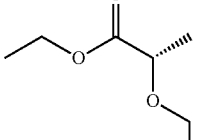

91
In some embodiments, the compound is
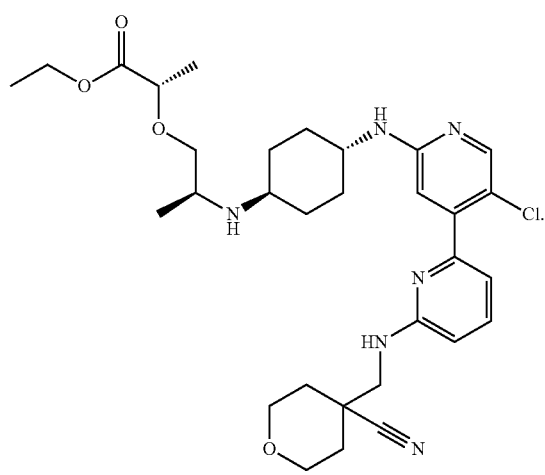 [SMILES: CCOC(=O)[C@H](C)OC[C@H](C)N[C@H]1CC[C@H](Nc2cc(-c3cccc(NCC4(C#N)CCOCC4)n3)c(Cl)cn2)CC1]
In some embodiments, the compound is
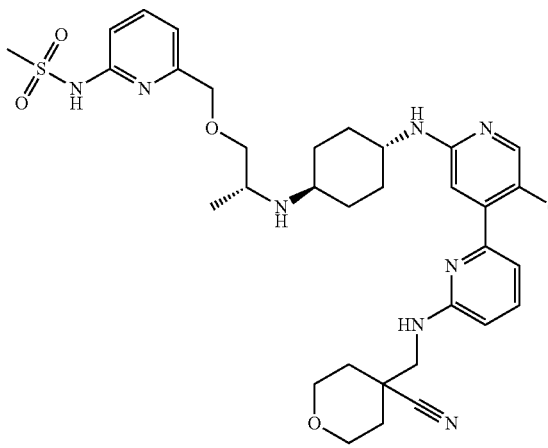
In some embodiments, the compound is
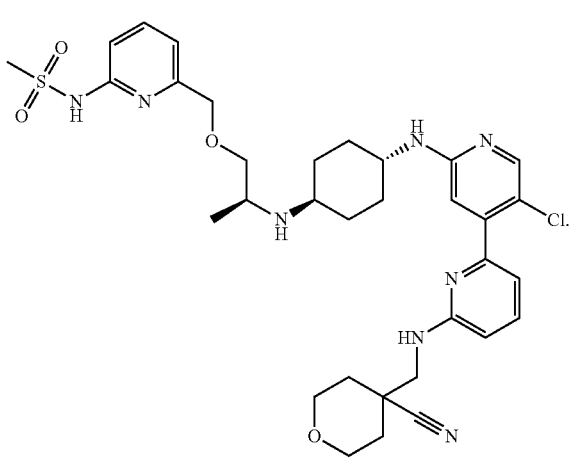 [SMILES: C[C@@H](COCc1cccc(NS(C)(=O)=O)n1)N[C@H]1CC[C@H](Nc2cc(-c3cccc(NCC4(C#N)CCOCC4)n3)c(Cl)cn2)CC1]
92
In some embodiments, the compound is
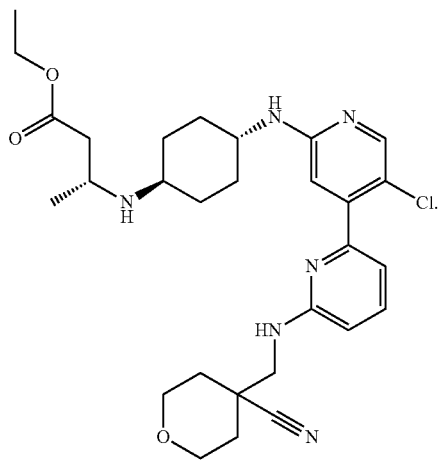 [SMILES: CCOC(=O)C[C@@H](C)N[C@H]1CC[C@H](Nc2cc(-c3cccc(NCC4(C#N)CCOCC4)n3)c(Cl)cn2)CC1]
In some embodiments, the compound is
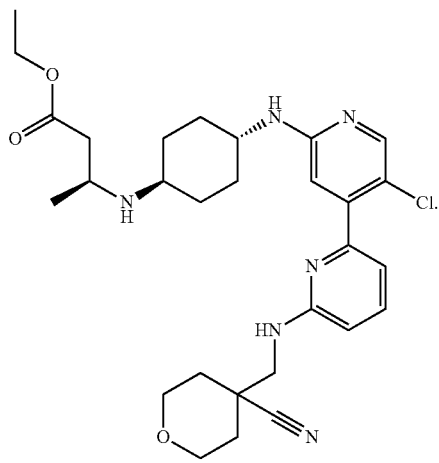 [SMILES: CCOC(=O)C[C@H](C)N[C@H]1CC[C@H](Nc2cc(-c3cccc(NCC4(C#N)CCOCC4)n3)c(Cl)cn2)CC1]
In some embodiments, the compound is
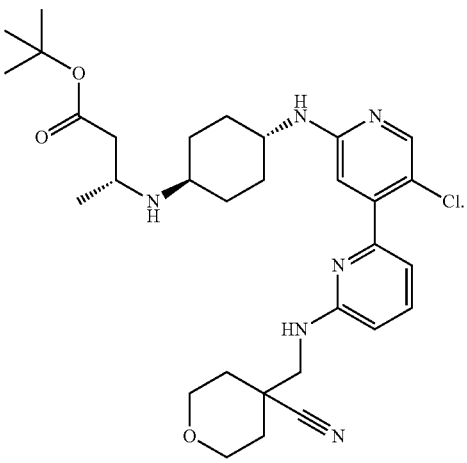 [SMILES: C[C@H](CC(=O)OC(C)(C)C)N[C@H]1CC[C@H](Nc2cc(-c3cccc(NCC4(C#N)CCOCC4)n3)c(Cl)cn2)CC1]

In some embodiments, the compound is
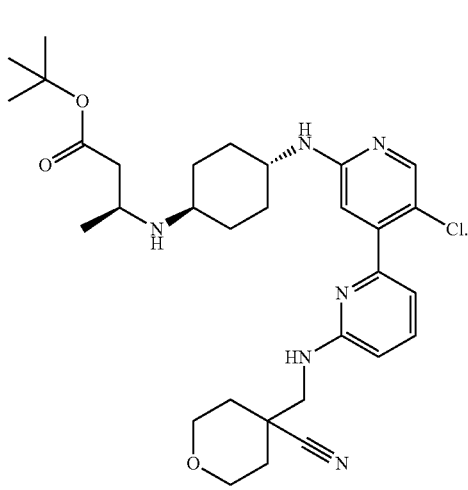 [SMILES: C[C@@H](CC(=O)OC(C)(C)C)N[C@H]1CC[C@H](Nc2cc(-c3cccc(NCC4(C#N)CCOCC4)n3)c(Cl)cn2)CC1]
In some embodiments, the compound is
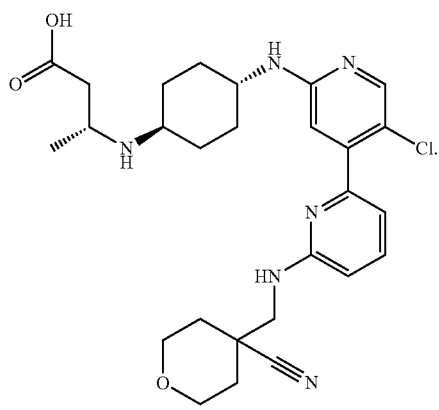 [SMILES: C[C@H](CC(=O)O)N[C@H]1CC[C@H](Nc2cc(-c3cccc(NCC4(C#N)CCOCC4)n3)c(Cl)cn2)CC1]
In some embodiments, the compound is
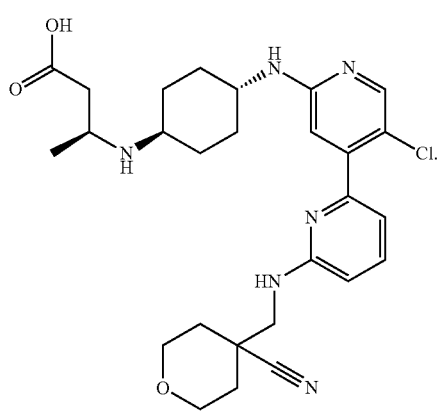 [SMILES: C[C@@H](CC(=O)O)N[C@H]1CC[C@H](Nc2cc(-c3cccc(NCC4(C#N)CCOCC4)n3)c(Cl)cn2)CC1]
In some embodiments, the compound is
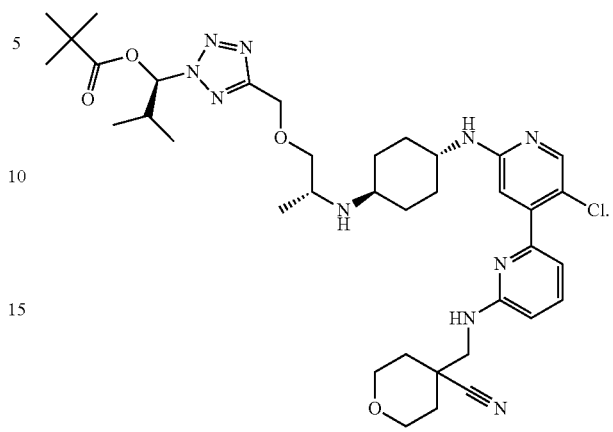
In some embodiments, the compound is
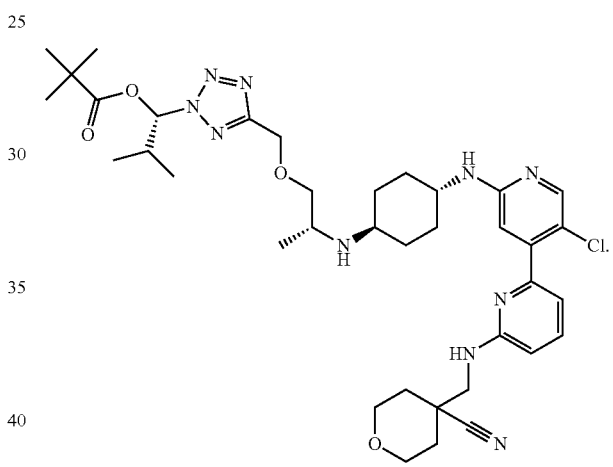
In some embodiments, the compound is
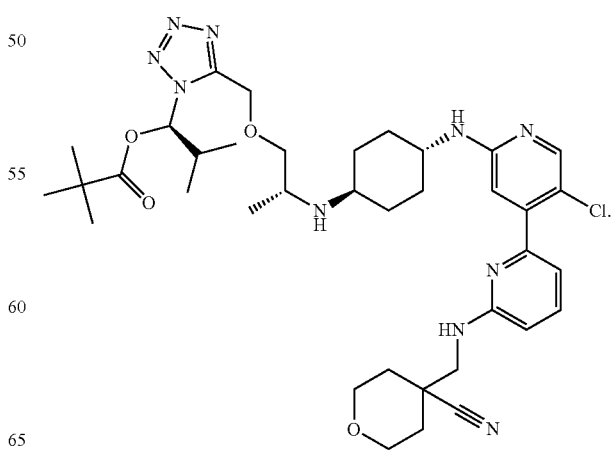

In some embodiments, the compound is
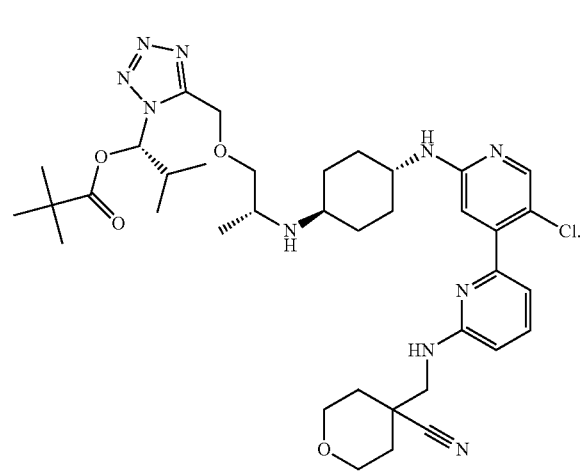 [SMILES: CC(C)[C@H](OC(=O)C(C)(C)C)n1nnnc1COC[C@@H](C)N[C@H]1CC[C@H](Nc2cc(-c3cccc(NCC4(C#N)CCOCC4)n3)c(Cl)cn2)CC1]
In some embodiments, the compound is
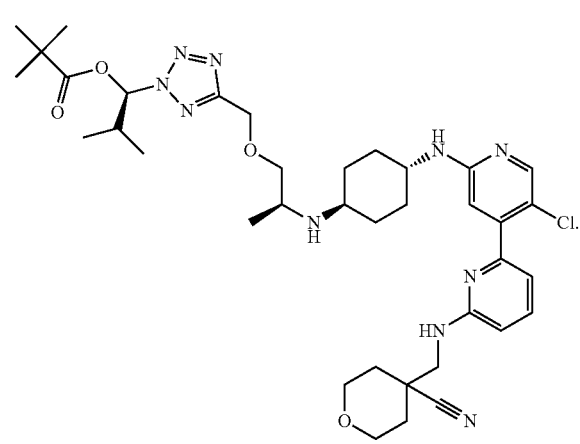 [SMILES: CC(C)[C@@H](OC(=O)C(C)(C)C)n1nnc(COC[C@H](C)N[C@H]2CC[C@H](Nc3cc(-c4cccc(NCC5(C#N)CCOCC5)n4)c(Cl)cn3)CC2)n1]
In some embodiments, the compound is
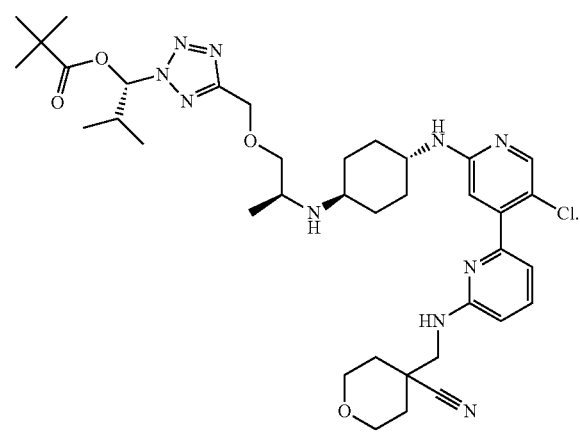 [SMILES: CC(C)[C@H](OC(=O)C(C)(C)C)n1nnc(COC[C@H](C)N[C@H]2CC[C@H](Nc3cc(-c4cccc(NCC5(C#N)CCOCC5)n4)c(Cl)cn3)CC2)n1]
In some embodiments, the compound is
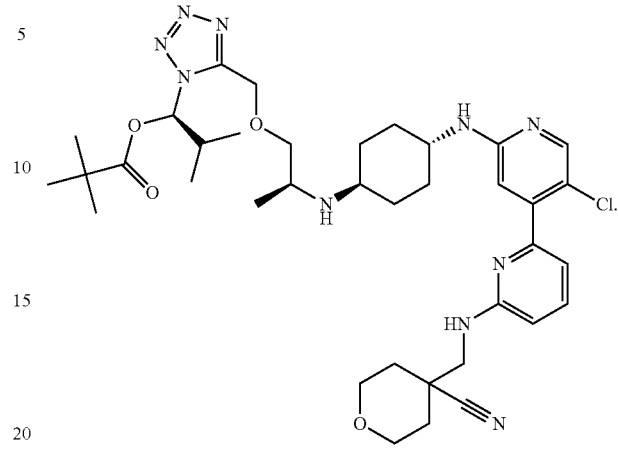
In some embodiments, the compound is
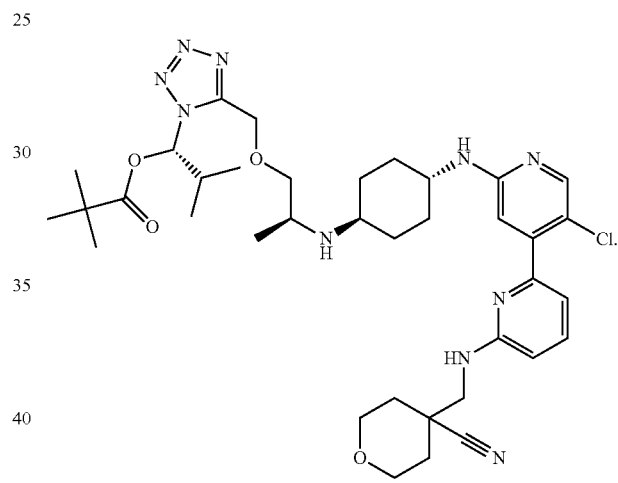
In some embodiments, the compound is
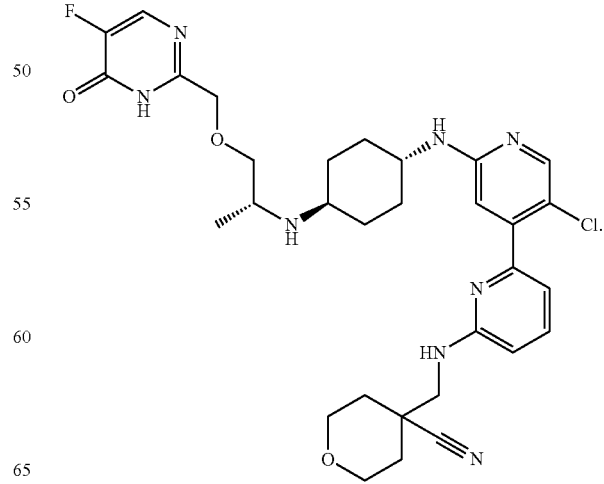

In some embodiments, the compound is
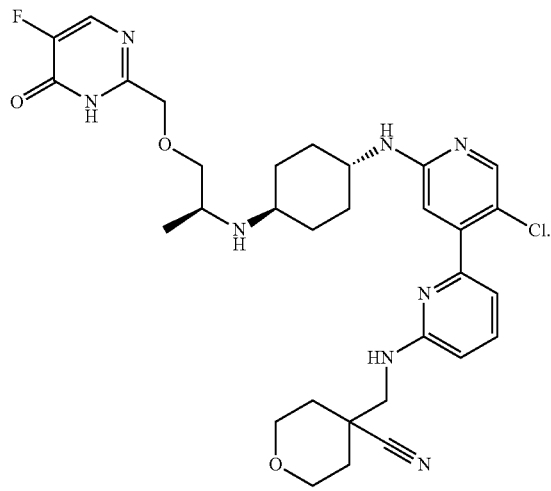 [SMILES: C[C@@H](COCc1ncc(F)c(=O)[nH]1)N[C@H]1CC[C@H](Nc2cc(-c3cccc(NCC4(C#N)CCOCC4)n3)c(Cl)cn2)CC1]
In some embodiments, the compound is
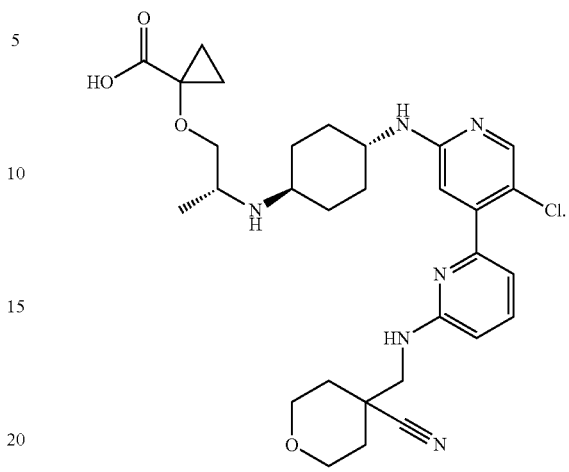
In some embodiments, the compound is
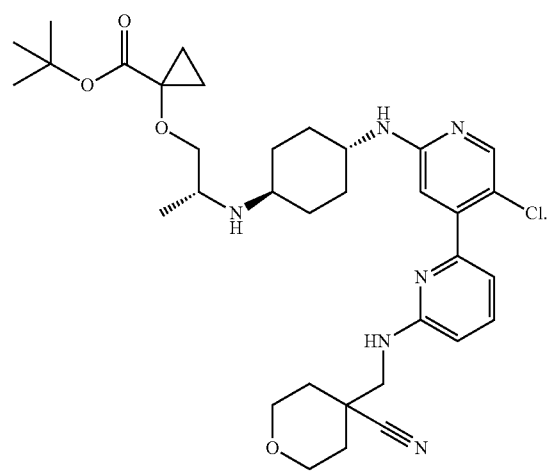 [SMILES: C[C@H](COC1(C(=O)OC(C)(C)C)CC1)N[C@H]1CC[C@H](Nc2cc(-c3cccc(NCC4(C#N)CCOCC4)n3)c(Cl)cn2)CC1]
In some embodiments, the compound is
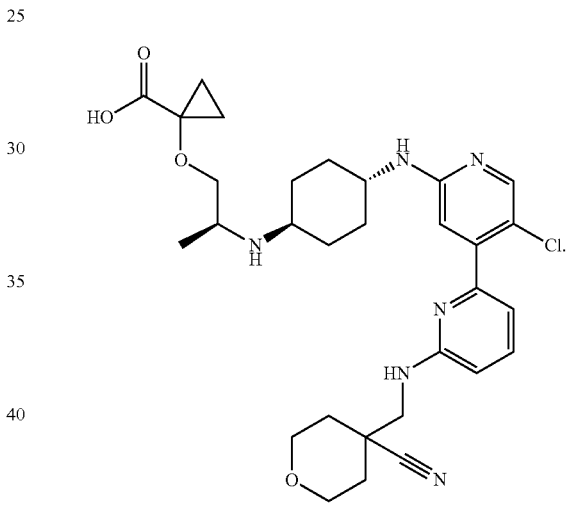
In some embodiments, the compound is
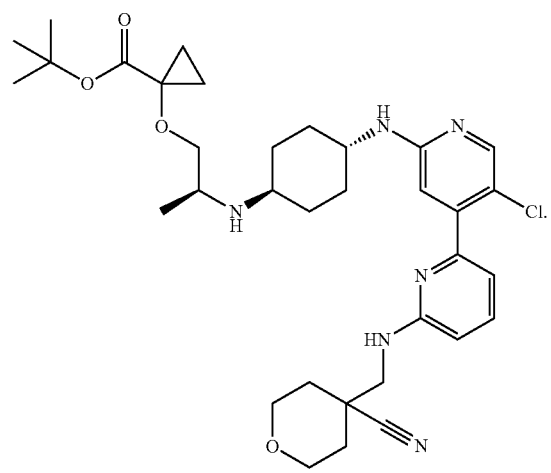 [SMILES: C[C@@H](COC1(C(=O)OC(C)(C)C)CC1)N[C@H]1CC[C@H](Nc2cc(-c3cccc(NCC4(C#N)CCOCC4)n3)c(Cl)cn2)CC1]
In some embodiments, the compound is
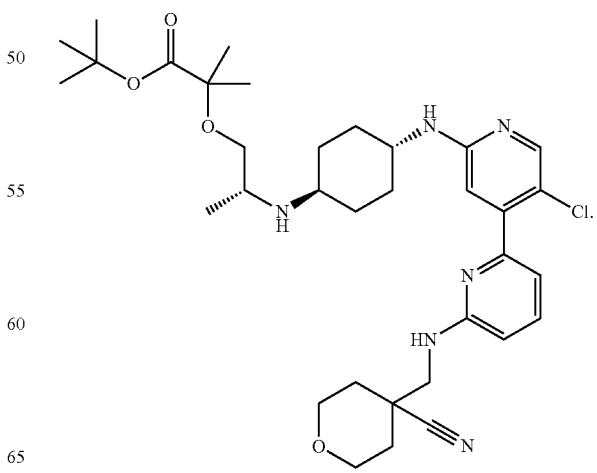

In some embodiments, the compound is
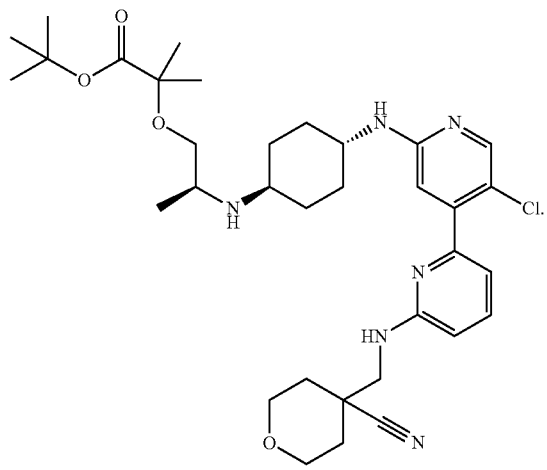 [SMILES: C[C@@H](COC(C)(C)C(=O)OC(C)(C)C)N[C@H]1CC[C@H](Nc2cc(-c3cccc(NCC4(C#N)CCOCC4)n3)c(Cl)cn2)CC1]
In some embodiments, the compound is
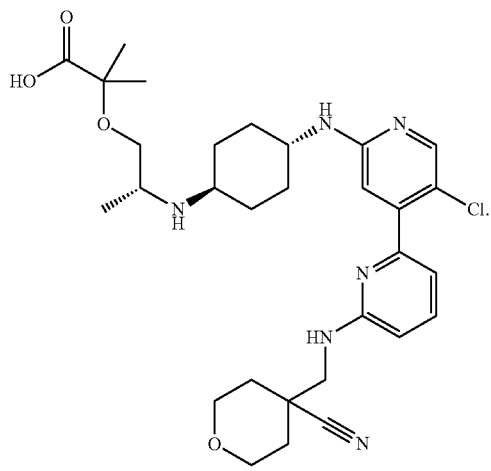 [SMILES: C[C@H](COC(C)(C)C(=O)O)N[C@H]1CC[C@H](Nc2cc(-c3cccc(NCC4(C#N)CCOCC4)n3)c(Cl)cn2)CC1]
In some embodiments, the compound is
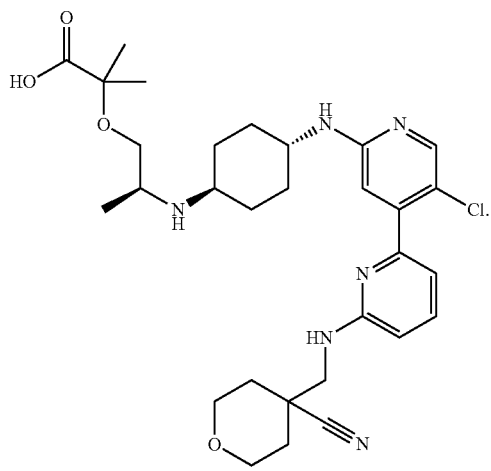 [SMILES: C[C@@H](COC(C)(C)C(=O)O)N[C@H]1CC[C@H](Nc2cc(-c3cccc(NCC4(C#N)CCOCC4)n3)c(Cl)cn2)CC1]
In some embodiments, the compound is
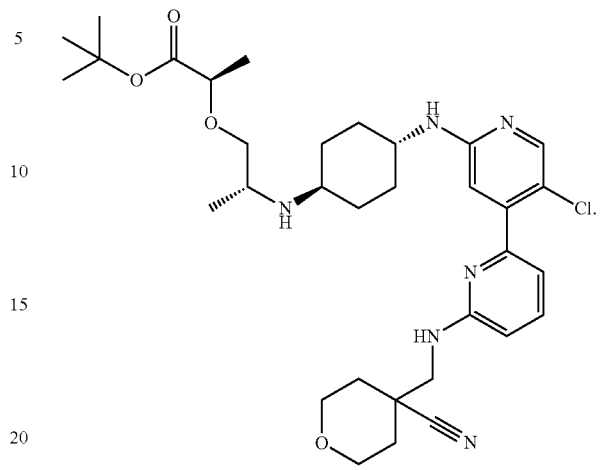
In some embodiments, the compound is
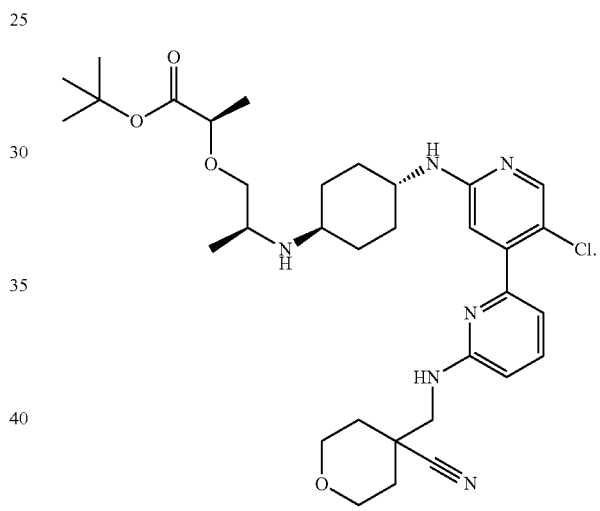
In some embodiments, the compound is
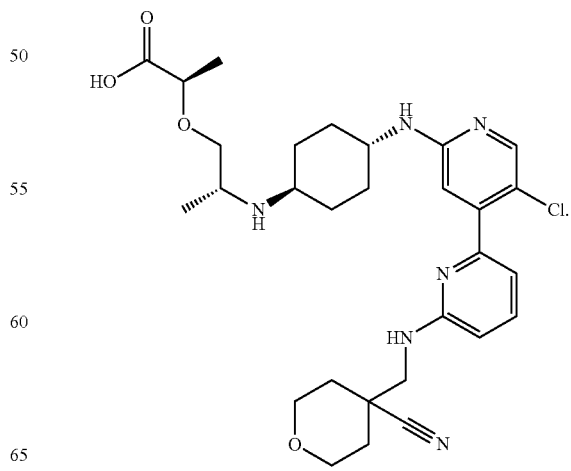

101
In some embodiments, the compound is
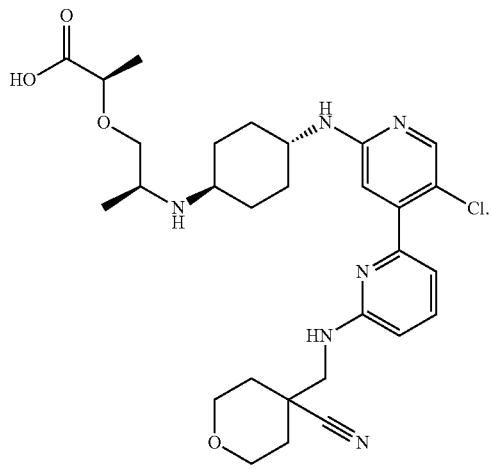 [SMILES: C[C@@H](CO[C@H](C)C(=O)O)N[C@H]1CC[C@H](Nc2cc(-c3cccc(NCC4(C#N)CCOCC4)n3)c(Cl)cn2)CC1]
In some embodiments, the compound is
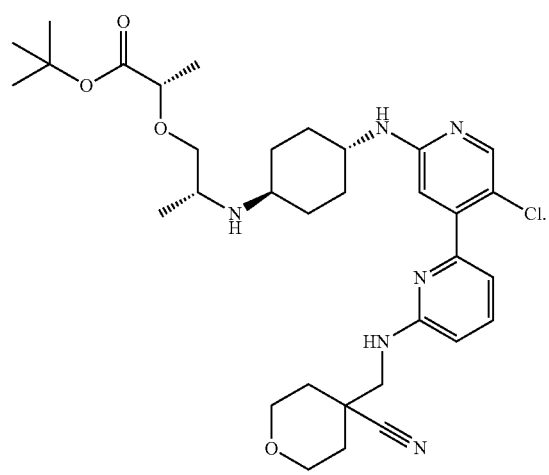 [SMILES: C[C@H](CO[C@@H](C)C(=O)OC(C)(C)C)N[C@H]1CC[C@H](Nc2cc(-c3cccc(NCC4(C#N)CCOCC4)n3)c(Cl)cn2)CC1]
In some embodiments, the compound is
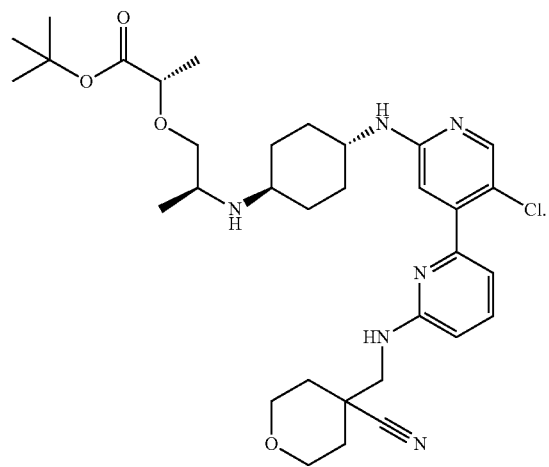 [SMILES: C[C@H](OC[C@H](C)N[C@H]1CC[C@H](Nc2cc(-c3cccc(NCC4(C#N)CCOCC4)n3)c(Cl)cn2)CC1)C(=O)OC(C)(C)C]
102
In some embodiments, the compound is
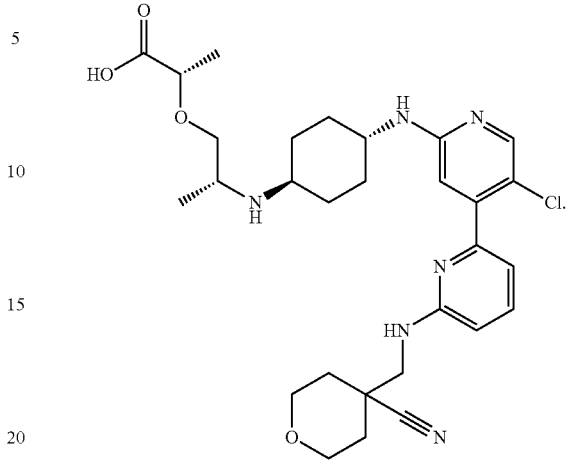
In some embodiments, the compound is
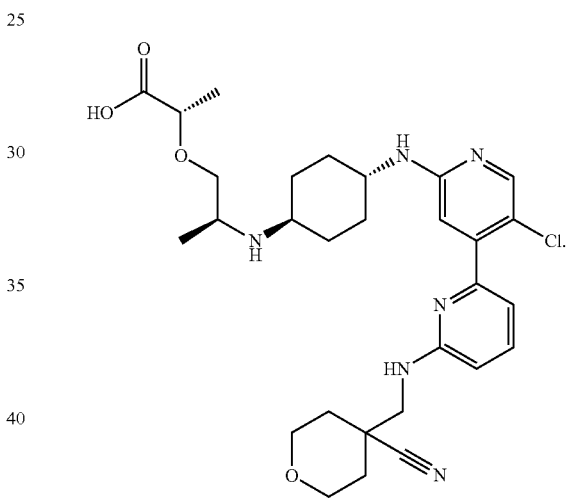
In some embodiments, the compound is
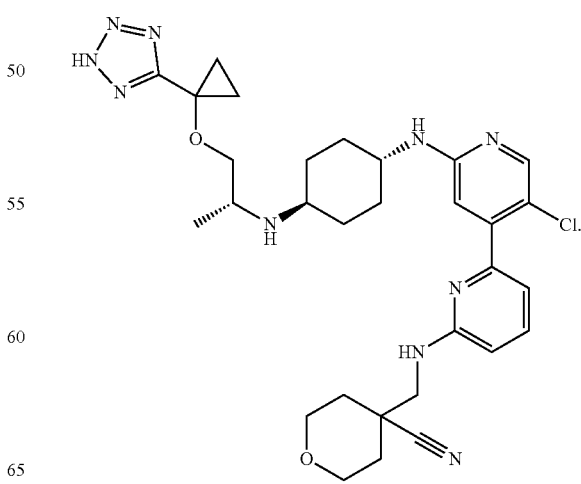

In some embodiments, the compound is
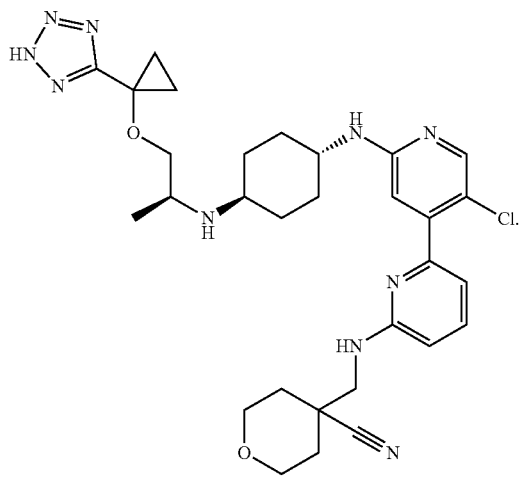 [SMILES: C[C@@H](COC1(c2nn[nH]n2)CC1)N[C@H]1CC[C@H](Nc2cc(-c3cccc(NCC4(C#N)CCOCC4)n3)c(Cl)cn2)CC1]
In some embodiments, the compound is
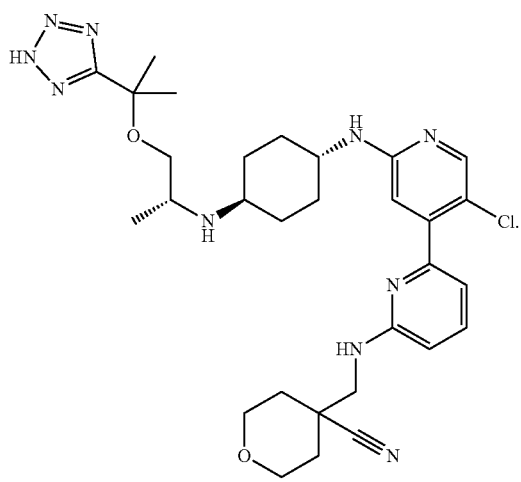 [SMILES: C[C@H](COC(C)(C)c1nn[nH]n1)N[C@H]1CC[C@H](Nc2cc(-c3cccc(NCC4(C#N)CCOCC4)n3)c(Cl)cn2)CC1]
In some embodiments, the compound is
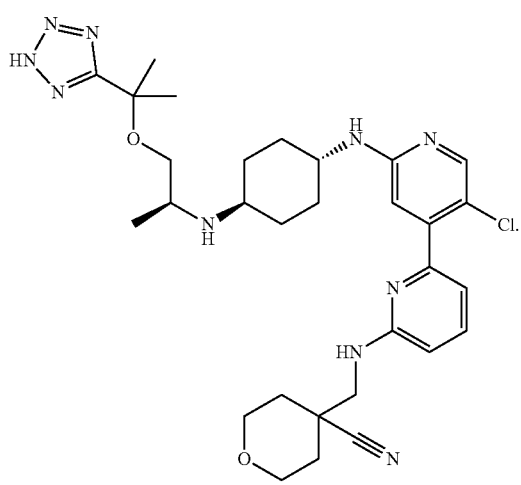 [SMILES: C[C@@H](COC(C)(C)c1nn[nH]n1)N[C@H]1CC[C@H](Nc2cc(-c3cccc(NCC4(C#N)CCOCC4)n3)c(Cl)cn2)CC1]
In some embodiments, the compound is
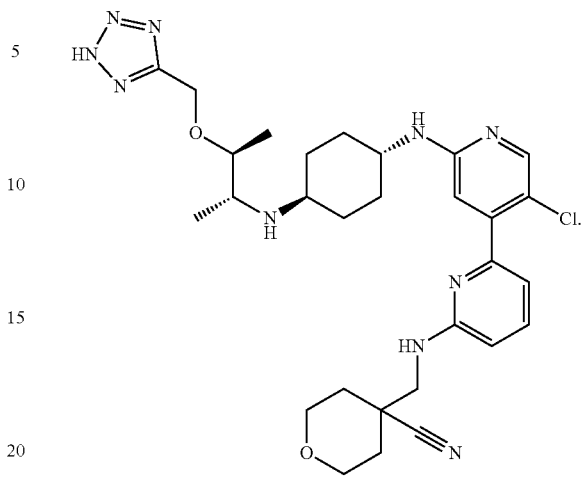
In some embodiments, the compound is
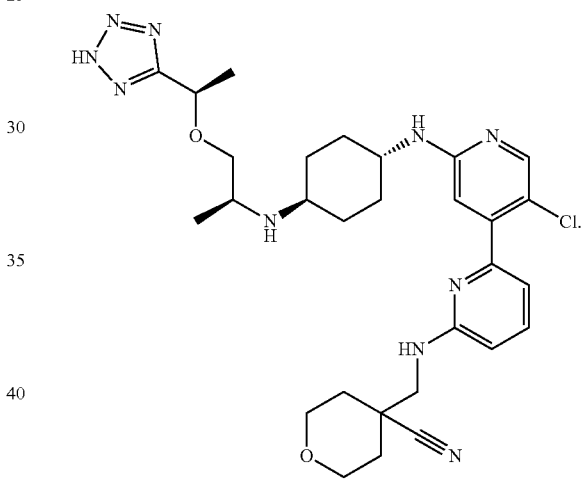
In some embodiments, the compound is
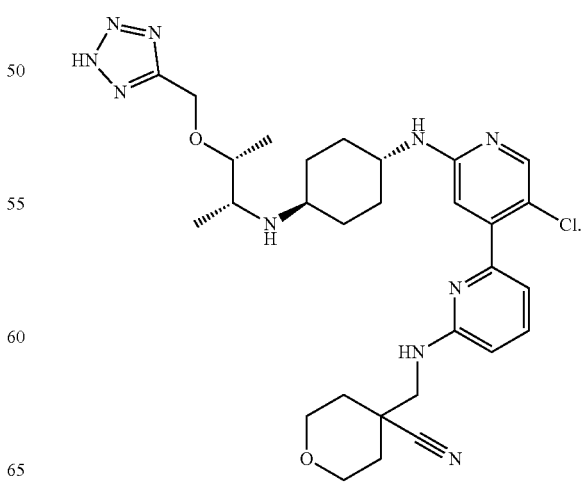

In some embodiments, the compound is

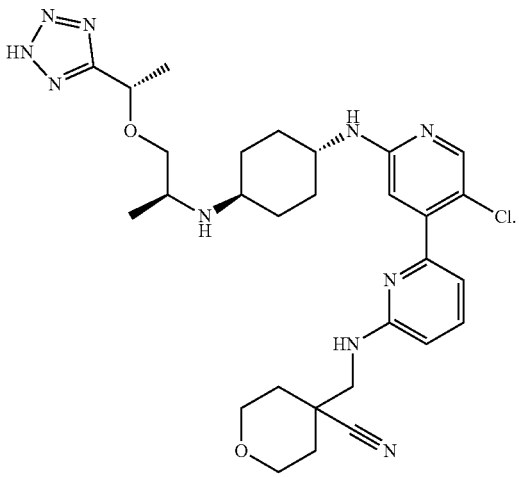 [SMILES: C[C@H](OC[C@H](C)N[C@H]1CC[C@H](Nc2cc(-c3cccc(NCC4(C#N)CCOCC4)n3)c(Cl)cn2)CC1)c1nn[nH]n1]

In some embodiments, the compound is

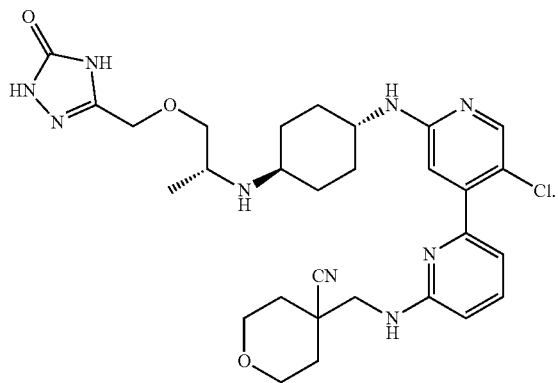 [SMILES: C[C@H](COCc1n[nH]c(=O)[nH]1)N[C@H]1CC[C@H](Nc2cc(-c3cccc(NCC4(C#N)CCOCC4)n3)c(Cl)cn2)CC1]

In some embodiments, the compound is

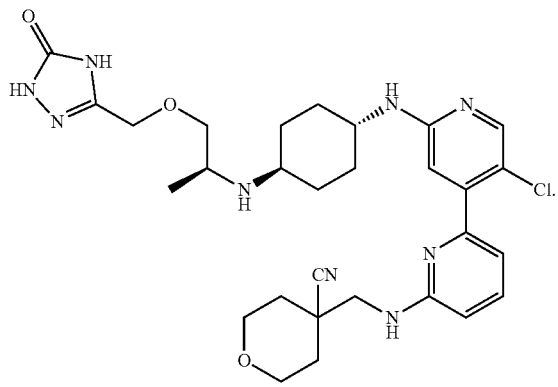 [SMILES: C[C@@H](COCc1n[nH]c(=O)[nH]1)N[C@H]1CC[C@H](Nc2cc(-c3cccc(NCC4(C#N)CCOCC4)n3)c(Cl)cn2)CC1]

Provided herein, in another aspect, is a pharmaceutical composition comprising a compound described herein, or a pharmaceutically acceptable salt thereof, and a pharmaceutically acceptable excipient.

Provided herein, in another aspect, is a method of treating a disease or disorder in a patient in need thereof, comprising administering to the subject a therapeutically effective amount of a compound described herein, or a pharmaceutically acceptable salt thereof, or a pharmaceutical composition described herein.

In some embodiments, the disease or disorder is cancer. In some embodiments, the cancer is selected from leukemia, breast cancer, prostate cancer, ovarian cancer, colon cancer, cervical cancer, lung cancer, lymphoma, and liver cancer. In some embodiments, the cancer is leukemia. In some embodiments, the cancer is breast cancer. In some embodiments, the cancer is prostate cancer. In some embodiments, the cancer is ovarian cancer. In some embodiments, the cancer is colon cancer. In some embodiments, the cancer is cervical cancer. In some embodiments, the cancer is lung cancer. In some embodiments, the cancer is lymphoma. In some embodiments, the cancer is liver cancer.

Methods of Use

In one aspect, the present invention provides a method for treating a proliferative disorder in a subject in need thereof, comprising administering to said subject a compound having Formula (I), as disclosed further herein. In some embodiments, the method for treating the proliferative disorder comprises administering to said subject a CDK9 inhibitor. In some embodiments, the compound having Formula (I) is the CDK9 inhibitor. In some embodiments, the proliferative disorder is a cancer condition. In some further embodiments, said cancer condition is a cancer selected from the group consisting of leukemia, breast cancer, prostate cancer, ovarian cancer, colon cancer, cervical cancer, lung cancer, lymphoma, and liver cancer. In some embodiments, said cancer condition is liver cancer.

In some embodiments, the CDK9 inhibitors disclosed herein are highly targeted to the liver. In some embodiments, the CDK9 inhibitors disclosed herein have superior liver targeting as compared with known CDK9 inhibitors. In some embodiments, the CDK9 inhibitors disclosed herein accumulate in the liver while avoiding peripheral exposure to nearby tissues. In some embodiments, the CDK9 inhibitors disclosed herein have reduced peripheral exposure to nearby tissues as compared with known CDK9 inhibitors. In some embodiments, the CDK9 inhibitors disclosed herein have reduced toxicity as compared with known CDK9 inhibitors.

In a further embodiment, the present invention provides a method of treating a cancer condition, wherein the compound having Formula (I) (e.g., a CDK9 inhibitor) is effective in one or more method of inhibiting proliferation of cancer cells, inhibiting metastasis of cancer cells, reducing severity or incidence of symptoms associated with the presence of cancer cells, and promoting an immune response to tumor cells. In some embodiments, said method comprises administering to the cancer cells a therapeutically effective amount of a compound having Formula (I). In some embodiments, the compound having Formula (I) is a CDK9 inhibitor. In some embodiments, the administration takes place in vitro. In other embodiments, the administration takes place in vivo.

As used herein, a therapeutically effective amount of a CDK9 inhibitor refers to an amount sufficient to effect the intended application, including but not limited to, disease treatment, as defined herein. Also contemplated in the subject methods is the use of a sub-therapeutic amount of a CDK9 inhibitor for treating an intended disease condition.

The amount of the CDK9 inhibitor administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring inhibition of biological effects of CDK9 can comprise performing an assay on a biological sample, such as a sample from a subject. Any of a variety of samples may be selected, depending on the assay. Examples of samples include, but are not limited to, blood samples (e.g. blood plasma or serum), exhaled breath condensate samples, bronchoalveolar lavage fluid, sputum samples, urine samples, and tissue samples.

A subject being treated with a CDK9 inhibitor may be monitored to determine the effectiveness of treatment, and the treatment regimen may be adjusted based on the subject's physiological response to treatment. For example, if inhibition of a biological effect of CDK9 degradation is above or below a threshold, the dosing amount or frequency may be decreased or increased, respectively. The methods can further comprise continuing the therapy if the therapy is determined to be efficacious. The methods can comprise maintaining, tapering, reducing, or stopping the administered amount of a compound in the therapy if the therapy is determined to be efficacious. The methods can comprise increasing the administered amount of a compound in the therapy if it is determined not to be efficacious. Alternatively, the methods can comprise stopping therapy if it is determined not to be efficacious. In some embodiments, treatment with a CDK9 inhibitor is discontinued if inhibition of the biological effect is above or below a threshold, such as in a lack of response or an adverse reaction. The biological effect may be a change in any of a variety of physiological indicators.

In general, a CDK9 inhibitor is a compound that inhibits one or more biological effects of CDK9. Such biological effects may be inhibited by about or more than about 10%, 20%, 30%, 40%, 50%, 60%, 70%, 80%, 90%, 95%, or more.

In some other embodiments, the subject methods are useful for treating a disease condition associated with CDK9. Any disease condition that results directly or indirectly from an abnormal activity or expression level of CDK9 can be an intended disease condition. In some embodiments, the disease condition is a proliferative disorder, such as described herein, including but not limited to cancer. In some embodiments, the disease condition is cancer. A role of CDK9 in tumorigenesis and tumor progression has been implicated in many human cancers. Consequently, agents that target CDK9 have therapeutic value.

The data presented in the Examples herein below demonstrate the anti-cancer effects of a CDK9 inhibitor. As such, the subject method is particularly useful for treating a proliferative disorder, such as a neoplastic condition.

In some embodiments, the methods of administering a CDK9 inhibitor described herein are applied to the treatment of cancers of the blood, breast, prostate, ovaries, colon, cervix, lungs, lymph nodes, liver, or any combination thereof.

Therapeutic Efficacy

In some embodiments, therapeutic efficacy is measured based on an effect of treating a proliferative disorder, such as cancer. In general, therapeutic efficacy of the methods and compositions of the invention, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, the reduction in the rate of growth of a tumor, and/or a reduction in the size of at least one tumor. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. The primary efficacy parameter used to evaluate the treatment of cancer by the inventive method and compositions preferably is a reduction in the size of a tumor. Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

In some desirable embodiments, the growth of a tumor is stabilized (i.e., one or more tumors do not increase more than 1%, 5%, 10%, 15%, or 20% in size, and/or do not metastasize) as a result of the inventive method and compositions. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the inventive method reduces the size of a tumor at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

In some embodiments, the efficacy of the inventive method in reducing tumor size can be determined by measuring the percentage of necrotic (i.e., dead) tissue of a surgically resected tumor following completion of the therapeutic period. In some further embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is 100%, that is, no tumor tissue is present or detectable.

The efficacy of the inventive method can be determined by a number of secondary parameters. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA), prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also can efficiently distinguish small tumors from surrounding tissue (see, for example, U.S. Pat. No. 4,932,412).

In additional desirable embodiments, the treatment of cancer in a human patient in accordance with the inventive method is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient by the inventive method. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the invention can be evidenced in terms of pain intensity, analgesic consumption, and/or the Karnofsky Performance Scale score. The treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced as a result of the inventive method preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. Desirably, the inventive method is associated with minimal adverse events, e.g. Grade 0, Grade 1, or Grade 2 adverse events, as graded by the CTEP/NCI. However, as discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Detection, monitoring and rating of various cancers in a human are further described in Cancer Facts and Figures 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

In some embodiments, administration of a CDK9 inhibitor provides improved therapeutic efficacy. Improved efficacy may be measured using any method known in the art, including but not limited to those described herein. In some embodiments, the improved therapeutic efficacy is an improvement of at least about 10%, 20%, 30%, 40%, 50%, 60%, 70%, 75%, 80%, 90%, 95%, 100%, 110%, 120%, 150%, 200%, 300%, 400%, 500%, 600%, 700%, 1000% or more, using an appropriate measure (e.g. tumor size reduction, duration of tumor size stability, duration of time free from metastatic events, duration of disease-free survival). Improved efficacy may also be expressed as fold improvement, such as at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold or more, using an appropriate measure (e.g. tumor size reduction, duration of tumor size stability, duration of time free from metastatic events, duration of disease-free survival).

Pharmaceutical Compositions

A composition of the present disclosure may be formulated in any suitable pharmaceutical formulation. A pharmaceutical composition of the present disclosure typically contains an active ingredient (e.g., a compound of Formula (I), or a pharmaceutically acceptable salt and/or coordination complex thereof), and one or more pharmaceutically acceptable excipients or carriers, including but not limited to: inert solid diluents and fillers, diluents, sterile aqueous solution and various organic solvents, permeation enhancers, solubilizers, and adjuvants. A composition of the present disclosure may be formulated in any suitable pharmaceutical formulation. In some embodiments, the pharmaceutical acceptable carriers or excipients are selected from water, alcohol, glycerol, chitosan, alginate, chondroitin, Vitamin E, mineral oil, and dimethyl sulfoxide (DMSO).

Pharmaceutical formulations may be provided in any suitable form, which may depend on the route of administration. In some embodiments, the pharmaceutical composition disclosed herein can be formulated in dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral administration. For example, the pharmaceutical composition can be formulated in the form of a pill, a tablet, a capsule, an inhaler, a liquid suspension, a liquid emulsion, a gel, or a powder. In some embodiments, the pharmaceutical composition can be formulated as a unit dosage in liquid, gel, semi-liquid, semi-solid, or solid form.

The amount of each compound administered will be dependent on the mammal being treated, the severity of the disorder or condition, the rate of administration, the disposition of the compound and the discretion of the prescribing physician. However, an effective dosage may be in the range of about 0.001 to about 100 mg per kg body weight per day, in single or divided doses. In some instances, dosage levels below the lower limit of the aforesaid range may be more than adequate, while in other cases still larger doses may be employed without causing any harmful side effect, e.g., by dividing such larger doses into several small doses for administration throughout the day. In some embodiments, an effective dosage may be provided in pulsed dosing (i.e., administration of the compound in consecutive days, followed by consecutive days of rest from administration).

In some embodiments, the composition is provided in one or more unit doses. For example, the composition can be administered in 1, 2, 3, 4, 5, 6, 7, 14, 30, 60, or more doses. Such amount can be administered each day, for example in individual doses administered once, twice, or three or more times a day. However, dosages stated herein on a per day basis should not be construed to require administration of the daily dose each and every day. For example, if one of the agents is provided in a suitably slow-release form, two or more daily dosage amounts can be administered at a lower frequency, e.g., as a depot injection or oral prodrug administered every second day to once a month or even longer. Most typically and conveniently for the subject, a CDK9 inhibitor can be administered once a day, for example in the morning, in the evening or during the day.

The unit doses can be administered simultaneously or sequentially. The composition can be administered for an extended treatment period. Illustratively, the treatment period can be at least about one month, for example at least about 3 months, at least about 6 months or at least about 1 year. In some cases, administration can continue for substantially the remainder of the life of the subject.

In some embodiments, the CDK9 inhibitor can be administered as part of a therapeutic regimen that comprises administering one or more second agents (e.g. 1, 2, 3, 4, 5, or more second agents), either simultaneously or sequentially with the CDK9 inhibitor. When administered sequentially, the CDK9 inhibitor may be administered before or after the one or more second agents. When administered simultaneously, the CDK9 inhibitor and the one or more second agents may be administered by the same route (e.g. injections to the same location; tablets taken orally at the same time), by a different route (e.g. a tablet taken orally while receiving an intravenous infusion), or as part of the same combination (e.g. a solution comprising a CDK9 inhibitor and one or more second agents).

A combination treatment according to the invention may be effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. The exact dosage will depend upon the agent selected, the route of administration, the form in which the compound is administered, the subject to be treated, the body weight of the subject to be treated, and the preference and experience of the attending physician.

Pharmaceutical Composition for Oral Administration

In some embodiments, the disclosure provides a pharmaceutical composition for oral administration containing at least one compound of the present disclosure and a pharmaceutical excipient suitable for oral administration. The composition may be in the form of a solid, liquid, gel, semi-liquid, or semi-solid. In some embodiments, the composition further comprises a second agent.

In some embodiments, the invention provides a solid pharmaceutical composition for oral administration containing: (i) a CDK9 inhibitor; and (ii) a pharmaceutical excipient suitable for oral administration. In some embodiments, the composition further contains: (iii) a third agent or even a fourth agent. In some embodiments, each compound or agent is present in a therapeutically effective amount. In other embodiments, one or more compounds or agents is present in a sub-therapeutic amount, and the compounds or agents act synergistically to provide a therapeutically effective pharmaceutical composition.

Pharmaceutical compositions of the disclosure suitable for oral administration can be presented as discrete dosage forms, such as hard or soft capsules, cachets, troches, lozenges, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, or dispersible powders or granules, or syrups or elixirs. Such dosage forms can be prepared by any of the methods of pharmacy, which typically include the step of bringing the active ingredient(s) into association with the carrier. In general, the composition are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient(s) in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This disclosure further encompasses anhydrous pharmaceutical composition and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the composition for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical composition and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical composition and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the composition of the disclosure to provide tablets that disintegrate when exposed to an aqueous environment. Too much of a disintegrant may produce tablets which may disintegrate in the bottle. Too little of a disintegrant may be insufficient for disintegration to occur and may alter the rate and extent of release of the active ingredient(s) from the dosage form. A sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical composition and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical composition and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical composition and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group of glycerides, vegetable oils, hydrogenated vegetable oils, fatty acids, and sterols; polyoxyethylene sterols, derivatives, and analogues thereof; polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of the group of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for composition for non-oral use, e.g., composition for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, 6-valerolactone and isomers thereof, 0-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. If present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

EXAMPLES

The following abbreviations are used in the examples: ATP=adenosine triphosphate, DBU=1,8-diazabicyclo[5.4.0] undec-7-ene, DCE=1,2-dichloroethane, DCM=dichloromethane, DEA=diethylamine, DHP=dihydropyran, DIPEA=N,N-diisopropylethylamine, DME=dimethoxyethane, DMF=dimethylformamide, DMSO=dimethyl sulfoxide, EtOH=ethanol, DTT=dithiothreitol, HPLC=high-performance liquid chromatography, PMB=para-methoxybenzyl, PPTS=pyridinium p-toluenesulfonate, SFC=supercritical fluid chromatography, TBME=tert-butyl methyl ether, TEA=triethylamine, TFA=trifluoroacetic acid, THF= tetrahydrofuran, THP=tetrahydropyran.

All chemicals, reagents, and solvents were purchased from commercial sources when available and used without further purification.

Example 1: Synthesis of 4-(((2'-(((1R,4R)-4-aminocyclohexyl)amino)-5'-chloro-[2,4'-bipyridin]-6-yl) amino)methyl)tetrahydro-2H-pyran-4-carbonitrile (Intermediate 1)

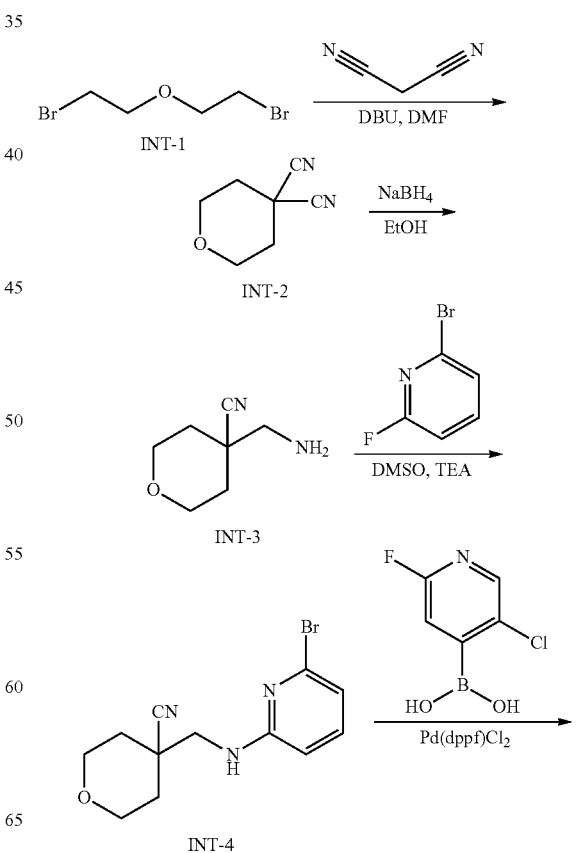

-continued

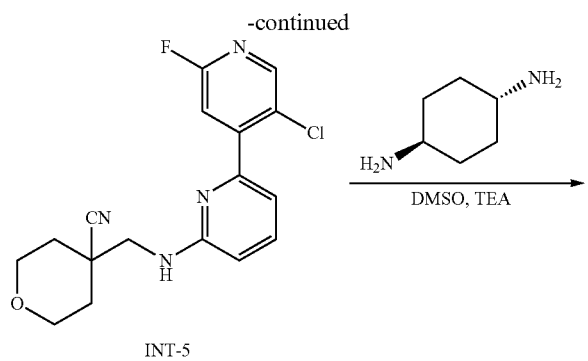

INT-5

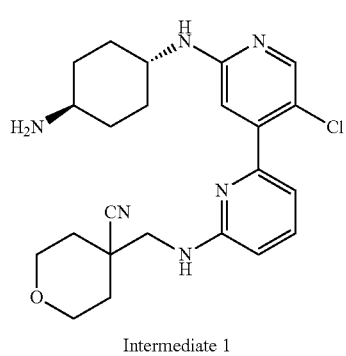

Intermediate 1

Step 1: Preparation of tetrahydro-4H-pyran-4,4-dicarbonitrile (INT-2)

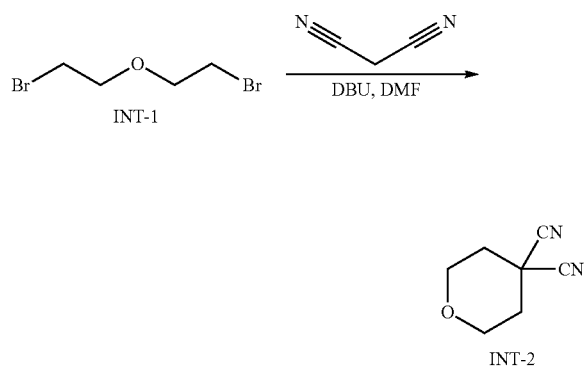

To a solution of 1-bromo-2-(2-bromoethoxy)ethane (INT-1, 20 g, 86.24 mmol) and propanedinitrile (6.27 g, 94.86 mmol) in DMF (30 mL) was added DBU (26.26 g, 172.48 mmol). The reaction mixture was stirred at 85° C. for 3 hours, cooled to ambient temperature, diluted with water (100 mL), and extracted with ethyl acetate (100 mL×3). The combined organic phase was washed with brine (50 mL), dried over anhydrous sodium sulfate, filtered, and concentrated under vacuum to provide tetrahydro-4H-pyran-4,4-dicarbonitrile (INT-2, 12.61 g, crude) as a brown solid. The crude product was used directly in the next step without further purification. $^1$H NMR (400 MHz, methanol-$d_4$) δ=3.86-3.77 (m, 4H), 2.32-2.21 (m, 4H).

Step 2: Preparation of 4-(aminomethyl)tetrahydro-2H-pyran-4-carbonitrile (INT-3)

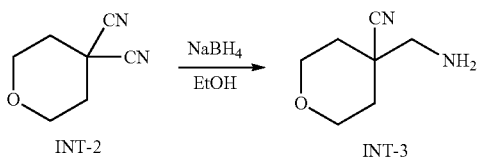

To a solution of tetrahydro-4H-pyran-4,4-dicarbonitrile (INT-2, 9.0 g, 66.10 mmol) in EtOH (270 mL) was added NaBH$_4$ (7.50 g, 198.31 mmol) in portions. The reaction mixture was stirred at 20° C. for 4 hours, quenched by water (200 mL), and extracted with ethyl acetate (200 mL×3). The combined organic phase was washed with brine (150 mL), dried over anhydrous sodium sulfate, filtered, and concentrated in vacuo to provide 4-(aminomethyl)tetrahydro-2H-pyran-4-carbonitrile (INT-3, 7.23 g, 78% yield) as a brown oil. The crude product was used directly in the next step without further purification.

Step 3: Preparation of 4-(((6-bromopyridin-2-yl)amino)methyl)tetrahydro-2H-pyran-4-carbonitrile (INT-4)

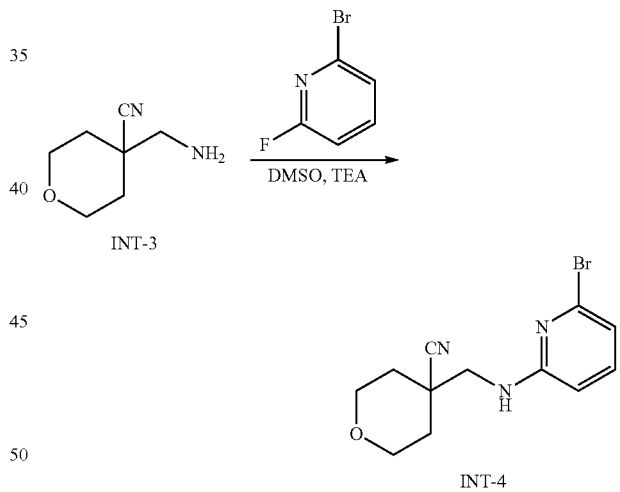

To a solution of 4-(aminomethyl)tetrahydro-2H-pyran-4-carbonitrile (INT-3, 7.23 g, 51.58 mmol) and 2-bromo-6-fluoro-pyridine (7.72 g, 43.84 mmol) in DMSO (80 mL) was added TEA (13.05 g, 128.94 mmol). The reaction mixture was stirred at 130° C. for 18 hours, cooled to ambient temperature, diluted with ethyl acetate (100 mL), washed with saturated NaHCO$_3$ solution and brine, dried over anhydrous sodium sulfate, filtered, and concentrated in vacuo. The resulting residue was purified by silica gel chromatography (Biotage 20 g Silica Flash Column; 0-25% petroleum ether in ethyl acetate @ 40 mL/min) to provide 4-(((6-bromopyridin-2-yl)amino)methyl)tetrahydro-2H-pyran-4-carbonitrile (INT-4, 3.8 g, 18.35% yield) as a light green solid. MS (ESI) m/z=296.1 [M+H]$^+$.

Step 4: Preparation of 4-(((5'-chloro-2'-fluoro-[2,4'-bipyridin]-6-yl)amino)methyl)tetrahydro-2H-pyran-4-carbonitrile (INT-5)

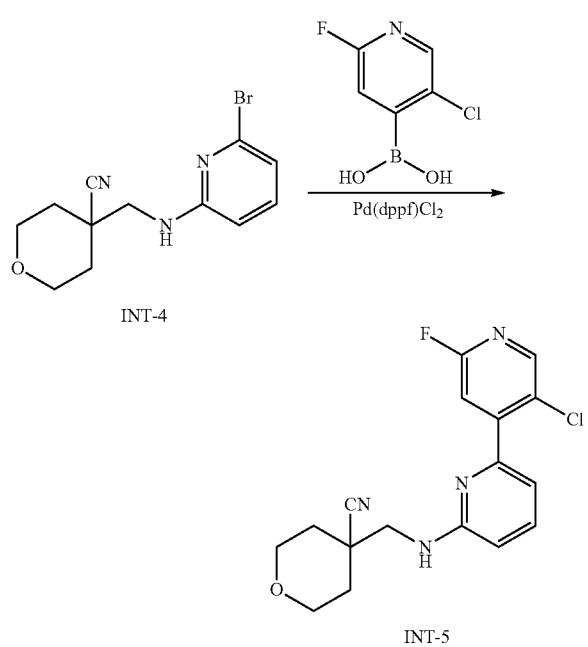

To a solution of 4-(((6-bromopyridin-2-yl)amino)methyl)tetrahydro-2H-pyran-4-carbonitrile (INT-4, 3.8 g, 12.83 mmol), (5-chloro-2-fluoro-4-pyridyl)boronic acid (3.37 g, 19.25 mmol), and Pd(dppf)Cl₂ (938.84 mg, 1.28 mmol) in DME (40 mL) was added Na₂CO₃ (2 M, 16.04 mL). The reaction mixture was sealed, stirred at 110° C. for 4 hr under N2, cooled to ambient temperature, diluted with water (40 mL), and extracted with ethyl acetate (70 mL×3). The combined organic phase was washed with brine (50 mL), dried over anhydrous sodium sulfate, filtered, and concentrated in vacuo. The resulting residue was purified by silica gel chromatography (Biotage 40 g Silica Flash Column; 20-26% petroleum ether in ethyl acetate @ 80 mL/min) to provide 4-(((5'-chloro-2'-fluoro-[2,4'-bipyridin]-6-yl)amino)methyl)tetrahydro-2H-pyran-4-carbonitrile (INT-5, 3.6 g, 73% yield) as a yellow oil. MS (ESI) m/z=347.1 [M+H]⁺.

Step 5: Preparation of 4-(((2'-(((1R,4R)-4-aminocyclohexyl)amino)-5'-chloro-[2,4'-bipyridin]-6-yl)amino)methyl)tetrahydro-2H-pyran-4-carbonitrile (Intermediate 1)

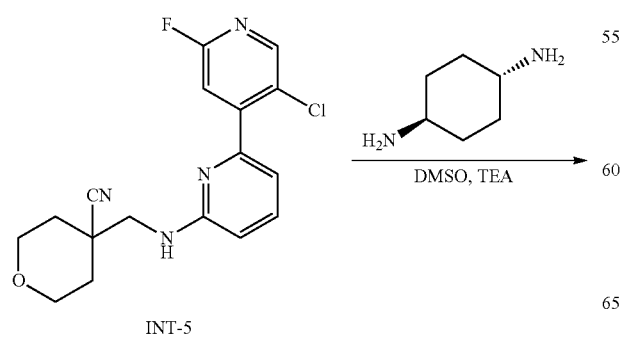

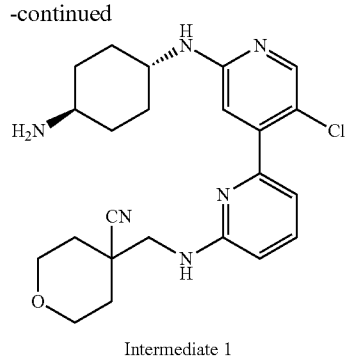

Intermediate 1

To a solution of 4-(((5'-chloro-2'-fluoro-[2,4'-bipyridin]-6-yl)amino)methyl)tetrahydro-2H-pyran-4-carbonitrile (INT-5, 4.33 g, 12.49 mmol) and cyclohexane-1,4-diamine (2.14 g, 18.73 mmol) in DMSO (50 mL) was added TEA (2.53 g, 24.97 mmol). The reaction mixture was stirred at 110° C. for 16 hours, diluted with water (40 mL), and extracted with ethyl acetate (100 mL×3). The combined organic phase was washed with brine (60 mL), dried over anhydrous sodium sulfate, filtered, and concentrated in vacuo. The resulting residue was dissolved in ethyl acetate (100 mL), added dropwise to HCl/dioxane (50 mL), filtered, and washed with ethyl acetate. The resulting solid was dissolved in water (150 mL), basified with NaHCO₃ to pH 9, and extracted with ethyl acetate (100 mL×3). The combined organic phase was washed with brine (60 mL), dried over anhydrous sodium sulfate, filtered, and concentrated in vacuo to provide 4-(((2'-(((1R,4R)-4-aminocyclohexyl)amino)-5'-chloro-[2,4'-bipyridin]-6-yl)amino)methyl)tetrahydro-2H-pyran-4-carbonitrile (Intermediate 1, 4.1 g, 61.11% yield) as a brown solid. MS (ESI) m/z=441.3 [M+H]⁺.

Example 2: Synthesis of 1-((2-(tetrahydro-2H-pyran-2-yl)-2H-tetrazol-5-yl)methoxy)propan-2-one (Intermediate 2)

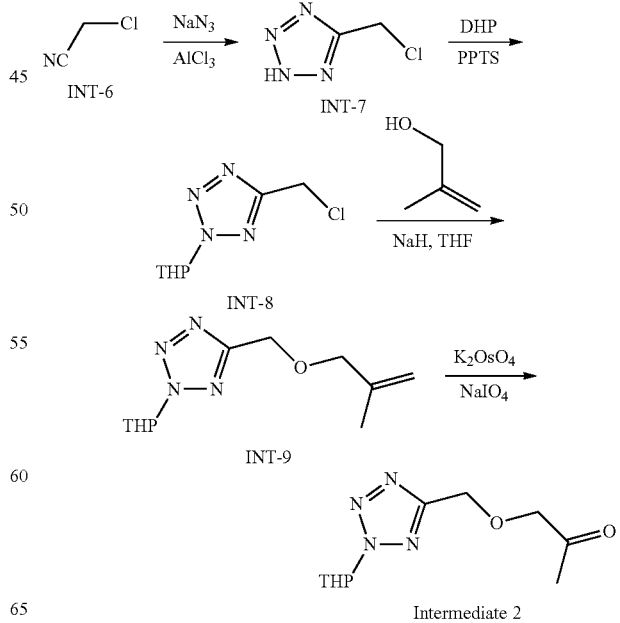

Intermediate 2

Step 1: Preparation of 5-(chloromethyl)-2H-tetrazole (INT-7)

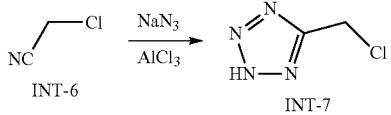

To a solution of AlCl₃ (3.67 g, 27.55 mmol) in THF (50 mL) was added NaN₃ (4.87 g, 74.97 mmol). The reaction mixture was stirred at 60° C. for 2 hours and cooled to 20° C. 2-chloroacetonitrile (INT-6, 2.0 g, 26.49 mmol) was added and the reaction mixture was heated to 70° C. and stirred for 24 hours. The reaction mixture was concentrated and the resulting residue was acidified with aq. HCl (37%) to pH 2 and extracted with EtOAc (100 mL×3). The combined organic layers were dried over Na₂SO₄, filtered, and concentrated to provide 5-(chloromethyl)-2H-tetrazole (INT-7, 3.0 g, crude) as a white solid. The crude product was used directly in the next step without further purification. ¹H NMR (400 MHz, DMSO-d₆): δ=5.08 (s, 2H).

Step 2: Preparation of 5-(chloromethyl)-2-(tetrahydro-2H-pyran-2-yl)-2H-tetrazole (INT-8)

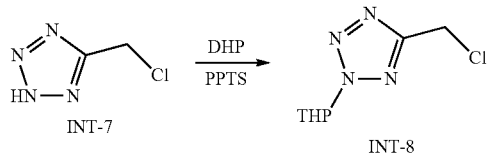

To a solution of 5-(chloromethyl)-2H-tetrazole (INT-7, 3.0 g, 25.31 mmol) and DHP (4.26 g, 50.62 mmol) in acetone (100 mL) was added PPTS (203.54 mg, 0.809 mmol). The reaction mixture was stirred at 45° C. for 3 hours and concentrated. The residue was purified by silica gel chromatography (Biotage 20 g Silica Flash Column; 0-10% petroleum ether in ethyl acetate @ 40 mL/min) to provide 5-(chloromethyl)-2-(tetrahydro-2H-pyran-2-yl)-2H-tetrazole (INT-8, 4.6 g, 89% yield) as a colorless oil. ¹H NMR (400 MHz, DMSO-d₆): δ=6.18 (dd, J=8.0, 2.8 Hz, 1H), 5.06 (s, 2H), 3.81-3.76 (m, 2H), 2.51-2.26 (m, 1H), 2.25-2.13 (m, 1H), 2.12-1.98 (m, 1H), 1.64-1.62 (m, 1H), 1.61-1.601 (m, 2H).

Step 3: Preparation of 5-(((2-methylallyl)oxy)methyl)-2-(tetrahydro-2H-pyran-2-yl)-2H-tetrazole (INT-9)

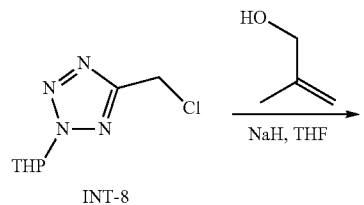

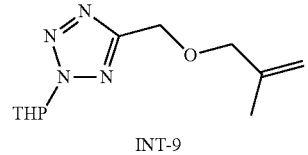

To a solution of 2-methylprop-2-en-1-ol (1.07 g, 14.80 mmol, 1.25 mL) in DMF (2 mL) was added NaH (789 mg, 19.74 mmol, 60% purity) and the reaction mixture was stirred at 0° C. for 0.5 hours. 5-(chloromethyl)-2-(tetrahydro-2H-pyran-2-yl)-2H-tetrazole (INT-8, 2.0 g, 9.87 mmol) was added and the reaction mixture was stirred at 25° C. for 2 hours, quenched with brine (50 mL), and extracted with EtOAc (50 mL×3). The combined organic layers were washed with brine (50 mL×7), dried over Na₂SO₄, filtered, and concentrated to provide 5-(((2-methylallyl)oxy)methyl)-2-(tetrahydro-2H-pyran-2-yl)-2H-tetrazole (INT-9, 2.3 g, 97% yield) as white solid. The crude product was used directly in the next step without further purification. ¹H NMR (400 MHz, DMSO-d₆): δ=6.15 (dd, J=8.0, 3.2 Hz, 1H), 4.95 (s, 1H), 4.89 (s, 1H), 4.71 (s, 2H), 3.95 (s, 2H), 3.82-3.75 (m, 2H), 2.26-2.25 (m, 1H), 2.25-2.24 (m, 1H), 2.16-2.10 (m, 1H), 1.67-1.66 (m, 1H), 1.64 (s, 3H), 1.62-1.58 (m, 2H).

Step 4: Preparation of 1-((2-(tetrahydro-2H-pyran-2-yl)-2H-tetrazol-5-yl)methoxy)propan-2-one (Intermediate 2)

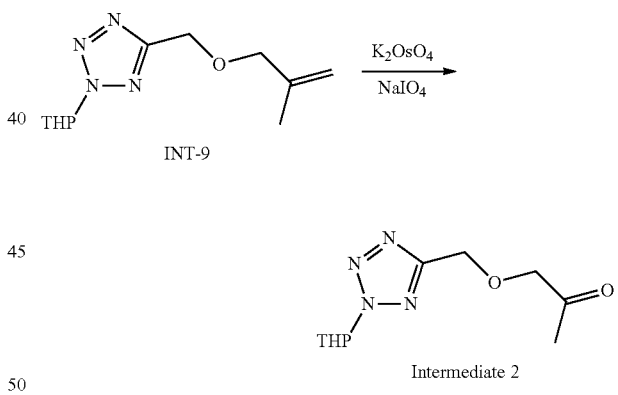

To a solution of 5-(((2-methylallyl)oxy)methyl)-2-(tetrahydro-2H-pyran-2-yl)-2H-tetrazole (INT-9, 1.0 g, 4.20 mmol) and K₂OsO₄·2H₂O (15.46 mg, 0.042 mmol) in H₂O (3.6 mL) and THF (4 mL) was added dropwise a solution of NaIO₄ (2.06 g, 9.65 mmol) in H₂O (8 mL). The reaction mixture was stirred at 25° C. for 12 hours, filtered, and extracted with EtOAc (30 mL×5). The combined organic layers were dried over Na₂SO₄, filtered, and concentrated to provide 1-((2-(tetrahydro-2H-pyran-2-yl)-2H-tetrazol-5-yl)methoxy)propan-2-one (Intermediate 2, 800 mg, 79% yield) as a yellow oil. ¹H NMR (400 MHz, DMSO-d₆): δ=6.17 (dd, J=8.0, 3.6 Hz, 1H), 5.06 (s, 2H), 3.84-3.73 (m, 3H), 2.24-2.15 (m, 1H), 2.15-2.13 (m, 1H), 1.99-1.75 (m, 1H), 1.74-1.72 (m, 4H), 1.64-1.59 (m, 3H). MS (ESI) m/z=263.3 [M+Na]⁺.

Example 3: Synthesis of ethyl 2-(2-oxopropoxy)acetate (Intermediate 3)

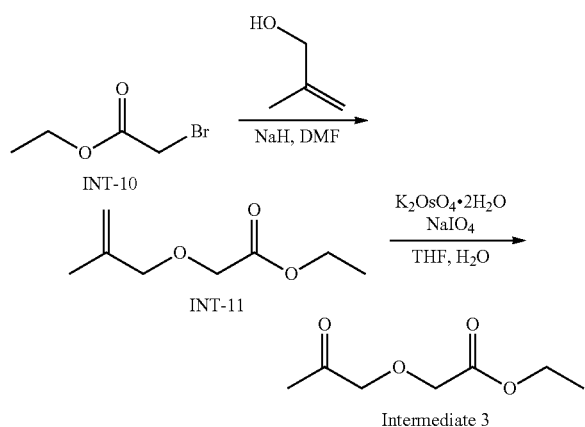

Step 1: Preparation of ethyl 2-((2-methylallyl)oxy)acetate (INT-11)

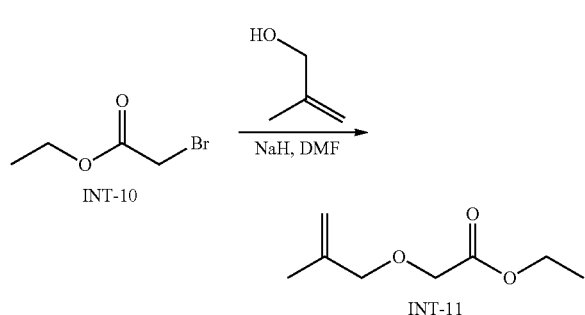

To a solution of 2-methylprop-2-en-1-ol (1.0 g, 13.87 mmol) in DMF (12 mL) was added NaH (610 mg, 15.26 mmol). The reaction mixture was stirred at 0° C. for 10 min, and ethyl 2-bromoacetate (INT-10, 2.32 g, 13.87 mmol) was added. The reaction mixture was stirred at 0° C. for 1 hour, quenched with water (5 mL) at 0° C., and extracted with ethyl acetate (20 mL×3). The combined organic phase was washed with brine (20 mL), dried over anhydrous sodium sulfate, filtered, and concentrated in vacuo. The resulting residue was purified by flash column chromatography on silica gel (0-20% ethyl acetate in petroleum ether) to provide ethyl 2-((2-methylallyl)oxy)acetate (INT-11, 780 mg, 36% yield) as a colorless liquid. $^1$H NMR (400 MHz, DMSO-$d_6$) δ=4.89-4.86 (m, 1H), 4.57-4.45 (m, 1H), 4.11 (s, 2H), 4.09-4.06 (m, 2H), 3.92-3.90 (m, 2H), 1.68-1.67 (m, 3H), 1.23-1.16 (m, 3H). MS (ESI) m/z=159.3 [M+H]$^+$.

Step 2: Preparation of ethyl 2-(2-oxopropoxy)acetate (Intermediate 3)

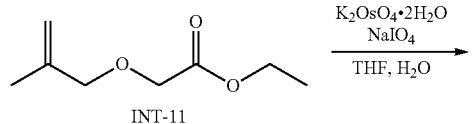

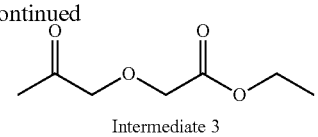

To a solution of ethyl 2-((2-methylallyl)oxy)acetate (INT-11, 1.5 g, 9.48 mmol) in THF (8 mL) were added K$_2$OsO$_4$·2H$_2$O (34.94 mg, 0.1 mmol) in a mixture of H$_2$O (4 mL) and THF (9 mL) and NaIO$_4$ (4.66 g, 21.81 mmol) in H$_2$O (12 mL). The reaction mixture was stirred at 20° C. for 11 hours and concentrated in vacuo. The resulting residue was purified by silica gel chromatography (Biotage 20 g Silica Flash Column; 0-10% petroleum ether in ethyl acetate @ 40 mL/min) to provide ethyl 2-(2-oxopropoxy)acetate (Intermediate 3, 850 mg, 56% yield) as a colorless liquid. $^1$H NMR (400 MHz, CDCl$_3$) δ=4.24-4.14 (m, 6H), 2.17 (s, 3H), 1.27 (t, J=7.2 Hz, 3H).

Example 4: Synthesis of 1-(1-(4-methoxybenzyl)-1H-tetrazol-5-yl)propan-2-one (Intermediate 4)

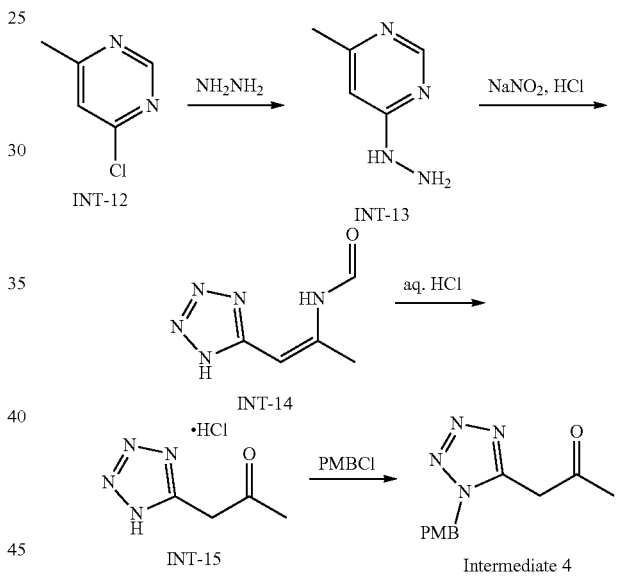

Step 1: Preparation of 4-hydrazine-6-methylpyrimidine (INT-13)

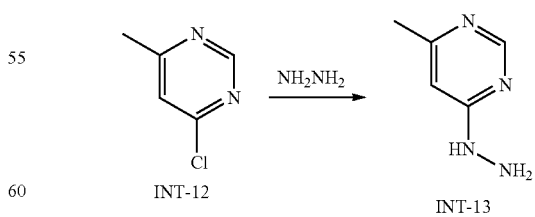

To a solution of 4-chloro-6-methyl-pyrimidine (INT-12, 2.5 g, 19.45 mmol) in dioxane (30 mL) was added NH$_2$NH$_2$·H$_2$O (1.67 g, 33.45 mmol) and K$_2$CO$_3$ (2.74 g, 19.84 mmol). The reaction mixture was stirred at 100° C. for 6 hr, diluted with H$_2$O (20 mL), and extracted with EtOAc (50 mL×3). The combined organic layers were washed with brine (50 mL), dried over Na₂SO₄, filtered, and concentrated in vacuo to provide 4-hydrazine-6-methylpyrimidine (INT-13, 2 g, 16.11 mmol, 82.85% yield) as a yellow solid. The crude product was used directly in the next step without further purification.

Step 2: Preparation of (Z)—N-(1-(1H-tetrazol-5-yl)prop-1-en-2-yl)formamide (INT-14)

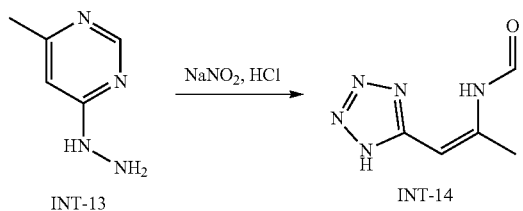

To a solution of 4-hydrazine-6-methylpyrimidine (INT-13, 0.9 g, 7.25 mmol) in H₂O (2 mL) were added HCl (2 M, 3.62 mL) and NaNO₂ (500.19 mg, 7.25 mmol). The reaction mixture was stirred at 0° C. for 8 hr and filtered, and the filter cake was concentrated under reduced pressure to provide (Z)—N-(1-(1H-tetrazol-5-yl)prop-1-en-2-yl)formamide (INT-14, 0.6 g, 3.92 mmol, 54.04% yield) as a brown solid. The crude product was used directly in the next step without further purification. MS (ESI) m/z=296.1 [M+H]⁺.

Step 3: Preparation of 5-(2-oxopropyl)-1H-tetrazol-1-ium chloride (INT-15)

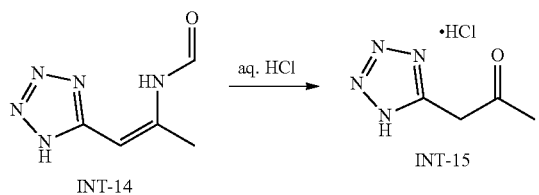

To a solution of (Z)—N-(1-(1H-tetrazol-5-yl)prop-1-en-2-yl)formamide (INT-14, 0.8 g, 5.22 mmol) in H₂O (4 mL) was added HCl (1 mL). The reaction mixture was stirred at 80° C. for 12 hr and concentrated under reduced pressure to provide 5-(2-oxopropyl)-1H-tetrazol-1-ium chloride (INT-15, 0.7 g, 4.31 mmol, 82.42% yield) as a yellow solid. The crude product was used directly in the next step without further purification.

Step 5: Preparation of 1-(1-(4-methoxybenzyl)-1H-tetrazol-5-yl)propan-2-one (Intermediate 4)

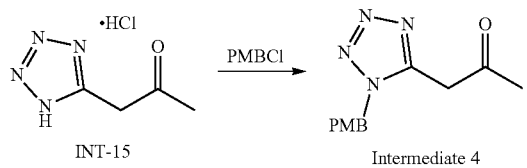

To a solution of 5-(2-oxopropyl)-1H-tetrazol-1-ium chloride (INT-15, 600 mg, 4.76 mmol, 1 eq) and 1-(chloromethyl)-4-methoxy-benzene (1.12 g, 7.14 mmol, 971.83 uL, 1.5 eq) in THF (15 mL) was added DIPEA (3.07 g, 23.79 mmol, 4.14 mL, 5 eq). The reaction mixture was stirred at 45° C. for 16 hr, diluted with water (20 mL), and extracted with DCM (30 mL×3). The combined organic layer was washed with brine (40 mL), dried over Na₂SO₄, filtered, and concentrated. The resulting residue was purified by flash silica gel chromatography (ISCO®; 20 g SepaFlash® Silica Flash Column, 0-6% methanol/dichloromethane @ 35 mL/min) to provide 1-(1-(4-methoxybenzyl)-1H-tetrazol-5-yl)propan-2-one (Intermediate 4, 440 mg, 1.14 mmol, 24.04% yield, 64% purity) as s light yellow oil. MS (ESI) m/z=247.2 [M+H]⁺.

Example 5: Synthesis of 4-(((2'-(((1R,4R)-4-(((R)-1-((2H-tetrazol-5-yl)methoxy)propan-2-yl)amino)cyclohexyl)amino)-5'-chloro-[2,4'-bipyridin]-6-yl)amino)methyl)tetrahydro-2H-pyran-4-carbonitrile (Compound 2) and 4-(((2'-(((1S,4R)-4-(((S)-1-((2H-tetrazol-5-yl)methoxy)propan-2-yl)amino)cyclohexyl)amino)-5'-chloro-[2,4'-bipyridin]-6-yl)amino)methyl)tetrahydro-2H-pyran-4-carbonitrile (Compound 3)

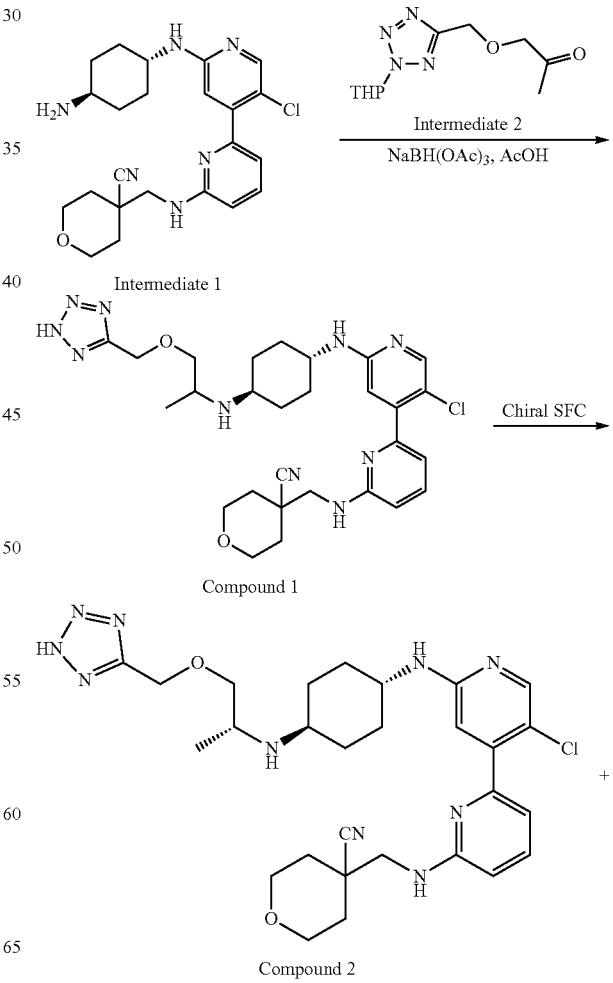

-continued

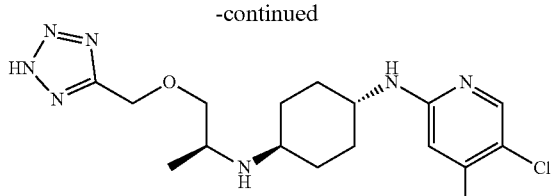

Compound 3

To a solution of 4-(((2'-(((1R,4R)-4-aminocyclohexyl)amino)-5'-chloro-[2,4'-bipyridin]-6-yl)amino)methyl)tetrahydro-2H-pyran-4-carbonitrile (Intermediate 1, 500 mg, 1.13 mmol) and 1-((2-(tetrahydro-2H-pyran-2-yl)-2H-tetrazol-5-yl)methoxy)propan-2-one (Intermediate 2, 354 mg, 1.47 mmol) in AcOH (204 mg, 3.40 mmol) and DCE (15 mL) was added NaBH(OAc)$_3$ (336 mg, 1.59 mmol) at 0° C. The mixture was stirred at 25° C. for 12 hours, quenched with MeOH (5 mL), and concentrated. The resulting residue was purified by preparative HPLC (Phenomenex Luna C18 75×30 mm (3 μm particle size); 0-35% acetonitrile/water (0.225% FA); 35 min; 25 mL/min) to provide 4-(((2'-((4-((1-((2H-tetrazol-5-yl)methoxy)propan-2-yl)amino)cyclohexyl)amino)-5'-chloro-[2,4'-bipyridin]-6-yl)amino)methyl)tetrahydro-2H-pyran-4-carbonitrile (Compound 1, 140 mg, 21% yield) as a white solid. MS (ESI) m/z=581.5 [M+H]$^+$.

4-(((2'-((4-((1-((2H-tetrazol-5-yl)methoxy)propan-2-yl)amino)cyclohexyl)amino)-5'-chloro-[2,4'-bipyridin]-6-yl)amino)methyl)tetrahydro-2H-pyran-4-carbonitrile (Compound 1) was separated by chiral SFC (Chiralpak OD-3 100×4.6 mm (3 μm particle size); 5-40% EtOH (0.05% DEA)/CO$_2$; 8 min; 2.8 mL/min) to provide 4-(((2'-(((1R,4R)-4-(((R)-1-((2H-tetrazol-5-yl)methoxy)propan-2-yl)amino)cyclohexyl)amino)-5'-chloro-[2,4'-bipyridin]-6-yl)amino)methyl)tetrahydro-2H-pyran-4-carbonitrile (Compound 2, 35 mg, 35% yield, 97% purity, >99% ee) and 4-(((2'-(((1S,4R)-4-(((S)-1-((2H-tetrazol-5-yl)methoxy)propan-2-yl)amino)cyclohexyl)amino)-5'-chloro-[2,4'-bipyridin]-6-yl)amino)methyl)tetrahydro-2H-pyran-4-carbonitrile (Compound 3, 35 mg, 35% yield, 99% purity, 97% ee).

Compound 2: $^1$H NMR (400 MHz, CDCl$_3$): δ=8.04 (s, 1H), 7.48 (t, J=7.6 Hz, 1H), 6.91 (d, J=7.6 Hz, 1H), 6.54 (s, 1H), 6.49 (d, J=8.0 Hz, 2H), 5.09-5.05 (m, 1H), 4.87-4.83 (m, 2H), 4.45 (d, J=8.0 Hz, 1H), 3.97-3.95 (m, 2H), 3.87-3.85 (m, 1H), 3.74-3.63 (m, 6H), 3.57-3.55 (m, 2H), 3.22-3.21 (m, 1H). 2.41-2.40 (m, 2H), 2.30-2.10 (m, 2H), 1.91-1.77 (m, 4H), 1.76-1.70 (m, 2H), 1.50-1.48 (m, 3H), 1.29-1.26 (m, 2H). MS (ESI) m/z=581.5 [M+H]$^+$.

Compound 3: $^1$H NMR (400 MHz, CDCl$_3$): δ=8.05 (s, 1H), 7.48 (t, J=7.6 Hz, 1H), 6.91 (d, J=7.6 Hz, 1H), 6.54 (s, 1H), 6.49 (d, J=8.0 Hz, 2H), 5.08-5.05 (m, 1H), 4.89-4.83 (m, 2H), 4.45 (d, J=8.0 Hz, 1H), 3.97-3.95 (m, 2H), 3.87-3.85 (m, 1H), 3.74-3.63 (m, 6H), 3.57-3.55 (m, 2H), 3.22-3.21 (m, 1H). 2.41-2.40 (m, 2H), 2.30-2.10 (m, 2H), 1.91-1.77 (m, 4H), 1.76-1.70 (m, 2H), 1.50-1.48 (m, 3H), 1.29-1.26 (m, 2H). MS (ESI) m/z=581.5 [M+H]$^+$.

Example 6: Synthesis of ethyl 2-((R)-2-(((1R,4R)-4-((5'-chloro-6-(((4-cyanotetrahydro-2H-pyran-4-yl)methyl)amino)-[2,4]-bipyridin]-2'-yl)amino)cyclohexyl)amino)propoxy)acetate (Compound 5) and ethyl 2-((S)-2-(((1R,4S)-4-((5'-chloro-6-(((4-cyanotetrahydro-2H-pyran-4-yl)methyl)amino)-[2,4]-bipyridin]-2'-yl)amino)cyclohexyl)amino)propoxy)acetate (Compound 6)

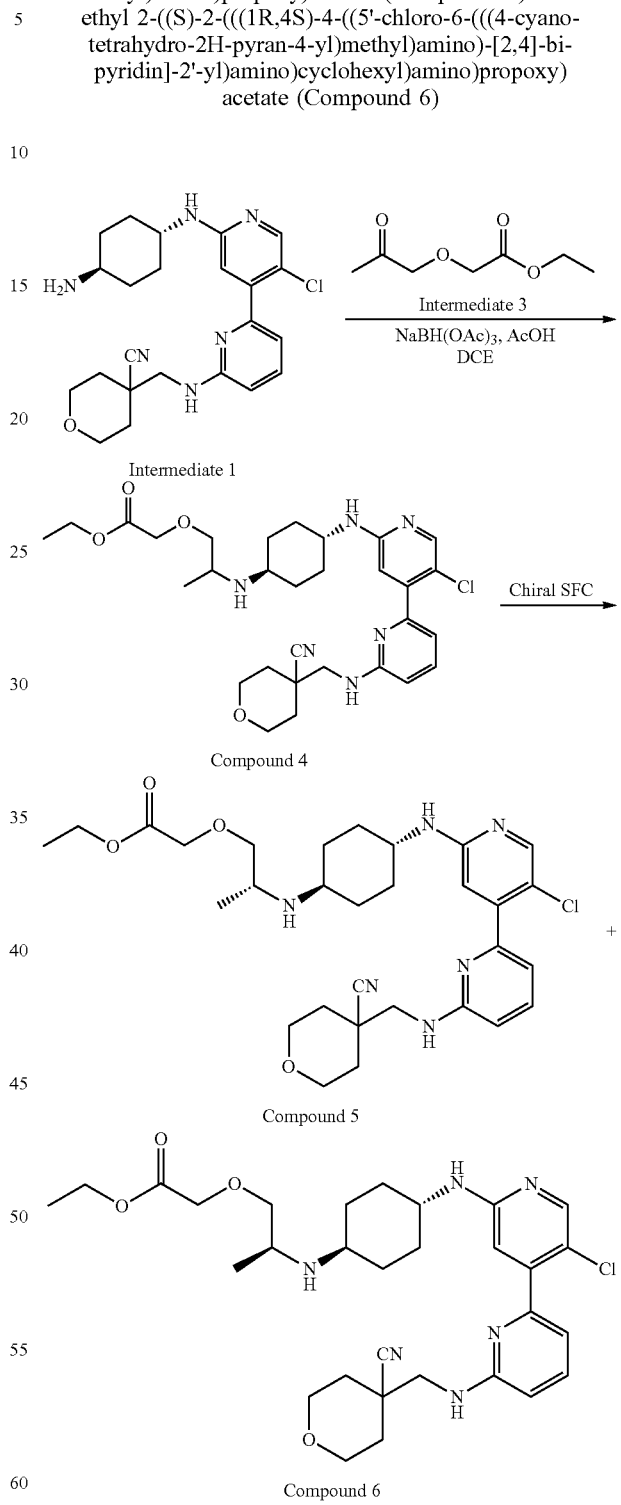

To a solution of 4-(((2'-(((1R,4R)-4-aminocyclohexyl)amino)-5'-chloro-[2,4'-bipyridin]-6-yl)amino)methyl)tetrahydro-2H-pyran-4-carbonitrile (Intermediate 1, 200 mg, 0.45 mmol), ethyl 2-(2-oxopropoxy)acetate (Intermediate 3, 80 mg, 0.5 mmol), and AcOH (82 mg, 1.36 mmol) in DCE (2 mL) was added NaBH(OAc)₃ (134 mg, 0.63 mmol) at 0° C. The reaction mixture was stirred at 20° C. for 20 hours, quenched with water (10 mL) at 0° C., and extracted with ethyl acetate (30 mL×3). The combined organic phase was washed with brine (30 mL), dried over anhydrous sodium sulfate, filtered, and concentrated in vacuo. The resulting residue was purified by preparative HPLC (Phenomenex Luna C18 100×30 mm (5 μm particle size); 10-40% acetonitrile/water (0.225% FA); 10 min; 25 mL/min) to provide ethyl 2-(2-((4-((5'-chloro-6-(((4-cyanotetrahydro-2H-pyran-4-yl)methyl)amino)-[2,4'-bipyridin]-2'-yl)amino)cyclohexyl)amino)propoxy)acetate (Compound 4) as a white solid.

Ethyl 2-(2-((4-((5'-chloro-6-(((4-cyanotetrahydro-2H-pyran-4-yl)methyl)amino)-[2,4'-bipyridin]-2'-yl)amino)cyclohexyl)amino)propoxy)acetate (Compound 4) was further separated by chiral SFC (Chiralpak AD-3 100×4.6 mm (3 μm particle size); 5-40% EtOH (0.05% DEA)/CO₂; 8 min; 2.8 mL/min) to afford ethyl 2-((R)-2-(((1R,4R)-4-((5'-chloro-6-(((4-cyanotetrahydro-2H-pyran-4-yl)methyl)amino)-[2,4]-bipyridin]-2'-yl)amino)cyclohexyl)amino)propoxy)acetate (Compound 5, 18.8 mg, 7% yield, >99% purity, >99% ee) and ethyl 2-((S)-2-(((1R,4S)-4-((5'-chloro-6-(((4-cyanotetrahydro-2H-pyran-4-yl)methyl)amino)-[2,4]-bipyridin]-2'-yl)amino)cyclohexyl)amino)propoxy)acetate (Compound 6, 21.8 mg, 8% yield, 99% purity, 90% ee) as white solids.

Compound 5: 1H NMR (400 MHz, CDCl₃) δ=8.11 (s, 1H), 7.53 (t, J=8.0 Hz, 1H), 6.97 (d, J=8.0 Hz, 1H), 6.55 (s, 1H), 6.51 (d, J=8.0 Hz, 1H), 4.78 (t, J=4.0 Hz, 1H), 4.43 (d, J=8.0 Hz, 1H), 4.30-4.17 (m, 2H), 4.11 (s, 2H), 4.05-3.97 (m, 2H), 3.81-3.76 (m, 2H), 3.74-3.66 (m, 2H), 3.61-3.49 (m, 2H), 3.47-3.34 (m, 1H), 3.19-3.01 (m, 1H), 2.82-2.47 (m, 1H), 2.22-2.13 (m, 2H), 2.11-2.00 (m, 2H), 1.97-1.90 (m, 2H), 1.80-1.72 (m, 2H), 1.32-1.20 (m, 7H), 1.15-1.06 (m, 3H). MS (ESI) m/z=585.4 [M+H]⁺.

Compound 6: ¹H NMR (400 MHz, CDCl₃) δ=8.44 (s, 1H), 8.10 (s, 1H), 7.52 (t, J=8.0 Hz, 1H), 6.97 (d, J=4.0 Hz, 1H), 6.57 (s, 1H), 6.52 (d, J=8.0 Hz, 1H), 4.82 (t, J=8.0 Hz, 1H), 4.28-4.20 (m, 2H), 4.17-4.11 (m, 2H), 4.03-3.97 (m, 2H), 3.81-3.64 (m, 7H), 3.31-3.27 (m, 1H), 3.02-2.92 (m, 1H), 2.28-2.11 (m, 4H), 1.97-1.89 (m, 2H), 1.81-1.72 (m, 2H), 1.67-1.46 (m, 2H), 1.33-1.25 (m, 8H). MS (ESI) m/z=585.4 [M+H]⁺.

Example 7: Synthesis of 2-((R)-2-(((1R,4R)-4-((5'-chloro-6-(((4-cyanotetrahydro-2H-pyran-4-yl)methyl)amino)-[2,4'-bipyridin]-2'-yl)amino)cyclohexyl)amino)propoxy)acetic acid (Compound 8) and 2-((S)-2-(((1R,4S)-4-((5'-chloro-6-(((4-cyanotetrahydro-2H-pyran-4-yl)methyl)amino)-[2,4'-bipyridin]-2'-yl)amino)cyclohexyl)amino)propoxy)acetic acid (Compound 9)

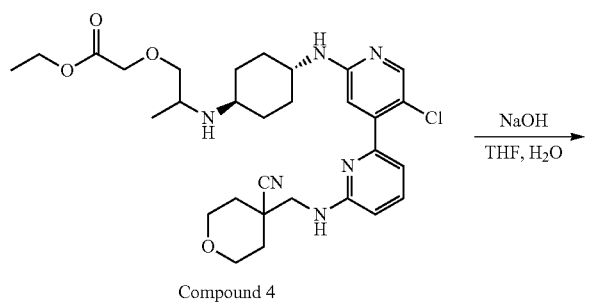

Compound 4

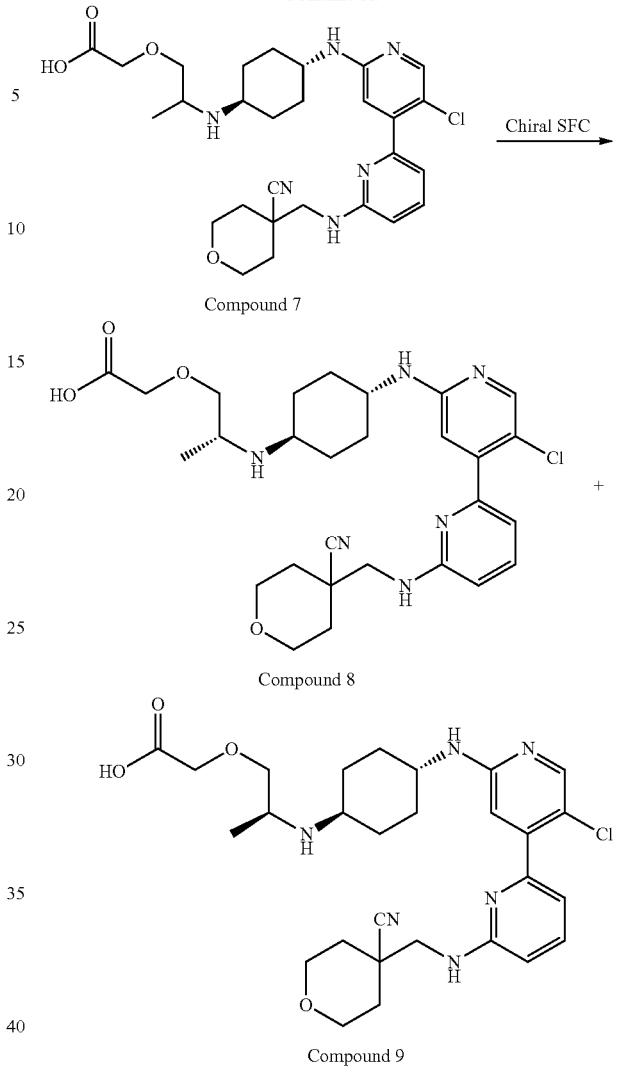

Compound 7

Compound 8

Compound 9

To a solution of ethyl 2-(2-((4-((5'-chloro-6-(((4-cyanotetrahydro-2H-pyran-4-yl)methyl)amino)-[2,4'-bipyridin]-2'-yl)amino)cyclohexyl)amino)propoxy)acetate (Compound 4, 210 mg, 0.35 mmol) in THF (3 mL) and H₂O (1 mL) was added NaOH (143 mg, 3.59 mmol). The reaction mixture was stirred at 25° C. for 2 hours. The aqueous phase was acidified with aqueous HCl (1 N) to pH 4 and concentrated in vacuo. The resulting residue was dissolved in DMF, filtered, concentrated in vacuo, and purified by preparative HPLC (Phenomenex Luna C18 100×40 mm (3 μm particle size); 15-45% acetonitrile/water (0.225% FA); 10 min; 25 mL/min) to provide 2-(2-((4-((5'-chloro-6-(((4-cyanotetrahydro-2H-pyran-4-yl)methyl)amino)-[2,4'-bipyridin]-2'-yl)amino)cyclohexyl)amino)propoxy)acetic acid (Compound 7).

2-(2-((4-((5'-chloro-6-(((4-cyanotetrahydro-2H-pyran-4-yl)methyl)amino)-[2,4'-bipyridin]-2'-yl)amino)cyclohexyl)amino)propoxy)acetic acid (Compound 7) was further purified by chiral SFC (Chiralpak AD-3 100×4.6 mm (3 μm particle size); 5-40% EtOH (0.05% DEA)/CO₂; 8 min; 2.8 mL/min) to provide 2-((R)-2-(((1R,4R)-4-((5'-chloro-6-(((4-cyanotetrahydro-2H-pyran-4-yl)methyl)amino)-[2,4'-bipyridin]-2'-yl)amino)cyclohexyl)amino)propoxy)acetic acid (Compound 8, 32.5 mg, 16% yield, 98% purity, >99% ee)

and 2-((S)-2-((((1R,4S)-4-((5'-chloro-6-(((4-cyanotetrahydro-2H-pyran-4-yl)methyl)amino)-[2,4'-bipyridin]-2'-yl)amino)cyclohexyl)amino)propoxy)acetic acid (Compound 9, 34.8 mg, 17% yield, 99% purity, >99% ee) as yellow solids.

Compound 8: $^1$H NMR (400 MHz, DMSO-$d_6$) δ=8.16 (s, 1H), 8.03 (s, 1H), 7.54-7.45 (m, 1H), 7.12-7.05 (m, 1H), 6.79-6.70 (m, 2H), 6.68-6.60 (m, 2H), 3.92-3.86 (m, 2H), 3.71-3.62 (m, 7H), 3.49-3.46 (m, 2H), 3.04-2.92 (m, 2H), 2.13-2.00 (m, 4H), 1.87-1.80 (m, 2H), 1.71-1.62 (m, 2H), 1.54-1.44 (m, 2H), 1.30-1.21 (m, 2H), 1.17-1.11 (m, 3H). MS (ESI) m/z=557.3 [M+H]$^+$.

Compound 9: 1H NMR (400 MHz, DMSO-$d_6$) δ=8.17 (s, 1H), 8.03 (s, 1H), 7.54-7.45 (m, 1H), 7.13-7.04 (m, 1H), 6.78-6.71 (m, 2H), 6.69-6.64 (m, 1H), 6.63-6.60 (m, 1H), 3.92-3.86 (m, 2H), 3.70-3.61 (m, 7H), 3.50-3.46 (m, 2H), 3.04-2.90 (m, 2H), 2.14-2.02 (m, 4H), 1.88-1.80 (m, 2H), 1.73-1.62 (m, 2H), 1.54-1.43 (m, 2H), 1.33-1.21 (m, 2H), 1.18-1.10 (m, 3H). MS (ESI) m/z=557.3 [M+H]$^+$.

Example 8: Synthesis of 4-(((2'-(((1R,4R)-4-(((R)-1-(1H-tetrazol-5-yl)propan-2-yl)amino)cyclohexyl)amino)-5'-chloro-[2,4'-bipyridin]-6-yl)amino)methyl)tetrahydro-2H-pyran-4-carbonitrile (Compound 12) and 4-(((2'-(((1S,4R)-4-(((S)-1-(1H-tetrazol-5-yl)propan-2-yl)amino)cyclohexyl)amino)-5'-chloro-[2,4'-bipyridin]-6-yl)amino)methyl)tetrahydro-2H-pyran-4-carbonitrile (Compound 13)

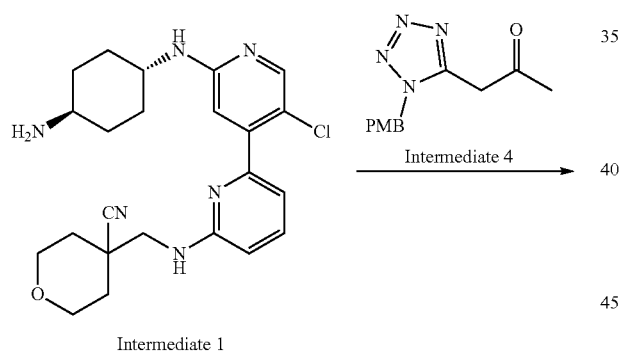

Intermediate 1

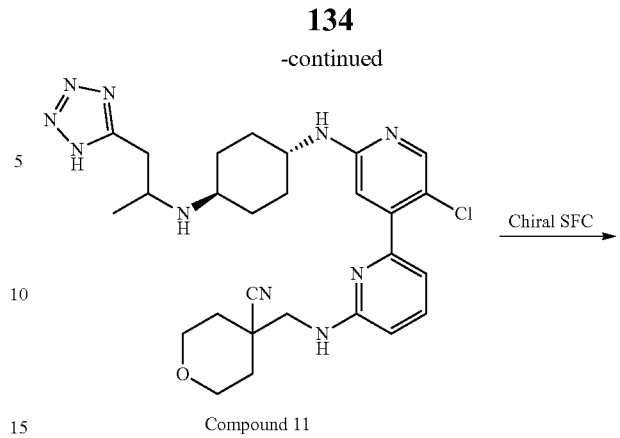

Compound 11

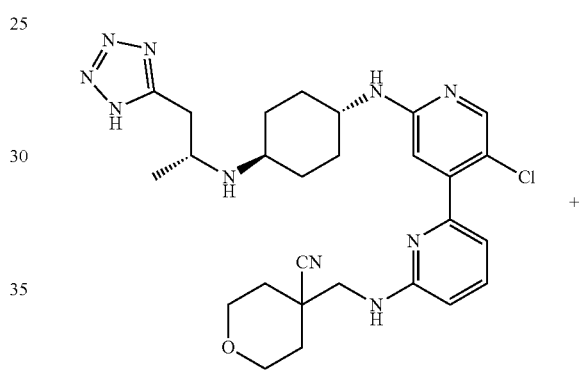

Compound 12

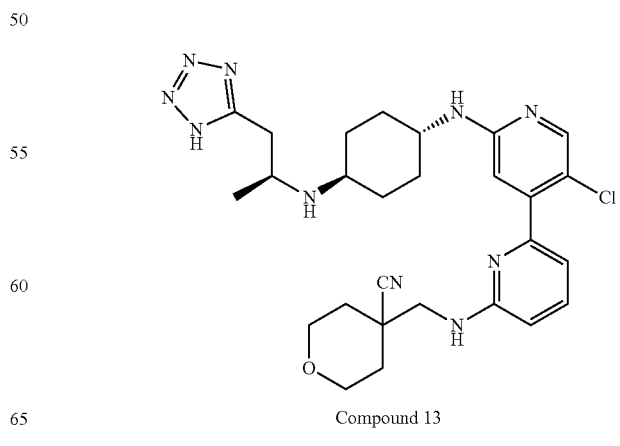

Compound 10

Compound 13

Step 1: Preparation of 4-(((5'-chloro-2'-(((1R,4R)-4-((1-(1-(4-methoxybenzyl)-1H-tetrazol-5-yl)propan-2-yl)amino)cyclohexyl)amino)-[2,4'-bipyridin]-6-yl)amino)methyl)tetrahydro-2H-pyran-4-carbonitrile (Compound 10)

Step 2: Preparation of 4-(((2'-(((1R,4R)-4-(((R)-1-(1H-tetrazol-5-yl)propan-2-yl)amino)cyclohexyl)amino)-5'-chloro-[2,4'-bipyridin]-6-yl)amino)methyl)tetrahydro-2H-pyran-4-carbonitrile (Compound 12) and 4-(((2'-(((1S,4R)-4-(((S)-1-(1H-tetrazol-5-yl)propan-2-yl)amino)cyclohexyl)amino)-5'-chloro-[2,4'-bipyridin]-6-yl)amino)methyl)tetrahydro-2H-pyran-4-carbonitrile (Compound 13)

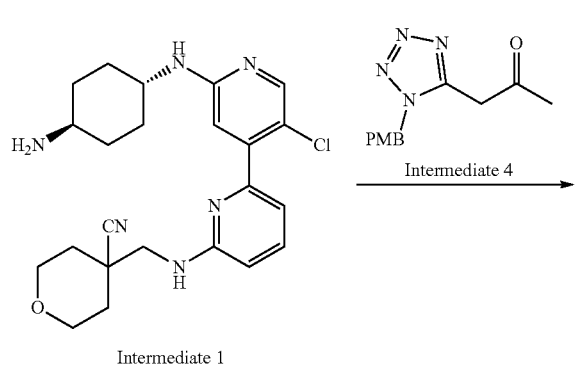

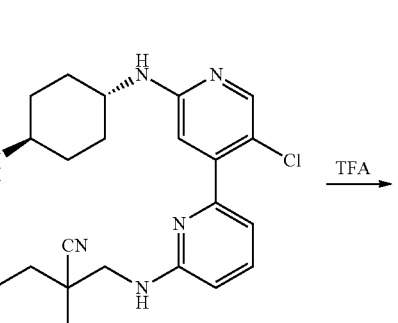

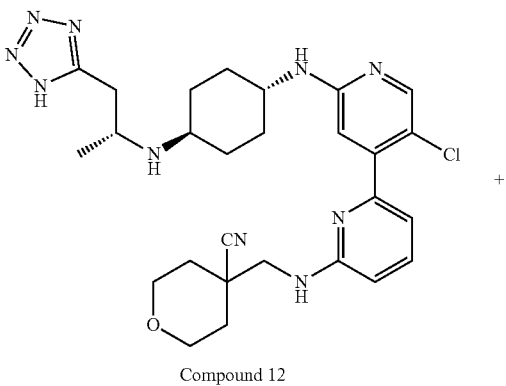

To a solution of 4-(((2'-(((1R,4R)-4-aminocyclohexyl)amino)-5'-chloro-[2,4'-bipyridin]-6-yl)amino)methyl)tetrahydro-2H-pyran-4-carbonitrile (Intermediate 1, 504.24 mg, 1.14 mmol, 1 eq) and 1-(1-(4-methoxybenzyl)-1H-tetrazol-5-yl)propan-2-one (Intermediate 4, 440 mg, 1.14 mmol, 64% purity, 1 eq) in DCE (20 mL) was added AcOH (137.34 mg, 2.29 mmol, 130.80 uL, 2 eq) and NaBH(OAc)$_3$ (727.05 mg, 3.43 mmol, 3 eq). The reaction mixture was stirred at 20° C. for 16 hr, diluted with water (40 mL), basified with sat. NaHCO$_3$ to pH 7-8, and extracted with DCM (60 mL×3). The combined organic layer was washed with brine (80 mL), dried over Na$_2$SO$_4$, filtered, and concentrated. The resulting residue was purified by flash silica gel chromatography (20 g SepaFlash® Silica Flash Column, 0-8% methanol/dichloromethane, 35 mL/min) to provide 4-(((5'-chloro-2'-(((1R,4R)-4-((1-(1-(4-methoxybenzyl)-1H-tetrazol-5-yl)propan-2-yl)amino)cyclohexyl)amino)-[2,4'-bipyridin]-6-yl)amino)methyl)tetrahydro-2H-pyran-4-carbonitrile (Compound 10, 150 mg, 207.83 umol, 18.17% yield, 93% purity) as a brown oil. MS (ESI) m/z=671.2 [M+H]$^+$.

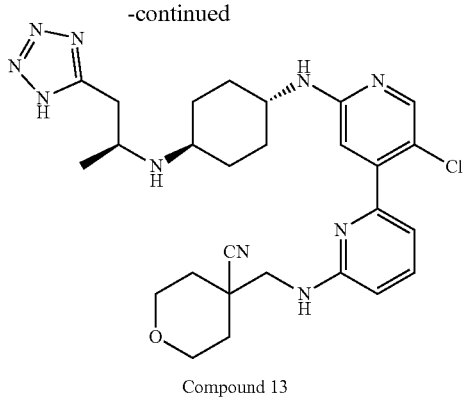

Compound 13

A solution of 4-(((5'-chloro-2'-(((1R,4R)-4-((1-(1-(4-methoxybenzyl)-1H-tetrazol-5-yl)propan-2-yl)amino)cyclohexyl)amino)-[2,4'-bipyridin]-6-yl)amino)methyl)tetrahydro-2H-pyran-4-carbonitrile (Compound 10, 140 mg, 208.57 umol, 1 eq) in TFA (38.50 g, 337.65 mmol, 25.00 mL, 1618.88 eq) was stirred at 40° C. for 12 hr, concentrated in vacuo, diluted with water (20 mL), and extracted with TBME (20 mL×2). The aqueous layer was basified with sat. NaHCO$_3$ to pH 8 and extracted with DCM (40 mL×5). The combined DCM layer was washed with brine (50 mL), dried over Na$_2$SO$_4$, filtered, and concentrated to provide 4-(((2'-(((1R,4R)-4-((1-(1H-tetrazol-5-yl)propan-2-yl)amino)cyclohexyl)amino)-5'-chloro-[2,4'-bipyridin]-6-yl)amino)methyl)tetrahydro-2H-pyran-4-carbonitrile (110 mg, crude) (Compound 11) as a yellow oil. MS (ESI) m/z=551.4 [M+H]$^+$.

4-(((2'-(((1R,4R)-4-((1-(1H-tetrazol-5-yl)propan-2-yl)amino)cyclohexyl)amino)-5'-chloro-[2,4'-bipyridin]-6-yl)amino)methyl)tetrahydro-2H-pyran-4-carbonitrile (Compound 11) was further purified by chiral SFC (Chiralpak IC 250×30 mm (10 μm particle size); 60% MeOH (0.1% NH$_3$/H$_2$O)/CO$_2$) to provide 4-(((2'-(((1R,4R)-4-(((R)-1-(1H-tetrazol-5-yl)propan-2-yl)amino)cyclohexyl)amino)-5'-chloro-[2,4'-bipyridin]-6-yl)amino)methyl)tetrahydro-2H-pyran-4-carbonitrile (Compound 12, 30 mg, 76.7% purity) and 4-(((2'-(((1S,4R)-4-(((S)-1-(1H-tetrazol-5-yl)propan-2-yl)amino)cyclohexyl)amino)-5'-chloro-[2,4'-bipyridin]-6-yl)amino)methyl)tetrahydro-2H-pyran-4-carbonitrile (Compound 13, 50 mg, 93.6% purity). Compound 12 was further purified by preparative HPLC (Phenomenex Luna C18 80×40 mm (3 μm particle size); 0-30% acetonitrile/water (0.05% HCl); 11 min) to provide the hydrochloride salt of Compound 12 (21 mg, 35.74 umol, 17.91% yield, >99% purity) as a yellow solid. Compound 13 was further purified by preparative HPLC (Phenomenex Luna C18 80×40 mm (3 μm particle size); 0-30% acetonitrile/water (0.05% HCl); 11 min) to provide the hydrochloride salt of Compound 13 (26 mg, 44.25 umol, 22.17% yield, >99% purity) as a yellow solid.

Compound 12: $^1$H NMR (400 MHz, methanol-d$_4$) δ=8.15 (s, 1H), 7.93 (t, J=8.1 Hz, 1H), 7.30 (s, 1H), 7.22 (d, J=8.8 Hz, 1H), 7.09 (d, J=7.2 Hz, 1H), 3.99 (dd, J=3.2, 11.2 Hz, 3H), 3.88-3.78 (m, 3H), 3.70-3.61 (m, 2H), 3.57-3.45 (m, 2H), 3.40-3.33 (m, 1H), 2.29 (t, J=14.4 Hz, 4H), 1.98 (d, J=13.6 Hz, 2H), 1.83-1.71 (m, 4H), 1.68-1.54 (m, 2H), 1.39 (d, J=6.4 Hz, 3H). MS (ESI) m/z=551.2 [M+H]$^+$.

Compound 13: $^1$H NMR (400 MHz, methanol-d$_4$) δ=8.17 (s, 1H), 8.03 (t, J=8.0 Hz, 1H), 7.35 (s, 2H), 7.13 (d, J=7.2 Hz, 1H), 4.00 (dd, J=3.2, 11.6 Hz, 3H), 3.89 (s, 2H), 3.87-3.79 (m, 1H), 3.70-3.61 (m, 2H), 3.57-3.47 (m, 2H), 3.41-3.33 (m, 1H), 2.30 (br t, J=14.4 Hz, 4H), 2.01 (br d, J=13.2 Hz, 2H), 1.85-1.73 (m, 4H), 1.69-1.56 (m, 2H), 1.40 (d, J=6.4 Hz, 3H). MS (ESI) m/z=551.2 [M+H]$^+$.

Example 9: Synthesis of isopropyl 2-(2-oxopropoxy)acetate (Intermediate 5)

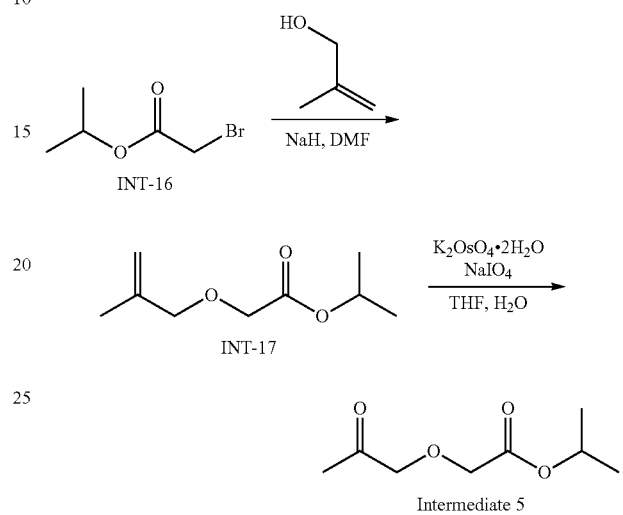

Step 1: Preparation of isopropyl 2-((2-methylallyl)oxy)acetate (INT-17)

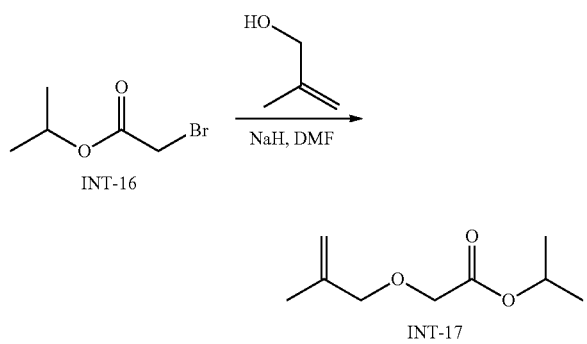

To a solution of 2-methylprop-2-en-1-ol (1.99 g, 27.62 mmol) in DMF (50 mL) was added NaH (1.66 g, 41.43 mmol, 60% purity) at 0° C. over 15 min, then isopropyl 2-bromoacetate (INT-16, 5 g, 27.62 mmol) was added slowly. The mixture was stirred at 0° C. for 1 hr. The mixture was quenched by water (25 mL) at 0° C., and then extracted with ethyl acetate (30 mL×3). The combined organic phase was washed with brine (20 mL), dried over anhydrous sodium sulfate, filtered and concentrated in vacuo, then purified by flash column chromatography on silica gel (ethyl acetate in petroleum ether from 0% to 3%) to afford isopropyl 2-(2-methylallyloxy)acetate (INT-17, 2.22 g, 46% yield) was obtained as a colorless liquid. $^1$H NMR (400 MHz, DMSO-d$_6$): δ=5.05-4.8 (m, 3H), 4.03 (s, 2H), 4.0-3.85 (m, 2H), 1.68 (s, 3H), 1.21 (s, 3H), 1.19 (s, 3H).

Step 2: Preparation of ethyl 2-(2-oxopropoxy)acetate (Intermediate 5)

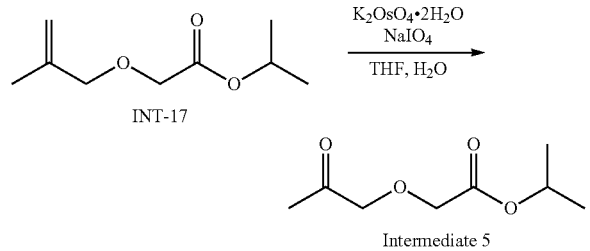

To a solution of isopropyl 2-(2-methylallyloxy)acetate (INT-17, 2.22 g, 12.89 mmol) in THF (25 mL) and H₂O (24 mL) was added K₂OsO₄·2H₂O (48 mg, 0.129 mmol) and NaIO₄ (6.07 g, 28.36 mmol). The mixture was stirred at 20° C. for 12 hr. The mixture was diluted with H₂O (10 mL) and extracted with DCM (20 mL×3). The organic phases were combined and washed with brine (50 mL) and dried over anhydrous Na₂SO₄, filtered and concentrated in vacuo to give the residue, which was purified by chromatography on silica gel (10-15% Ethyl acetate in Petroleum ether) to give the isopropyl 2-acetonyloxyacetate (Intermediate 5, 1.06 g, 47% yield) was obtained as a light yellow liquid. ¹H NMR (400 MHz, DMSO-d₆): δ=5.13-5.04 (m, 1H), 4.19 (s, 2H), 4.13 (s, 2H), 2.17 (s, 3H), 1.26 (s, 3H), 1.24 (s, 3H).

Example 10: Synthesis of isopropyl 2-((R)-2-(((1r,4R)-4-((5'-Chloro-6-(((4-Cyanotetrahydro-2H-pyran-4-yl)methyl)amino)-[2,4'-bipyridin]-2'-yl)amino)cyclohexyl)amino)propoxy)acetate (Compound 15) and isopropyl 2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)acetate (Compound 16)

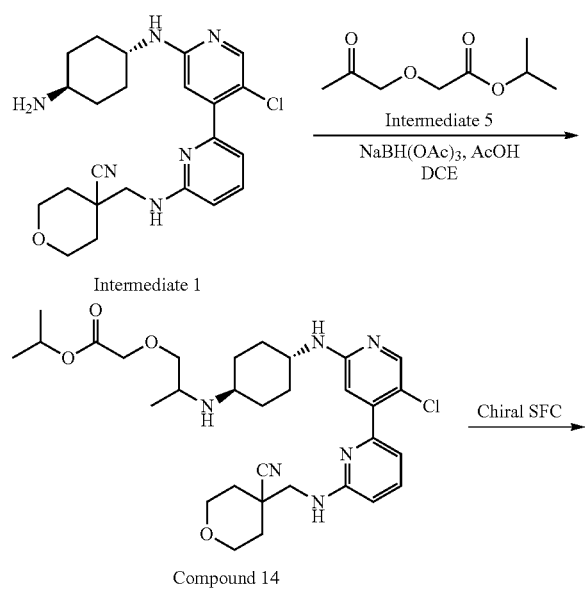

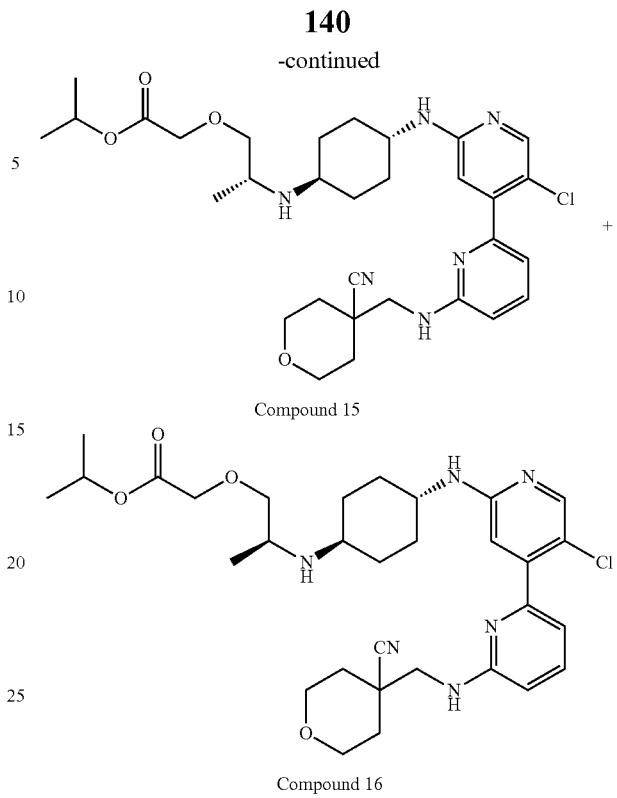

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1, 100 mg, 0.227 mmol), isopropyl 2-acetonyloxyacetate (Intermediate 5, 43 mg, 0.249 mmol) and AcOH (41 mg, 0.680 mmol) in DCE (2 mL) was added NaBH(OAc)₃ (67 mg, 0.317 mmol) at 0° C. The mixture was stirred at 20° C. for 20 hr. The mixture was quenched with H₂O (5 mL). The resulting mixture was extracted with EtOAc (20 mL×3). The organic phases were combined and washed with brine (50 mL) and dried over anhydrous Na₂SO₄, filtered and concentrated in vacuo, which was purified by chromatography on silica gel (15-20% MeOH in DCM) to give the isopropyl 2-[2-[[4-[[5-chloro-4-[6-[(4-cyanotetrahydropyran-4-yl)methylamino]-2-pyridyl]-2-pyridyl]amino]cyclohexyl]amino]propoxy]acetate (Compound 14, 50 mg, 12% yield) as a black brown solid.

Racemic isopropyl 2-[2-[[4-[[5-chloro-4-[6-[(4-cyanotetrahydropyran-4-yl)methylamino]-2-pyridyl]-2-pyridyl]amino]cyclohexyl]amino]propoxy]acetate (Compound 14, 50 mg, 0.083 mmol) was separated by chiral SFC (Chiralpak AD 250×30 mm (10 μm particle size); 70% EtOH/CO₂) and further purified by prep-HPLC (HCOOH condition) to afford isopropyl 2-[(2R)-2-[[4-[[5-chloro-4-[6-[(4-cyanotetrahydropyran-4-yl)methylamino]-2-pyridyl]-2-pyridyl]amino]cyclohexyl]amino]propoxy]acetate (Compound 15, 3.9 mg, 8% yield) as a white solid and isopropyl 2-[(2S)-2-[[4-[[5-chloro-4-[6-[(4-cyanotetrahydropyran-4-yl)methylamino]-2-pyridyl]-2-pyridyl]amino]cyclohexyl]amino]propoxy]acetate (Compound 16, 11.2 mg, 21% yield) as a brown solid.

Compound 15: ¹H NMR (400 MHz, CDCl₃): δ=8.49 (s, 1H), 8.09 (s, 1H), 7.52 (t, J=7.6 Hz, 1H), 6.97 (d, J=7.2 Hz, 1H), 6.6-6.5 (m, 2H), 5.15-5.0 (m, 1H), 4.86 (t, J=6.8 Hz, 1H), 4.56 (s, 1H), 4.15-4.0 (m, 2H), 4.0-3.9 (m, 2H), 3.78 (d, J=6.8 Hz, 2H), 3.75-3.7 (m, 2H), 3.7-3.5 (m, 3H), 3.4-3.25

(m, 1H), 3.05-2.9 (m, 1H), 2.3-2.1 (m, 4H), 1.95-1.85 (m, 2H), 1.8-1.7 (m, 2H), 1.65-1.45 (m, 2H), 1.3-1.2 (m, 11H).

Compound 16: ¹H NMR (400 MHz, CDCl₃): δ=8.1 (s, 1H), 7.51-7.5 (m, 1H), 6.97 (d, J=7.2 Hz, 1H), 6.51-6.5 (m, 2H), 5.2-5.0 (m, 1H), 4.82 (t, J=7.6 Hz, 1H), 4.45 (d, J=8.4 Hz, 1H), 4.05 (d, J=0.8 Hz, 2H), 4.05-3.95 (m, 2H), 3.77 (d, J=7.6 Hz, 2H), 3.75-3.65 (m, 2H), 3.6-3.45 (m, 2H), 3.4-3.3 (m, 1H), 3.15-3.0 (m, 1H), 2.65-2.5 (m, 1H), 2.2-2.1 (m, 2H), 2.1-1.95 (m, 2H), 1.95-1.85 (m, 2H), 1.8-1.75 (m, 2H), 1.3-1.25 (m, 8H), 1.25-1.15 (m, 2H), 1.06 (d, J=6.4 Hz, 3H).

Example 11: Synthesis of tert-butyl 2-(2-oxopropoxy)acetate (Intermediate 6)

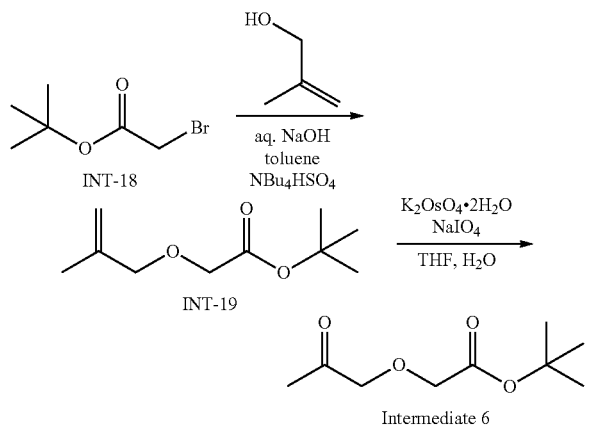

Step 1: Preparation of tert-butyl 2-((2-methylallyl)oxy)acetate (INT-19)

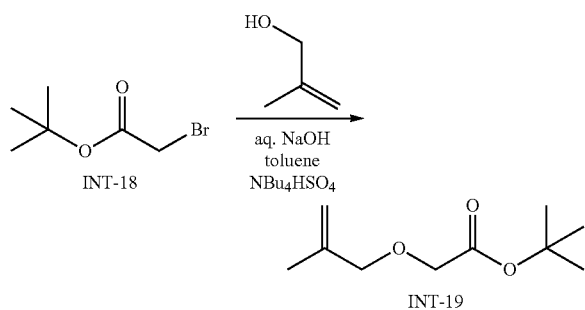

To a solution of 2-methylprop-2-en-1-ol (296 mg, 4.10 mmol) in toluene (18 mL) was added 50% aqueous NaOH (18 mL), then NBu₄HSO₄ (1.13 g, 3.33 mmol) was added, the mixture was stirred for 30 min at 15-20° C., then tert-butyl 2-bromoacetate (INT-18, 500 mg, 2.56 mmol) was added slowly, the mixture was stirred at 15-20° C. for 1.5 hr. The mixture was extracted with ethyl acetate (300 mL×3). The combined organic phase was washed with brine (200 mL), dried over anhydrous sodium sulfate, filtered and concentrated in vacuo, then which was purified by chromatography on silica gel (3% ethyl acetate in Petroleum ether) to give tert-butyl 2-(2-methylallyloxy)acetate (INT-19, 0.35 g, 72% yield) as colorless liquid. ¹H NMR (400 MHz, CDCl₃): δ=4.98 (s, 1H), 4.92 (s, 1H), 3.98 (s, 2H), 3.94 (s, 2H), 1.75 (s, 3H), 1.48 (s, 9H).

Step 2: Preparation of tert-butyl 2-(2-oxopropoxy)acetate (Intermediate 6)

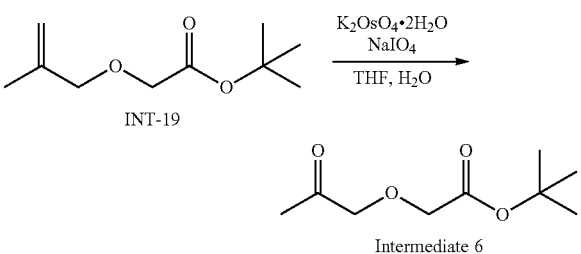

To a solution of tert-butyl 2-(2-methylallyloxy)acetate (INT-19, 4.5 g, 24.16 mmol) in THF (50 mL) and H₂O (50 mL) was added K₂OsO4.2H₂O (89 mg, 0.242 mmol) and NaIO₄ (11.37 g, 53.16 mmol). The mixture was stirred at 20° C. for 12 hr. The mixture was diluted with H₂O (100 mL) and extracted with DCM (200 mL×3). The organic phases were combined and washed with brine (50 mL) and dried over anhydrous Na₂SO₄, filtered and concentrated in vacuo, which was purified by chromatography on silica gel (6-10% ethyl acetate in petroleum ether) to give the tert-butyl 2-acetonyloxyacetate (Intermediate 6, 2.99 g, 66% yield) as light yellow liquid. ¹H NMR (400 MHz, CDCl₃): δ=4.17 (s, 2H), 4.05 (s, 2H), 2.20 (s, 3H), 1.46 (s, 9H).

Example 12: Synthesis of tert-butyl 2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)acetate (Compound 18) and tert-butyl 2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)acetate (Compound 19)

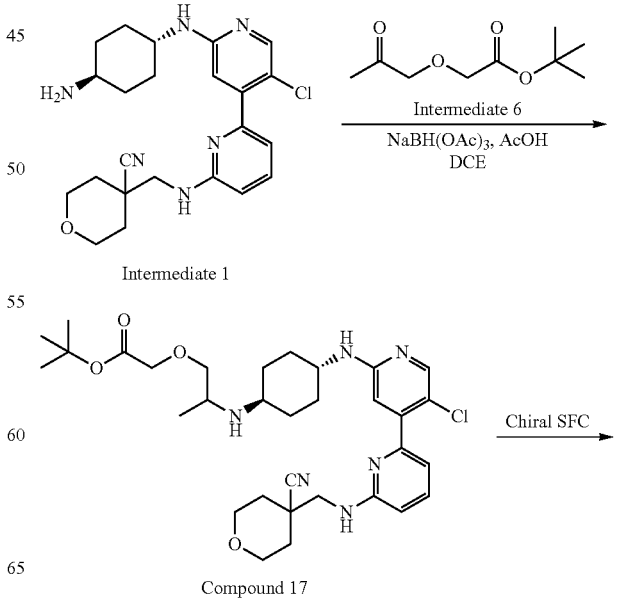

143

-continued

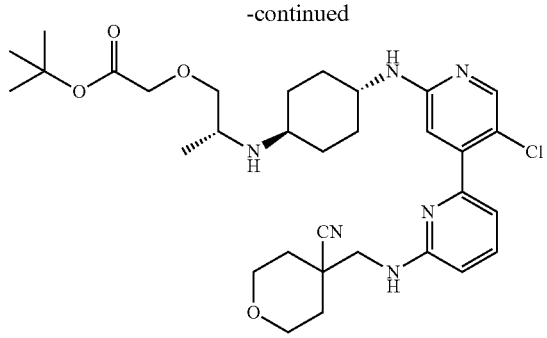

Compound 18

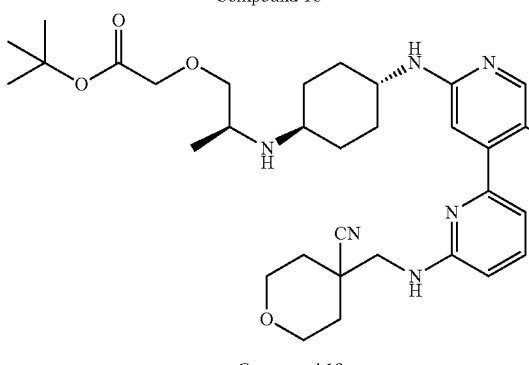

Compound 19

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1, 200 mg, 0.454 mmol), tert-butyl 2-acetonyloxyacetate (94 mg, 0.499 mmol) and AcOH (82 mg, 1.36 mmol) in DCE (2 mL) was added NaBH(OAc)$_3$ (Intermediate 6, 135 mg, 0.635 mmol) at 0° C. The mixture was stirred at 20° C. for 20 hr. The mixture was quenched with H$_2$O (5 mL). The resulting mixture was extracted with EtOAc (20 mL×3). The organic phases were combined and washed with brine (50 mL) and dried over anhydrous Na$_2$SO$_4$, filtered and concentrated in vacuo, which was purified by chromatography on silica gel (15-20% MeOH in DCM) to give the tert-butyl 2-[2-[[4-[[5-chloro-4-[6-[(4-cyanotetrahydropyran-4-yl)methylamino]-2-pyridyl]-2-pyridyl]amino]cyclohexyl]amino]propoxy] acetate (Compound 17, 110 mg, 25% yield) as a black brown solid.

Racemic tert-butyl 2-[2-[[4-[[5-chloro-4-[6-[(4-cyanotetrahydropyran-4-yl)methylamino]-2-pyridyl]-2-pyridyl] amino]cyclohexyl]amino]propoxy]acetate (Compound 17, 92 mg) was separated by chiral SFC (Chiralpak AD 250×30 mm (10 μm particle size); 75% EtOH/CO$_2$) and further purified by pre-HPLC (HCOOH condition) to afford tert-butyl 2-[(2R)-2-[[4-[[5-chloro-4-[6-[(4-cyanotetrahydropyran-4-yl)methylamino]-2-pyridyl]-2-pyridyl]amino]cyclohexyl]amino]propoxy]acetate (Compound 18, 20.3 mg, 22% yield) as a white solid and tert-butyl 2-[(2S)-2-[[4-[[5-chloro-4-[6-[(4-cyanotetrahydropyran-4-yl)methylamino]-2-pyridyl]-2-pyridyl]amino]cyclohexyl]amino]propoxy]acetate (Compound 19, 26.2 mg, 28% yield) as a white solid.

Compound 18: $^1$H NMR (400 MHz, CDCl$_3$): δ=8.47 (s, 1H), 8.09 (s, 1H), 7.52 (t, J=7.2 Hz, 1H), 6.97 (d, J=7.2 Hz, 1H), 6.6-6.5 (m, 2H), 5.0-4.8 (m, 1H), 4.58 (s, 1H), 4.1-3.9 (m, 4H), 3.8-3.75 (m, 2H), 3.75-3.65 (m, 4H), 3.65-3.55 (m, 1H), 3.4-3.3 (m, 1H), 3.05-2.95 (m, 1H), 2.3-2.1 (m, 4H), 1.97-1.87 (m 2H), 1.8-1.7 (m, 2H), 1.7-1.5 (m, 2H), 1.49 (s, 9H), 1.32-1.22 (m, 5H).

144

Compound 19: $^1$H NMR (400 MHz, CDCl$_3$): δ=8.1 (s, 1H), 7.51 (t, J=8.0 Hz, 1H), 6.97 (d, J=7.2 Hz, 1H), 6.6-6.4 (m, 2H), 4.81 (t, J=6.4 Hz, 1H), 4.44 (d, J=7.6 Hz, 1H), 4.1-4.0 (m, 4H), 3.77 (d, J=7.2 Hz, 2H), 3.7 (t, J=11.2 Hz, 2H), 3.6-3.45 (m, 2H), 3.4-3.3 (m, 1H), 3.15-3.0 (m, 1H), 2.7-2.45 (m, 1H), 2.2-2.1 (m, 2H), 2.1-1.95 (m, 2H), 1.95-1.9 (m, 2H), 1.8-1.75 (m, 2H), 1.48 (s, 9H), 1.3-1.25 (m, 2H), 1.25-1.2 (m, 2H), 1.06 (d, J=6.4 Hz, 3H).

Example 13: Synthesis of ethyl (1-(5-(((2-methylallyl)oxy)methyl)-2H-tetrazol-2-yl)ethyl) carbonate (INT-21) and ethyl (1-(5-(((2-methylallyl)oxy) methyl)-1H-tetrazol-1-yl)ethyl) carbonate (INT-22)

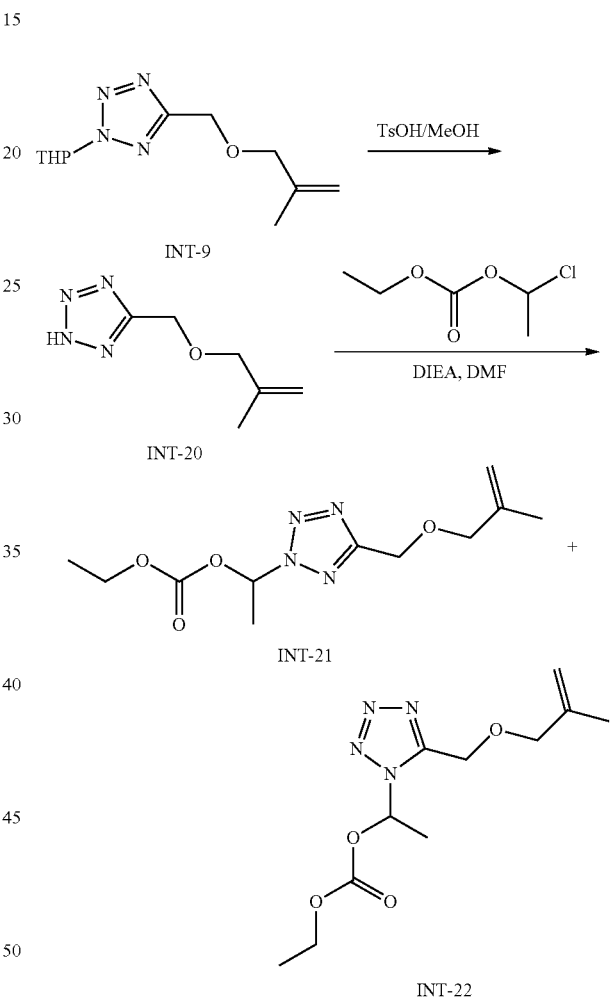

Step 1: Preparation of 5-(((2-methylallyl)oxy) methyl)-2H-tetrazole (INT-20)

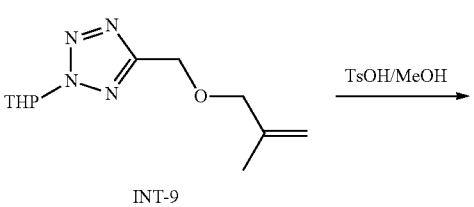

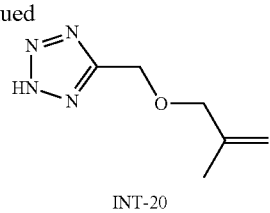

INT-20

To a solution of 5-(2-methylallyloxymethyl)-2-tetrahydropyran-2-yl-tetrazole (INT-9, 5.09 g, 21.36 mmol) in MeOH (50 mL) was added 4-methylbenzenesulfonic acid (3.68 g, 21.36 mmol). The mixture was stirred at 20° C. for 12 hours. The mixture was concentrated under reduced pressure. The residue was purified by silica gel chromatography (0-50% ethyl acetate in petroleum ether) to afford 5-(2-methylallyloxymethyl)-2H-tetrazole (INT-20, 600 mg, 18% yield) as white solid. $^1$H NMR (400 MHz, CDCl$_3$) δ=5.02 (d, J=6.0 Hz, 2H), 4.91 (s, 2H), 4.07 (s, 2H), 1.77 (s, 3H).

Step 2: Preparation of ethyl (1-(5-(((2-methylallyl)oxy)methyl)-2H-tetrazol-2-yl)ethyl) carbonate (INT-21) and ethyl (1-(5-(((2-methylallyl)oxy)methyl)-1H-tetrazol-1-yl)ethyl) carbonate (INT-22)

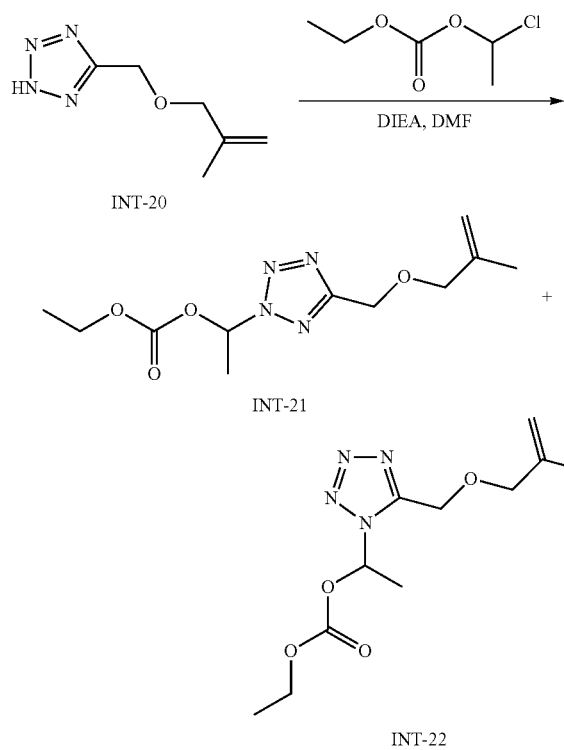

To a solution of 5-(2-methylallyloxymethyl)-2H-tetrazole (INT-20, 600 mg, 3.89 mmol) in DMF (6 mL) was added DIEA (5.03 g, 38.92 mmol) and 1-chloroethyl ethyl carbonate (5.94 g, 38.92 mmol). The mixture was stirred at 70° C. for 16 hours. The mixture was diluted with ethyl acetate (100 mL), which was washed with brine (100 mL×3). The organic layer was dried over anhydrous sodium sulfate, filtered and concentrated in vacuo to give the residue, which was purified by flash column chromatography (silica gel, 100-200 mesh, 0-10% ethyl acetate in petroleum ether) to afford ethyl 1-[5-(2-methylallyloxymethyl)tetrazol-1-yl]ethyl carbonate (INT-21, 326 mg, 31% yield) as yellow oil and ethyl 1-[5-(2-methylallyloxymethyl)tetrazol-2-yl]ethyl carbonate (INT-22, 464 mg, 44% yield) as yellow oil.

INT-21: $^1$H NMR (400 MHz, CDCl$_3$): δ=7.00 (q, J=6.4 Hz, 1H), 5.06-4.88 (m, 4H), 4.254.14 (m, 2H), 3.96 (q, J=12.4 Hz, 2H), 1.98 (d, J=6.0 Hz, 3H), 1.74 (s, 3H), 1.31-1.27 (m, 3H).

INT-22: $^1$H NMR (400 MHz, CDCl$_3$) δ=7.19 (q, J=6.4 Hz, 1H), 5.00 (d, J=27.2 Hz, 2H), 4.76 (s, 2H), 4.29-4.19 (m, 2H), 4.05 (s, 2H), 2.04-2.01 (m, 3H), 1.77 (s, 3H), 1.31-1.28 (m, 3H).

Example 14: Synthesis of (R)-ethyl (1-(5-((2-oxopropoxy)methyl)-2H-tetrazol-2-yl)ethyl) carbonate (Intermediate 7) and (S)-ethyl (1-(5-((2-oxopropoxy)methyl)-2H-tetrazol-2-yl)ethyl) carbonate (Intermediate 8)

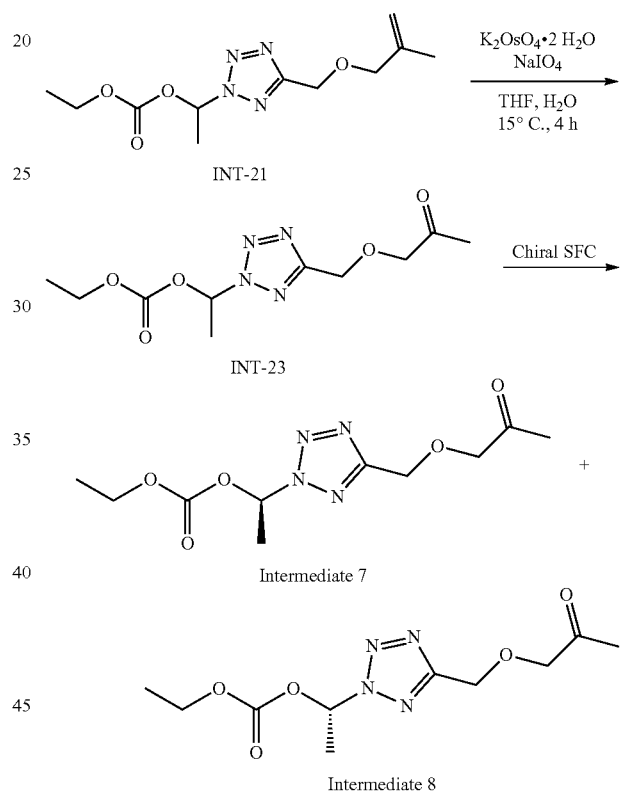

To a solution of ethyl 1-[5-(2-methylallyloxymethyl)tetrazol-2-yl]ethyl carbonate (INT-21, 464 mg, 1.72 mmol) in THF (10 mL) and H$_2$O (10 mL) was added K$_2$OsO$_4$.2H$_2$O (32 mg, 0.086 mmol) and NaIO$_4$ (845 mg, 3.95 mmol). The mixture was stirred at 15° C. for 4 hours. The mixture was diluted with water (50 mL), which was extracted with ethyl acetate (50 mL×3). The combined organic phase was washed with brine (100 mL), dried over anhydrous sodium sulfate, filtered and concentrated in vacuo to give the residue, which was purified by flash column chromatography (silica gel, 100-200 mesh, 0-20% ethyl acetate in petroleum ether) to afford 1-[5-(acetonyloxymethyl)tetrazol-2-yl]ethyl ethyl carbonate (INT-23, 400 mg, 86% yield) as yellow oil.

1-[5-(acetonyloxymethyl)tetrazol-2-yl]ethyl ethyl carbonate (INT-23, 400 mg, 1.47 mmol) was separated by chiral SFC to afford [(1R)-1-[5-(acetonyloxymethyl)tetrazol-2-yl]ethyl]ethyl carbonate (Intermediate 7, 143 mg, 36% yield, 90% purity) as yellow oil and [(1S)-1-[5-(acetonyloxymethyl)tetrazol-2-yl]ethyl] ethyl carbonate (Intermediate 8, 290 mg, 73% yield) as yellow oil.

Intermediate 7: 1H NMR (400 MHz, MeOD): δ=7.23 (q, J=6.0 Hz, 1H), 4.87 (s, 2H), 4.29 (s, 2H), 4.26-4.18 (m, 2H), 2.12 (s, 3H), 1.96 (d, J=6.0 Hz, 3H), 1.27 (t, J=7.2 Hz, 3H).

Intermediate 8: $^1$H NMR (400 MHz, MeOD): δ=7.23 (q, J=6.0 Hz, 1H), 4.87 (s, 2H), 4.30 (s, 2H), 4.25-4.17 (m, 2H), 2.12 (s, 3H), 1.96 (d, J=6.4 Hz, 3H), 1.27 (t, J=6.8 Hz, 3H).

Example 15: Synthesis of (R)-ethyl (1-(5-((2-oxo-propoxy)methyl)-1H-tetrazol-1-yl)ethyl) carbonate (Intermediate 9) and (S)-ethyl (1-(5-((2-oxo-propoxy)methyl)-1H-tetrazol-1-yl)ethyl) carbonate (Intermediate 10)

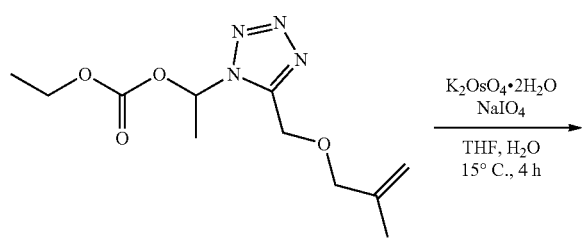

INT-22

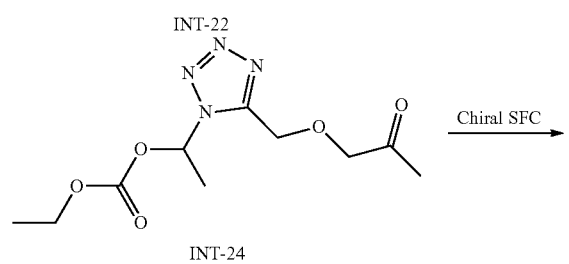

INT-24

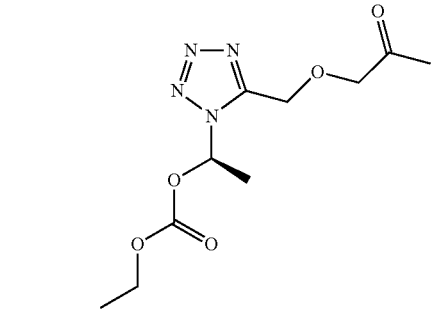

Intermediate 9

+

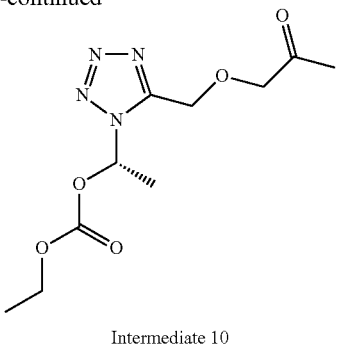

Intermediate 10

To a solution of ethyl 1-[5-(2-methylallyloxymethyl)tetrazol-1-yl]ethyl carbonate (INT-22, 326 mg, 1.21 mmol) in THF (7 mL) and H$_2$O (7 mL) was added K$_2$OsO$_4$·2H$_2$O (22 mg, 0.060 mmol) and NaIO$_4$ (593 mg, 2.77 mmol). The mixture was stirred at 15° C. for 4 hours. The reaction mixture was diluted with water (50 mL), which was extracted with ethyl acetate (50 mL×3). The combined organic phase was washed with brine (100 mL), dried over anhydrous sodium sulfate, filtered and concentrated in vacuo to give the residue, which was purified by flash column chromatography (silica gel, 100-200 mesh, 0-25% ethyl acetate in petroleum ether) followed by chiral SFC to afford [(1R)-1-[5-(acetonyloxymethyl)tetrazol-1-yl]ethyl] ethyl carbonate (Intermediate 9, 142 mg, 43% yield) as yellow oil and [(1S)-1-[5-(acetonyloxymethyl)tetrazol-1-yl]ethyl] ethyl carbonate (Intermediate 10, 195 mg, 59% yield) as yellow oil.

Intermediate 9: 1H NMR (400 MHz, MeOD): δ=7.16 (q, J=6.0 Hz, 1H), 5.16-4.97 (m, 2H), 4.35 (d, J=2.8 Hz, 1H), 4.22-4.14 (m, 2H), 2.09 (s, 3H), 1.95 (d, J=6.0 Hz, 3H), 1.25 (t, J=6.8 Hz, 3H).

Intermediate 10: $^1$H NMR (400 MHz, MeOD): δ=7.16 (q, J=6.0 Hz, 1H), 5.17-4.96 (m, 2H), 4.35 (d, J=2.8 Hz, 2H), 4.23-4.12 (m, 2H), 2.09 (s, 3H), 1.95 (d, J=6.0 Hz, 3H), 1.25 (t, J=7.2 Hz, 3H).

Example 16: Synthesis of (R)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)ethyl ethyl carbonate (Compound 21) and (R)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)ethyl ethyl carbonate (Compound 22)

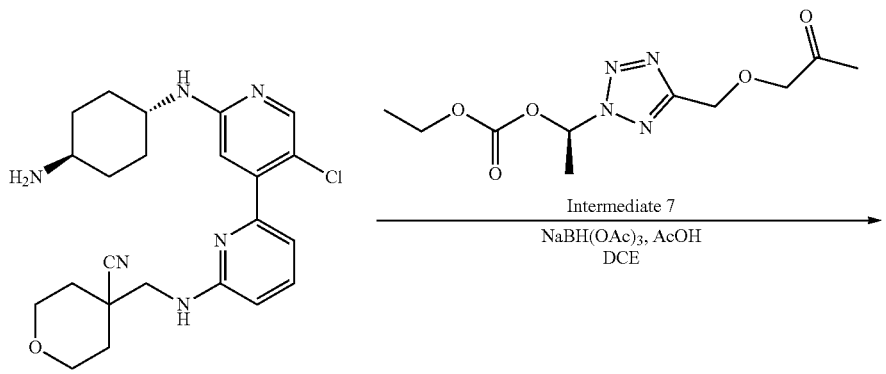

Intermediate 1

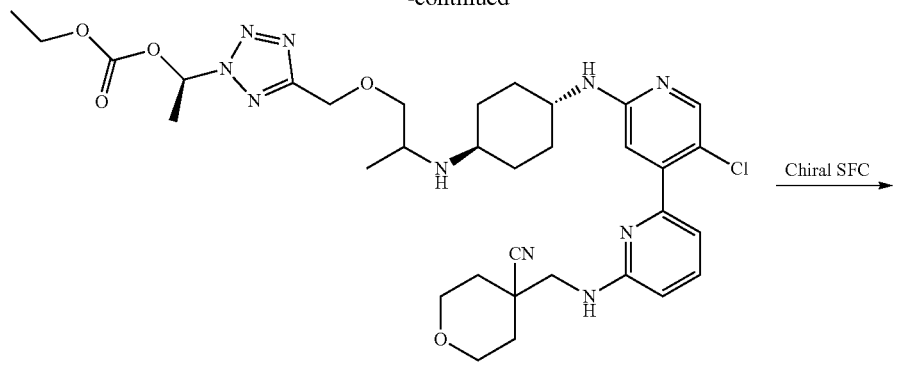

Compound 20

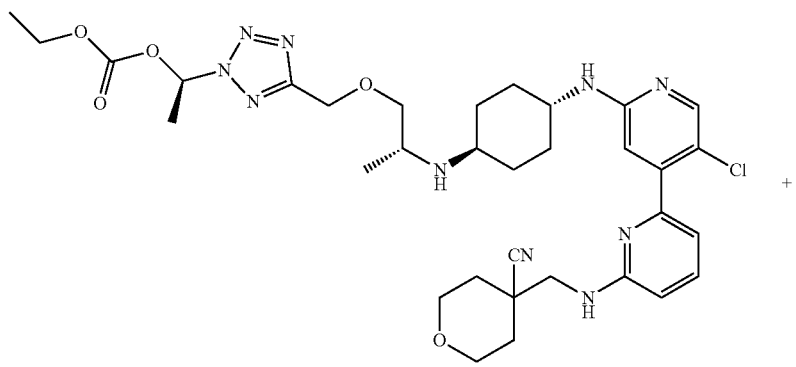

Compound 21

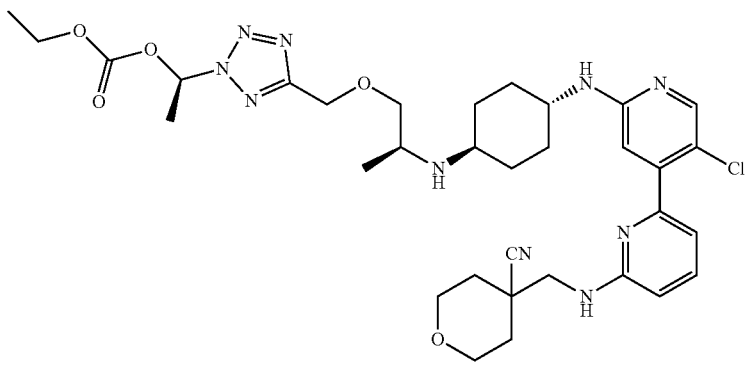

Compound 22

To a solution of [(1R)-1-[5-(acetonyloxymethyl)tetrazol-2-yl]ethyl] ethyl carbonate (Intermediate 7, 123 mg, 0.45 mmol) and 4-[[[6-[2-[(4-aminocyclohexyl)amino]-5-chloro-4-pyridyl]-2-pyridyl]amino]methyl]tetrahydropyran-4-carbonitrile (Intermediate 1, 166 mg, 0.38 mmol) in DCE (2 mL) was added HOAc (68 mg, 1.13 mmol) and NaBH(OAc)$_3$ (112 mg, 0.53 mmol) at 0° C. The mixture was stirred at 20° C. for 16 hours. The mixture was quenched by water (50 mL) at 0° C., which was extracted with DCM (50 mL×3). The combined organic phase was washed with saturated brine (50 mL), dried over anhydrous sodium sulfate, filtered and concentrated in vacuo to give the residue, which was purified by RP-HPLC (16 to 46% acetonitrile in water and 0.225% formic acid) to afford [(1R)-1-[5-[2-[[4-[[5-chloro-4-[6-[(4-cyanotetrahydropyran-4-yl)methylamino]-2-pyridyl]-2-pyridyl]amino]cyclohexyl]amino]propoxymethyl]tetrazol-2-yl]ethyl] ethyl carbonate (Compound 20, 168 mg, 63% yield) as yellow oil.

[(1R)-1-[5-[2-[[4-[[5-chloro-4-[6-[(4-cyanotetrahydropyran-4-yl)methylamino]-2-pyridyl]-2-pyridyl]amino]cyclohexyl]amino]propoxymethyl]tetrazol-2-yl]ethyl] ethyl carbonate (Compound 20, 100 mg, 0.14 mmol) was separated by chiral SFC to afford [(1R)-1-[5-[[(2R)-2-[[4-[[5-chloro-4-[6-[(4-cyanotetrahydropyran-4-yl)methylamino]-2-pyridyl]-2-pyridyl]amino]cyclohexyl]amino]propoxy]methyl]tetrazol-2-yl]ethyl] ethyl carbonate (Compound 21, 11.6 mg, 11% yield) as a white solid and [(1R)-1-[5-[[(2S)-2-[[4-[[5-chloro-4-[6-[(4-cyanotetrahydropyran-4-yl)methylamino]-2-pyridyl]-2-pyridyl]amino]cyclohexyl]amino]propoxy]methyl]tetrazol-2-yl]ethyl] ethyl carbonate (Compound 22, 22.4 mg, 20% yield) as a white solid.

Compound 21: 1H NMR (400 MHz, MeOD): δ=8.54 (s, 1H), 7.97 (s, 1H), 7.53-7.40 (m, 1H), 7.25 (q, J=6.0 Hz, 1H), 6.84 (d, J=7.2 Hz, 1H), 6.70 (s, 1H), 6.63 (d, J=8.4 Hz, 1H), 4.98-4.92 (m, 2H), 4.28-4.13 (m, 2H), 4.00-3.83 (m, 3H), 3.75 (s, 2H), 3.73-3.55 (m, 6H), 2.25-2.11 (m, 4H), 1.96 (d, J=6.0 Hz, 3H), 1.93-1.85 (m, 2H), 1.82-1.71 (m, 2H), 1.60-1.46 (m, 2H), 1.38-1.21 (m, 8H).

Compound 22: 1H NMR (400 MHz, MeOD): δ=8.55 (s, 1H), 7.97 (s, 1H), 7.53-7.45 (m, 1H), 7.25 (q, J=6.0 Hz, 1H), 6.84 (d, J=7.2 Hz, 1H), 6.70 (s, 1H), 6.62 (d, J=8.0 Hz, 1H), 4.87 (s, 2H), 4.26-4.15 (m, 2H), 3.99-3.92 (m, 2H), 3.82-3.74 (m, 3H), 3.69-3.59 (m, 4H), 3.51-3.42 (m, 1H), 3.15-2.99 (m, 1H), 2.21-2.07 (m, 4H), 1.96 (d, J=6.4 Hz, 3H), 1.93-1.86 (m, 2H), 1.82-1.72 (m, 2H), 1.50-1.23 (m, 10H).

Example 17: Synthesis of (S)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)ethyl ethyl carbonate (Compound 24) and (S)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)ethyl ethyl carbonate (Compound 25)

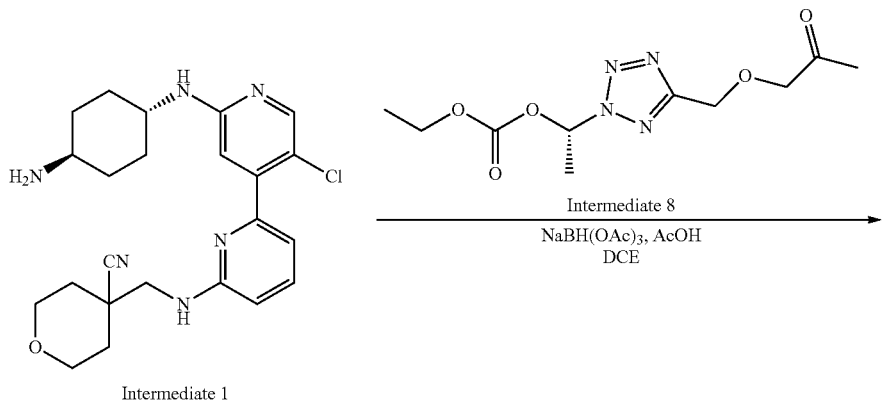

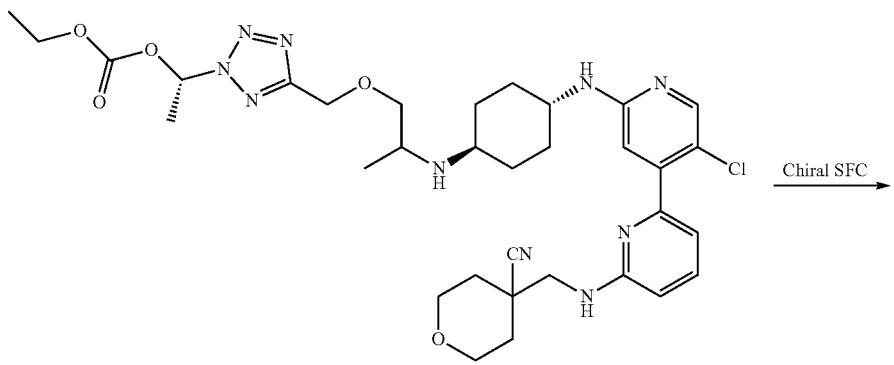

Compound 23

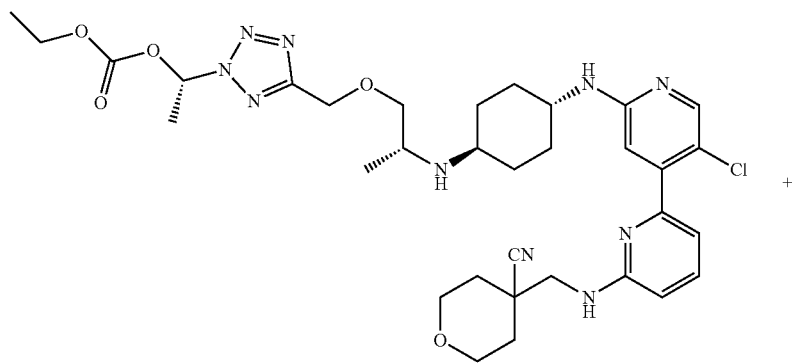

Compound 24

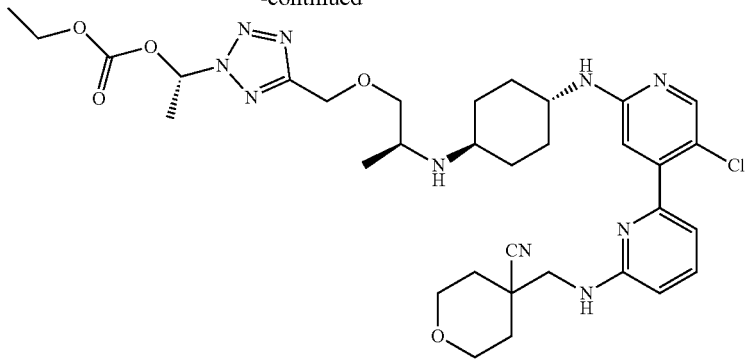

Compound 25

To a solution of [(1S)-1-[5-(acetonyloxymethyl)tetrazol-2-yl]ethyl] ethyl carbonate (Intermediate 8, 270 mg, 0.99 mmol) and 4-[[[6-[2-[(4-aminocyclohexyl)amino]-5-chloro-4-pyridyl]-2-pyridyl]amino]methyl]tetrahydropyran-4-carbonitrile (Intermediate 1, 364 mg, 0.83 mmol) in DCE (3 mL) was added HOAc (149 mg, 2.48 mmol) and NaBH(OAc)₃ (245 mg, 1.16 mmol) at 0° C. The mixture was stirred at 20° C. for 16 hours. The mixture was quenched by water (50 mL) at 0° C., which was extracted with DCM (50 mL×3). The combined organic phase was washed with saturated brine (50 mL), dried over anhydrous sodium sulfate, filtered and concentrated in vacuo to give the residue, which was purified by RP-HPLC (16 to 46% acetonitrile in water and 0.225% formic acid) to afford [(1S)-1-[5-[2-[[4-[[5-chloro-4-[6-[(4-cyanotetrahydropyran-4-yl)methylamino]-2-pyridyl]-2-pyridyl]amino]cyclohexyl]amino]propoxymethyl]tetrazol-2-yl]ethyl] ethyl carbonate (Compound 23, 260 mg, 44% yield) as yellow oil.

[(1S)-1-[5-[2-[[4-[[5-chloro-4-[6-[(4-cyanotetrahydropyran-4-yl)methylamino]-2-pyridyl]-2-pyridyl]amino]cyclohexyl]amino]propoxymethyl]tetrazol-2-yl]ethyl] ethyl carbonate (Compound 23, 100 mg, 0.14 mmol) was separated by chiral SFC to afford [(1S)-1-[5-[[(2R)-2-[[4-[[5-chloro-4-[6-[(4-cyanotetrahydropyran-4-yl)methylamino]-2-pyridyl]-2-pyridyl]amino]cyclohexyl]amino]propoxy]methyl]tetrazol-2-yl]ethyl] ethyl carbonate (Compound 24, 17.3 mg, 16% yield) as a white solid and [(1S)-1-[5-[[(2S)-2-[[4-[[5-chloro-4-[6-[(4-cyanotetrahydropyran-4-yl)methylamino]-2-pyridyl]-2-pyridyl]amino]cyclohexyl]amino]propoxy]methyl]tetrazol-2-yl]ethyl] ethyl carbonate (Compound 25, 28.5 mg, 26% yield) as a white solid.

Compound 24: 1H NMR (400 MHz, MeOD): δ=8.53 (s, 1H), 7.98 (s, 1H), 7.53-7.45 (m, 1H), 7.25 (q, J=6.0 Hz, 1H), 6.83 (d, J=7.2 Hz, 1H), 6.70 (s, 1H), 6.63 (d, J=8.4 Hz, 1H), 4.92 (s, 2H), 4.26-4.14 (m, 2H), 3.99-3.86 (m, 3H), 3.75 (s, 2H), 3.72-3.60 (m, 5H), 3.28-3.20 (m, 1H), 2.25-2.12 (m, 4H), 1.97 (d, J=6.0 Hz, 3H), 1.93-1.86 (m, 2H), 1.83-1.72 (m, 2H), 1.61-1.47 (m, 2H), 1.40-1.31 (m, 5H), 1.26 (t, J=7.2 Hz, 3H).

Compound 25: 1H NMR (400 MHz, MeOD): δ=8.55 (s, 1H), 7.97 (s, 1H), 7.53-7.44 (m, 1H), 7.25 (q, J=6.4 Hz, 1H), 6.84 (d, J=6.8 Hz, 1H), 6.69 (s, 1H), 6.62 (d, J=8.4 Hz, 1H), 4.89 (s, 2H), 4.26-4.14 (m, 2H), 3.99-3.92 (m, 2H), 3.82-3.74 (m, 3H), 3.70-3.59 (m, 4H), 3.52-3.42 (m, 1H), 3.12-3.00 (m, 1H), 2.20-2.07 (m, 4H), 1.96 (d, J=6.4 Hz, 3H), 1.93-1.86 (m, 2H), 1.82-1.71 (m, 2H), 1.54-1.25 (m, 10H).

Example 18: Synthesis of (R)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-1H-tetrazol-1-yl)ethyl ethyl carbonate (Compound 27) and (R)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-1H-tetrazol-1-yl)ethyl ethyl carbonate (Compound 28)

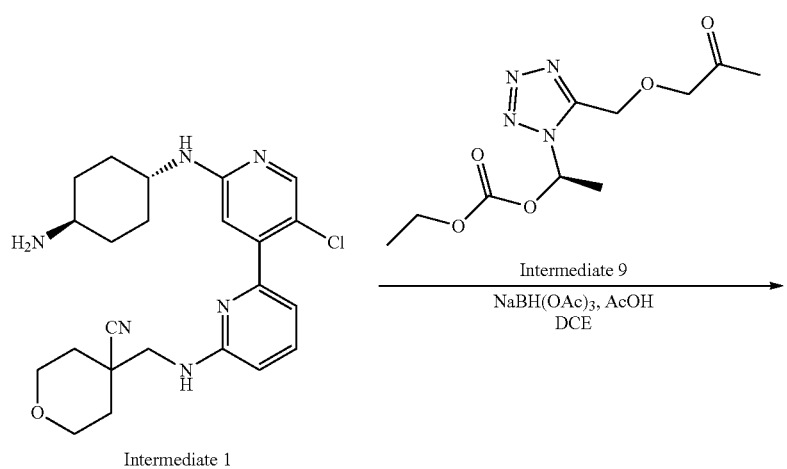

Intermediate 1

-continued

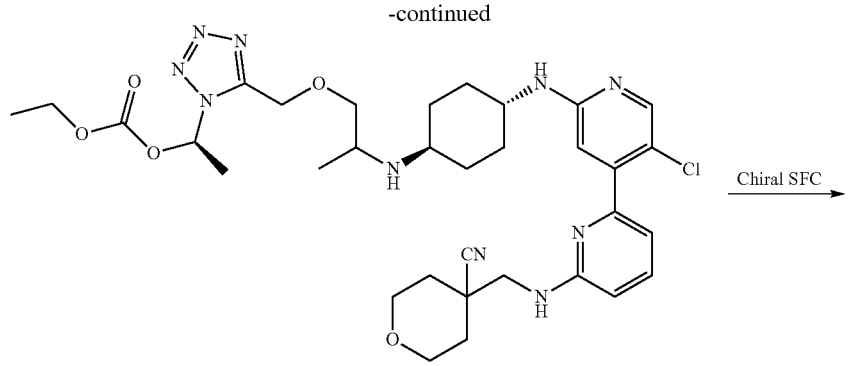

Compound 26

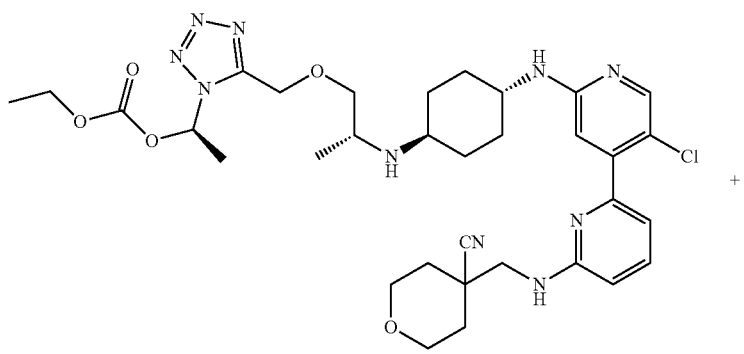

Compound 27

+

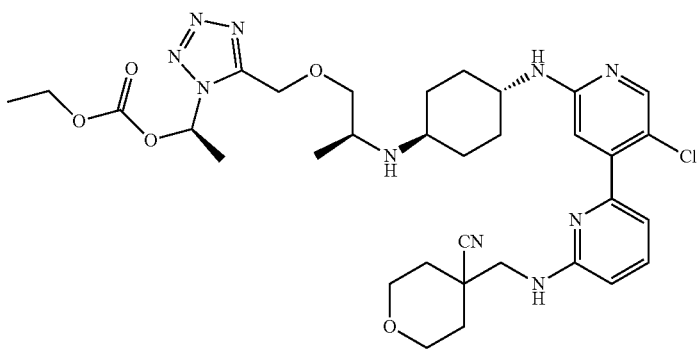

Compound 28

To a solution of [(1R)-1-[5-(acetonyloxymethyl)tetrazol-1-yl]ethyl] ethyl carbonate (Intermediate 9, 122 mg, 0.45 mmol) and 4-[[[6-[2-[(4-aminocyclohexyl)amino]-5-chloro-4-pyridyl]-2-pyridyl]amino]methyl]tetrahydropyran-4-carbonitrile (Intermediate 1, 165 mg, 0.37 mmol) in DCE (2 mL) was added HOAc (67 mg, 1.12 mmol) and NaBH(OAc)$_3$ (111 mg, 0.52 mmol) at 0° C. The mixture was stirred at 20° C. for 16 hours under N2. The mixture was quenched by water (50 mL) at 0° C., which was extracted with DCM (50 mL×3). The combined organic phase was washed with saturated brine (50 mL), dried over anhydrous sodium sulfate, filtered and concentrated in vacuo to give the residue, which was purified by prep-HPLC (45 to 75% acetonitrile in water and 0.225% formic acid) to afford [(1R)-1-[5-[2-[[4-[[5-chloro-4-[6-[(4-cyanotetrahydropyran-4-yl)methylamino]-2-pyridyl]-2-pyridyl]amino]cyclohexyl]amino]propoxymethyl]tetrazol-1-yl]ethyl] ethyl carbonate (Compound 26, 73 mg, 27% yield) as yellow oil.

[(1R)-1-[5-[2-[[4-[[5-chloro-4-[6-[(4-cyanotetrahydropyran-4-yl)methylamino]-2-pyridyl]-2-pyridyl]amino]cyclohexyl]amino]propoxymethyl]tetrazol-1-yl]ethyl] ethyl carbonate (Compound 26, 73 mg, 0.11 mmol) was separated by chiral SFC to afford [(1R)-1-[5-[[(2R)-2-[[4-[[5-chloro-4-[6-[(4-cyanotetrahydropyran-4-yl)methylamino]-2-pyridyl]-2-pyridyl]amino]cyclohexyl]amino]propoxy]methyl]tetrazol-1-yl]ethyl] ethyl carbonate (Compound 27, 14.5 mg, 19% yield) as a white solid and [(1R)-1-[5-[[(2S)-2-[[4-[[5-chloro-4-[6-[(4-cyanotetrahydropyran-4-yl)methylamino]-2-pyridyl]-2-pyridyl]amino]cyclohexyl]amino]propoxy]methyl]tetrazol-1-yl]ethyl] ethyl carbonate (Compound 28, 17.1 mg, 21% yield) as a white solid.

Compound 27: 1H NMR (400 MHz, MeOD): δ=7.95 (s, 1H), 7.52-7.46 (m, 1H), 7.02 (q, J=6.0 Hz, 1H), 6.85 (d, J=6.8 Hz, 1H), 6.69 (s, 1H), 6.62 (d, J=8.4 Hz, 1H), 5.12-5.00 (m, 2H), 4.26-4.14 (m, 2H), 3.99-3.92 (m, 2H), 3.75 (s, 2H), 3.69-3.59 (m, 4H), 3.51-3.45 (m, 1H), 3.29-3.27 (m, 1H), 3.18-3.12 (m, 1H), 2.16-1.99 (m, 4H), 1.95 (d, J=6.0 Hz, 3H), 1.92-1.90 (m, 1H), 1.89-1.85 (m, 1H), 1.82-1.72 (m, 2H), 1.35-1.24 (m, 7H), 1.16-1.06 (m, 3H).

Compound 28: $^1$H NMR (400 MHz, MeOD): δ=8.54 (s, 1H), 7.97 (s, 1H), 7.52-7.46 (m, 1H), 6.93 (q, J=6.0 Hz, 1H), 6.84 (d, J=7.2 Hz, 1H), 6.70 (s, 1H), 6.62 (d, J=8.4 Hz, 1H), 5.18-5.06 (m, 2H), 4.25-4.13 (m, 2H), 3.99-3.91 (m, 2H), 3.86-3.77 (m, 1H), 3.75 (s, 2H), 3.73-3.46 (m, 5H), 3.21-3.10 (m, 1H), 2.25-2.08 (m, 4H), 1.96 (d, J=6.0 Hz, 3H), 1.92-1.86 (m, 2H), 1.82-1.71 (m, 2H), 1.60-1.42 (m, 2H), 1.38-1.24 (m, 8H).

Example 19: Synthesis of (S)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-1H-tetrazol-1-yl)ethyl ethyl carbonate (Compound 30) and (S)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-1H-tetrazol-1-yl)ethyl ethyl carbonate (Compound 31)

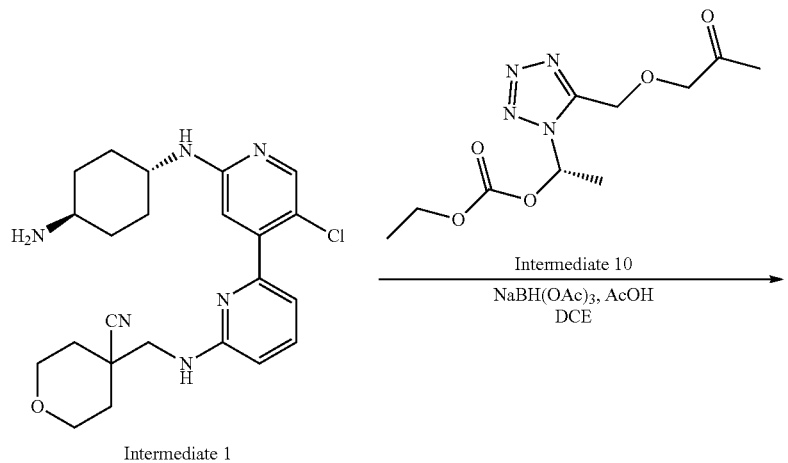

Intermediate 1

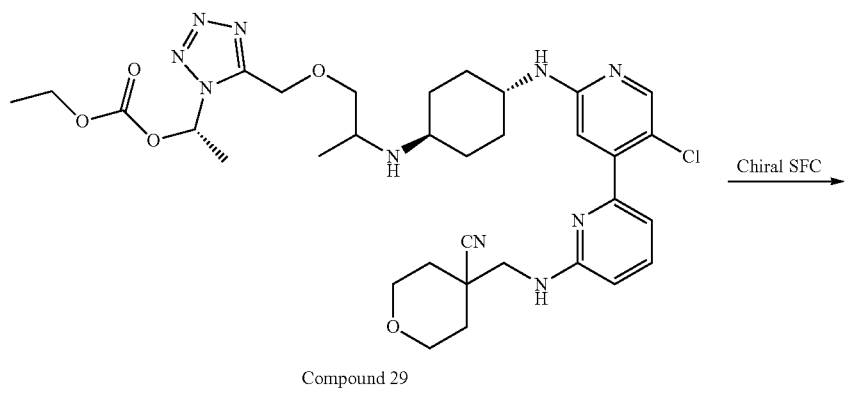

Compound 29

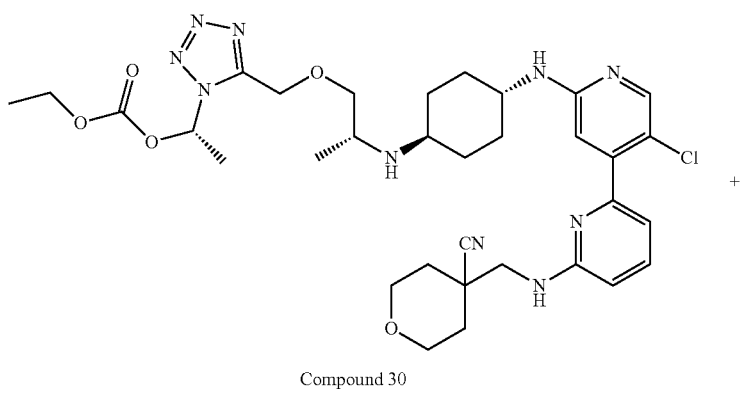

Compound 30

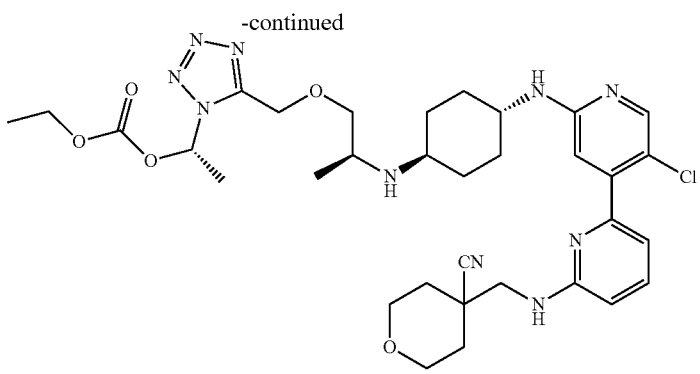

Compound 31

To a solution of [(1S)-1-[5-(acetonyloxymethyl)tetrazol-1-yl]ethyl] ethyl carbonate (Intermediate 10, 175 mg, 0.64 mmol) and 4-[[[6-[2-[(4-aminocyclohexyl)amino]-5-chloro-4-pyridyl]-2-pyridyl]amino]methyl]tetrahydropyran-4-carbonitrile (Intermediate 1, 236 mg, 0.54 mmol) in DCE (2 mL) was added HOAc (97 mg, 1.61 mmol) and NaBH(OAc)$_3$ (159 mg, 0.75 mmol) at 0° C. The mixture was stirred at 20° C. for 16 hours under N2. The mixture was quenched by water (50 mL) at 0° C., which was extracted with DCM (50 mL×3). The combined organic phase was washed with saturated brine (50 mL), dried over anhydrous sodium sulfate, filtered and concentrated in vacuo to give the residue, which was purified by RP-HPLC (15 to 45% acetonitrile in water and 0.225% formic acid) to afford [(1S)-1-[5-[2-[[4-[[5-chloro-4-[6-[(4-cyanotetrahydropyran-4-yl)methylamino]-2-pyridyl]-2-pyridyl]amino]cyclohexyl]amino]propoxymethyl]tetrazol-1-yl]ethyl] ethyl carbonate (Compound 29, 204 mg, 54% yield) as yellow oil.

[(1S)-1-[5-[2-[[4-[[5-chloro-4-[6-[(4-cyanotetrahydropyran-4-yl)methylamino]-2-pyridyl]-2-pyridyl]amino]cyclohexyl]amino]propoxymethyl]tetrazol-1-yl]ethyl] ethyl carbonate (Compound 29, 100 mg, 0.14 mmol) was separated by chiral SFC to afford [(1S)-1-[5-[[(2R)-2-[[4-[[5-chloro-4-[6-[(4-cyanotetrahydropyran-4-yl)methylamino]-2-pyridyl]-2-pyridyl]amino]cyclohexyl]amino]propoxy]methyl]tetrazol-1-yl]ethyl] ethyl carbonate (Compound 30, 25.4 mg, 25% yield) as a white solid and [(1S)-1-[5-[[(2S)-2-[[4-[[5-chloro-4-[6-[(4-cyanotetrahydropyran-4-yl)methylamino]-2-pyridyl]-2-pyridyl]amino]cyclohexyl]amino]propoxy]methyl]tetrazol-1-yl]ethyl] ethyl carbonate (Compound 31, 27.1 mg, 24% yield) as a white solid.

Compound 30: 1H NMR (400 MHz, MeOD): δ=7.95 (s, 1H), 7.52-7.45 (m, 1H), 7.06-6.98 (m, 1H), 6.89-6.81 (m, 1H), 6.69 (s, 1H), 6.62 (d, J=8.4 Hz, 1H), 5.11-4.95 (m, 2H), 4.26-4.14 (m, 2H), 3.99-3.92 (m, 2H), 3.75 (s, 2H), 3.70-3.44 (m, 6H), 3.16-3.10 (m, 1H), 2.14-1.98 (m, 4H), 1.95 (d, J=6.4 Hz, 3H), 1.92-1.85 (m, 2H), 1.81-1.72 (m, 2H), 1.34-1.21 (m, 7H), 1.15-1.04 (m, 3H).

Compound 31: 1H NMR (400 MHz, MeOD): δ=8.54 (s, 1H), 7.97 (s, 1H), 7.52-7.45 (m, 1H), 6.94 (q, J=6.4 Hz, 1H), 6.84 (d, J=6.8 Hz, 1H), 6.69 (s, 1H), 6.63 (d, J=8.0 Hz, 1H), 5.21-5.06 (m, 2H), 4.28-4.12 (m, 2H), 3.99-3.92 (m, 2H), 3.88-3.83 (m, 1H), 3.75 (s, 2H), 3.70-3.52 (m, 5H), 3.26-3.12 (m, 1H), 2.23-2.10 (m, 4H), 1.96 (d, J=6.0 Hz, 3H), 1.92-1.85 (m, 2H), 1.81-1.72 (m, 2H), 1.59-1.44 (m, 2H), 1.43-1.23 (m, 8H).

Example 20: Synthesis of 2-methyl-5-(((2-methylallyl)oxy)methyl)-2H-tetrazole (INT-26) and 1-methyl-5-(((2-methylallyl)oxy)methyl)-1H-tetrazole (INT-27)

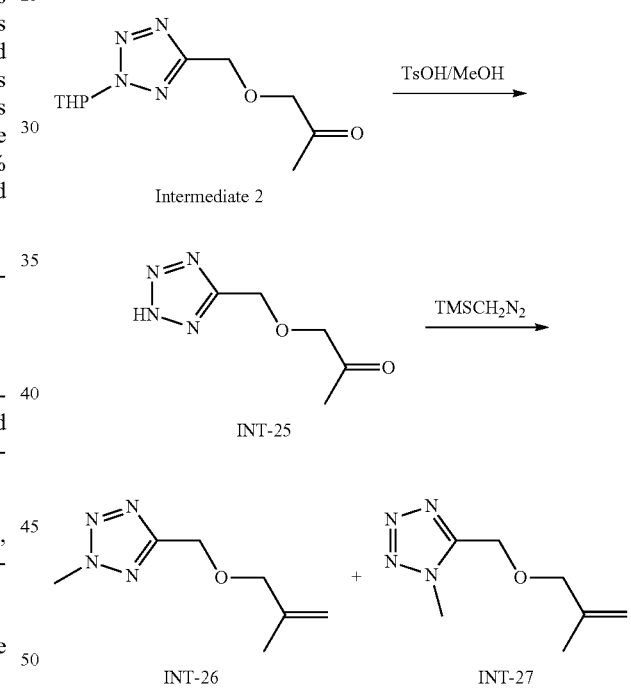

Step 1: Preparation of 1-((2H-tetrazol-5-yl)methoxy)propan-2-one (INT-25)

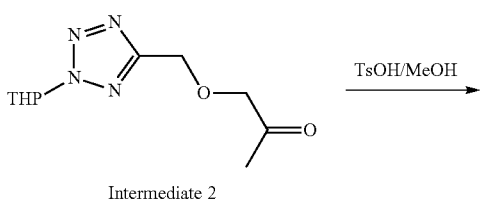

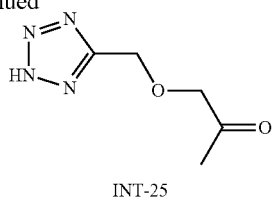

INT-25

To a solution of 5-(2-methylallyloxymethyl)-2-tetrahydropyran-2-yl-tetrazole (Intermediate 2, 3.0 g, 12.59 mmol) in MeOH (1 mL) was added 4-methylbenzenesulfonic acid (2.2 g, 12.59 mmol). The mixture was stirred at 20° C. for 12 hours. The mixture was concentrated under reduced pressure. The residue was purified by flash silica gel chromatography (silica gel, 100-200 mesh, 0-40% ethyl acetate in petroleum ether) to afford 5-(2-methylallyloxymethyl)-2H-tetrazole (INT-25, 2.1 g, 13.62 mmol, 54% yield) as colorless oil. $^1$H NMR (400 MHz, CDCl$_3$): δ 5.00-4.85 (m, 4H), 3.95 (s, 2H), 1.62 (s, 3H).

Step 2: Preparation of 2-methyl-5-(((2-methylallyl)oxy)methyl)-2H-tetrazole (INT-26) and 1-methyl-5-(((2-methylallyl)oxy)methyl)-1H-tetrazole (INT-27)

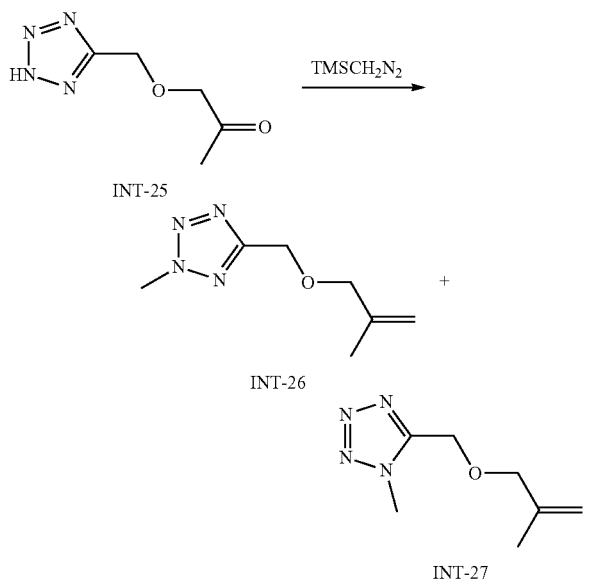

To a solution of 5-(2-methylallyloxymethyl)-2H-tetrazole (INT-25, 1.0 g, 6.49 mmol) in THF (10 mL) was added diazomethyl(trimethyl)silane (2 M, 9.73 mL). The mixture was stirred at 20° C. for 2 hours. The mixture was filtered and the filtrate was concentrated under reduced pressure. The residue was purified by flash column chromatography (silica gel, 100-200 mesh, 10-30% ethyl acetate in petroleum ether) to afford 2-methyl-5-(2-methylallyloxymethyl)tetrazole (INT-26, 470 mg, 2.79 mmol, 43% yield) as colorless oil and 1-methyl-5-(2-methylallyloxymethyl)tetrazole (INT-27, 330 mg, 1.96 mmol, 30% yield) as colorless oil.

INT-26: $^1$H NMR (400 MHz, CDCl$_3$) δ 5.00 (d, J=24.0 Hz, 2H), 4.74 (s, 2H), 4.36 (s, 3H), 4.05 (s, 2H), 1.77 (s, 3H).

INT-27: $^1$H NMR (400 MHz, CDCl$_3$) δ 4.99 (d, J=6.0 Hz, 2H), 4.83 (s, 2H), 4.14 (s, 3H), 3.95 (s, 2H), 1.75 (s, 3H).

Example 21: Synthesis of 1-((2-methyl-2H-tetrazol-5-yl)methoxy)propan-2-one (Intermediate 11)

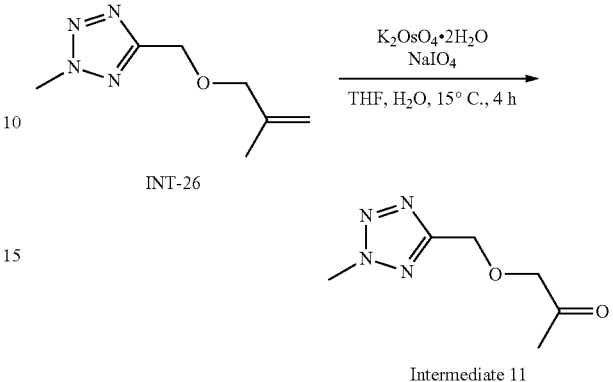

To a solution of 2-methyl-5-(2-methylallyloxymethyl) tetrazole (INT-26, 450 mg, 2.68 mmol) in THF (4 mL) and H$_2$O (3 mL) was added K$_2$OsO$_4$.2H$_2$O (49 mg, 0.13 mmol) and NaIO$_4$ (1.32 g, 6.15 mmol). The mixture was stirred at 20° C. for 4 hours. The mixture was diluted with ethyl acetate (100 mL), which was washed with brine (100 mL). The organic extract was dried over anhydrous sodium sulphate and filtered. The filtrate was concentrated under reduced pressure. The residue was purified by flash column chromatography (silica gel, 100-200 mesh, 0-5% methanol in dichloromethane) to afford 1-[(2-methyltetrazol-5-yl)methoxy]propan-2-one (Intermediate 11, 310 mg, 1.82 mmol, 68% yield) as colorless oil. $^1$H NMR (400 MHz, CDCl$_3$): δ 4.87 (s, 2H), 4.37 (s, 3H), 4.22 (s, 2H), 2.18 (s, 2H).

Example 22: Synthesis of 1-((1-methyl-1H-tetrazol-5-yl)methoxy)propan-2-one (Intermediate 12)

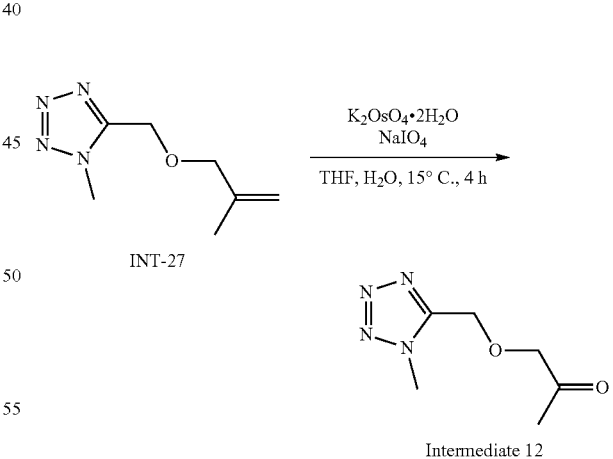

To a solution of 1-methyl-5-(2-methylallyloxymethyl) tetrazole (INT-27, 310 mg, 1.84 mmol) in THF (3 mL) and H$_2$O (2 mL) was added K$_2$OsO4.2H$_2$O (34 mg, 0.09 mmol) and NaIO$_4$ (907 mg, 4.24 mmol). The mixture was stirred at 20° C. for 4 hours. The mixture was diluted with ethyl acetate (100 mL), which was washed with brine (100 mL). The organic extract was dried over anhydrous sodium sulphate and filtered. The filtrate was concentrated under reduced pressure. The residue was purified by flash column chromatography (silica gel, 100-200 mesh, 0-80% methanol in dichloromethane) to afford 1-[(1-methyltetrazol-5-yl)methoxy]propan-2-one (Intermediate 12, 210 mg, 1.23 mmol, 67% yield) as black oil. $^1$H NMR (400 MHz, CDCl$_3$) δ 4.86 (s, 2H), 4.16 (s, 3H), 4.15 (s, 2H), 2.05 (s, 2H).

Example 23: Synthesis of 4-(((5'-chloro-2'-(((1R,4r)-4-(((R)-1-((2-methyl-2H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 33) and 4-(((5'-chloro-2'-(((1S,4r)-4-(((S)-1-((2-methyl-2H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 34)

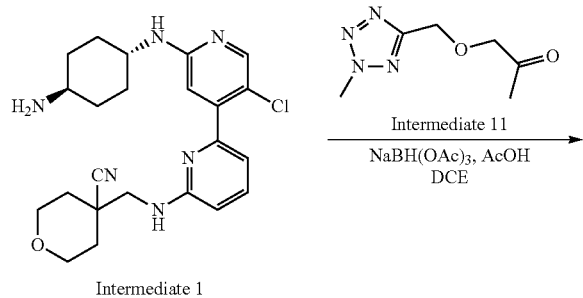

Intermediate 1

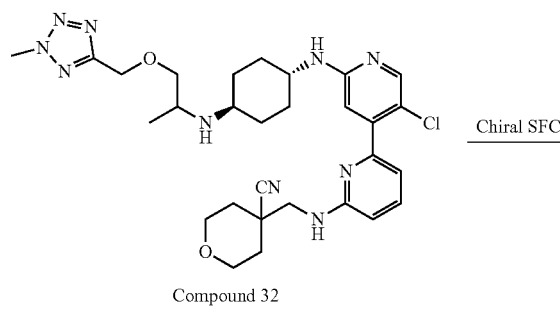

Compound 32

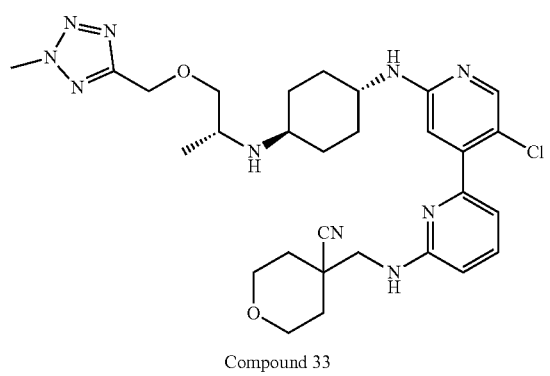

Compound 33

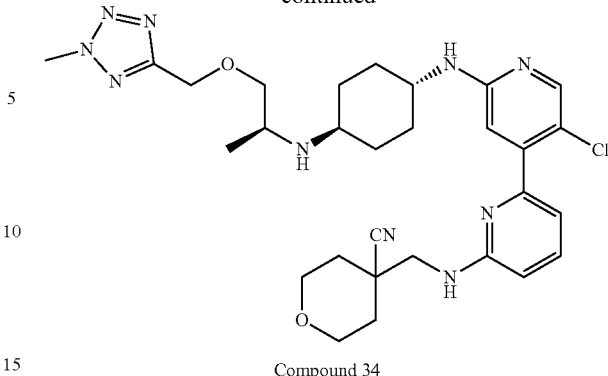

Compound 34

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1, 600 mg, 1.36 mmol) and 1-[(2-methyltetrazol-5-yl)methoxy]propan-2-one (Intermediate 11, 278 mg, 1.63 mmol) in DCE (5 mL) was added HOAc (245 mg, 4.08 mmol) and NaBH(OAc)$_3$ (404 mg, 1.90 mmol). The mixture was stirred at 20° C. for 36 hours. The mixture was quenched by water (50 mL) at 0° C., which was extracted with DCM (50 mL×3). The combined organic phase was washed with brine (50 mL), dried over anhydrous sodium sulfate, filtered and concentrated to dryness under reduced pressure. The residue was purified by prep-HPLC (column: Xtimate C18 150*40 mm*10 um; mobile phase: [water (0.225% FA)-ACN]; B %: 10%-40%, 10 min) to afford 4-[[[6-[5-chloro-2-[[4-[[1-methyl-2-[(2-methyltetrazol-5-yl)methoxy]ethyl]amino]cyclohexyl]amino]-4-pyridyl]-2-pyridyl]amino]methyl]tetrahydropyran-4-carbonitrile (Compound 32, 600 mg, 736 umol, 54% yield) as yellow oil.

4-(((5'-chloro-2'-(((1r,4r)-4-((1-((2-methyl-2H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 32, 100 mg, 0.17 mmol) was separated by chiral SFC to afford 4-(((5'-chloro-2'-(((1S,4r)-4-(((S)-1-((2-methyl-2H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 33, 11.2 mg, 10.5% yield, 94% purity) and 4-(((5'-chloro-2'-(((1R,4r)-4-(((R)-1-((2-methyl-2H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 34.22 mg, 21.6% yield, 98% purity) as a white solid.

Compound 33: $^1$H NMR (400 MHz, CDCl$_3$): δ=7.95 (s, 1H), 7.50-7.46 (m, 1H), 6.85 (d, J=7.2 Hz, 1H), 6.69 (s, 1H), 6.62 (d, J=8.4 Hz, 1H), 4.76 (s, 2H), 4.37 (s, 3H), 3.97-3.93 (m, 2H), 3.75 (s, 2H), 3.66-3.55 (m, 4H), 3.45-3.41 (m, 1H), 3.12-3.08 (m, 1H), 2.64-2.63 (m, 1H). 2.11-1.97 (m, 4H), 1.90-1.87 (m, 2H), 1.80-1.72 (m, 2H), 1.32-1.22 (m, 4H), 1.05 (d, J=6.4 Hz, 3H).

Compound 34: 1H NMR (400 MHz, CDCl$_3$): δ=8.54 (s, 1H), 7.97 (s, 1H), 7.51-7.47 (m, 1H), 6.83 (d, J=6.8 Hz, 1H), 6.69 (s, 1H), 6.62 (d, J=8.4 Hz, 1H), 4.89 (s, 2H), 4.39 (s, 3H), 3.97-3.94 (m, 2H), 3.90-3.80 (m, 1H), 3.75 (s, 2H), 3.67-3.61 (m, 5H), 3.23-3.17 (m, 1H), 2.21-2.12 (m, 5H), 1.91-1.87 (m, 2H), 1.80-1.73 (m, 2H), 1.54-1.51 (m, 2H), 1.39-1.36 (m, 1H), 1.32 (d, J=6.4 Hz, 3H).

Example 24: Synthesis of 4-(((5'-chloro-2'-(((1R,4r)-4-(((R)-1-((1-methyl-1H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 36) and 4-(((5'-chloro-2'-(((1S,4r)-4-(((S)-1-((1-methyl-1H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 37)

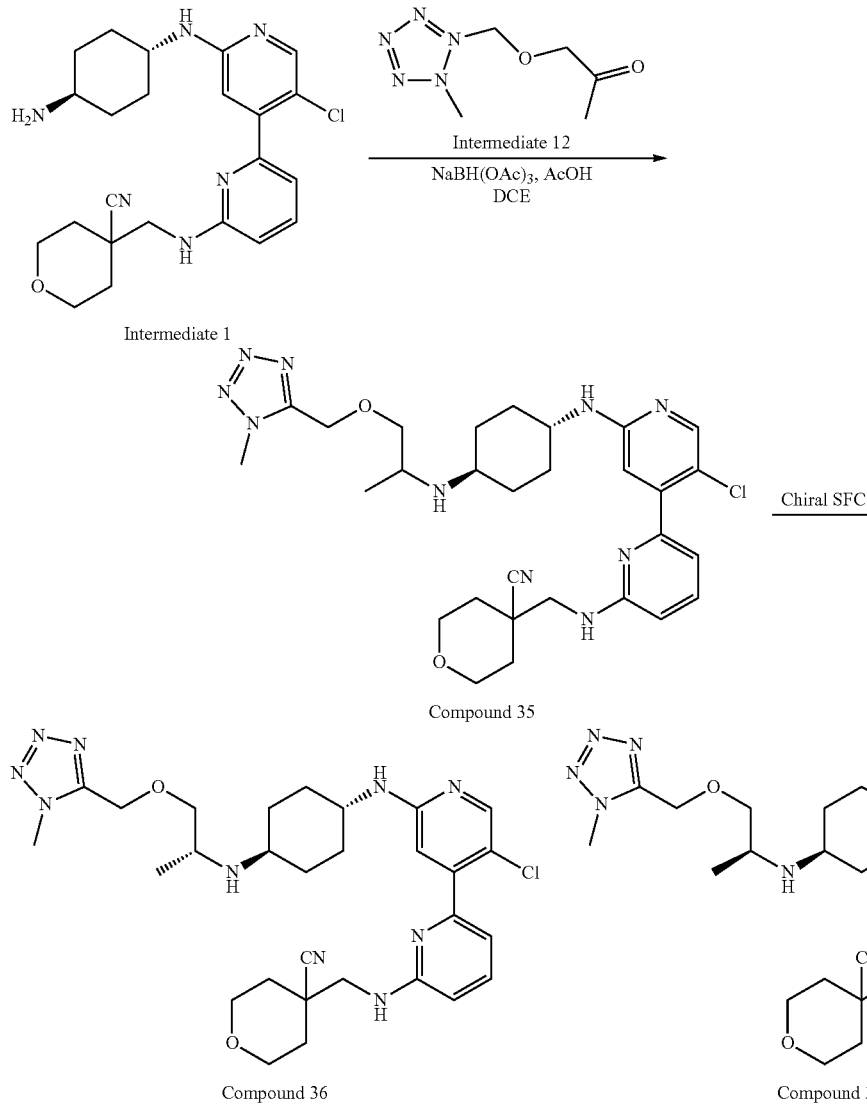

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1, 410 mg, 0.93 mmol) and 1-[(1-methyltetrazol-5-yl)methoxy]propan-2-one (Intermediate 12, 190 mg, 1.12 mmol) in DCE (5 mL) was added HOAc (168 mg, 2.79 mmol) and NaBH(OAc)₃ (276 mg, 1.30 mmol). The mixture was stirred at 20° C. for 36 hours. The mixture was quenched by water (50 mL) at 0° C., which was extracted with DCM (50 mL×3). The combined organic phase was washed with brine (50 mL), dried over anhydrous sodium sulfate, filtered and concentrated under reduced pressure. The residue was purified by prep-HPLC (column: Xtimate C18 150*40 mm*10 um; mobile phase: [water (0.225% FA)-ACN];B %: 10%-40%, 10 min) to afford 4-[[[6-[5-chloro-2-[[4-[[1-methyl-2-[(1-methyltetrazol-5-yl)methoxy]ethyl]amino]cyclohexyl]amino]-4-pyridyl]-2-pyridyl]amino]methyl]tetrahydropyran-4-carbonitrile (Compound 35, 300 mg, 367.98 umol, 40% yield) as yellow oil.

4-[[[6-[5-chloro-2-[[4-[[1-methyl-2-[(1-methyltetrazol-5-yl)methoxy]ethyl]amino]cyclohexyl]amino]-4-pyridyl]-2-pyridyl]amino]methyl]tetrahydropyran-4-carbonitrile (Compound 35, 100 mg, 0.17 mmol) was separated by chiral SFC to afford 4-[[[6-[5-chloro-2-[[4-[[(1S)-1-methyl-2-[(1-methyltetrazol-5-yl)methoxy]ethyl]amino]cyclohexyl]amino]-4-pyridyl]-2-pyridyl]amino]methyl]tetrahydropyran-4-carbonitrile (Compound 36, 18.7 mg, 18.2% yield, 97% purity) and 4-[[[6-[5-chloro-2-[[4-[[(1R)-1-methyl-2-[(1-methyltetrazol-5-yl)methoxy]ethyl]amino]cyclohexyl]amino]-4-pyridyl]-2-pyridyl]amino]methyl]tetrahydropyran-4-carbonitrile (Compound 37, 21.6 mg, 21.6% yield, 98% purity) as a white solid.

Compound 36: 1H NMR (400 MHz, MeOD): δ=7.95 (s, 1H), 7.50-7.46 (m, 1H), 6.85 (d, J=7.2 Hz, 1H), 6.69 (s, 1H), 6.62 (d, J=8.4 Hz, 1H), 4.90 (s, 2H), 4.13 (s, 3H), 3.97-3.93 (m, 2H), 3.75 (s, 2H), 3.66-3.61 (m, 3H), 3.56-3.52 (m, 1H), 3.48-3.44 (m, 1H), 3.17-3.13 (m, 1H). 2.66 (s, 1H), 2.11-2.09 (m, 2H), 2.03-1.98 (m, 2H), 1.90-1.87 (m, 2H), 1.80-1.73 (m, 2H), 1.31-1.24 (m, 4H), 1.10 (d, J=6.4 Hz, 3H).

Compound 37: ¹H NMR (400 MHz, MeOD): δ=7.96 (s, 1H), 7.51-7.47 (m, 1H), 6.84 (d, J=7.2 Hz, 1H), 6.69 (s, 1H), 6.62 (d, J=8.0 Hz, 1H), 4.93 (s, 2H), 4.13 (s, 3H), 3.97-3.93 (m, 2H), 3.75 (s, 2H), 3.67-3.61 (m, 4H), 3.56-3.52 (m, 1H), 2.87-2.84 (m, 1H), 2.15-2.01 (m, 5H), 1.90-1.87 (m, 2H), 1.80-1.72 (m, 2H), 1.39-1.29 (m, 4H), 1.19 (d, J=6.4 Hz, 3H).

Example 25: Synthesis of tert-butyl (2-(2-oxopropoxy)ethyl)carbamate (Intermediate 13)

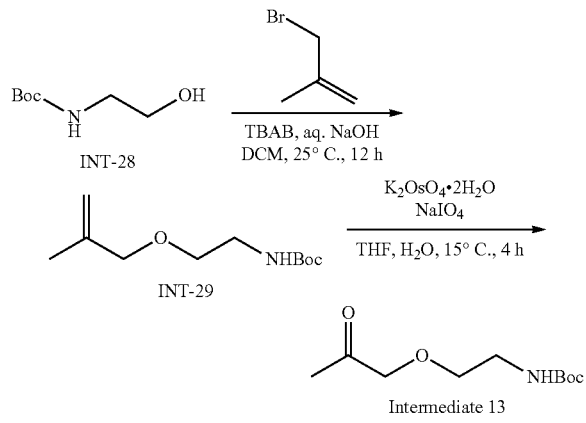

Step 1: Preparation of tert-butyl (2-((2-methylallyl)oxy)ethyl)carbamate (INT-29)

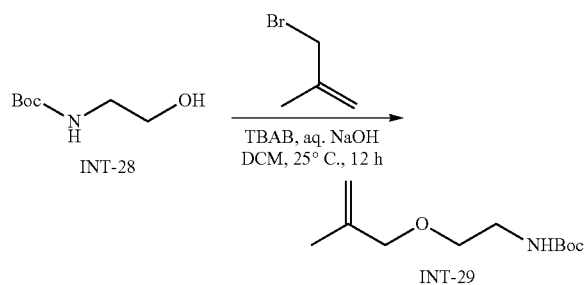

To a solution of tert-butyl N-(2-hydroxyethyl)carbamate (INT-28, 1.0 g, 6.20 mmol) in DCM (12 mL) was added 3-bromo-2-methyl-prop-1-ene (921 mg, 6.82 mmol), TBAB (1.40 g, 4.34 mmol) and aq. NaOH (10 M, 6 mL). The mixture was stirred at 25° C. for 12 hours. The mixture was diluted with water (10 mL) and extracted with DCM (20 mL×2). The combined organic layers were dried over Na₂SO₄, filtered and concentrated in vacuo to give a residue which was purified by silica gel chromatography (Biotage 4 g Silica Flash Column; Eluent of gradient 0-10% Petroleum ether in Ethyl acetate @ 40 mL/min) to afford tert-butyl N-[2-(2-methylallyloxy)ethyl]carbamate (INT-29, 880 mg, 66% yield) as colorless oil. ¹H NMR (400 MHz, CDCl₃): δ=4.96 (s, 1H), 4.91 (s, 1H), 3.89 (s, 2H), 3.49-3.46 (m, 2H), 3.35-3.32 (m, 2H), 1.74 (s, 3H), 1.45 (s, 9H).

Step 2: Preparation of tert-butyl (2-(2-oxopropoxy)ethyl)carbamate (Intermediate 13)

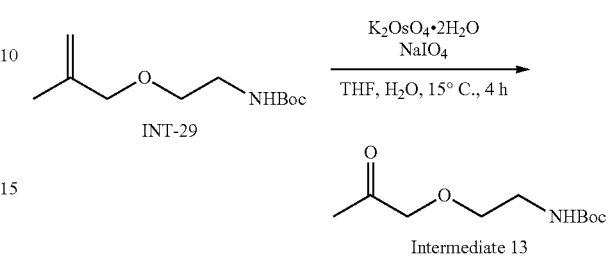

To a solution of tert-butyl N-[2-(2-methylallyloxy)ethyl] carbamate (200 mg, 0.93 mmol) in THF (3 mL) and H₂O (3 mL) was added K₂OsO₄.2H₂O (17 mg, 0.05 mmol) and NaIO₄ (457 mg, 2.14 mmol). The mixture was stirred at 15° C. for 4 hours. The mixture was diluted with water (20 mL), and extracted with ethyl acetate (25 mL×2). The combined organic phases were washed with aq. Na2S2O3 (20 mL), brine (20 mL), dried over anhydrous sodium sulfate, filtered and concentrated in vacuo to give the residue which was purified by silica gel chromatography (Biotage 4 g Silica Flash Column; Eluent of gradient 0-50% Petroleum ether in Ethyl acetate @40 mL/min) to afford tert-butyl N-(2-acetonyloxyethyl)carbamate (Intermediate 13, 200 mg, 99% yield) as light yellow oil. ¹H NMR (400 MHz, CDCl₃): δ=4.10 (s, 2H), 3.58-3.56 (m, 2H), 3.37-3.35 (m, 2H), 2.15 (s, 3H), 1.46 (s, 9H).

Example 26: Preparation of N-(2-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)ethyl)-1,1,1-trifluoromethanesulfonamide (Compound 40)

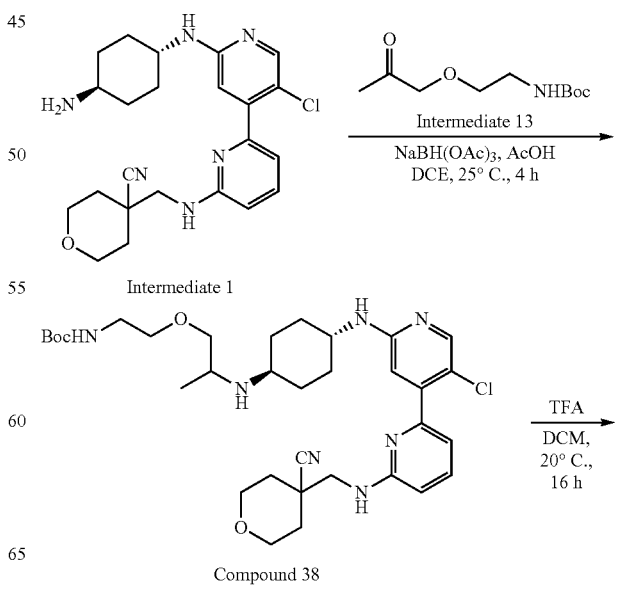

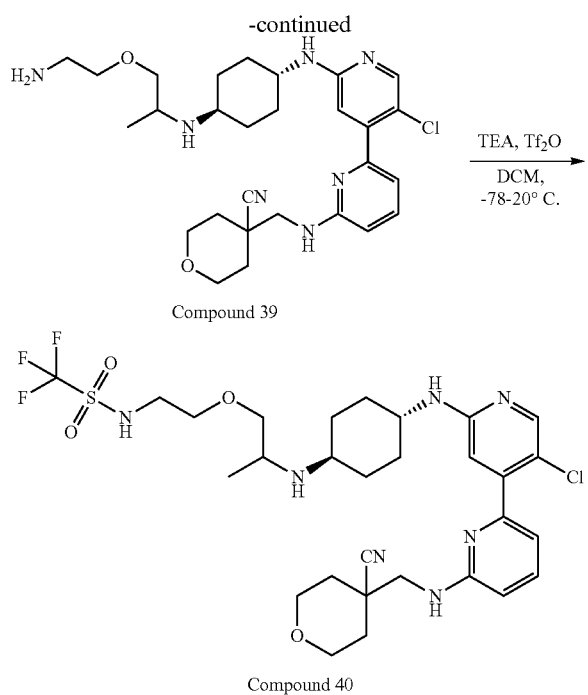

Step 1: Preparation of tert-butyl (2-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)ethyl)carbamate (Compound 38)

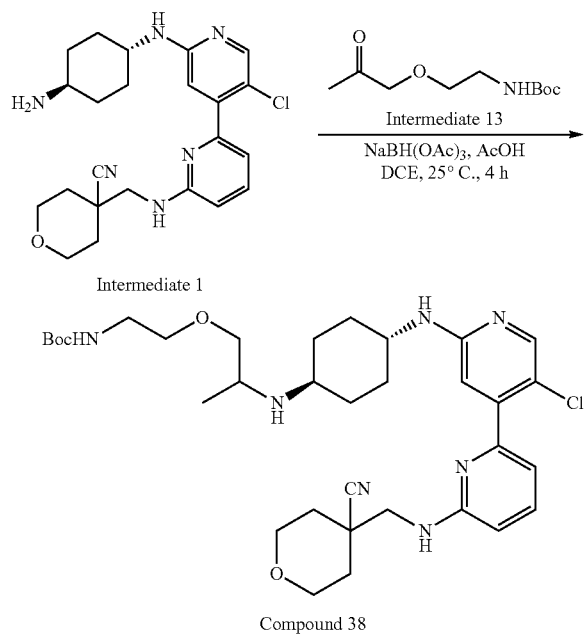

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1, 300 mg, 0.68 mmol) in DCE (5 mL) was added tert-butyl N-(2-acetonyloxyethyl)carbamate (Intermediate 13, 163 mg, 0.75 mmol), HOAc (123 mg, 2.04 mmol) and NaBH(OAc)₃ (202 mg, 0.95 mmol) at 0° C. The mixture was stirred at 20° C. under nitrogen for 4 hours. The mixture was quenched by water (5 mL) at 0° C., and then extracted with DCM (50 mL×3). The combined organic phases were washed with saturated Na₂CO₃ aq. (50 mL), brine (50 mL), dried over anhydrous sodium sulfate, filtered and concentrated, which was purified by silica gel chromatography (Biotage 4 g Silica Flash Column; Eluent of gradient 0-15% methanol in dichloromethane @ 40 mL/min) to afford tert-butyl N-[2-[2-[[4-[[5-chloro-4-[6-[(4-cyanotetrahydropyran-4-yl)methylamino]-2-pyridyl]-2-pyridyl]amino]cyclohexyl]amino] propoxy]ethyl]carbamate (Compound 38, 250 mg, 58% yield) as yellow oil.

Step 2: Preparation of 4-((((2'-(((1r,4r)-4-((1-(2-aminoethoxy)propan-2-yl)amino)cyclohexyl)amino)-5'-chloro-[2,4'-bipyridin]-6-yl)amino)methyl)tetrahydro-2H-pyran-4-carbonitrile (Compound 39)

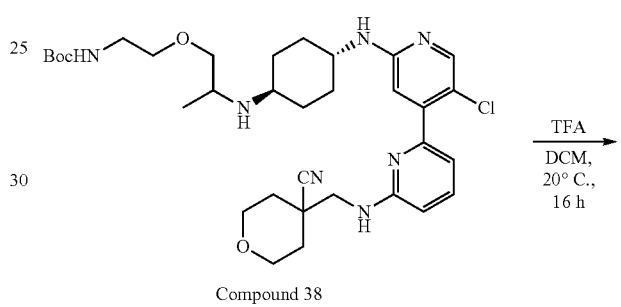

To a solution of tert-butyl N-[2-[2-[[4-[[5-chloro-4-[6-[(4-cyanotetrahydropyran-4-yl)methylamino]-2-pyridyl]-2-pyridyl]amino]cyclohexyl]amino]propoxy]ethyl]carbamate (Compound 38, 200 mg, 0.31 mmol) in DCM (5 mL) was added TFA (710.17 mg, 6.23 mmol). The mixture was stirred at 20° C. for 2 hours. The mixture was concentrated and then extracted with DCM (30 mL×3). The combined organic phases were washed with saturated aq. Na₂CO₃ (30 mL), brine (30 mL), dried over anhydrous sodium sulfate, filtered and concentrated to give 4-[[[6-[2-[[4-[[2-(2-aminoethoxy)-1-methyl-ethyl]amino]cyclohexyl]amino]-5-chloro-4-pyridyl]-2-pyridyl]amino]methyl]tetrahydropyran-4-carbonitrile (Compound 39, 210 mg, crude) as a yellow solid.

Step 3: Preparation of N-(2-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)ethyl)-1,1,1-trifluoromethanesulfonamide (Compound 40)

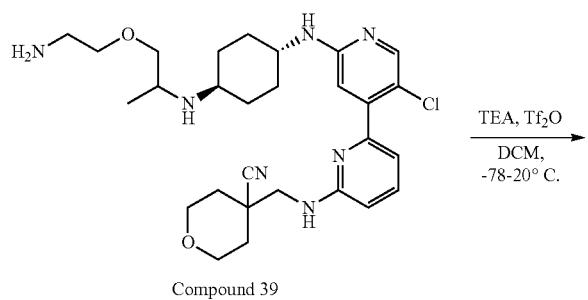

Compound 39

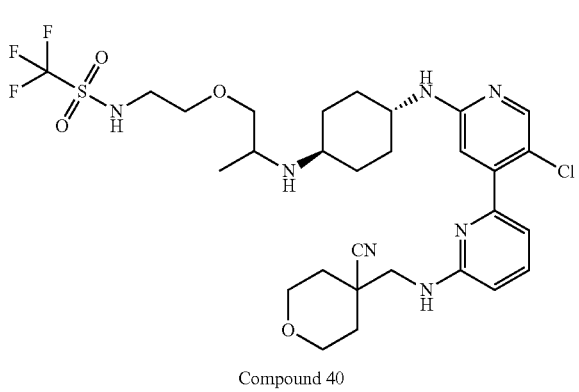

Compound 40

To a solution of 4-[[[6-[2-[[4-[[2-(2-aminoethoxy)-1-methyl-ethyl]amino]cyclohexyl]amino]-5-chloro-4-pyridyl]-2-pyridyl]amino]methyl]tetrahydropyran-4-carbonitrile (Compound 39, 165 mg, 0.30 mmol) in DCM (5 mL) was added TEA (77 mg, 0.76 mmol) and Tf$_2$O (94 mg, 0.33 mmol) at −78° C. The mixture was stirred at 20° C. for 3 hours. The mixture was quenched by water (5 mL), and then extracted with DCM (30 mL×3). The combined organic phases were washed with saturated Na$_2$CO$_3$ aq. (30 mL), brine (30 mL), dried over anhydrous sodium sulfate, filtered and concentrated. The reaction was concentrated and purified by prep-TLC (dichloromethane:methanol=10:1, R$_f$=0.24) to give the crude which was further purified by pre-HPLC (instrument: PREP-HPLC-WI column: Phenomenex Luna C18 100*30 mm*3 um; mobile phase: water (0.225% FA)-ACN; begin B: 6%, end B: 56%, Gradient Time (8 min)) to give N-[2-[2-[[4-[[5-chloro-4-[6-[(4-cyanotetrahydropyran-4-yl)methylamino]-2-pyridyl]-2-pyridyl]amino]cyclohexyl]amino]propoxy]ethyl]-1,1,1-trifluoromethanesulfonamide (Compound 40, 83 mg, 60% yield, FA salt) as a light yellow solid. $^1$H NMR (400 MHz, CDCl$_3$): δ=8.37 (s, 1H), 8.04 (s, 1H), 7.51 (t, J=7.6 Hz, 1H), 6.95 (d, J=7.2 Hz, 1H), 6.59 (s, 1H), 6.52 (d, J=8.4 Hz, 1H), 5.01-4.97 (m, 1H), 4.00-3.96 (m, 2H), 3.77-3.55 (m, 9H), 3.46 (brs, 3H), 3.08-3.02 (m, 1H), 2.28-2.13 (m, 4H), 1.90 (d, J=13.6 Hz, 2H), 1.80-1.63 (m, 4H), 1.40 (d, J=6.4 Hz, 3H), 1.35-1.26 (m, 2H).

Example 27: Synthesis of N-(2-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)ethyl)-1,1-difluoromethanesulfonamide (Compound 41)

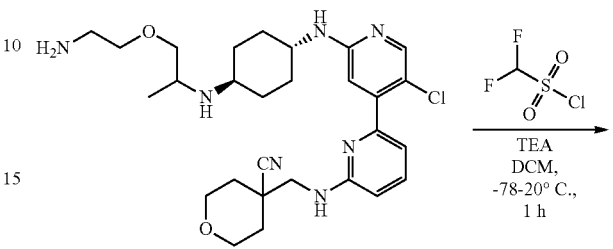

Compound 39

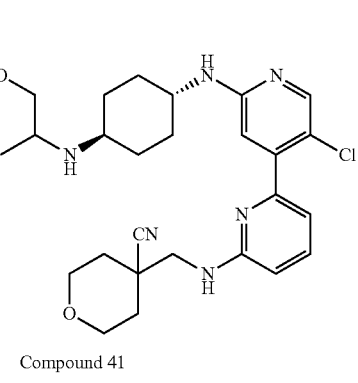

Compound 41

To a solution of 4-[[[6-[2-[[4-[[2-(2-aminoethoxy)-1-methyl-ethyl]amino]cyclohexyl]amino]-5-chloro-4-pyridyl]-2-pyridyl]amino]methyl]tetrahydropyran-4-carbonitrile (Compound 39, 240 mg, 0.44 mmol) in DCM (3 mL) was added TEA (90 mg, 0.89 mmol) and difluoromethanesulfonyl chloride (67 mg, 0.44 mmol) under −78° C. The mixture was stirred at 20° C. for 1 hour. The mixture was quenched by water (8 mL), and then extracted with DCM (50 mL×3). The combined organic phases were washed with saturated Na$_2$CO$_3$ (50 mL), brine (100 mL), dried over anhydrous sodium sulfate, filtered and concentrated. The reaction was concentrated and purified by prep-TLC (dichloromethane:methanol=10:1, R$_f$=0.13) to give the crude which was further purified by pre-HPLC (instrument: PREP-HPLC-WI column: Phenomenex Luna C18 100*30 mm*30 um; mobile phase: water (0.225% FA)-ACN; begin B: 6%, end B: 56%, Gradient Time (8 min)) to give N-[2-[2-[[4-[[5-chloro-4-[6-[(4-cyanotetrahydropyran-4-yl)methylamino]-2-pyridyl]-2-pyridyl]amino]cyclohexyl]amino]propoxy]ethyl]-1,1-difluoro-methanesulfonamide (Compound 41, 50.5 mg, 62% yield, FA salt) as a light yellow solid. $^1$H NMR (400 MHz, CDCl$_3$): δ=8.37 (s, 1H), 8.06 (s, 1H), 7.53 (t, J=7.2 Hz, 1H), 6.97 (d, J=7.6 Hz, 1H), 6.60 (s, 1H), 6.52 (d, J=8.0 Hz, 1H), 6.20 (t, J=54.0 Hz, 1H), 4.92-4.90 (m, 1H), 4.00-3.96 (m, 2H), 3.77-3.61 (m, 10H), 3.46 (brs, 3H), 3.08-3.02 (m, 1H), 2.29-2.21 (m, 4H), 1.90 (d, J=13.6 Hz, 2H), 1.80-1.63 (m, 4H), 1.41 (d, J=6.8 Hz, 3H), 1.35-1.26 (m, 2H).

Example 28: Synthesis of 1-(2-oxopropoxy)-N-(2,2,2-trifluoroethyl)methanesulfonamide (Intermediate 14)

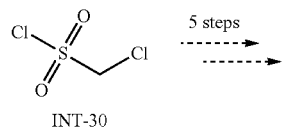

Chloromethanesulfonyl chloride (INT-30) is converted to 1-(2-oxopropoxy)-N-(2,2,2-trifluoroethyl)methanesulfonamide (Intermediate 14) in five synthetic steps.

Example 29: Synthesis of 1-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)-N-(2,2,2-trifluoroethyl)methanesulfonamide (Compound 43) and 1-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)-N-(2,2,2-trifluoroethyl)methanesulfonamide (Compound 44)

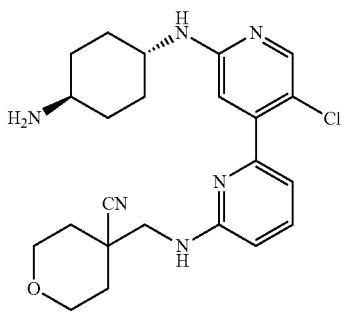

Intermediate 1

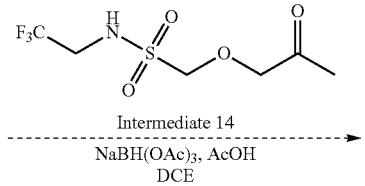

Intermediate 14

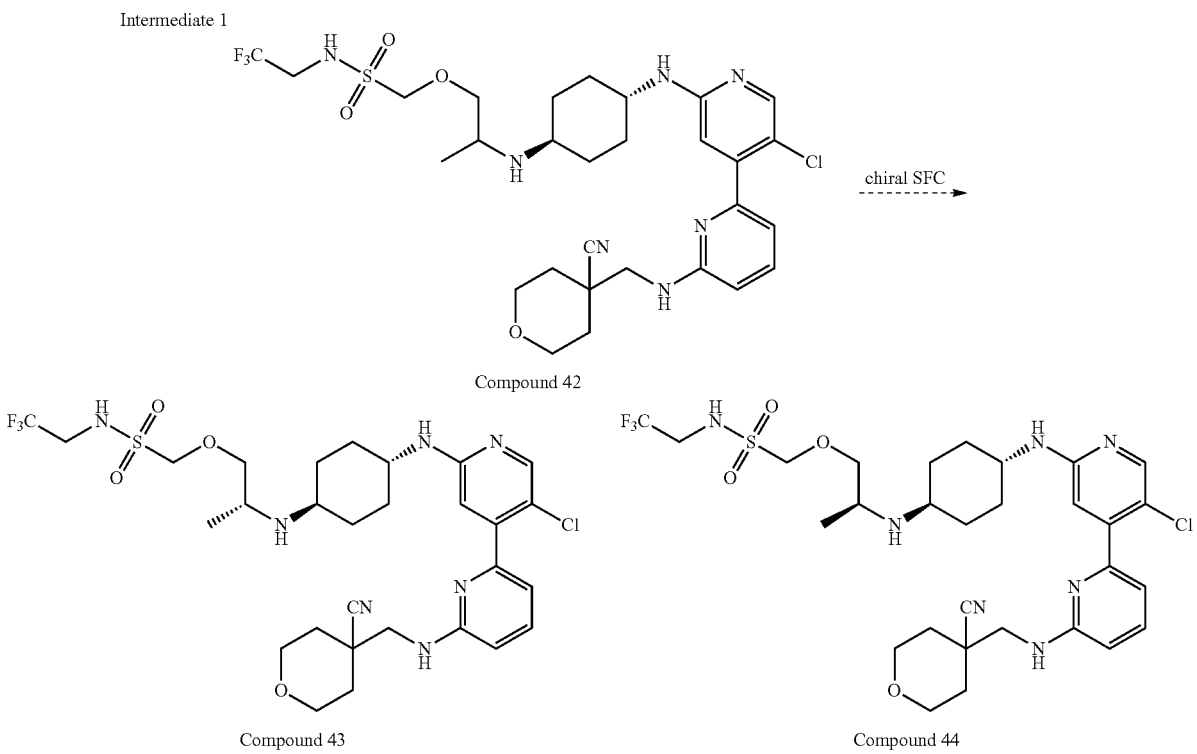

-continued

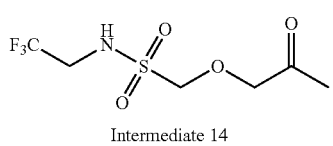

Intermediate 14

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and 1-(2-oxopropoxy)-N-(2,2,2-trifluoroethyl)methanesulfonamide (Intermediate 14) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford 1-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)-N-(2,2,2-trifluoroethyl)methanesulfonamide (Compound 42).

1-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)-N-(2,2,2-trifluoroethyl)methanesulfonamide (Compound 42) is separated by chiral SFC to afford 1-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)-N-(2,2,2-trifluoroethyl)methanesulfonamide (Compound 43) and 1-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)-N-(2,2,2-trifluoroethyl)methanesulfonamide (Compound 44).

Example 30: Synthesis of ethyl 1-(2-oxopropoxy)cyclopropane-1-carboxylate (Intermediate 15)

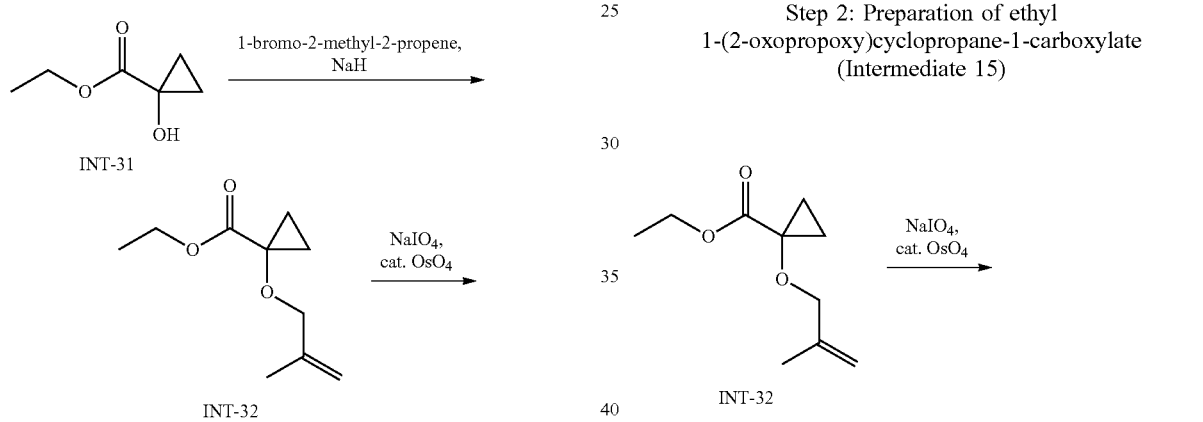

Step 1: Preparation of ethyl 1-((2-methylallyl)oxy)cyclopropane-1-carboxylate (INT-32)

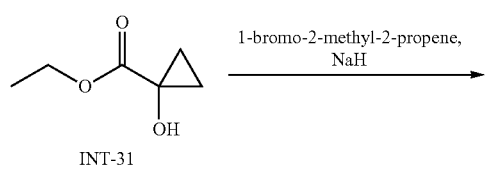

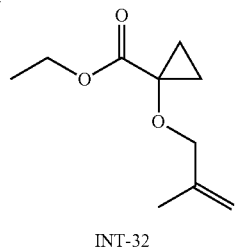

To a solution of ethyl 1-hydroxycyclopropane-1-carboxylate (INT-31) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na₂SO₄, filtered, and concentrated to provide ethyl 1-((2-methylallyl)oxy)cyclopropane-1-carboxylate (INT-32). The crude product is used directly in the next step without further purification.

Step 2: Preparation of ethyl 1-(2-oxopropoxy)cyclopropane-1-carboxylate (Intermediate 15)

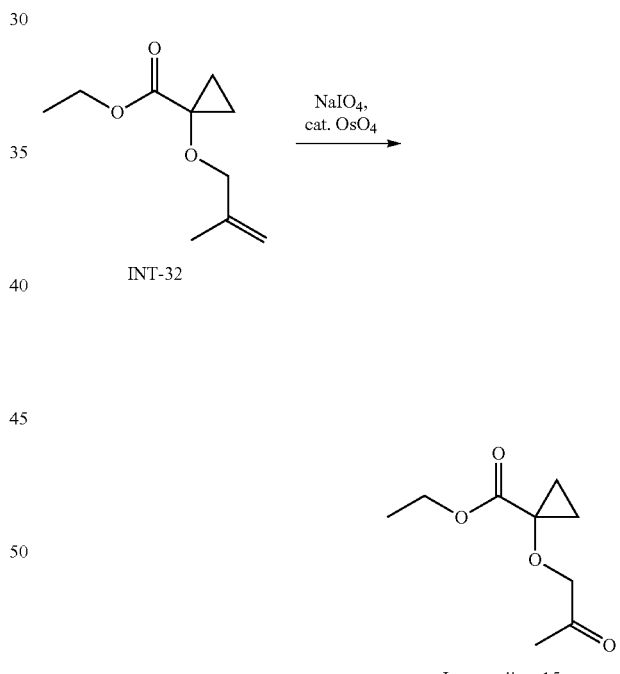

To a solution of ethyl 1-((2-methylallyl)oxy)cyclopropane-1-carboxylate (INT-32) in THF and H₂O is added K₂OsO₄·2H₂O and NaIO₄. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford ethyl 1-(2-oxopropoxy)cyclopropane-1-carboxylate (Intermediate 15).

Example 31: Synthesis of ethyl 1-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 46) and ethyl 1-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 47)
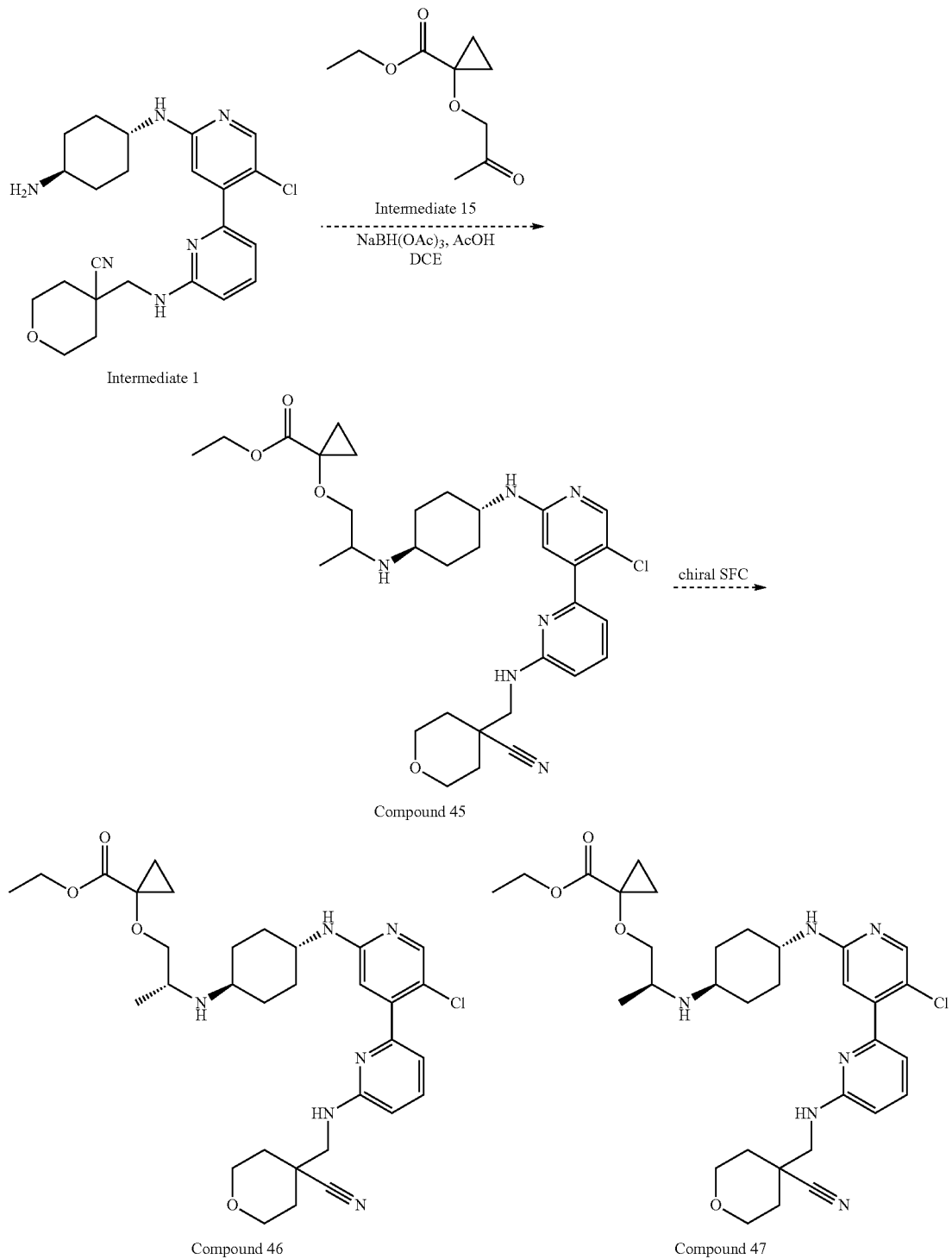

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and ethyl 1-(2-oxopropoxy)cyclopropane-1-carboxylate (Intermediate 15) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford ethyl 1-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 45).

Ethyl 1-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 45) is separated by chiral SFC to afford ethyl 1-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 46) and ethyl 1-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 47).

Example 32: Synthesis of ethyl 2-methyl-2-(2-oxopropoxy)propanoate (Intermediate 16)

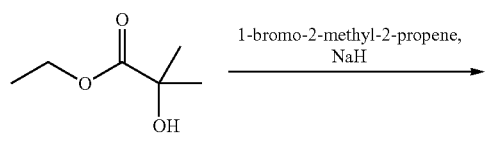

INT-33

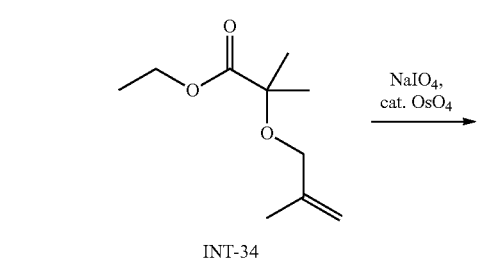

INT-34

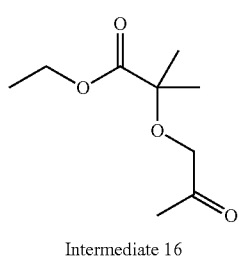

Intermediate 16

Step 1: Preparation of ethyl 2-methyl-2-((2-methylallyl)oxy)propanoate (INT-34)

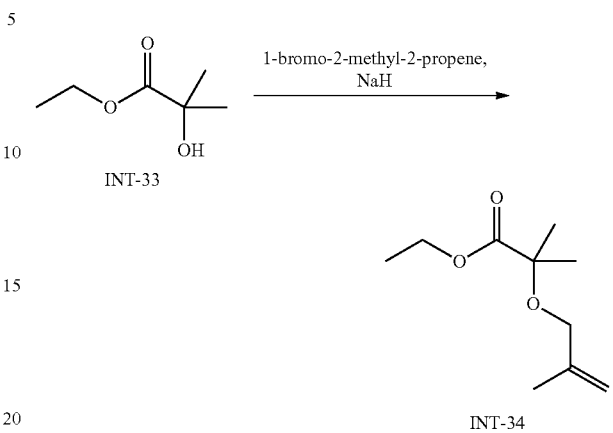

To a solution of ethyl 2-hydroxy-2-methylpropanoate (INT-33) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na₂SO₄, filtered, and concentrated to provide ethyl 2-methyl-2-((2-methylallyl)oxy)propanoate (INT-34). The crude product is used directly in the next step without further purification.

Step 2: Preparation of ethyl 2-methyl-2-(2-oxopropoxy)propanoate (Intermediate 16)

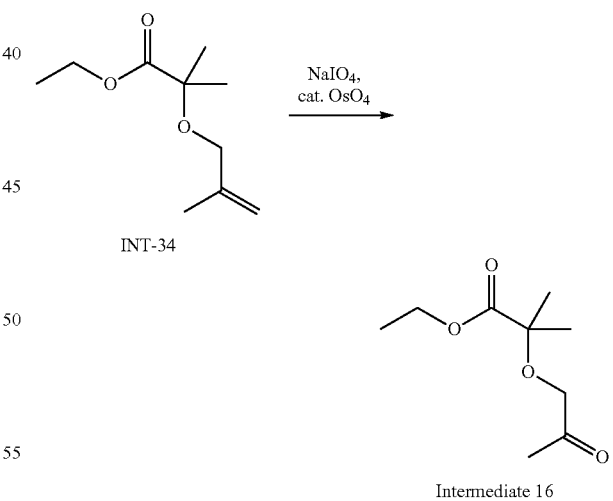

To a solution of ethyl 2-methyl-2-((2-methylallyl)oxy)propanoate (INT-34) in THF and H₂O is added K₂OsO₄·2H₂O and NaIO₄. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford ethyl 2-methyl-2-(2-oxopropoxy)propanoate (Intermediate 16).

Example 33: Synthesis of ethyl 2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 49) and ethyl 2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 50)
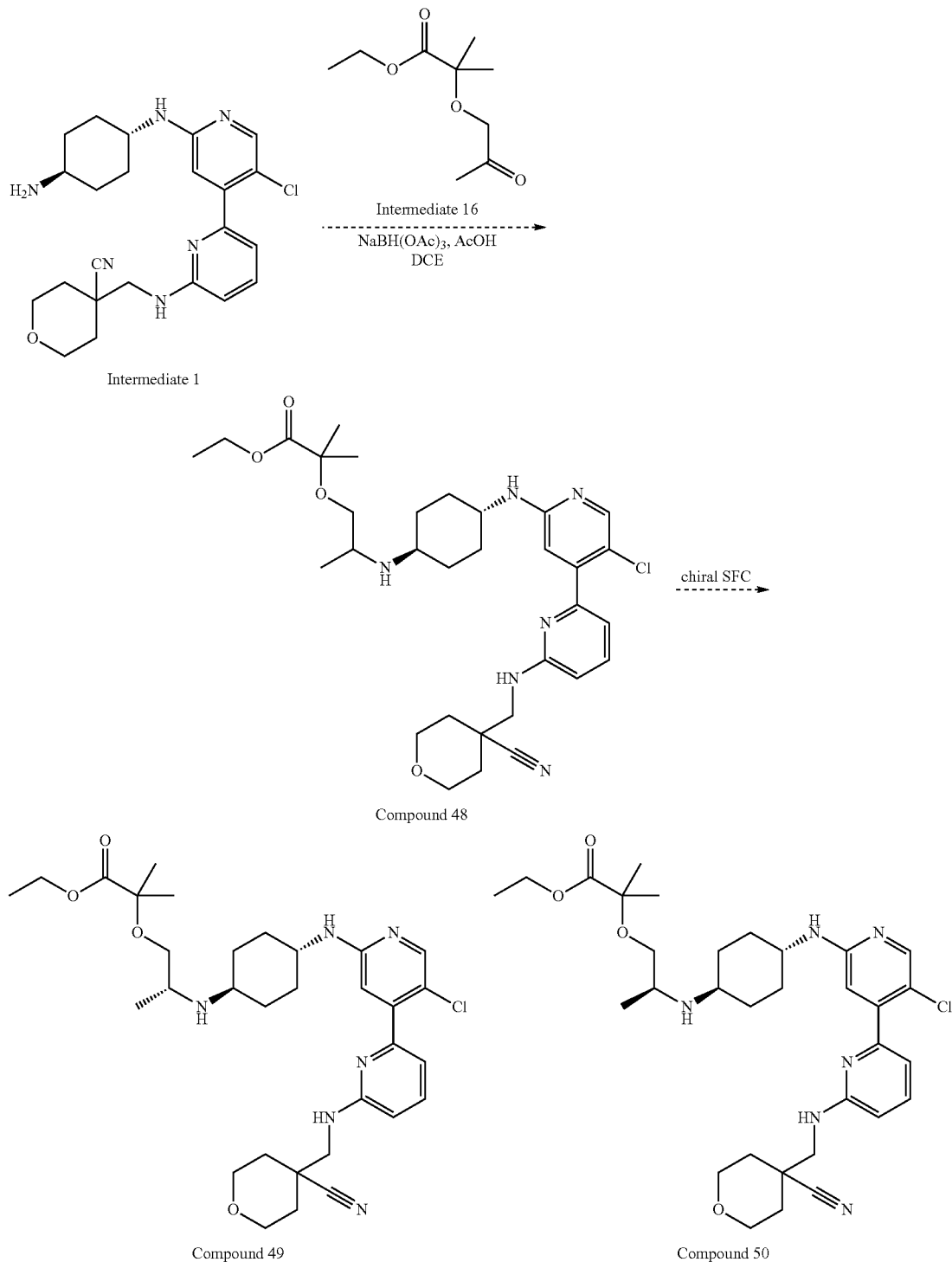

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and ethyl 2-methyl-2-(2-oxopropoxy)propanoate (Intermediate 16) in DCE is added HOAc and NaBH(OAc)$_3$. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford ethyl 2-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 48).

Ethyl 2-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 48) is separated by chiral SFC to afford ethyl 2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 49) and ethyl 2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 50).

Example 34: Synthesis of ethyl (R)-2-(2-oxopropoxy)propanoate (Intermediate 17)

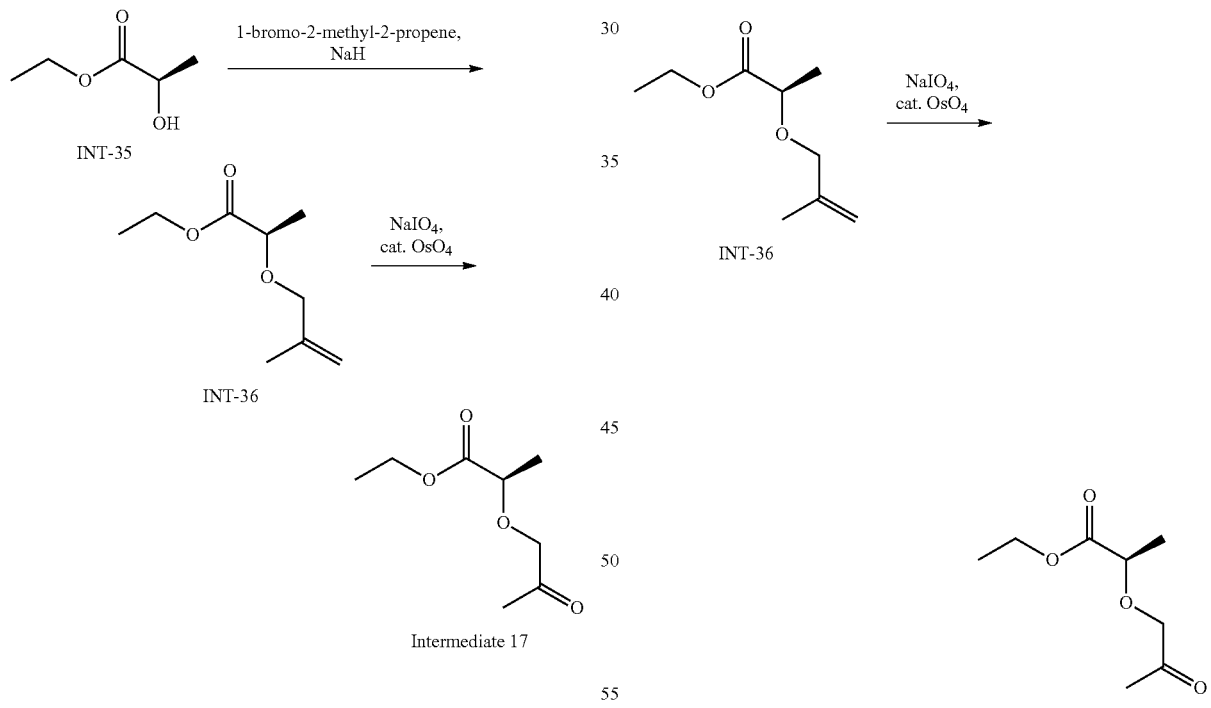

Step 1: Preparation of ethyl (R)-2-((2-methylallyl)oxy)propanoate (INT-36)

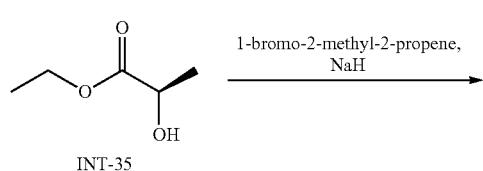

To a solution of ethyl (R)-2-hydroxypropanoate (INT-35) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na$_2$SO$_4$, filtered, and concentrated to provide ethyl (R)-2-((2-methylallyl)oxy)propanoate (INT-36). The crude product is used directly in the next step without further purification.

Step 2: Preparation of ethyl (R)-2-(2-oxopropoxy)propanoate (Intermediate 17)

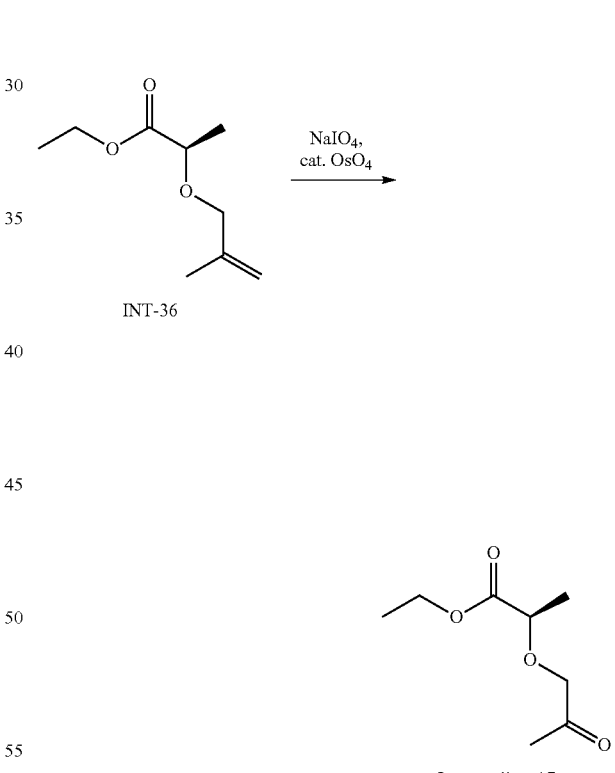

To a solution of ethyl (R)-2-((2-methylallyl)oxy)propanoate (INT-36) in THF and H$_2$O is added K$_2$OsO$_4$.2H$_2$O and NaIO$_4$. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford ethyl (R)-2-(2-oxopropoxy)propanoate (Intermediate 17).

Example 35: Synthesis of ethyl (R)-2-((R)-2-(((1r,4R)-4-((5'-chloro-6-((((4-cyanotetrahydro-2H-pyran-4-yl)methyl)amino)-[2,4'-bipyridin]-2'-yl)amino)cyclohexyl)amino)propoxy)propanoate (Compound 52) and ethyl (R)-2-((S)-2-(((1r,4S)-4-((5'-chloro-6-((((4-cyanotetrahydro-2H-pyran-4-yl)methyl)amino)-[2,4'-bipyridin]-2'-yl)amino)cyclohexyl)amino)propoxy)propanoate (Compound 53)
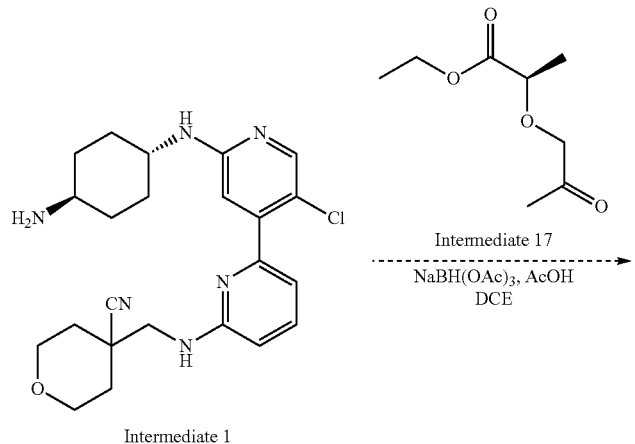
Intermediate 1
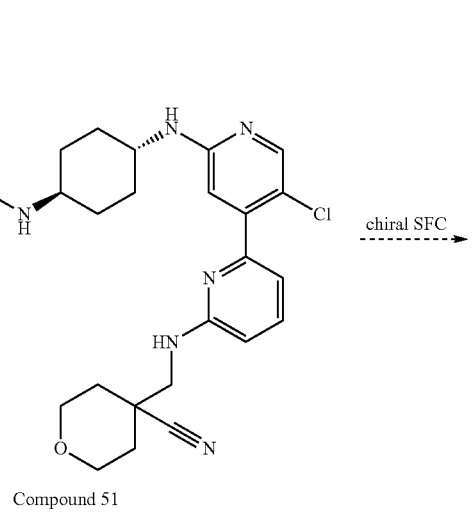
Compound 51
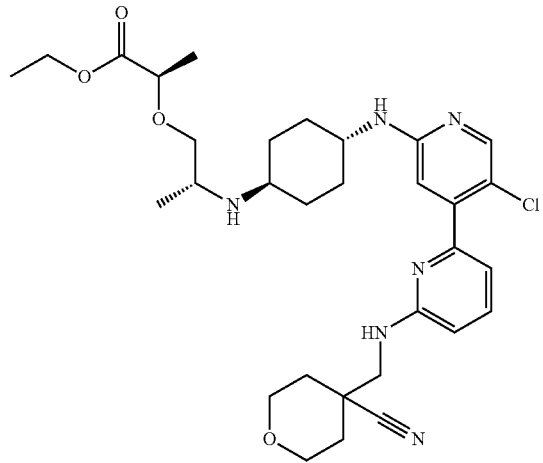
Compound 52
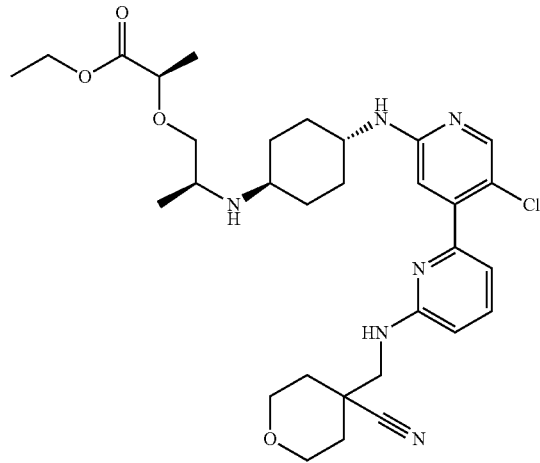
Compound 53

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and ethyl (R)-2-(2-oxopropoxy)propanoate (Intermediate 17) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford ethyl (2R)-2-(2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 51).

Ethyl (2R)-2-(2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 51) is separated by chiral SFC to afford ethyl (R)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 52) and ethyl (R)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 53).

Example 36: Synthesis of ethyl (S)-2-(2-oxopropoxy)propanoate (Intermediate 18)

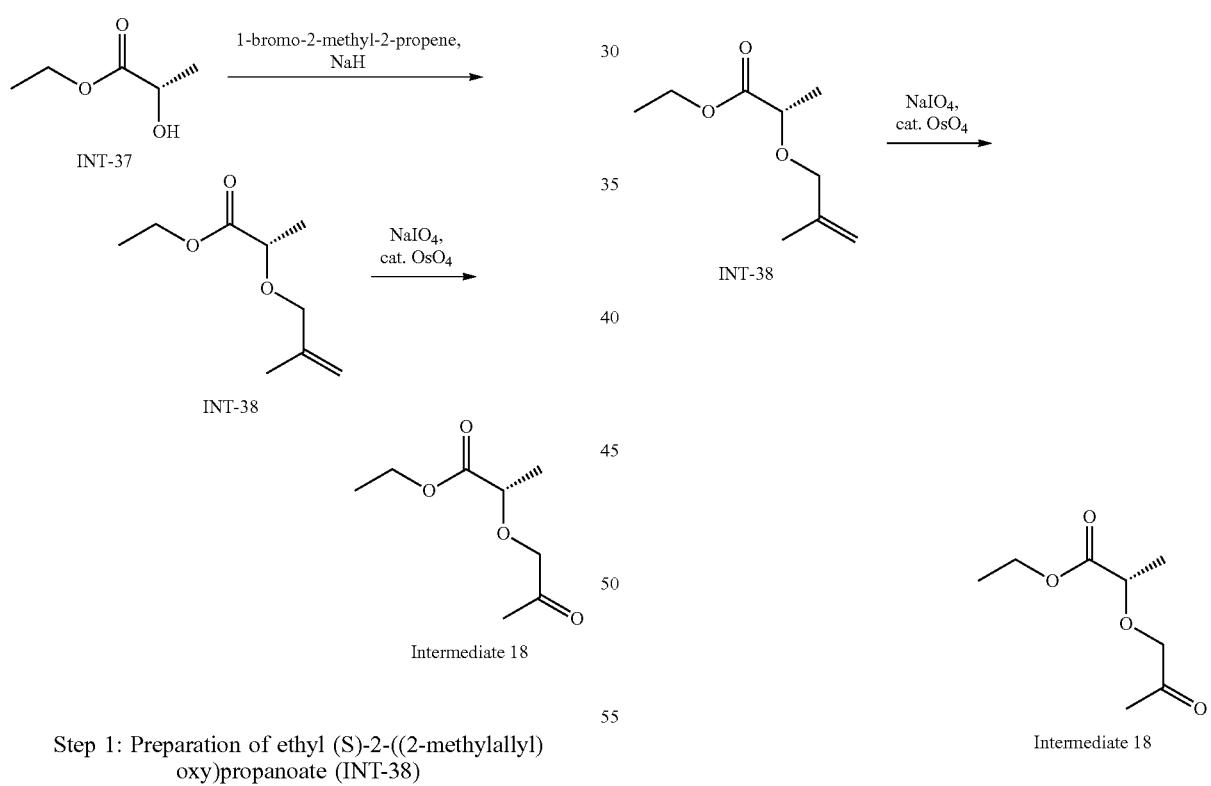

Step 1: Preparation of ethyl (S)-2-((2-methylallyl)oxy)propanoate (INT-38)

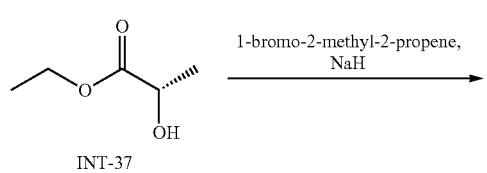

To a solution of ethyl (S)-2-hydroxypropanoate (INT-37) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na₂SO₄, filtered, and concentrated to provide ethyl (S)-2-((2-methylallyl)oxy)propanoate (INT-38). The crude product is used directly in the next step without further purification.

Step 2: Preparation of ethyl (S)-2-(2-oxopropoxy)propanoate (Intermediate 18)

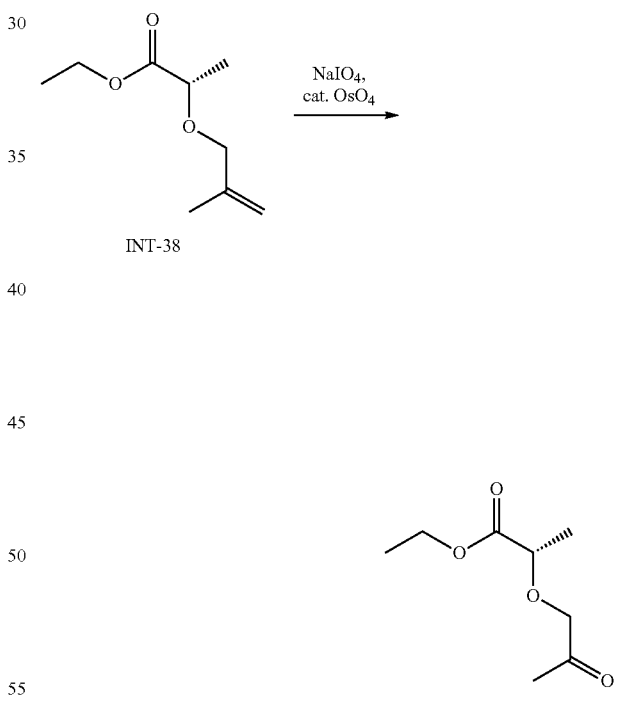

To a solution of ethyl (S)-2-((2-methylallyl)oxy)propanoate (INT-38) in THF and H₂O is added K₂OsO₄·2H₂O and NaIO₄. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford ethyl (S)-2-(2-oxopropoxy)propanoate (Intermediate 18).

Example 37: Synthesis of ethyl (S)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 55) and ethyl (S)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 56)
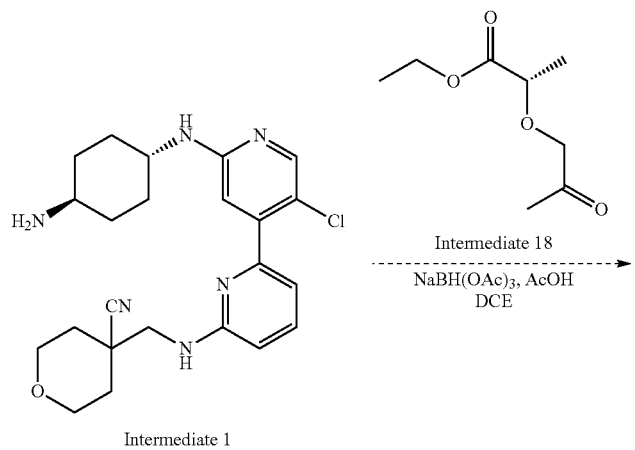
Intermediate 1
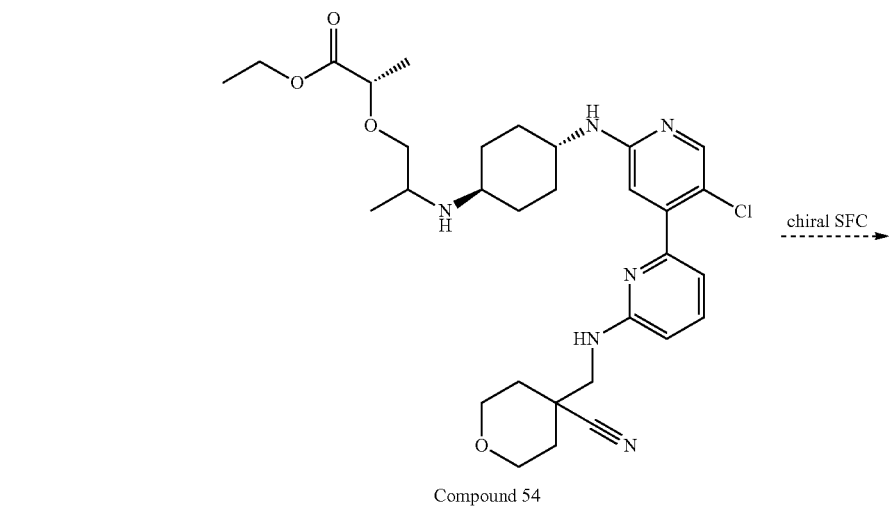
Compound 54
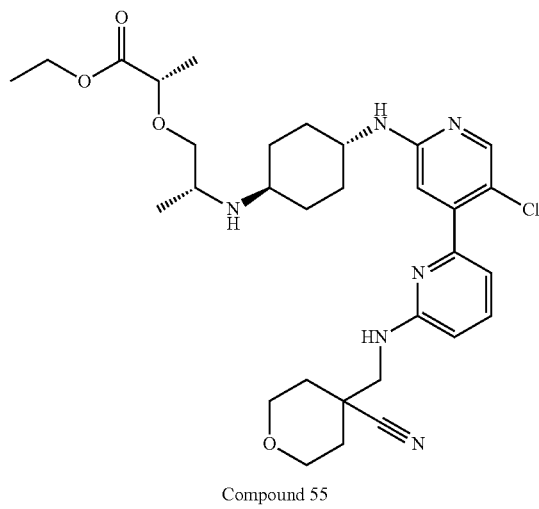
Compound 55      Compound 56

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and ethyl (S)-2-(2-oxopropoxy)propanoate (Intermediate 18) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford ethyl (2S)-2-(2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 54).

Ethyl (2S)-2-(2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 54) is separated by chiral SFC to afford ethyl (S)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 55) and ethyl (S)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 56).

Example 38: Synthesis of 1-((6-nitropyridin-2-yl)methoxy)propan-2-one (Intermediate 19)

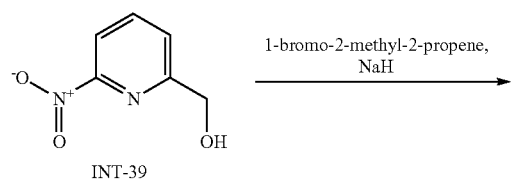

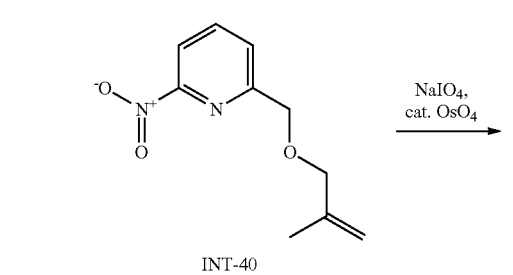

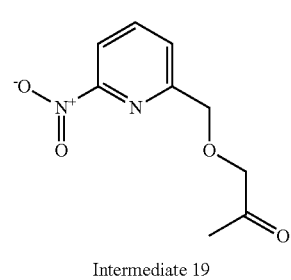

Intermediate 19

Step 1: Preparation of 2-(((2-methylallyl)oxy)methyl)-6-nitropyridine (INT-40)

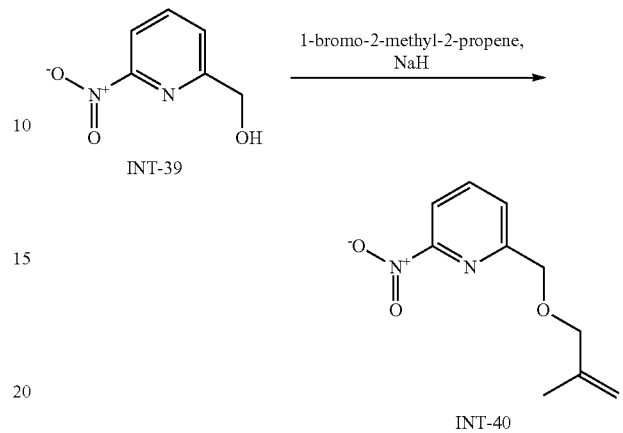

To a solution of (6-nitropyridin-2-yl)methanol (INT-39) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na₂SO₄, filtered, and concentrated to provide 2-(((2-methylallyl)oxy)methyl)-6-nitropyridine (INT-40). The crude product is used directly in the next step without further purification.

Step 2: Preparation of ethyl (S)-2-(2-oxopropoxy)propanoate (Intermediate 19)

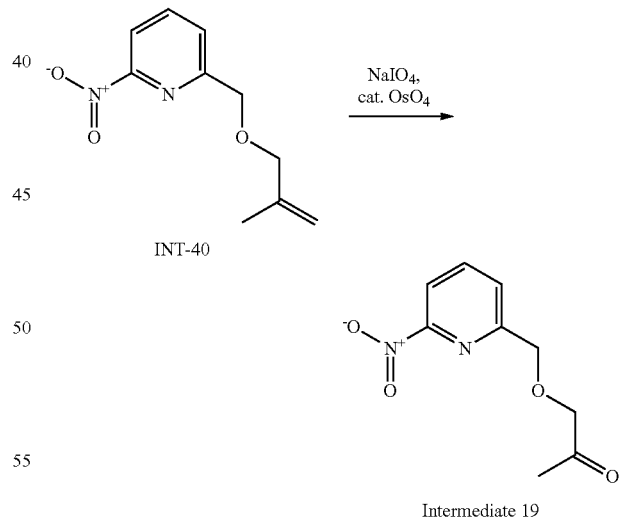

Intermediate 19

To a solution of 2-(((2-methylallyl)oxy)methyl)-6-nitropyridine (INT-40) in THF and H₂O is added K₂OsO₄·2H₂O and NaIO₄. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford ethyl (S)-2-(2-oxopropoxy)propanoate (Intermediate 19).

Example 39: Synthesis of N-(6-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)pyridin-2-yl)methanesulfonamide (Compound 58) and N-(6-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)pyridin-2-yl)methanesulfonamide (Compound 59)
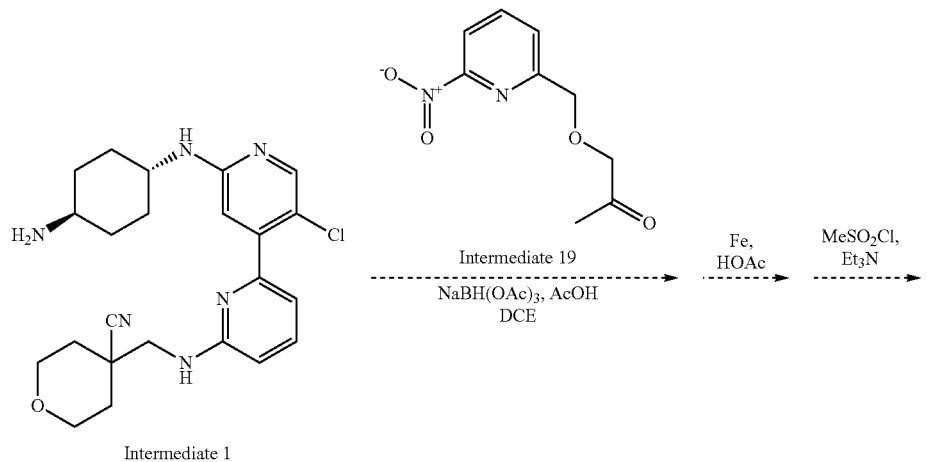
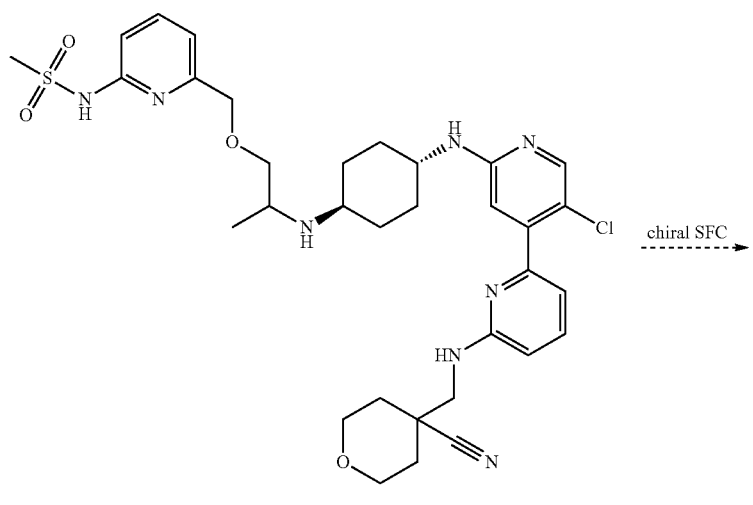
Compound 57

-continued

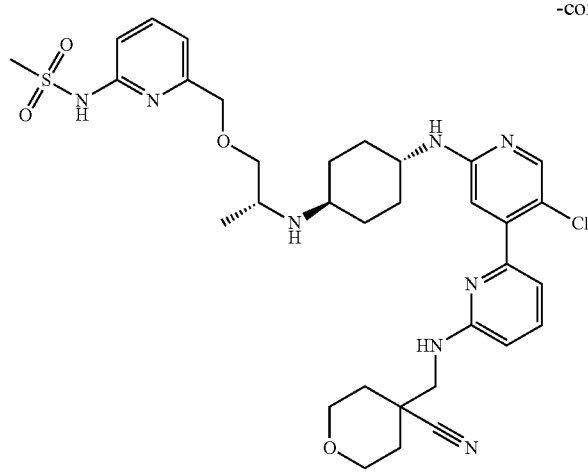

Compound 58

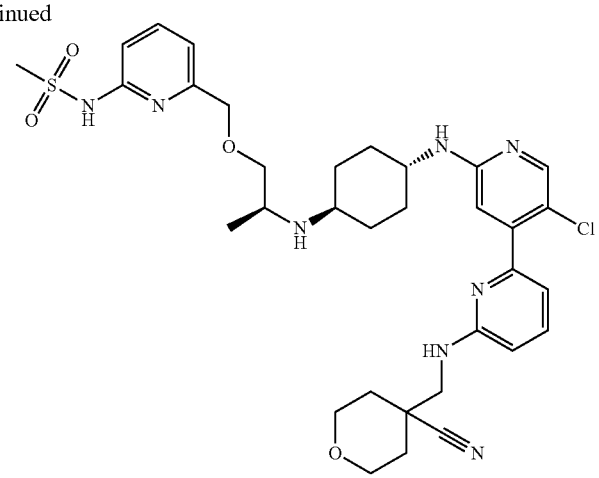

Compound 59

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and ethyl (S)-2-(2-oxopropoxy)propanoate (Intermediate 19) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC, reduced with iron and acetic acid, and mesylated with methanesulfonyl chloride and triethylamine to afford N-(6-((2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)pyridin-2-yl)methanesulfonamide (Compound 57).

N-(6-((2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)pyridin-2-yl)methanesulfonamide (Compound 57) is separated by chiral SFC to afford N-(6-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)pyridin-2-yl)methanesulfonamide (Compound 58) and N-(6-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)pyridin-2-yl)methanesulfonamide (Compound 59).

Example 40: Synthesis of ethyl (R)-3-(((1r,4R)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 61) and ethyl (S)-3-(((1r,4S)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 62)

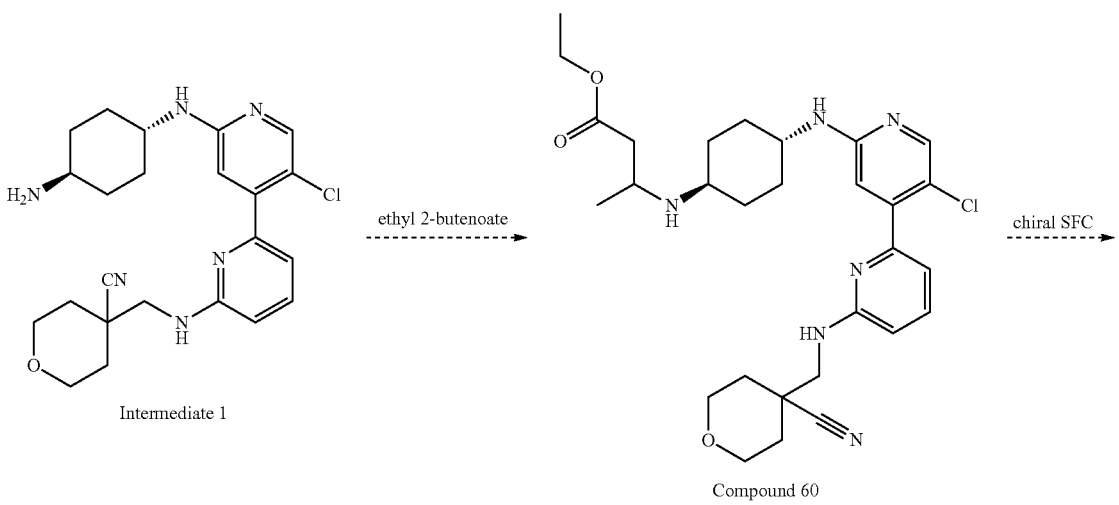

Compound 60

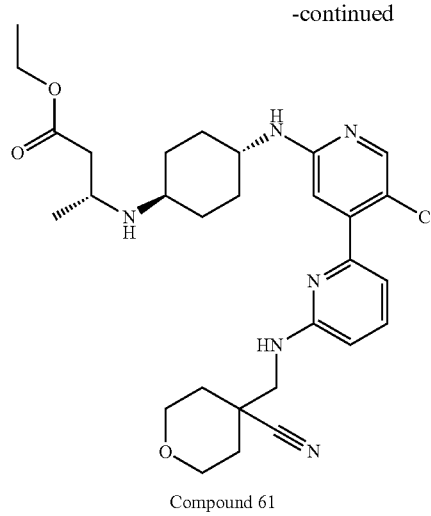

Compound 61

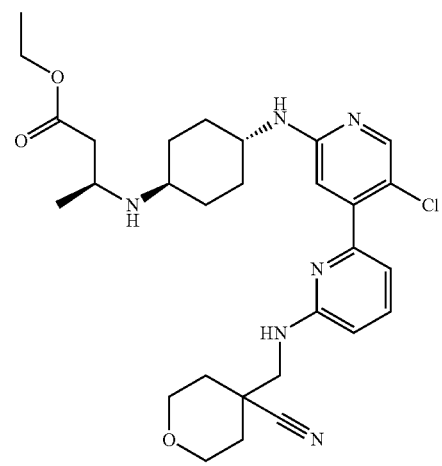

Compound 62

4-[[[6-[2-[(4-aminocyclohexyl)amino]-5-chloro-4-pyridyl]-2-pyridyl]amino]methyl]tetrahydropyran-4-carbonitrile (Intermediate 1) is treated with ethyl 2-butenoate to afford ethyl 3-(((1r,4r)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 60).

Ethyl 3-(((1r,4r)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 60) is separated by chiral SFC to afford ethyl (R)-3-(((1r,4R)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 61) and ethyl (S)-3-(((1r,4S)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 62).

Example 41: Synthesis of tert-butyl (R)-3-(((1r,4R)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 64) and tert-butyl (S)-3-(((1r,4S)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 65)

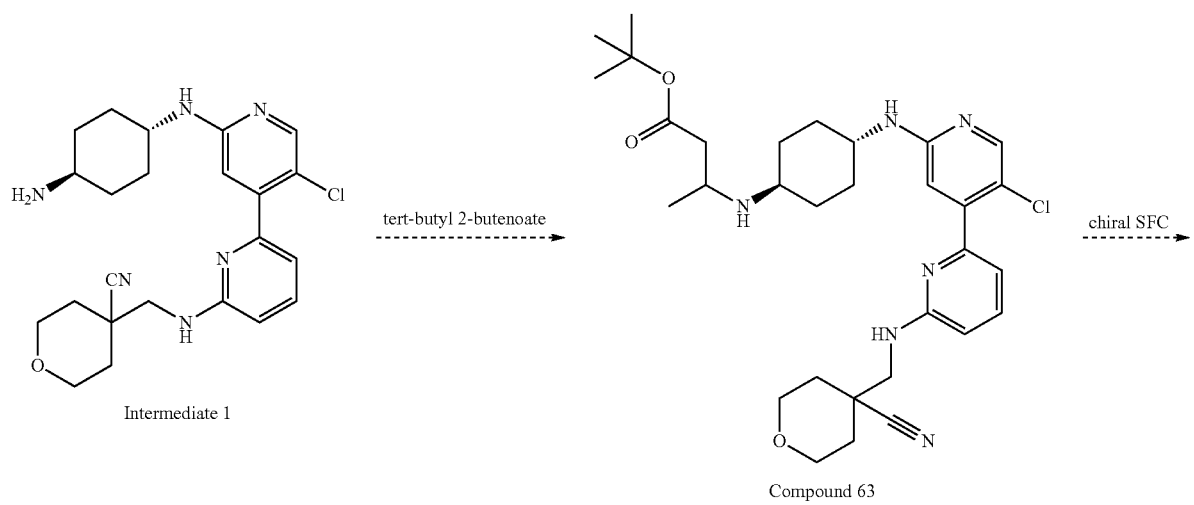

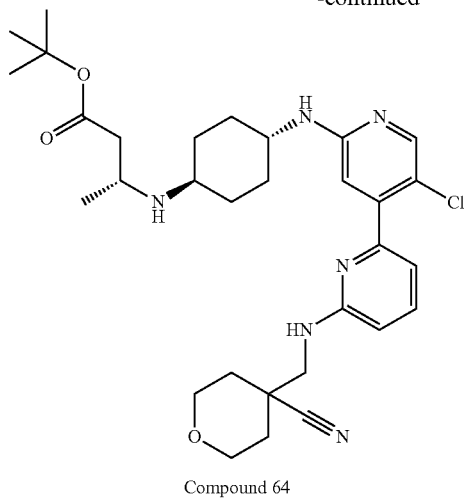

Compound 64

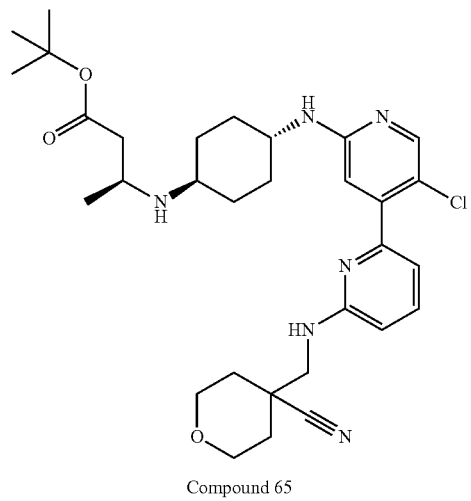

Compound 65

4-[[[6-[2-[(4-aminocyclohexyl)amino]-5-chloro-4-pyridyl]-2-pyridyl]amino]methyl]tetrahydropyran-4-carbonitrile (Intermediate 1) is treated with tert-butyl 2-butenoate to afford tert-butyl 3-(((1r,4r)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 63).

tert-butyl 3-(((1r,4r)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 63) is separated by chiral SFC to afford tert-butyl (R)-3-(((1r,4R)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 64) and tert-butyl (S)-3-(((1r,4S)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 65).

Example 42: Synthesis of (R)-3-(((1r,4R)-4-((5'-chloro-6-(((4-cyanotetrahydro-2H-pyran-4-yl)methyl)amino)-[2,4'-bipyridin]-2'-yl)amino)cyclohexyl)amino)butanoic acid (Compound 66)

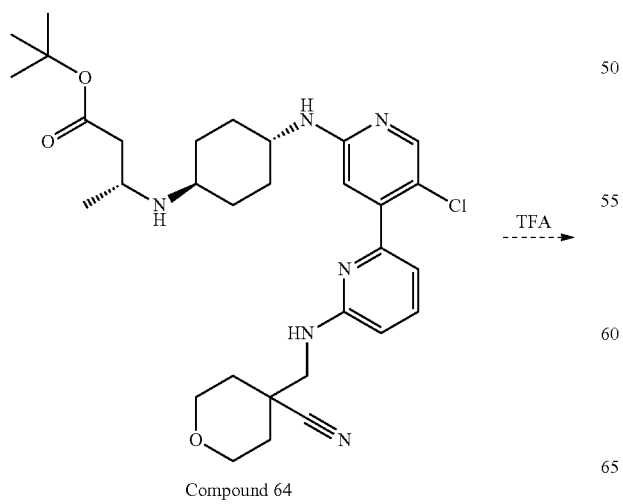

Compound 64

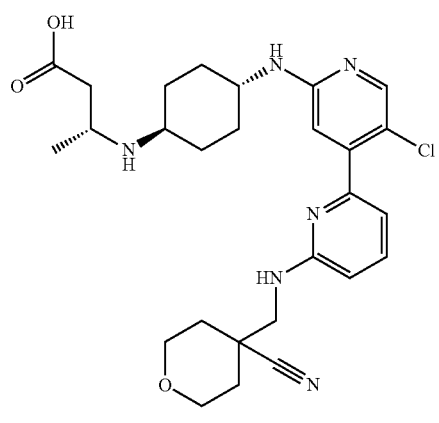

Compound 66 tert-butyl (R)-3-(((1R,4R)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 64) is treated with trifluoroacetic acid to afford (R)-3-(((1r,4R)-4-((5'-chloro-6-(((4-cyanotetrahydro-2H-pyran-4-yl)methyl)amino)-[2,4'-bipyridin]-2'-yl)amino)cyclohexyl)amino)butanoic acid (Compound 66).

Example 43: Synthesis of (S)-3-(((1r,4S)-4-((5'-chloro-6-(((4-cyanotetrahydro-2H-pyran-4-yl)methyl)amino)-[2,4'-bipyridin]-2'-yl)amino)cyclohexyl)amino)butanoic acid (Compound 67)

tert-butyl (S)-3-(((1R,4S)-4-((5'-chloro-6-(((4-cyanotetrahydro-2H-pyran-4-yl)methyl)amino)-[2,4'-bipyridin]-2'-yl)amino)cyclohexyl)amino)butanoate (Compound 65) is treated with trifluoroacetic acid to afford (S)-3-(((1r,4S)-4-((5'-chloro-6-(((4-cyanotetrahydro-2H-pyran-4-yl)methyl)amino)-[2,4'-bipyridin]-2'-yl)amino)cyclohexyl)amino)butanoic acid (Compound 67).

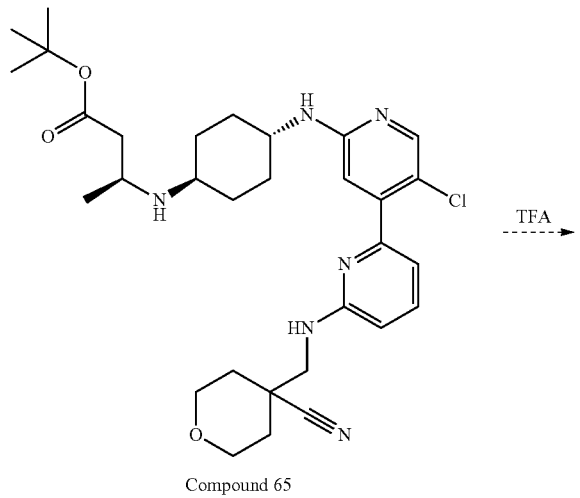

Example 44: Synthesis of (R)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)-2-methylpropyl pivalate (Compound 68), (S)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)-2-methylpropyl pivalate (Compound 69), 4-(((5'-chloro-2'-(((1R,4r)-4-(((R)-1-((R)-1-((3,3-dimethylbut-1-en-2-yl)oxy)-2-methylpropyl)-1H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 70), and (S)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-1H-tetrazol-1-yl)-2-methylpropyl pivalate (Compound 71)

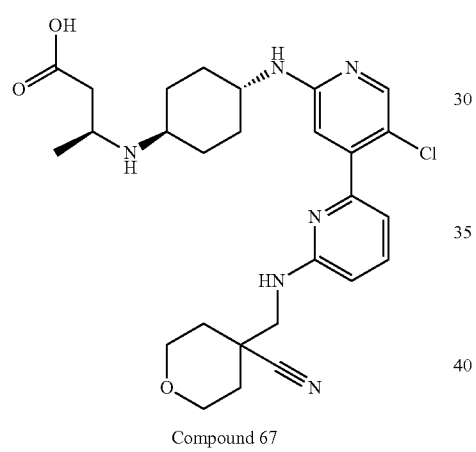

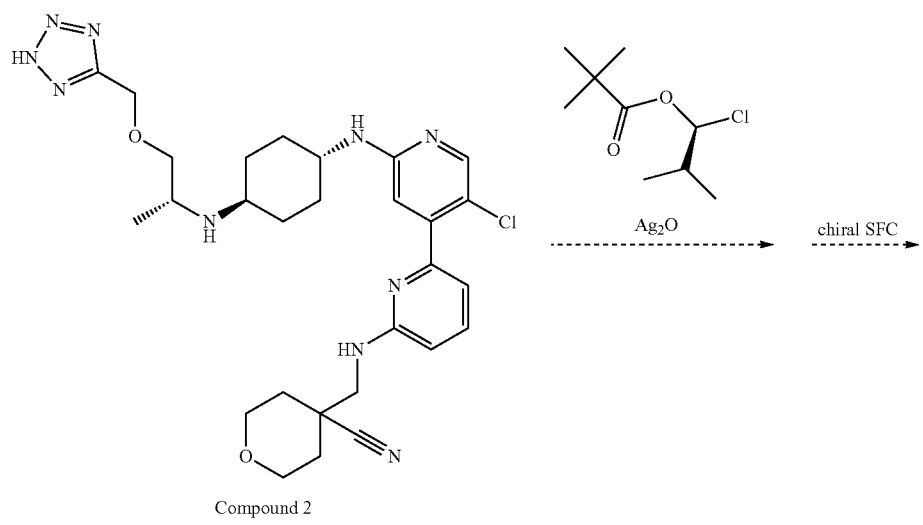

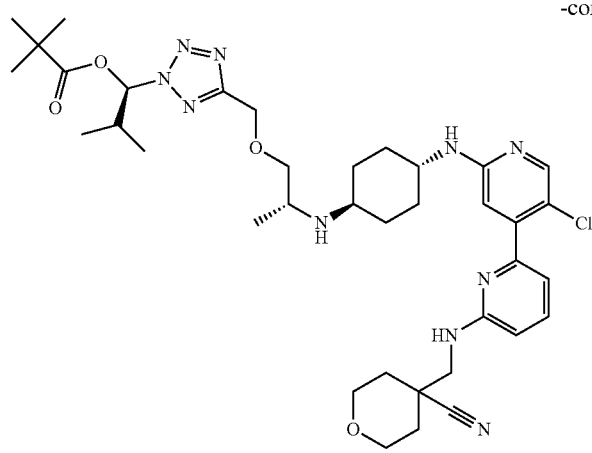

Compound 68

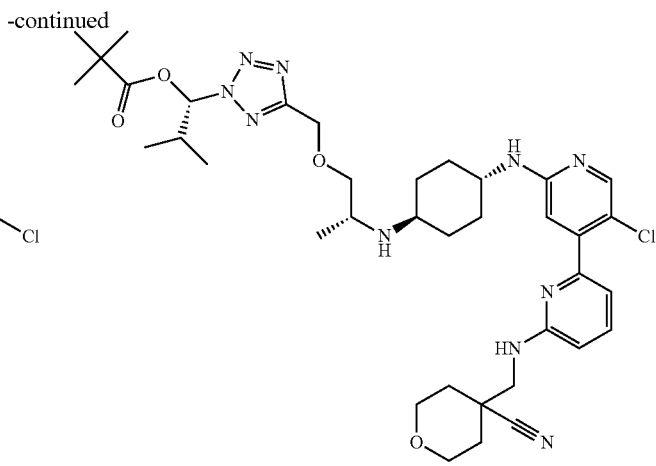

Compound 69

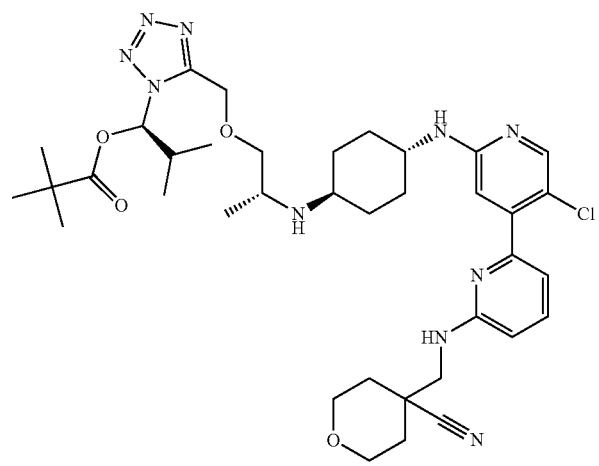

Compound 70

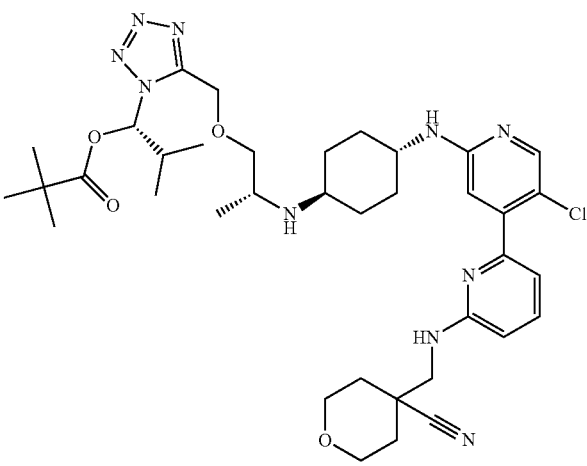

Compound 71

4-(((2'-(((1R,4r)-4-(((R)-1-((2H-tetrazol-5-yl)methoxy)propan-2-yl)amino)cyclohexyl)amino)-5'-chloro-[2,4'-bipyridin]-6-yl)amino)methyl)tetrahydro-2H-pyran-4-carbonitrile (Compound 2) is treated with (S)-1-chloro-2-methylpropyl pivalate and A920 and separated by chiral SFC to afford (R)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)-2-methylpropyl pivalate (Compound 68), (S)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)-2-methylpropyl pivalate (Compound 69), 4-(((5'-chloro-2'-(((1R,4r)-4-(((R)-1-((1-((R)-1-((3,3-dimethylbut-1-en-2-yl)oxy)-2-methylpropyl)-1H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 70), and (S)-1-(5-(((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-1H-tetrazol-1-yl)-2-methylpropyl pivalate (Compound 71).

Example 45: Synthesis of (R)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)-2-methylpropyl pivalate (Compound 72), (S)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)-2-methylpropyl pivalate (Compound 73), 4-(((5'-chloro-2'-(((1S,4r)-4-(((S)-1-((1-((R)-1-((3,3-dimethylbut-1-en-2-yl)oxy)-2-methylpropyl)-1H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 74), and (S)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-1H-tetrazol-1-yl)-2-methylpropyl pivalate (Compound 75)

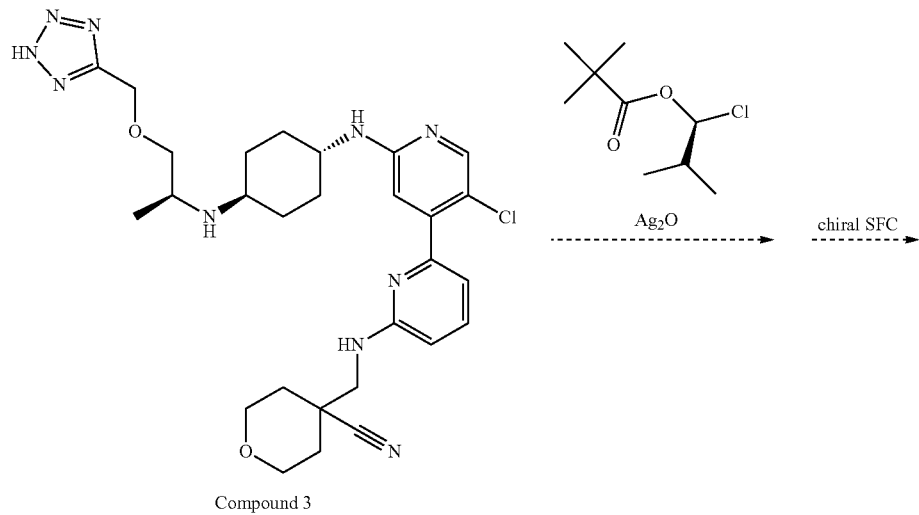

Compound 3

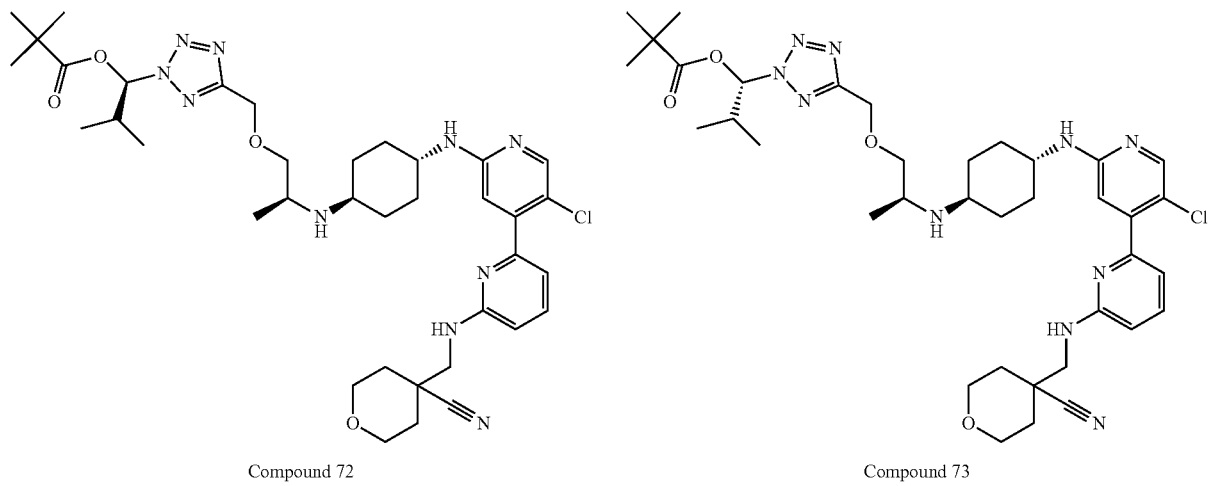

Compound 72

Compound 73

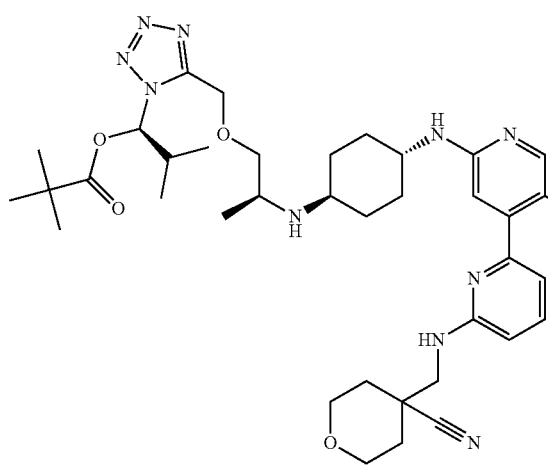

Compound 74

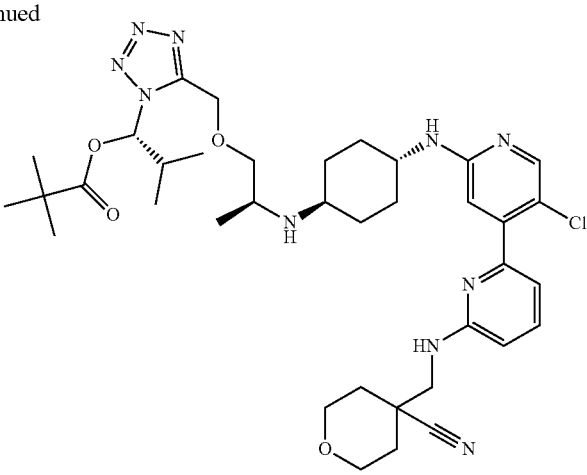

Compound 75

4-(((2'-(((1S,4r)-4-(((S)-1-((2H-tetrazol-5-yl)methoxy)propan-2-yl)amino)cyclohexyl)amino)-5'-chloro-[2,4'-bipyridin]-6-yl)amino)methyl)tetrahydro-2H-pyran-4-carbonitrile (Compound 3) is treated with (S)-1-chloro-2-methylpropyl pivalate and Ag$_2$O and separated by chiral SFC to afford (R)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)-2-methylpropyl pivalate (Compound 72), (S)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-2H-tetrazol-2-yl)-2-methylpropyl pivalate (Compound 73), 4-(((5'-chloro-2'-(((1S,4r)-4-(((S)-1-((1-((R)-1-((3,3-dimethylbut-1-en-2-yl)oxy)-2-methylpropyl)-1H-tetrazol-5-yl)methoxy)propan-2-yl)amino)cyclohexyl)amino)-[2,4'-bipyridin]-6-yl)amino)methyl)tetrahydro-2H-pyran-4-carbonitrile (Compound 74), and (S)-1-(5-(((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)methyl)-1H-tetrazol-1-yl)-2-methylpropyl pivalate (Compound 75).

Example 46: Synthesis of 1-((4-methoxypyrimidin-2-yl)methoxy)propan-2-one (Intermediate 20)

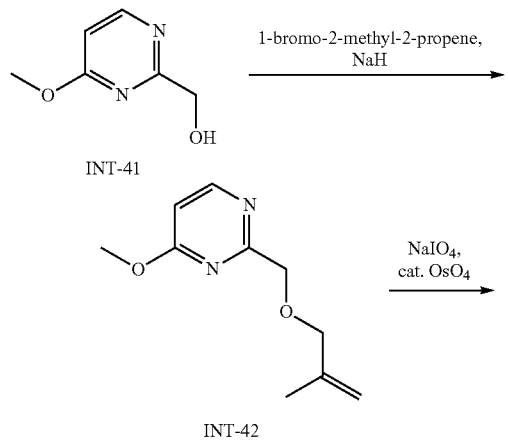

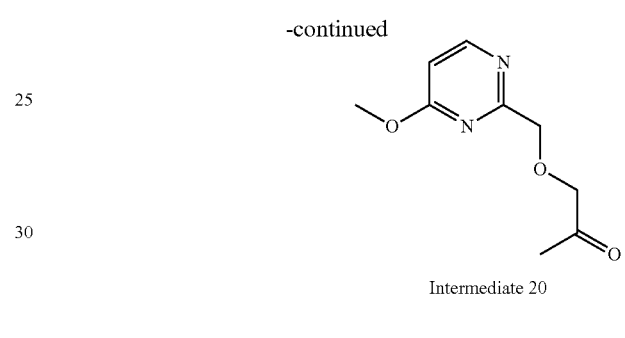

Intermediate 20

Step 1: Preparation of 4-methoxy-2-(((2-methylallyl)oxy)methyl)pyrimidine (INT-42)

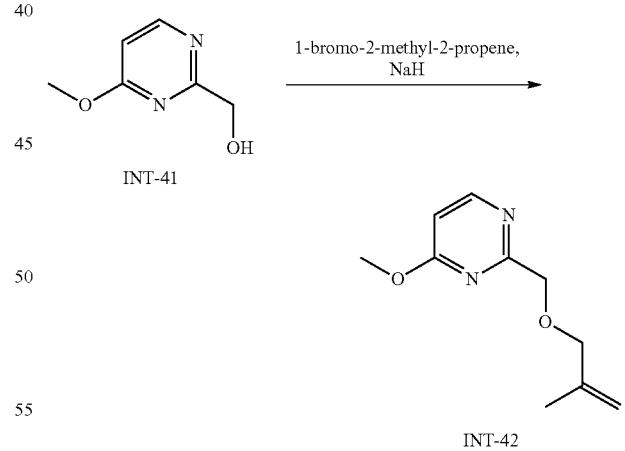

To a solution of (4-methoxypyrimidin-2-yl)methanol (INT-41) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na$_2$SO$_4$, filtered, and concentrated to provide 4-methoxy-2-(((2-methylallyl)oxy)methyl)pyrimidine (INT-42). The crude product is used directly in the next step without further purification.

Step 2: Preparation of 1-((4-methoxypyrimidin-2-yl)methoxy)propan-2-one (Intermediate 20)

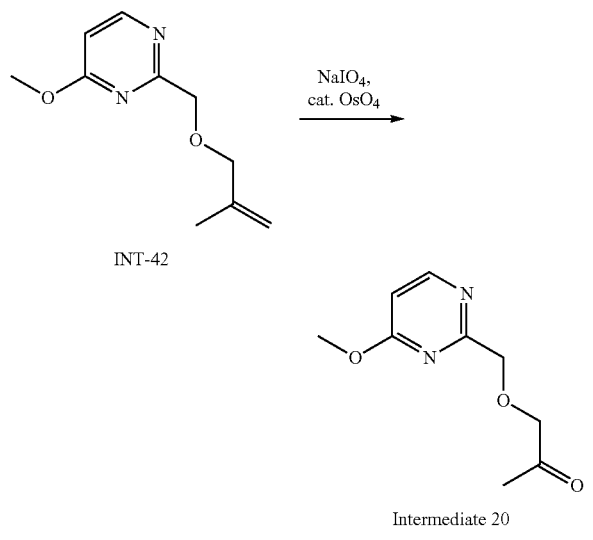

To a solution of 4-methoxy-2-(((2-methylallyl)oxy)methyl)pyrimidine (INT-42) in THF and H$_2$O is added K$_2$OsO$_4$.2H$_2$O and NaIO$_4$. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford 1-((4-methoxypyrimidin-2-yl)methoxy)propan-2-one (Intermediate 20).

Example 47: Synthesis of 4-(((5'-chloro-2'-(((1R,4r)-4-(((R)-1-((5-fluoro-6-oxo-1,6-dihydropyrimidin-2-yl)methoxy)propan-2-yl)amino)cyclohexyl)amino)-[2,4'-bipyridin]-6-yl)amino)methyl)tetrahydro-2H-pyran-4-carbonitrile (Compound 77) and 4-(((5'-chloro-2'-(((1S,4r)-4-(((S)-1-((5-fluoro-6-oxo-1,6-dihydropyrimidin-2-yl)methoxy)propan-2-yl)amino)cyclohexyl)amino)-[2,4'-bipyridin]-6-yl)amino)methyl)tetrahydro-2H-pyran-4-carbonitrile (Compound 78)

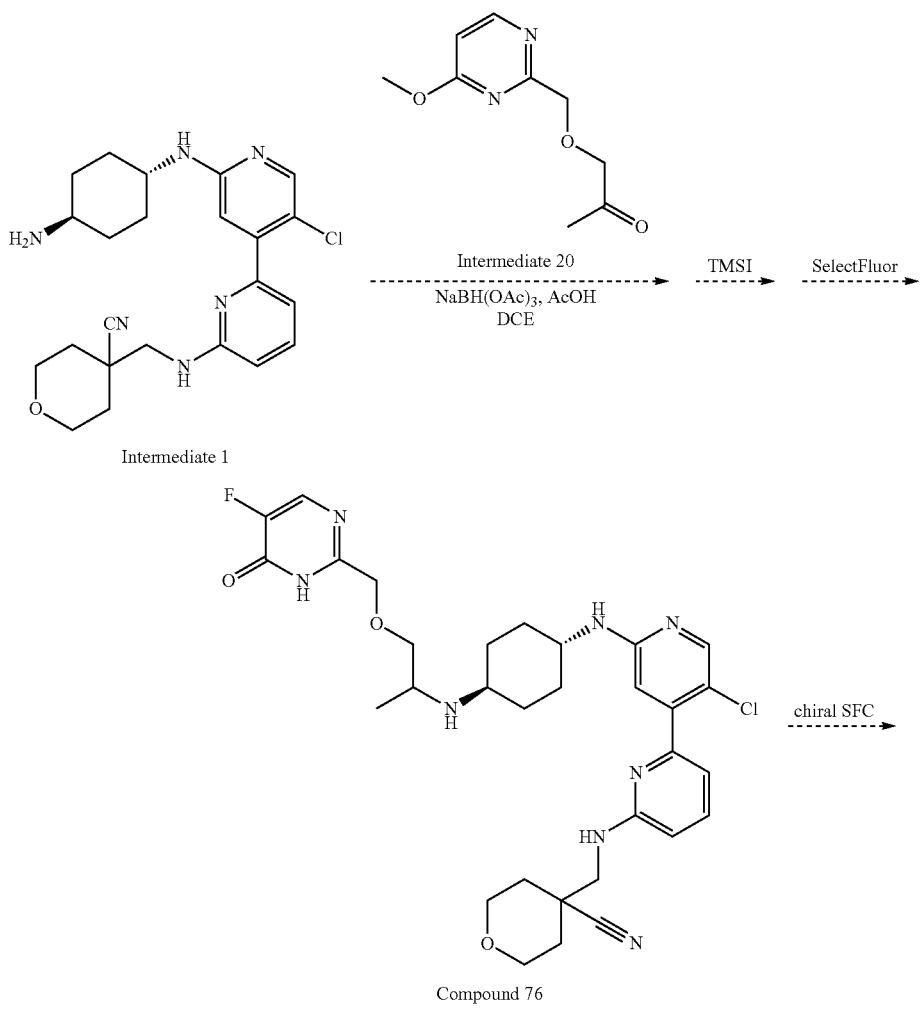

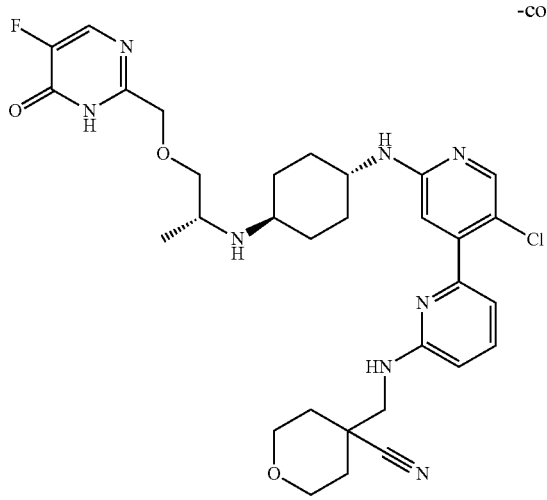

Compound 77

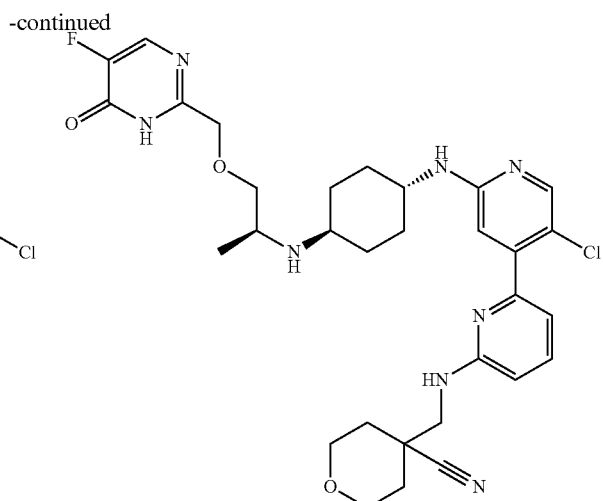

Compound 78

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and 1-((4-methoxypyrimidin-2-yl)methoxy)propan-2-one (Intermediate 20) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC, silylated with TMSI, and fluorinated with SelectFluor to afford 4-(((5'-chloro-2'-(((1r,4r)-4-((1-((5-fluoro-6-oxo-1,6-dihydropyrimidin-2-yl)methoxy)propan-2-yl)amino)cyclohexyl)amino)-[2,4'-bipyridin]-6-yl)amino)methyl)tetrahydro-2H-pyran-4-carbonitrile (Compound 76).

4-(((5'-chloro-2'-(((1r,4r)-4-((1-((5-fluoro-6-oxo-1,6-dihydropyrimidin-2-yl)methoxy)propan-2-yl)amino)cyclohexyl)amino)-[2,4'-bipyridin]-6-yl)amino)methyl)tetrahydro-2H-pyran-4-carbonitrile (Compound 76) is separated by chiral SFC to afford 4-(((5'-chloro-2'-(((1R,4r)-4-(((R)-1-((5-fluoro-6-oxo-1,6-dihydropyrimidin-2-yl)methoxy)propan-2-yl)amino)cyclohexyl)amino)-[2,4'-bipyridin]-6-yl)amino)methyl)tetrahydro-2H-pyran-4-carbonitrile (Compound 77) and 4-(((5'-chloro-2'-(((1S,4r)-4-(((S)-1-((5-fluoro-6-oxo-1,6-dihydropyrimidin-2-yl)methoxy)propan-2-yl)amino)cyclohexyl)amino)-[2,4'-bipyridin]-6-yl)amino)methyl)tetrahydro-2H-pyran-4-carbonitrile (Compound 78).

Example 48: Synthesis of tert-butyl 1-(2-oxopropoxy)cyclopropane-1-carboxylate (Intermediate 21)

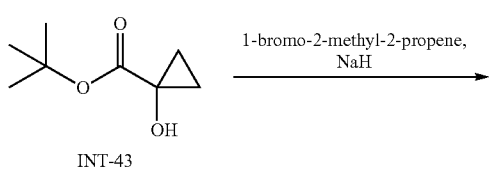

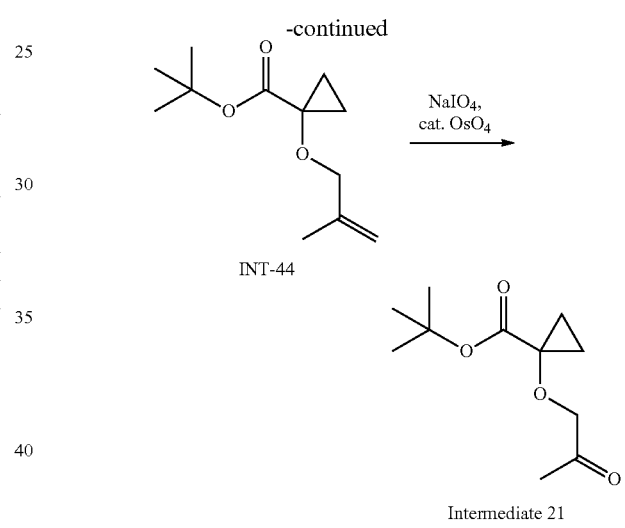

Step 1: Preparation of tert-butyl 1-((2-methylallyl)oxy)cyclopropane-1-carboxylate (INT-44)

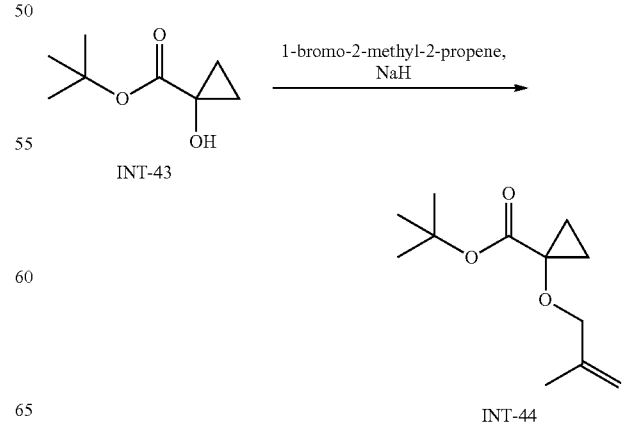

To a solution of tert-butyl 1-hydroxycyclopropane-1-carboxylate (INT-43) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na₂SO₄, filtered, and concentrated to provide tert-butyl 1-((2-methylallyl)oxy)cyclopropane-1-carboxylate (INT-44). The crude product is used directly in the next step without further purification.

Step 2: Preparation of tert-butyl 1-(2-oxopropoxy)cyclopropane-1-carboxylate (Intermediate 21)

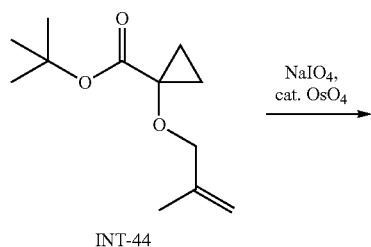

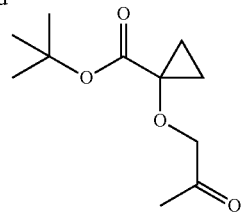

Intermediate 21

To a solution of tert-butyl 1-((2-methylallyl)oxy)cyclopropane-1-carboxylate (INT-44) in THF and H₂O is added K₂OsO₄·2H₂O and NaIO₄. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford tert-butyl 1-(2-oxopropoxy)cyclopropane-1-carboxylate (Intermediate 21).

Example 49: Synthesis of tert-butyl 1-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 80) and tert-butyl 1-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 81)

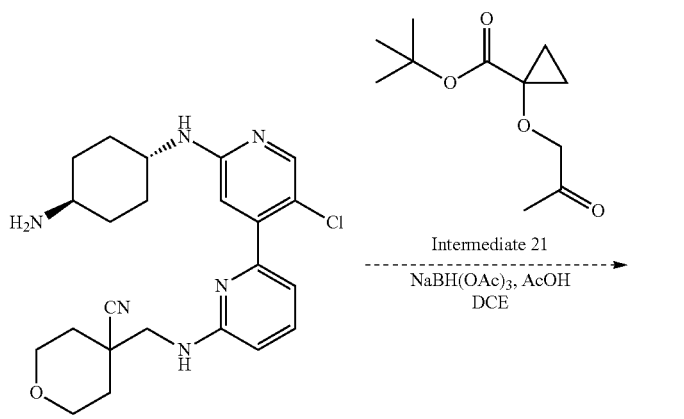

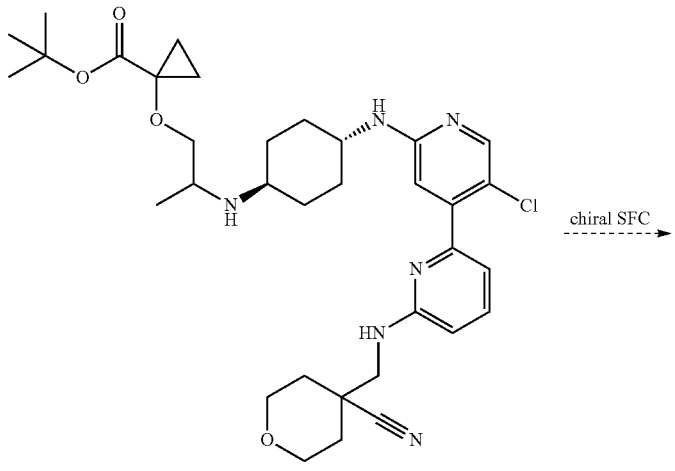

Compound 79

215

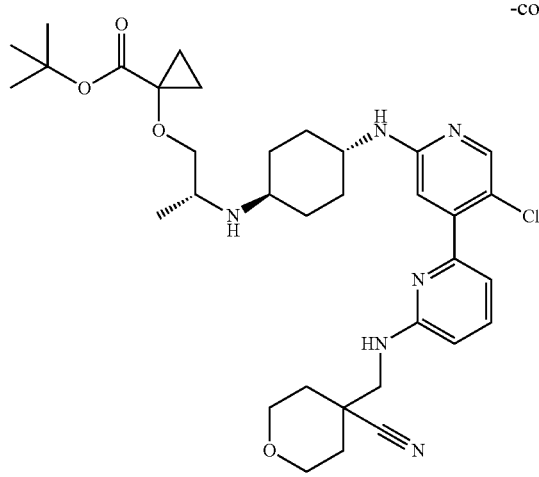

Compound 80

216

-continued

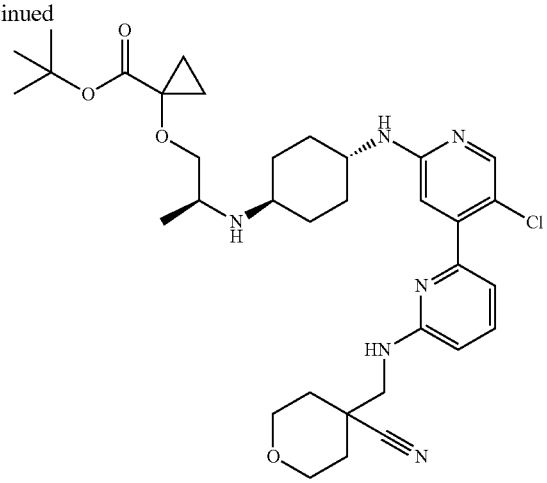

Compound 81

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and tert-butyl 1-(2-oxopropoxy)cyclopropane-1-carboxylate (Intermediate 21) in DCE is added HOAc and NaBH(OAc)$_3$. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford tert-butyl 1-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 79).

tert-butyl 1-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 79) is separated by chiral SFC to afford tert-butyl 1-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 80) and tert-butyl 1-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 81).

Example 50: Synthesis of (R)-3-(((1r,4R)-4-((5'-chloro-6-(((4-cyanotetrahydro-2H-pyran-4-yl)methyl)amino)-[2,4'-bipyridin]-2'-yl)amino)cyclohexyl)amino)butanoic acid (Compound 66)

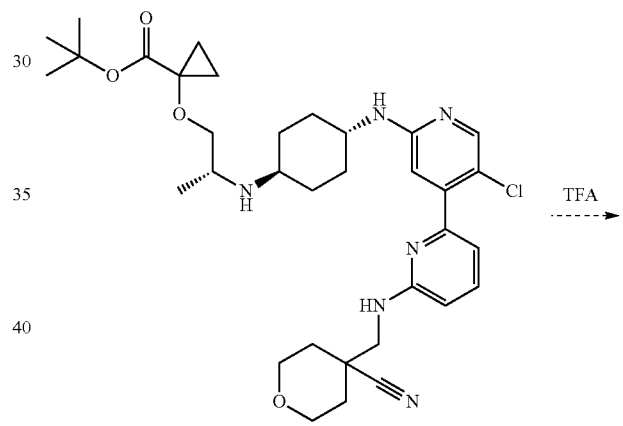

Compound 80

TFA

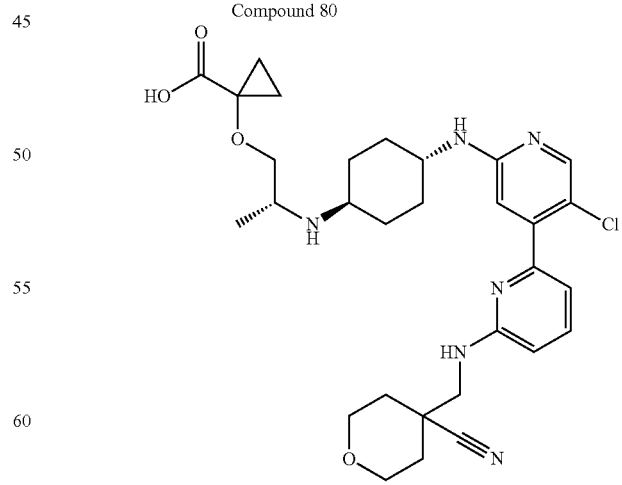

Compound 82 tert-butyl 1-((R)-2-(((1r,4R)-4-((5'-chloro-6-(((4-cyanotetrahydro-2H-pyran-4-yl)methyl)amino)-[2,4'-bipyridin]-

2'-yl)amino)cyclohexyl)amino)propoxy)cyclopropane-1-carboxylate (Compound 80) is treated with trifluoroacetic acid to afford 1-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylic acid (Compound 82).

Example 51: Synthesis of (S)-3-(((1r,4S)-4-((5'-chloro-6-(((4-cyanotetrahydro-2H-pyran-4-yl)methyl)amino)-[2,4'-bipyridin]-2'-yl)amino)cyclohexyl)amino)butanoic acid (Compound 67)

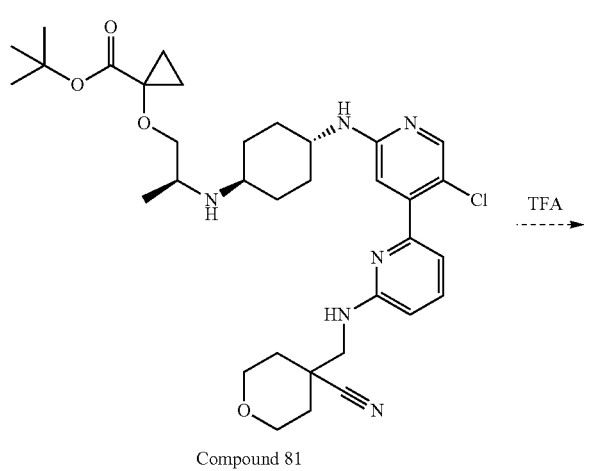

Compound 81

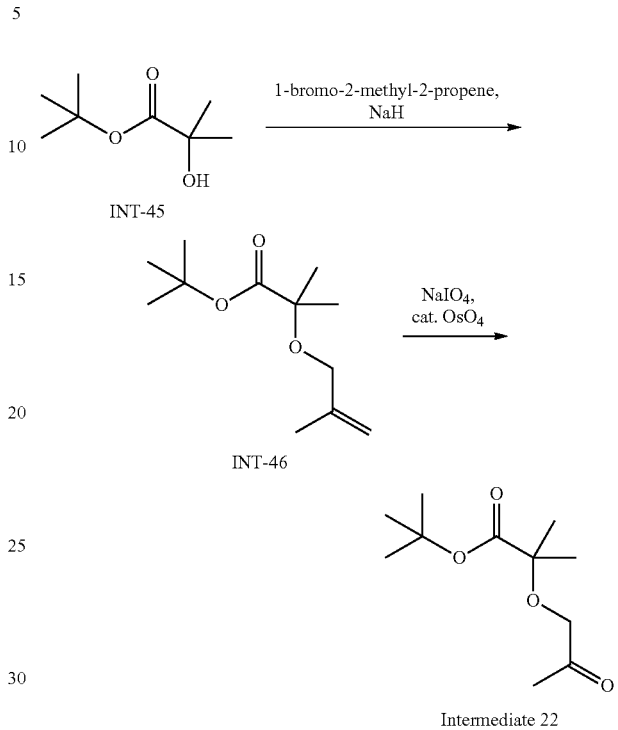

tert-butyl 1-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylate (Compound 81) is treated with trifluoroacetic acid to afford 1-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)cyclopropane-1-carboxylic acid (Compound 83).

Example 52: Synthesis of tert-butyl 2-methyl-2-(2-oxopropoxy)propanoate (Intermediate 22)

Step 1: Preparation of tert-butyl 2-methyl-2-((2-methylallyl)oxy)propanoate (INT-46)

To a solution of tert-butyl 2-hydroxy-2-methylpropanoate (INT-45) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na$_2$SO$_4$, filtered, and concentrated to provide tert-butyl 2-methyl-2-((2-methylallyl)oxy)propanoate (INT-46). The crude product is used directly in the next step without further purification.

Step 2: Preparation of tert-butyl 2-methyl-2-(2-oxopropoxy)propanoate (Intermediate 22)

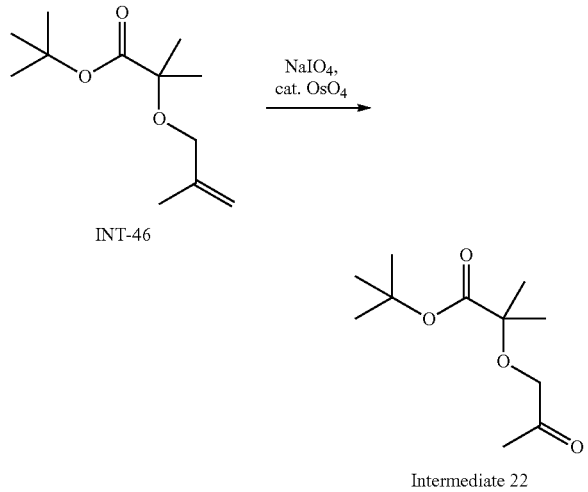

To a solution of tert-butyl 2-methyl-2-((2-methylallyl)oxy)propanoate (INT-46) in THF and H₂O is added K₂OsO₄·2H₂O and NaIO₄. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford tert-butyl 2-methyl-2-(2-oxopropoxy)propanoate (Intermediate 22).

Example 53: Synthesis of tert-butyl 2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 85) and tert-butyl 2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 86)

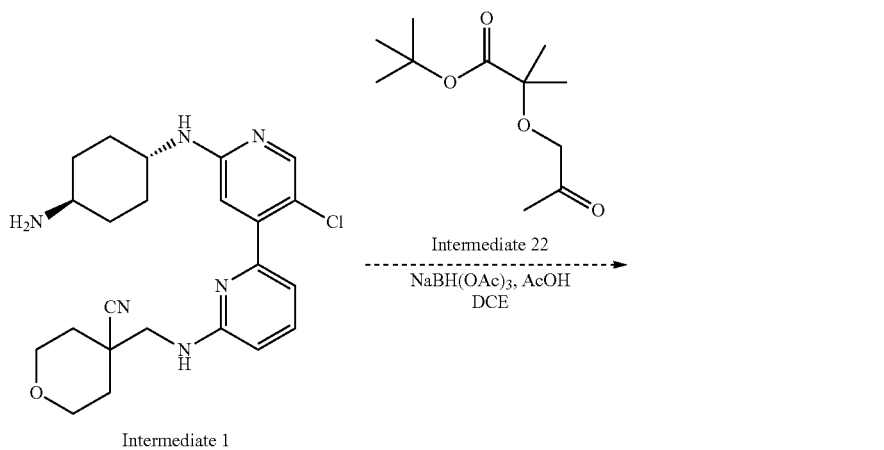

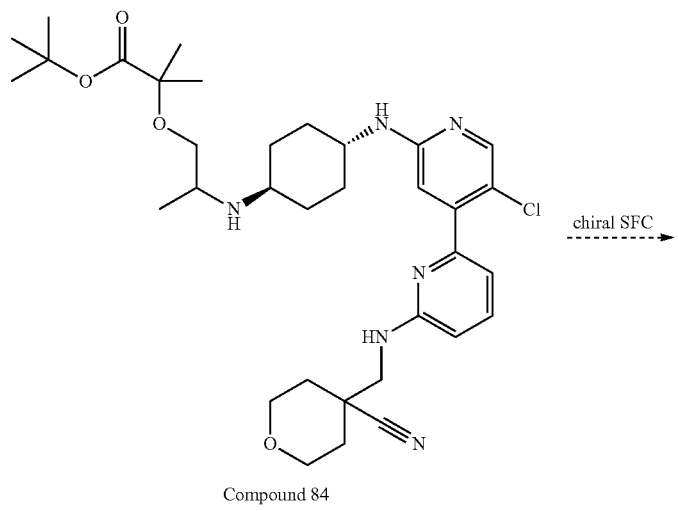

Compound 84

221

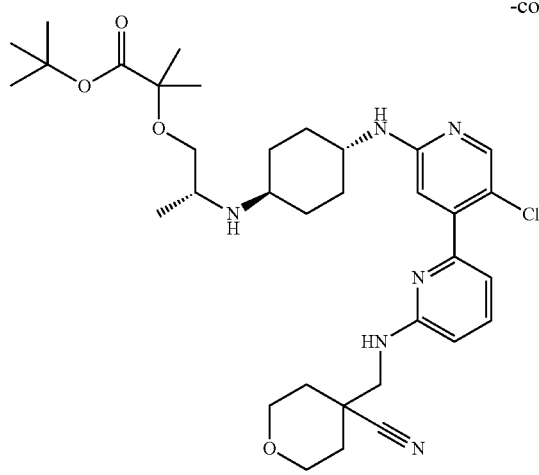

Compound 85

222

-continued

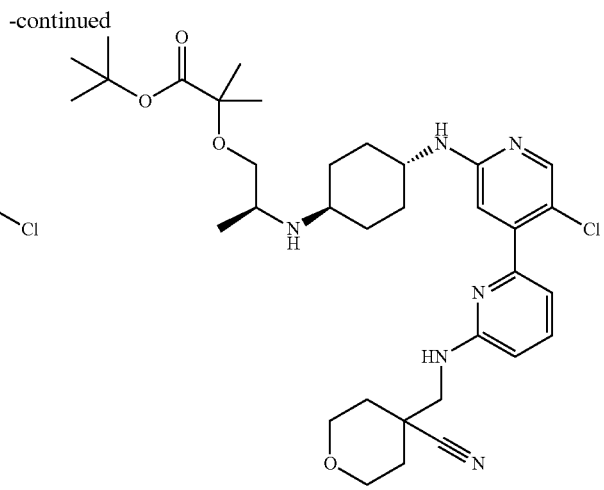

Compound 86

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and tert-butyl 2-methyl-2-(2-oxopropoxy)propanoate (Intermediate 22) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford tert-butyl 2-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 84).

tert-butyl 2-(2-(((1r,4r)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 84) is separated by chiral SFC to afford tert-butyl 2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 85) and tert-butyl 2-((S)-2-(((1R,4S)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 86).

Example 54: Synthesis of tert-butyl 2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoic acid (Compound 87)

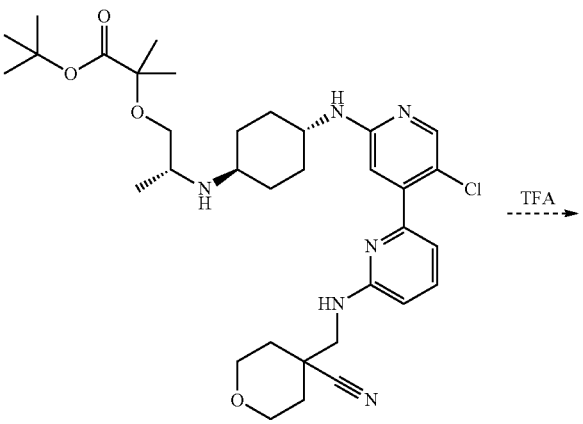

Compound 85

TFA

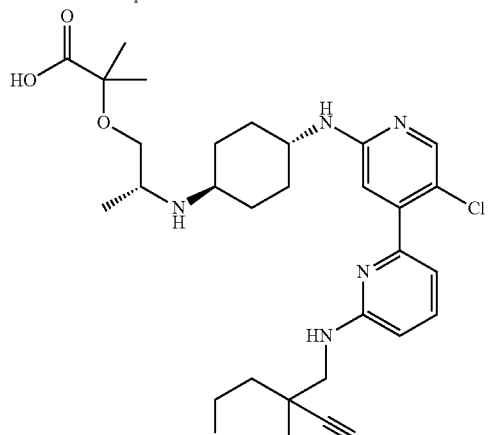

Compound 87 tert-butyl 2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 85) is treated with trifluoroacetic acid to afford 2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoic acid (Compound 87).

Example 55: Synthesis of tert-butyl 2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoic acid (Compound 88)

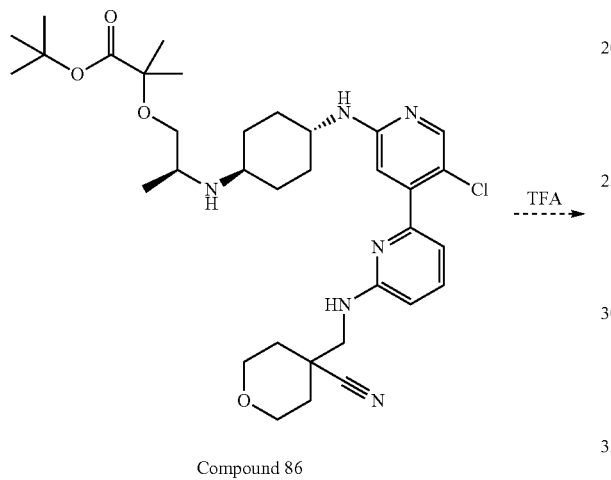

Compound 86

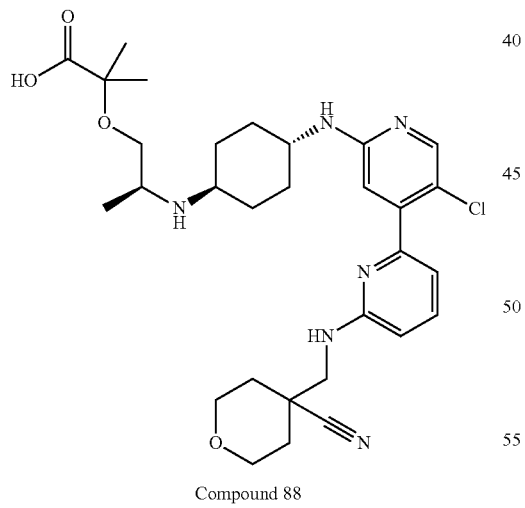

Compound 88 tert-butyl 2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoate (Compound 86) is treated with trifluoroacetic acid to afford 2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)-2-methylpropanoic acid (Compound 88).

Example 56: Synthesis of tert-butyl (R)-2-(2-oxopropoxy)propanoate (Intermediate 23)

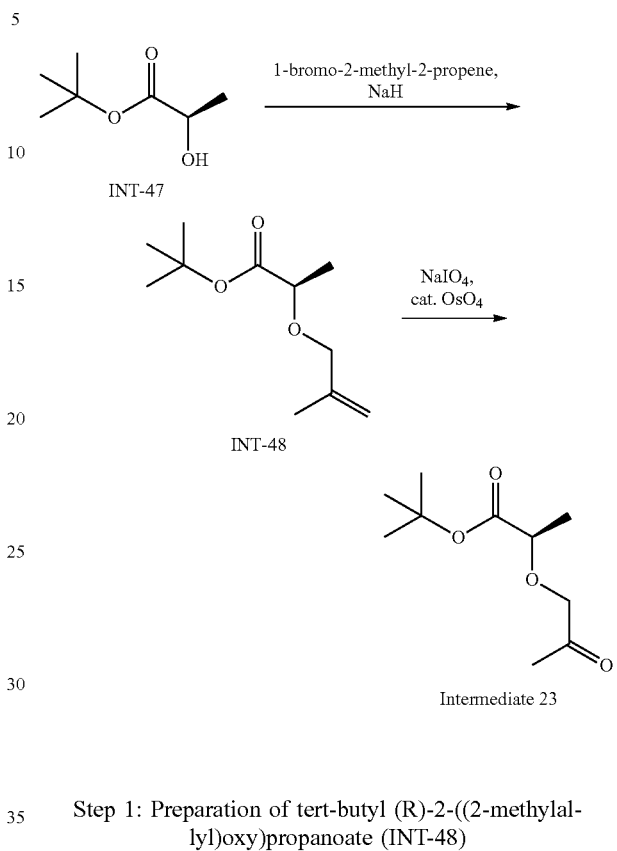

Step 1: Preparation of tert-butyl (R)-2-((2-methylallyl)oxy)propanoate (INT-48)

To a solution of tert-butyl (R)-2-hydroxypropanoate (INT-47) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na$_2$SO$_4$, filtered, and concentrated to provide tert-butyl (R)-2-((2-methylallyl)oxy)propanoate (INT-48). The crude product is used directly in the next step without further purification.

Step 2: Preparation of tert-butyl (R)-2-(2-oxopropoxy)propanoate (Intermediate 23)

To a solution of tert-butyl (R)-2-((2-methylallyl)oxy)propanoate (INT-48) in THF and H$_2$O is added K$_2$OsO$_4$·2H$_2$O and NaIO$_4$. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford tert-butyl (R)-2-(2-oxopropoxy)propanoate (Intermediate 23).

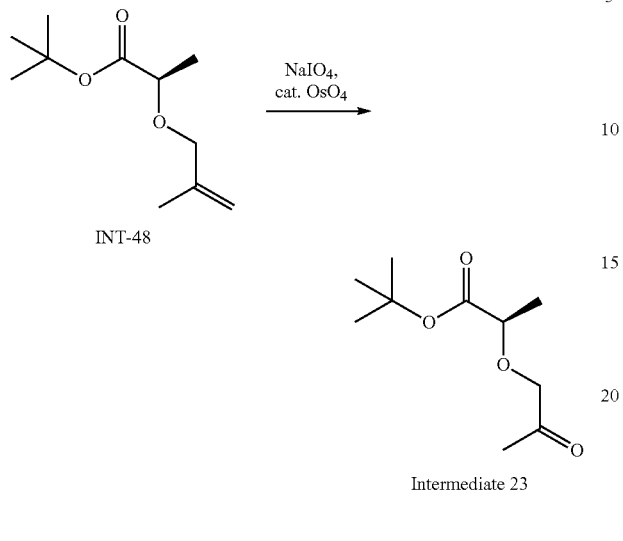

Example 57: Synthesis of tert-butyl (R)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 90) and tert-butyl (R)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 91)

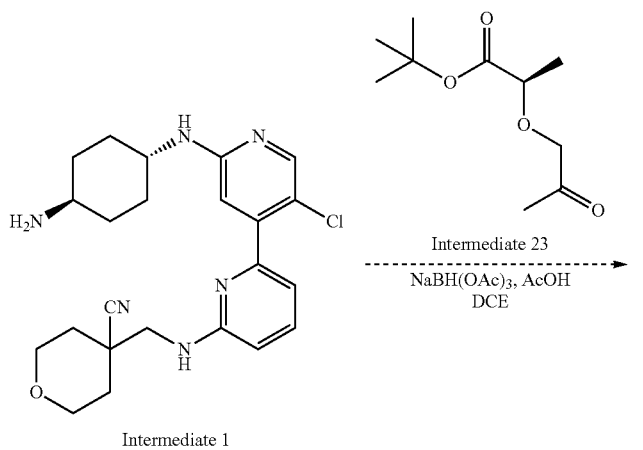

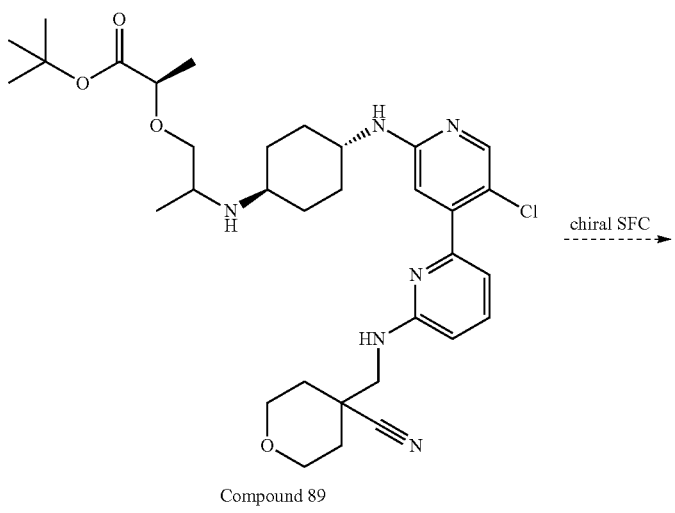

227

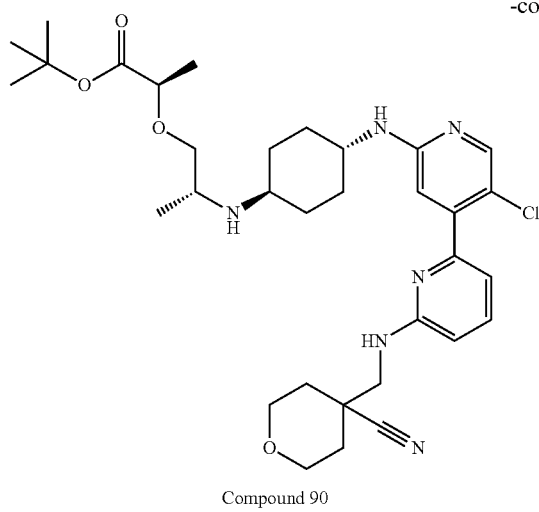

Compound 90

228

-continued

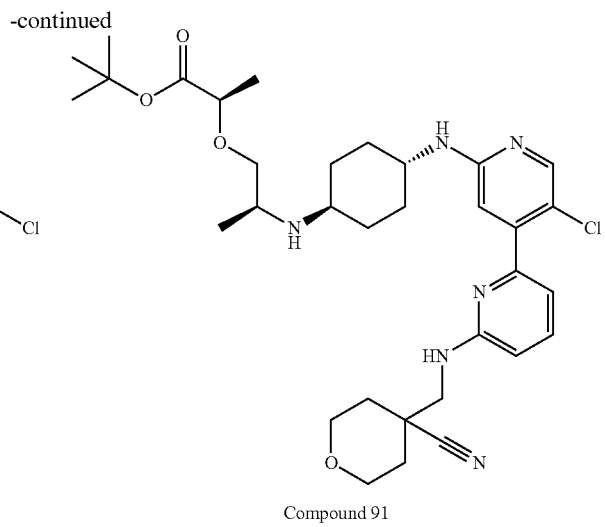

Compound 91

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and tert-butyl (R)-2-(2-oxopropoxy)propanoate (Intermediate 23) in DCE is added HOAc and NaBH(OAc)$_3$. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford tert-butyl (2R)-2-(2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 89).

tert-butyl (2R)-2-(2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 89) is separated by chiral SFC to afford tert-butyl (R)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 90) and tert-butyl (R)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 91).

Example 58: Synthesis of (R)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoic acid (Compound 92)

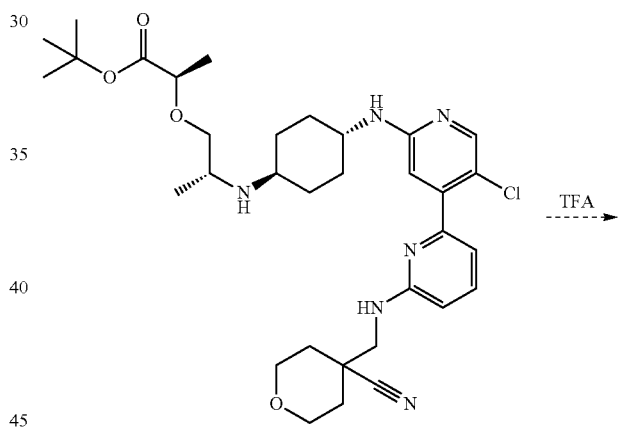

Compound 92 tert-butyl (R)-2-((R)-2-(((1R,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 90) is treated with trifluoroacetic acid to afford (R)-2-((R)-2-(((1R,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoic acid (Compound 92).

Example 59: Synthesis of (R)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoic acid (Compound 93)

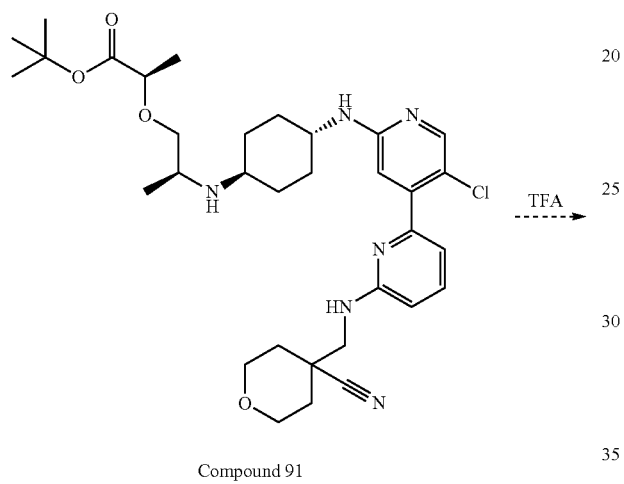

Compound 91

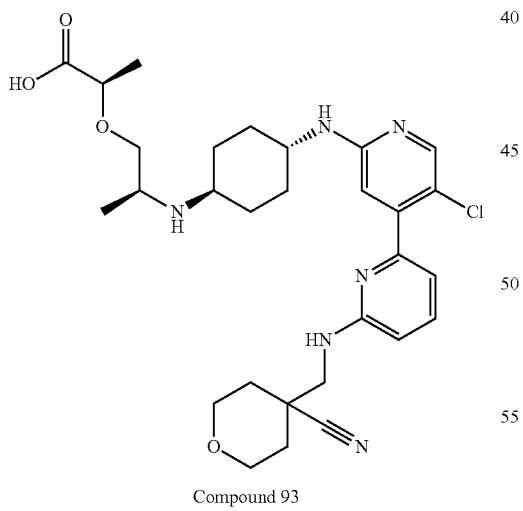

Compound 93 tert-butyl (R)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 91) is treated with trifluoroacetic acid to afford (R)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoic acid (Compound 93).

Example 60: Synthesis of tert-butyl (S)-2-(2-oxopropoxy)propanoate (Intermediate 24)

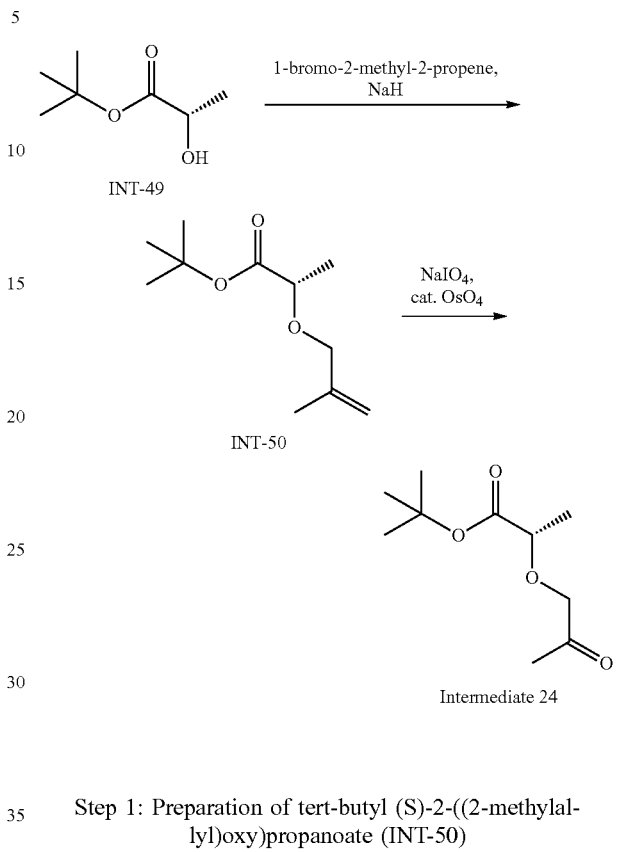

Step 1: Preparation of tert-butyl (S)-2-((2-methylallyl)oxy)propanoate (INT-50)

To a solution of tert-butyl (S)-2-hydroxypropanoate (INT-49) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na$_2$SO$_4$, filtered, and concentrated to provide tert-butyl (S)-2-((2-methylallyl)oxy)propanoate (INT-50). The crude product is used directly in the next step without further purification.

Step 2: Preparation of tert-butyl (S)-2-(2-oxopropoxy)propanoate (Intermediate 24)

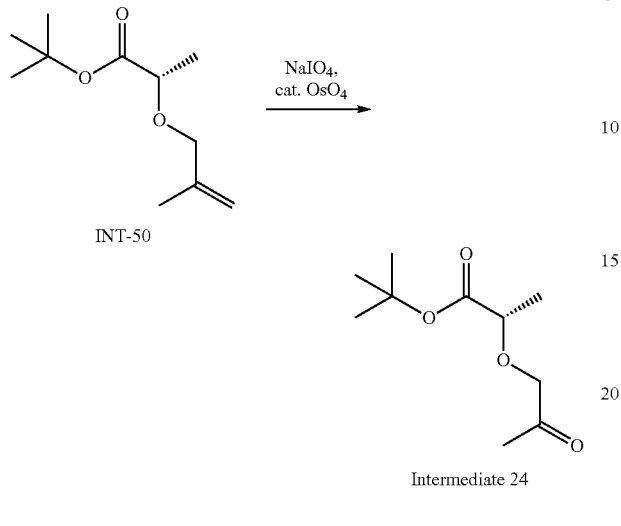

To a solution of tert-butyl (S)-2-((2-methylallyl)oxy)propanoate (INT-50) in THF and H₂O is added K₂OsO₄.2H₂O and NaIO₄. The mixture is stirred at 15° C. for 4 hours. The mixture is diluted with water and extracted with ethyl acetate. The combined organic phases are washed with aq. Na₂S₂O₃, brine, dried over anhydrous sodium sulfate, filtered and concentrated in vacuo to give the residue which is purified by silica gel chromatography to afford tert-butyl (S)-2-(2-oxopropoxy)propanoate (Intermediate 24).

Example 61: Synthesis of tert-butyl (S)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 95) and tert-butyl (S)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 96)

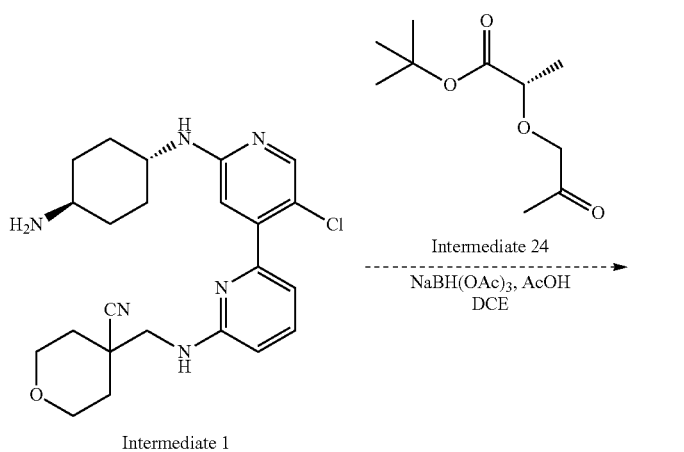

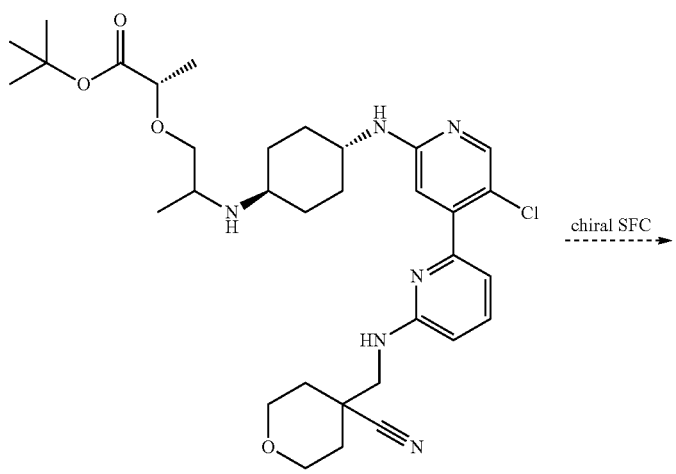

Compound 94

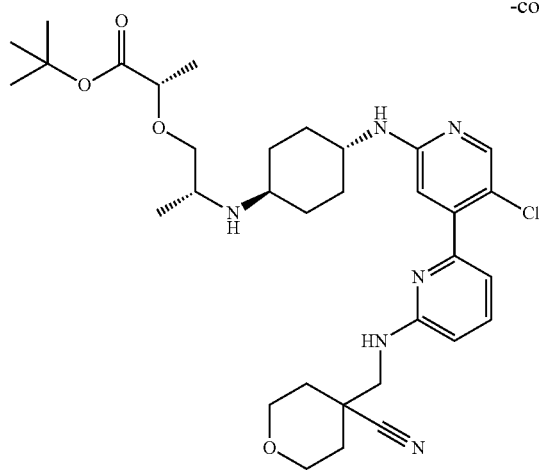

Compound 95

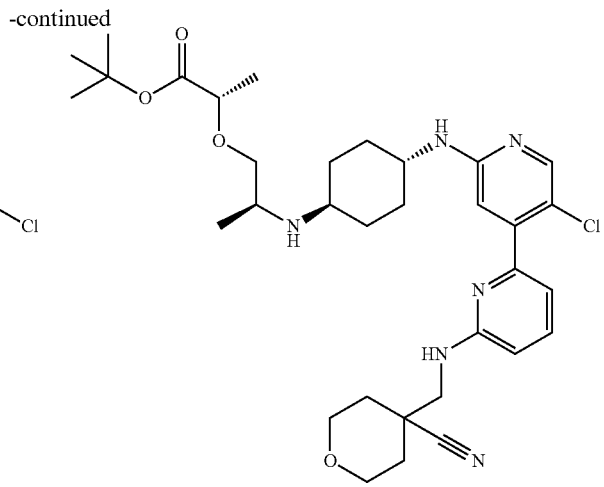

Compound 96

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and tert-butyl (S)-2-(2-oxopropoxy)propanoate (Intermediate 24) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford tert-butyl (2S)-2-(2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 94).

tert-butyl (2S)-2-(2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 94) is separated by chiral SFC to afford tert-butyl (S)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 95) and tert-butyl (S)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 96).

Example 62: Synthesis of (S)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoic acid (Compound 97)

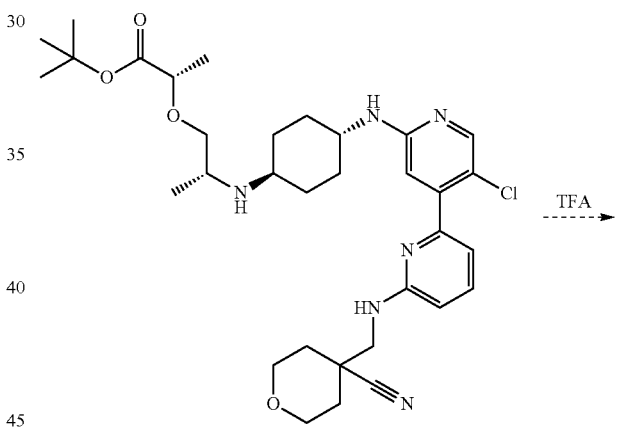

Compound 95

TFA

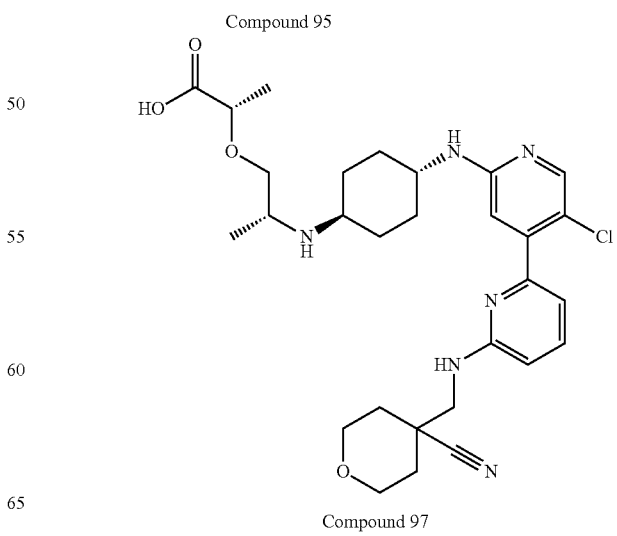

Compound 97 tert-butyl (S)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 95) is treated with trifluoroacetic acid to afford (S)-2-((R)-2-(((1r,4R)-4-((5'-chloro-6-(((4-cyanotetrahydro-2H-pyran-4-yl)methyl)amino)-[2,4'-bipyridin]-2'-yl)amino)cyclohexyl)amino)propoxy)propanoic acid (Compound 97).

Example 63: Synthesis of (S)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoic acid (Compound 98)

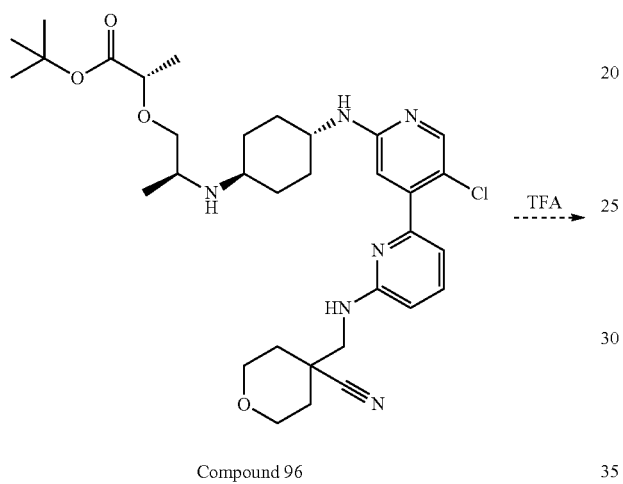

Compound 96

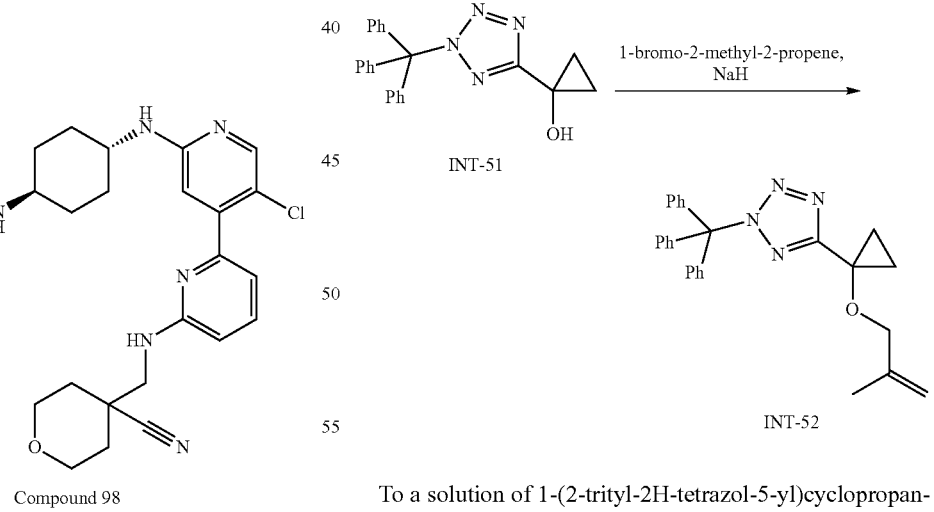

Compound 98 tert-butyl (S)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoate (Compound 96) is treated with trifluoroacetic acid to afford (S)-2-((S)-2-(((1r,4S)-4-((5'-chloro-6-(((4-cyanotetrahydro-2H-pyran-4-yl)methyl)amino)-[2,4'-bipyridin]-2'-yl)amino)cyclohexyl)amino)propoxy)propanoic acid (Compound 98).

Example 64: Synthesis of 1-(1-(2-trityl-2H-tetrazol-5-yl)cyclopropoxy)propan-2-one (Intermediate 25)

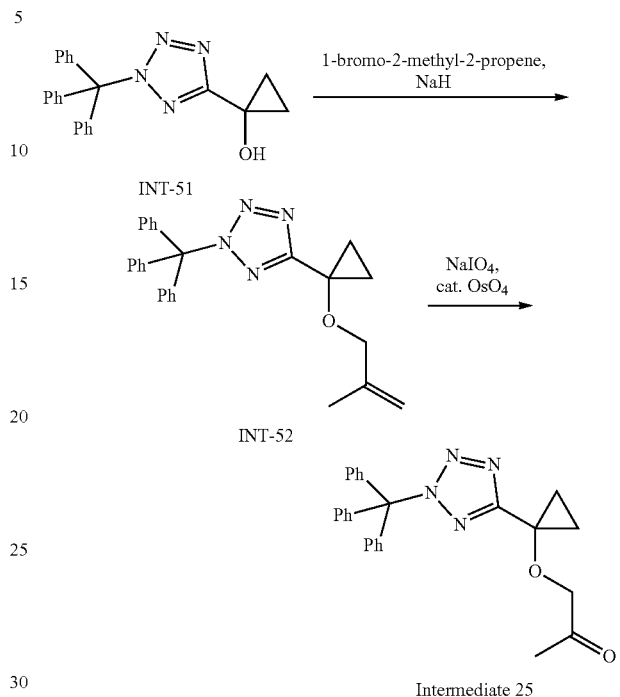

Step 1: Preparation of 5-(1-((2-methylallyl)oxy)cyclopropyl)-2-trityl-2H-tetrazole (INT-52)

To a solution of 1-(2-trityl-2H-tetrazol-5-yl)cyclopropan-1-ol (INT-51) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na$_2$SO$_4$, filtered, and concentrated to provide 5-(1-((2-methylallyl)oxy)cyclopropyl)-2-trityl-2H-tetrazole (INT-52). The crude product is used directly in the next step without further purification.

237

Step 2: Preparation of 1-(1-(2-trityl-2H-tetrazol-5-yl)cyclopropoxy)propan-2-one (Intermediate 25)

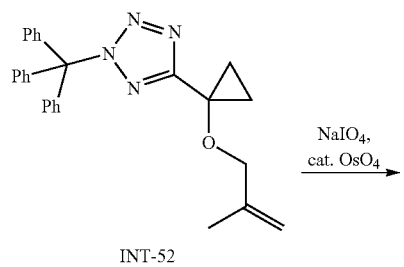

INT-52

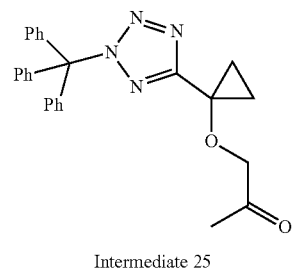

Intermediate 25

To a solution of 5-(1-((2-methylallyl)oxy)cyclopropyl)-2-trityl-2H-tetrazole (INT-52) in THF and H₂O is added K₂OsO₄·2H₂O and NaIO₄. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford 1-(1-(2-trityl-2H-tetrazol-5-yl)cyclopropoxy)propan-2-one (Intermediate 25).

Example 65: Synthesis of 4-(((2'-(((1R,4r)-4-(((R)-1-(1-(2H-tetrazol-5-yl)cyclopropoxy)propan-2-yl)amino)cyclohexyl)amino)-5'-chloro-[2,4'-bipyridin]-6-yl)amino)methyl)tetrahydro-2H-pyran-4-carbonitrile (Compound 100) and 4-(((2'-(((1S,4r)-4-(((S)-1-(1-(2H-tetrazol-5-yl)cyclopropoxy)propan-2-yl)amino)cyclohexyl)amino)-5'-chloro-[2,4'-bipyridin]-6-yl)amino)methyl)tetrahydro-2H-pyran-4-carbonitrile (Compound 101)

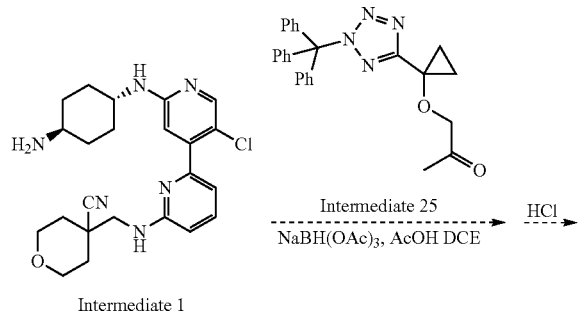

Intermediate 1 + Intermediate 25 → (NaBH(OAc)₃, AcOH DCE; HCl)

238

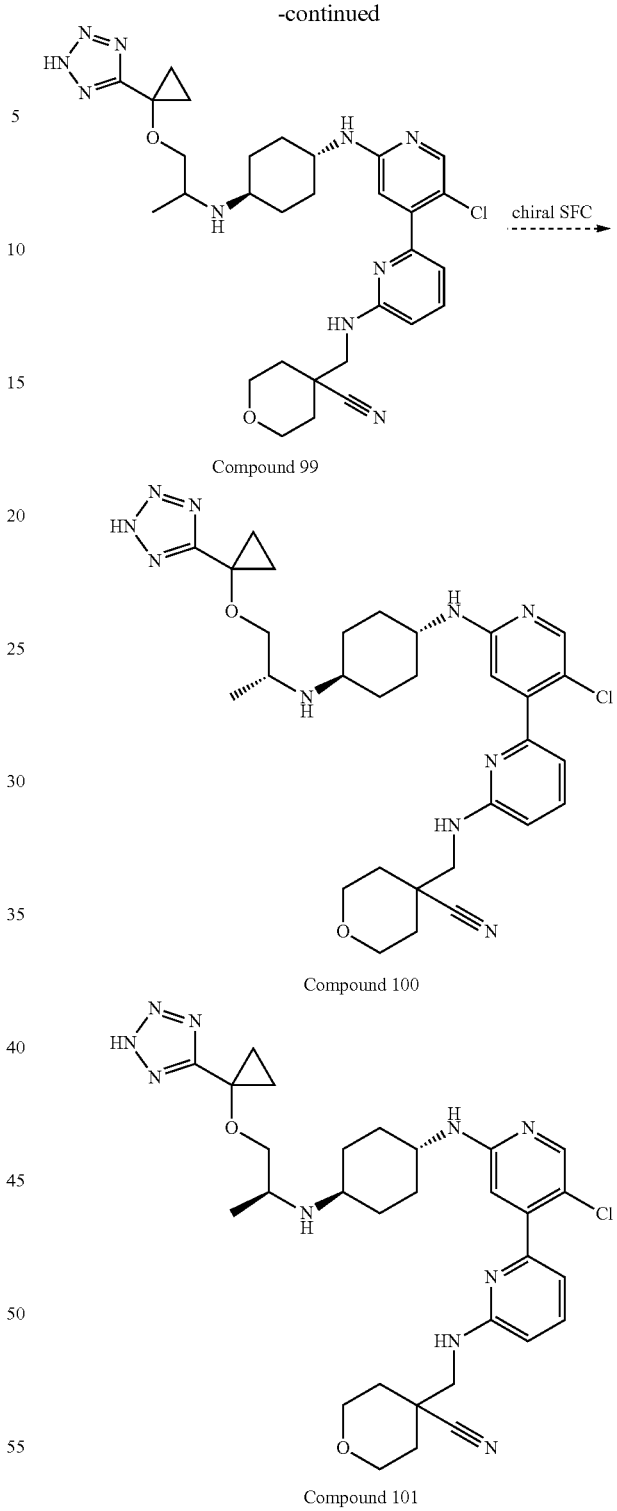

Compound 99

Compound 100

Compound 101

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and 1-(1-(2-trityl-2H-tetrazol-5-yl)cyclopropoxy)propan-2-one (Intermediate 25) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC and deprotected with HCl to afford 4-(((2'-(((1r,4r)-4-((1-(1-(2H-tetrazol-5-yl)cyclopropoxy)propan-2-yl)amino)cyclohexyl)amino)-5'-chloro-[2,4'-bipyridin]-6-yl)amino)methyl)tetrahydro-2H-pyran-4-carbonitrile (Compound 99).

4-(((2'-(((1r,4r)-4-((1-(1-(2H-tetrazol-5-yl)cyclopropoxy)propan-2-yl)amino)cyclohexyl)amino)-5'-chloro-[2,4'-bipyridin]-6-yl)amino)methyl)tetrahydro-2H-pyran-4-carbonitrile (Compound 99) is separated by chiral SFC to afford 4-(((2'-(((1R,4r)-4-(((R)-1-(1-(2H-tetrazol-5-yl)cyclopropoxy)propan-2-yl)amino)cyclohexyl)amino)-5'-chloro-[2,4'-bipyridin]-6-yl)amino)methyl)tetrahydro-2H-pyran-4-carbonitrile (Compound 100) and 4-(((2'-(((1S,4r)-4-(((S)-1-(1-(2H-tetrazol-5-yl)cyclopropoxy)propan-2-yl)amino)cyclohexyl)amino)-5'-chloro-[2,4'-bipyridin]-6-yl)amino)methyl)tetrahydro-2H-pyran-4-carbonitrile (Compound 101).

Example 66: Synthesis of 1-((2-(2-trityl-2H-tetrazol-5-yl)propan-2-yl)oxy)propan-2-one (Intermediate 26)

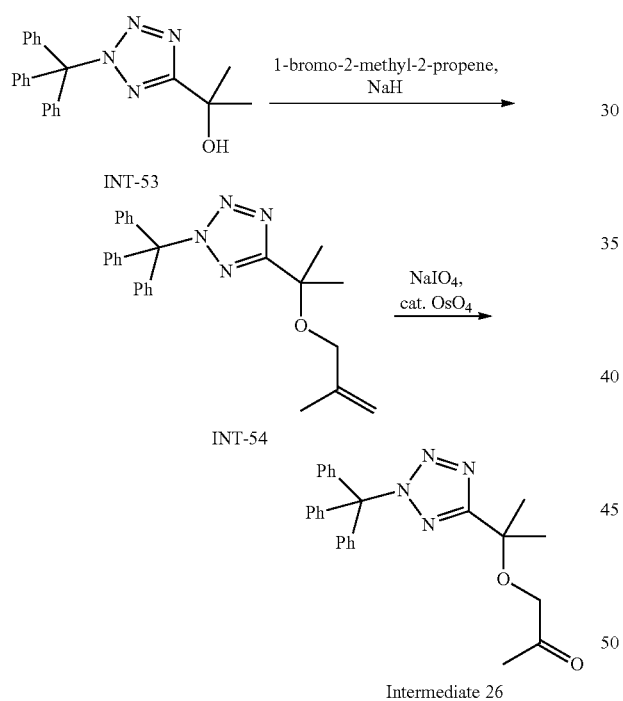

Step 1: Preparation of 5-(2-((2-methylallyl)oxy)propan-2-yl)-2-trityl-2H-tetrazole (INT-54)

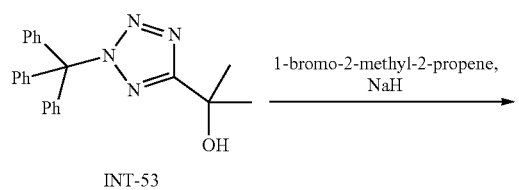

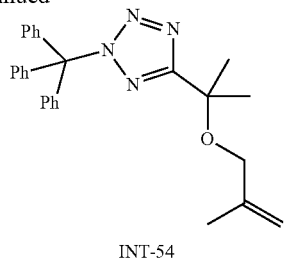

To a solution of 2-(2-trityl-2H-tetrazol-5-yl)propan-2-ol (INT-53) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na₂SO₄, filtered, and concentrated to provide 5-(2-((2-methylallyl)oxy)propan-2-yl)-2-trityl-2H-tetrazole (INT-54). The crude product is used directly in the next step without further purification.

Step 2: Preparation of 1-((2-(2-trityl-2H-tetrazol-5-yl)propan-2-yl)oxy)propan-2-one (Intermediate 26)

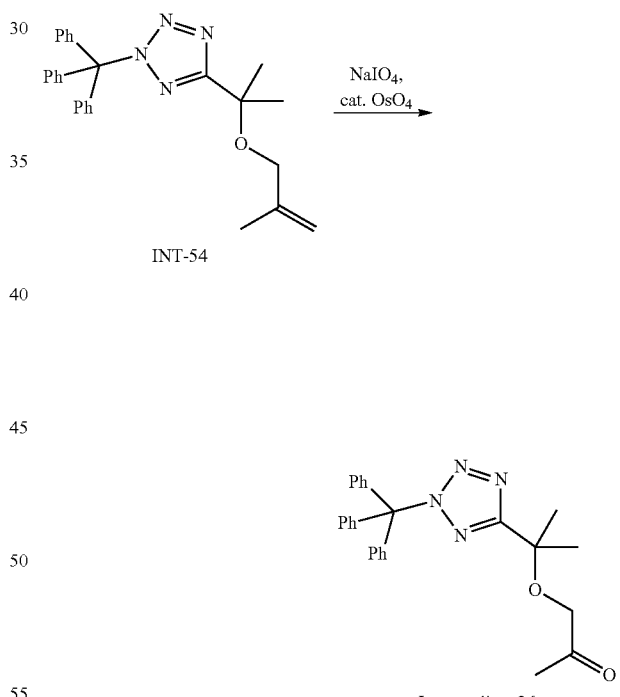

To a solution of 5-(2-((2-methylallyl)oxy)propan-2-yl)-2-trityl-2H-tetrazole (INT-54) in THF and H₂O is added K₂OsO₄.2H₂O and NaIO₄. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford 1-((2-(2-trityl-2H-tetrazol-5-yl)propan-2-yl)oxy)propan-2-one (Intermediate 26).

Example 67: Synthesis of 4-(((2'-(((1R,4r)-4-(((R)-1-((2-(2H-tetrazol-5-yl)propan-2-yl)oxy)propan-2-yl)amino)cyclohexyl)amino)-5'-chloro-[2,4'-bipyridin]-6-yl)amino)methyl)tetrahydro-2H-pyran-4-carbonitrile (Compound 103) and 4-(((2'-(((1S,4r)-4-(((S)-1-((2-(2H-tetrazol-5-yl)propan-2-yl)oxy)propan-2-yl)amino)cyclohexyl)amino)-5'-chloro-[2,4'-bipyridin]-6-yl)amino)methyl)tetrahydro-2H-pyran-4-carbonitrile (Compound 104)

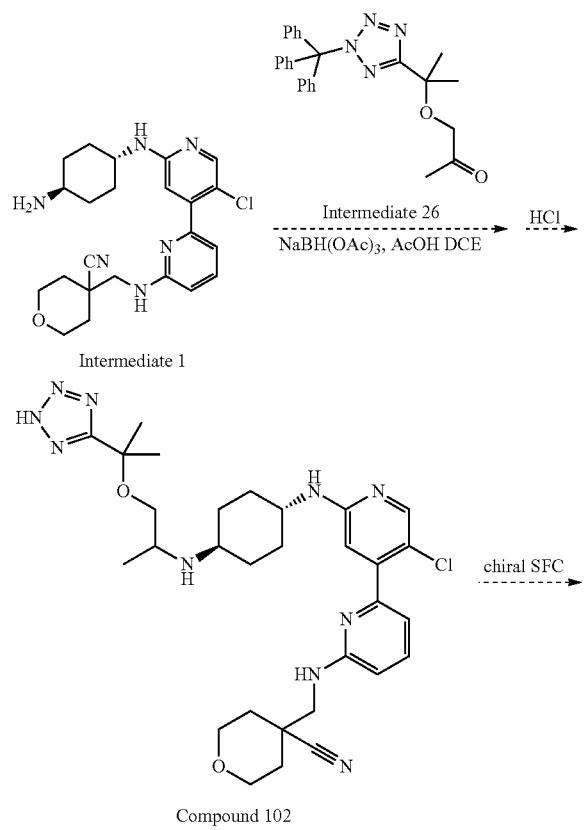
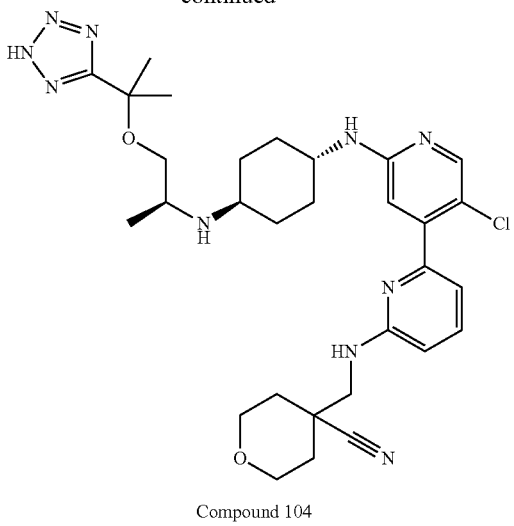

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and 1-((2-(2-ttyl-2H-tetrazol-5-yl)propan-2-yl)oxy)propan-2-one (Intermediate 26) in DCE is added HOAc and NaBH(OAc)₃. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC and deprotected with HCl to afford 4-(((2'-(((1r,4r)-4-((1-((2-(2H-tetrazol-5-yl)propan-2-yl)oxy)propan-2-yl)amino)cyclohexyl)amino)-5'-chloro-[2,4'-bipyridin]-6-yl)amino)methyl)tetrahydro-2H-pyran-4-carbonitrile (Compound 102).

4-(((2'-(((1r,4r)-4-((1-((2-(2H-tetrazol-5-yl)propan-2-yl)oxy)propan-2-yl)amino)cyclohexyl)amino)-5'-chloro-[2,4'-bipyridin]-6-yl)amino)methyl)tetrahydro-2H-pyran-4-carbonitrile (Compound 102) is separated by chiral SFC to afford 4-(((2'-(((1R,4r)-4-(((R)-1-((2-(2H-tetrazol-5-yl)propan-2-yl)oxy)propan-2-yl)amino)cyclohexyl)amino)-5'-chloro-[2,4'-bipyridin]-6-yl)amino)methyl)tetrahydro-2H-pyran-4-carbonitrile (Compound 103) and 4-(((2'-(((1S,4r)-4-(((S)-1-((2-(2H-tetrazol-5-yl)propan-2-yl)oxy)propan-2-yl)amino)cyclohexyl)amino)-5'-chloro-[2,4'-bipyridin]-6-yl)amino)methyl)tetrahydro-2H-pyran-4-carbonitrile (Compound 104).

Example 68: Synthesis of 1-(1-(2-trityl-2H-tetrazol-5-yl)ethoxy)propan-2-one (Intermediate 27)

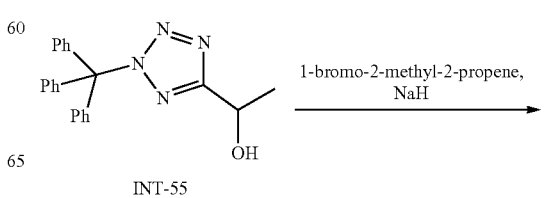

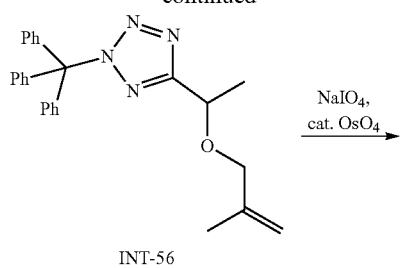

INT-56

Step 1: Preparation of 5-(1-((2-methylallyl)oxy)ethyl)-2-trityl-2H-tetrazole (INT-56)

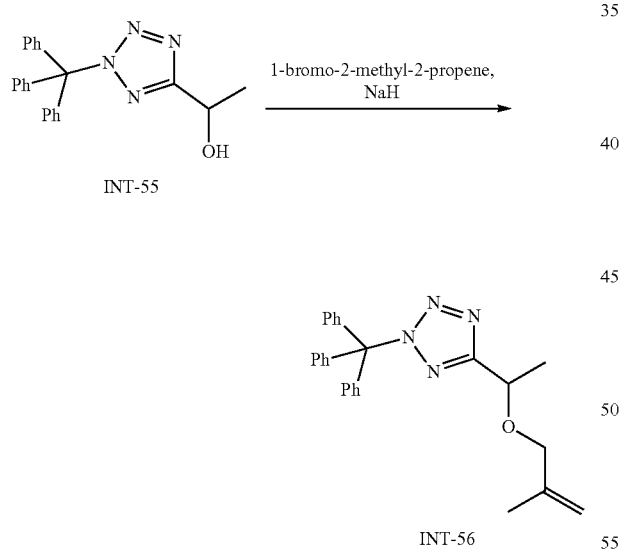

To a solution of 1-(2-trityl-2H-tetrazol-5-yl)ethan-1-ol (INT-55) in DMF is added NaH and the reaction mixture is stirred at 0° C. for 0.5 hours. 1-bromo-2-methyl-2-propene is added and the reaction mixture is stirred at 25° C. for 2 hours, quenched with brine, and extracted with EtOAc. The combined organic layers are washed with brine, dried over Na₂SO₄, filtered, and concentrated to provide 5-(1-((2-methylallyl)oxy)ethyl)-2-trityl-2H-tetrazole (INT-56). The crude product is used directly in the next step without further purification.

Step 2: Preparation of 1-(1-(2-trityl-2H-tetrazol-5-yl)ethoxy)propan-2-one (Intermediate 27)

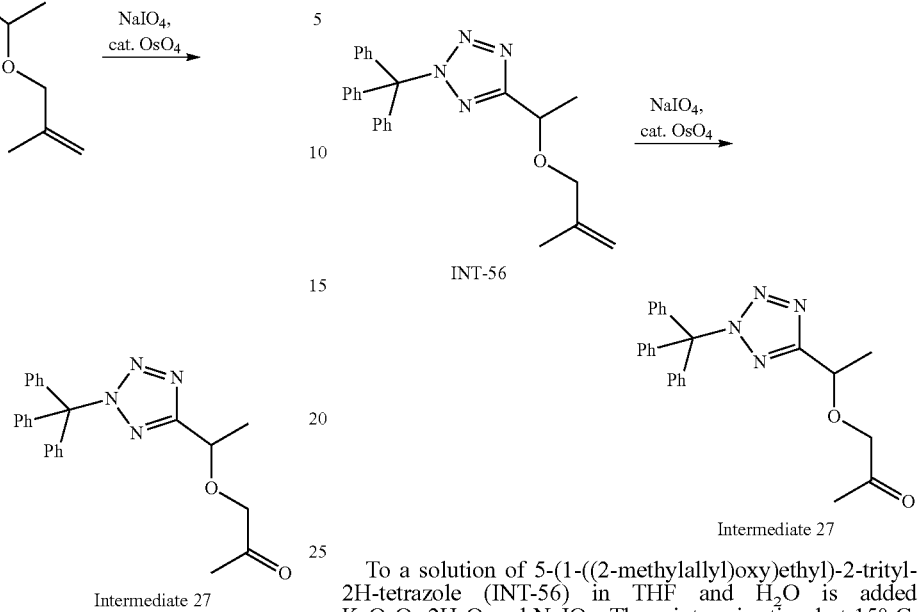

To a solution of 5-(1-((2-methylallyl)oxy)ethyl)-2-trityl-2H-tetrazole (INT-56) in THF and H₂O is added K₂OsO₄·2H₂O and NaIO₄. The mixture is stirred at 15° C. for 4 hours. The mixture is diluted with water and extracted with ethyl acetate. The combined organic phases are washed with aq. Na2S2O3, brine, dried over anhydrous sodium sulfate, filtered and concentrated in vacuo to give the residue which is purified by silica gel chromatography to afford 1-(1-(2-trityl-2H-tetrazol-5-yl)ethoxy)propan-2-one (Intermediate 27).

Example 69: Synthesis of 4-(((2'-(((1R,4r)-4-(((2R,3S)-3-((2H-tetrazol-5-yl)methoxy)butan-2-yl)amino)cyclohexyl)amino)-5'-chloro-[2,4'-bipyridin]-6-yl)amino)methyl)tetrahydro-2H-pyran-4-carbonitrile (Compound 106), 4-(((2'-(((1S,4r)-4-(((S)-1-((R)-1-(2H-tetrazol-5-yl)ethoxy)propan-2-yl)amino)cyclohexyl)amino)-5'-chloro-[2,4'-bipyridin]-6-yl)amino)methyl)tetrahydro-2H-pyran-4-carbonitrile (Compound 107), 4-(((2'-(((1R,4r)-4-(((2R,3R)-3-((2H-tetrazol-5-yl)methoxy)butan-2-yl)amino)cyclohexyl)amino)-5'-chloro-[2,4'-bipyridin]-6-yl)amino)methyl)tetrahydro-2H-pyran-4-carbonitrile (Compound 108), and 4-(((2'-(((1S,4r)-4-(((S)-1-((S)-1-(2H-tetrazol-5-yl)ethoxy)propan-2-yl)amino)cyclohexyl)amino)-5'-chloro-[2,4'-bipyridin]-6-yl)amino)methyl)tetrahydro-2H-pyran-4-carbonitrile (Compound 109)

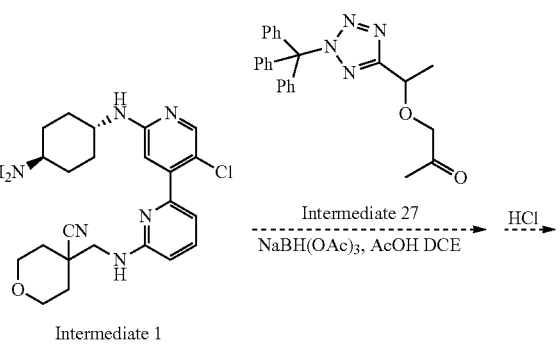

-continued

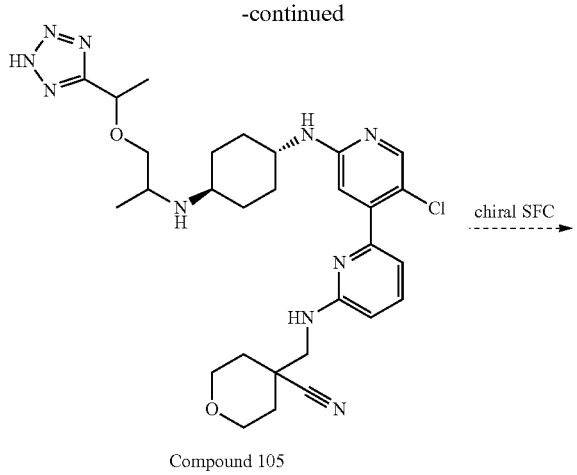

Compound 105

→ chiral SFC

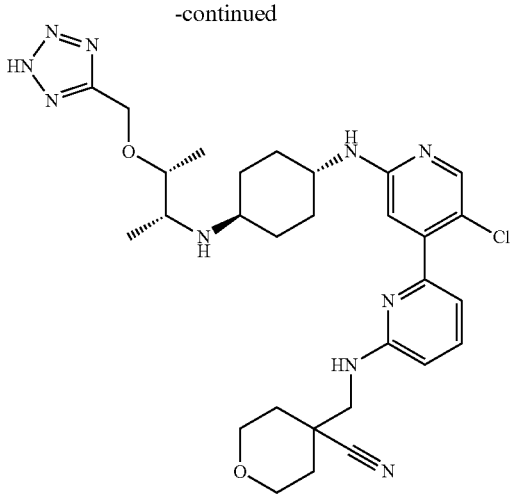

Compound 108

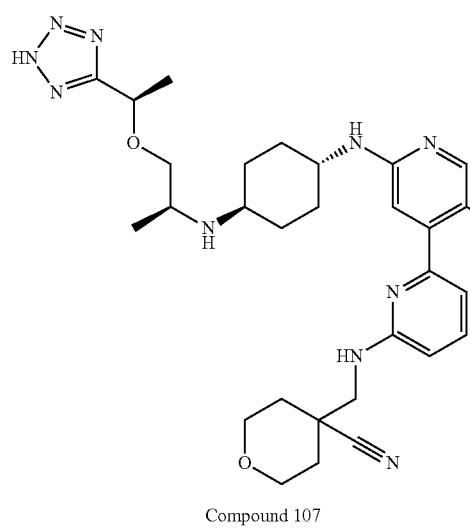

Compound 106

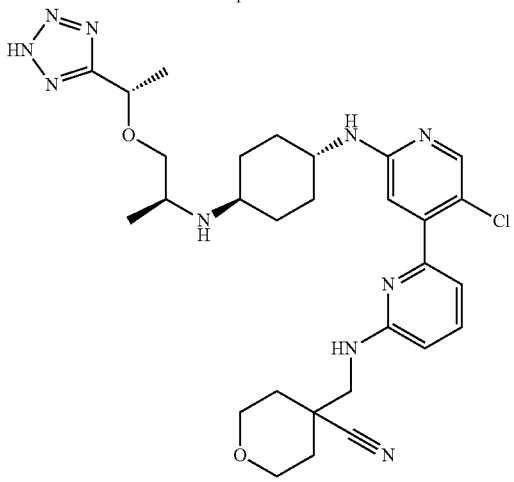

Compound 109

Compound 107

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and 1-(1-(2-trityl-2H-tetrazol-5-yl)ethoxy)propan-2-one (Intermediate 27) in DCE is added HOAc and NaBH(OAc)$_3$. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC and deprotected with HCl to afford 4-(((2'-(((1r,4r)-4-((1-((2-(2H-tetrazol-5-yl)propan-2-yl)oxy)propan-2-yl)amino)cyclohexyl)amino)-5'-chloro-[2,4'-bipyridin]-6-yl)amino)methyl)tetrahydro-2H-pyran-4-carbonitrile (Compound 102).

4-(((2'-(((1r,4r)-4-((1-((2-(2H-tetrazol-5-yl)propan-2-yl)oxy)propan-2-yl)amino)cyclohexyl)amino)-5'-chloro-[2,4'-bipyridin]-6-yl)amino)methyl)tetrahydro-2H-pyran-4-carbonitrile (Compound 102) is separated by chiral SFC to afford 4-(((2'-(((1R,4r)-4-(((2R,3S)-3-((2H-tetrazol-5-yl)methoxy)butan-2-yl)amino)cyclohexyl)amino)-5'-chloro-[2,4'-bipyridin]-6-yl)amino)methyl)tetrahydro-2H-pyran-4-carbonitrile (Compound 106), 4-(((2'-(((1S,4r)-4-(((S)-1-((R)-1-(2H-tetrazol-5-yl)ethoxy)propan-2-yl)amino)cyclohexyl)amino)-5'-chloro-[2,4'-bipyridin]-6-yl)amino)methyl)tetrahydro-2H-pyran-4-carbonitrile (Compound 107), 4-(((2'-(((1R,4r)-4-(((2R,3R)-3-((2H-tetrazol-5-yl)methoxy)butan-2-yl)amino)cyclohexyl)amino)-5'-chloro-[2,4'-bipyridin]-6-yl)amino)methyl)tetrahydro-2H-pyran-4-carbonitrile (Compound 108), and 4-(((2'-(((1S,4r)-4-(((S)-1-((S)-1-(2H-tetrazol-5-yl)ethoxy)propan-2-yl)amino)cyclohexyl)amino)-5'-chloro-[2,4'-bipyridin]-6-yl)amino)methyl)tetrahydro-2H-pyran-4-carbonitrile (Compound 109).

Example 70: Synthesis of 5-((2-oxopropoxy)methyl)-2,4-dihydro-3H-1,2,4-triazol-3-one (Intermediate 28)

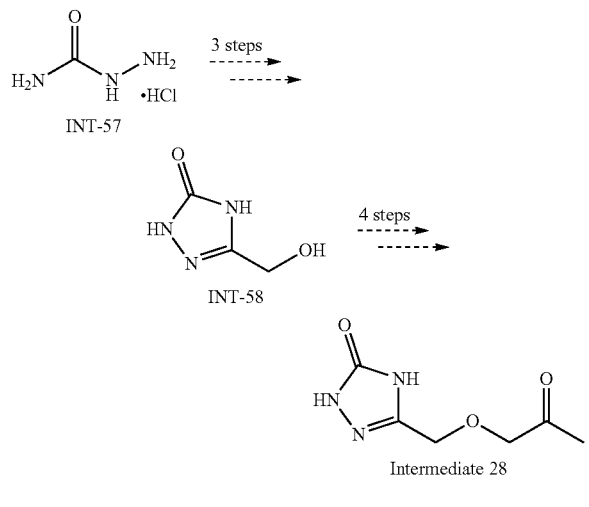

Step 1: Preparation of 5-(hydroxymethyl)-2,4-dihydro-3H-1,2,4-triazol-3-one (INT-58)

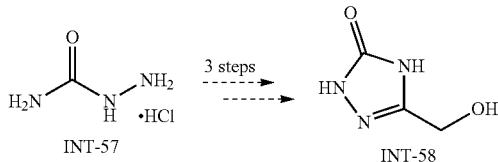

Hydrazinecarboxamide hydrochloride (INT-57) is converted to 5-(hydroxymethyl)-2,4-dihydro-3H-1,2,4-triazol-3-one (INT-58) in three synthetic steps.

Step 2: Preparation of 5-((2-oxopropoxy)methyl)-2,4-dihydro-3H-1,2,4-triazol-3-one (Intermediate 28)

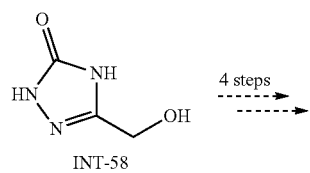

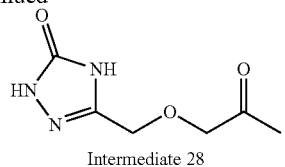

Intermediate 28

5-hydroxymethyl)-2,4-dihydro-3H-1,2,4-triazol-3-one (INT-58) is converted to 5-((2-oxopropoxy)methyl)-2,4-dihydro-3H-1,2,4-triazol-3-one (Intermediate 28) in four synthetic steps.

Example 71: Synthesis of 4-(((5'-chloro-2'-(((1R,4r)-4-(((R)-1-((5-oxo-4,5-dihydro-1H-1,2,4-triazol-3-yl)methoxy)propan-2-yl)amino)cyclohexyl)amino)-[2,4'-bipyridin]-6-yl)amino)methyl)tetrahydro-2H-pyran-4-carbonitrile (Compound 111) and 4-(((5'-chloro-2'-(((1S,4r)-4-(((S)-1-((5-oxo-4,5-dihydro-1H-1,2,4-triazol-3-yl)methoxy)propan-2-yl)amino)cyclohexyl)amino)-[2,4'-bipyridin]-6-yl)amino)methyl)tetrahydro-2H-pyran-4-carbonitrile (Compound 112)

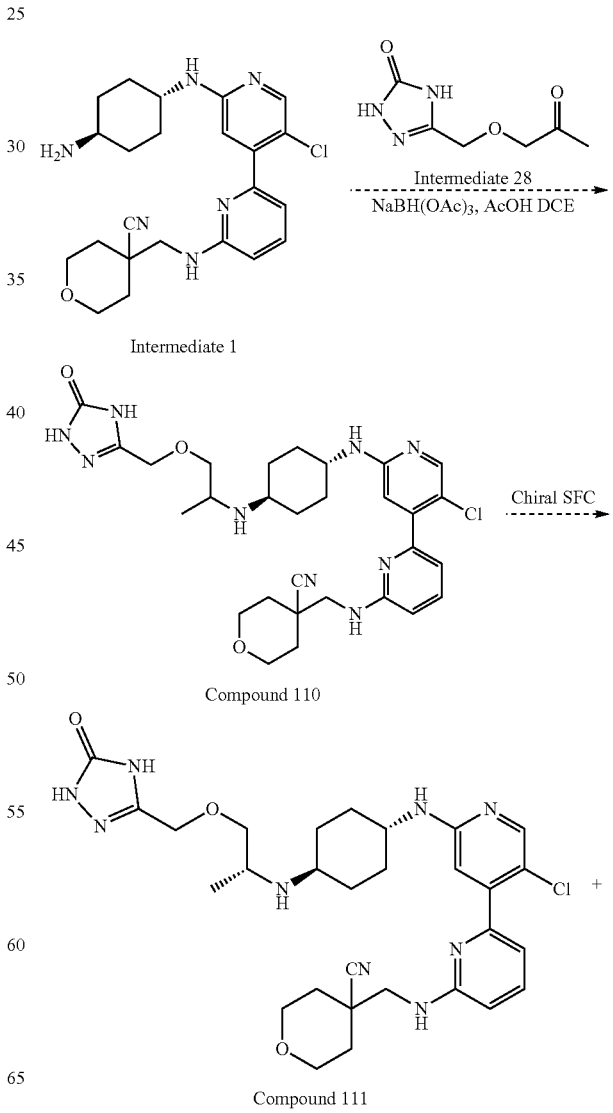

-continued

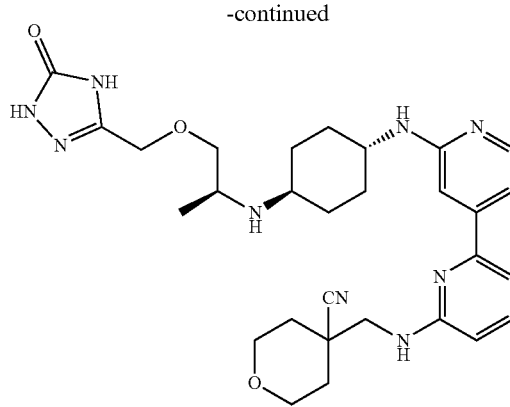

Compound 112

To a solution of 4-[[[6-[2-[(4-aminocyclohexyl)amino]-5-chloro-4-pyridyl]-2-pyridyl]amino]methyl]tetrahydropyran-4-carbonitrile (Intermediate 1) and 5-((2-oxopropoxy)methyl)-2,4-dihydro-3H-1,2,4-triazol-3-one (Intermediate 28) in DCE is added HOAc and $NaBH(OAc)_3$. The mixture is stirred at 20° C. for 36 hours. The mixture is quenched by water at 0° C., which is extracted with DCM. The combined organic phase is washed with brine, dried over anhydrous sodium sulfate, filtered and concentrated under reduced pressure. The residue is purified by prep-HPLC to afford 4-(((5'-chloro-2'-(((1r,4r)-4-((1-((5-oxo-4,5-dihydro-1H-1,2,4-triazol-3-yl)methoxy)propan-2-yl)amino)cyclohexyl)amino)-[2,4'-bipyridin]-6-yl)amino)methyl)tetrahydro-2H-pyran-4-carbonitrile (Compound 110).

4-(((5'-chloro-2'-(((1r,4r)-4-((1-((5-oxo-4,5-dihydro-1H-1,2,4-triazol-3-yl)methoxy)propan-2-yl)amino)cyclohexyl)amino)-[2,4'-bipyridin]-6-yl)amino)methyl)tetrahydro-2H-pyran-4-carbonitrile (Compound 110) is separated by chiral SFC to afford 4-(((5'-chloro-2'-(((1R,4r)-4-(((R)-1-((5-oxo-4,5-dihydro-1H-1,2,4-triazol-3-yl)methoxy)propan-2-yl)amino)cyclohexyl)amino)-[2,4'-bipyridin]-6-yl)amino)methyl)tetrahydro-2H-pyran-4-carbonitrile (Compound 111) and 4-(((5'-chloro-2'-(((1S,4r)-4-(((S)-1-((5-oxo-4,5-dihydro-1H-1,2,4-triazol-3-yl)methoxy)propan-2-yl)amino)cyclohexyl)amino)-[2,4'-bipyridin]-6-yl)amino)methyl)tetrahydro-2H-pyran-4-carbonitrile (Compound 112).

Example 72: CDK9 Biochemical Assay

To each well of a 96-well plate was added 5× kinase assay buffer with 10 mM DTT (6 µL), 500 µM ATP (1 µL), 5×CDK substrate (10 µL), and water (8 µL). 5 µL of compound were added to the test and positive control groups, while 5 µL of solvent was added to the blank groups. 100 ng of CDK9/CyclinT in 20 µL water was added to the test and positive control groups, while 20 µL of 1× kinase assay buffer was added to the blank groups. The reaction mixtures were incubated at 30° C. for 45 minutes, and 50 µL of Kinase-Glo® Max was added to each well and the plates were shielded from light and incubated for 15 minutes at room temperature. Luminescence was measured on a microplate reader and $IC_{50}$ values were calculated using Prism 9 software.

The $IC_{50}$ values obtained according to the above procedure are summarized in Table 1:

| Compound | $IC_{50}$ (nM) |
|---|---|
| NVP-2 | B |
| 2 | D |
| 3 | D |
| 5 | A |
| 6 | A |
| 8 | B |
| 9 | C |
| 12 | D |
| 13 | D |
| 15 | B |
| 16 | C |
| 18 | D |
| 19 | B |
| 21 | A |
| 22 | B |
| 24 | D |
| 25 | D |
| 27 | A |
| 28 | D |
| 30 | A |
| 31 | A |
| 33 | C |
| 34 | D |
| 36 | A |
| 37 | A |
| 40 | B |
| 41 | C |

A: < 2.50 nM; 2.50 nM ≤ B < 5.00 nM; 5.00 nM ≤ C < 10.00 nM; 10.00 nM < D

Example 73: Cancer Cell Viability Assay

Human liver cancer cell lines HepG2, Hep3B, Huh7, and SK-HEP-1 cells were rinsed and trypsinized with 0.25% trypsin (Corning #25-053-CI) in an incubator at 37° C. until detached. The cells were resuspended and seeded in 96-well plates to a density of 5,000 cells per well. Following cell adhesion, compounds were added to a final concentration of 2× dilution. 72 hours following compound treatment, CellTiter-Glo® 2.0 was added to the well in a 2:1 ratio of media/CellTiter-Glo® 2.0. The plates were shielded from light, shaken for 2 minutes, and incubated for 10 minutes. Luminescence was measured on a microplate reader and $EC_{50}$ values were calculated using Prism 9 software.

The $EC_{50}$ values obtained according to the above procedure are summarized in Table 2:

| Compound | HepG2 $EC_{50}$ (nM) | Hep3B $EC_{50}$ (nM) | Huh7 $EC_{50}$ (nM) | SK-HEP-1 $EC_{50}$ (nM) |
|---|---|---|---|---|
| 2 | D | D | C | D |
| 3 | D | ND | D | D |
| 5 | C | ND | A | A |
| 6 | C | B | A | A |
| 8 | D | ND | D | D |
| 9 | D | D | D | D |
| 12 | D | ND | ND | ND |
| 13 | D | ND | ND | ND |
| 15 | A | ND | A | A |
| 16 | B | ND | A | A |
| 18 | A | A | A | A |
| 19 | A | ND | A | A |
| 21 | D | C | ND | ND |
| 22 | D | C | ND | ND |
| 24 | D | D | ND | ND |
| 25 | D | D | ND | ND |
| 27 | D | D | ND | ND |
| 28 | D | D | ND | ND |
| 30 | C | D | ND | ND |
| 31 | D | D | ND | ND |
| 33 | A | B | ND | ND |
| 34 | A | B | ND | ND |

-continued

| Compound | HepG2 EC$_{50}$ (nM) | Hep3B EC$_{50}$ (nM) | Huh7 EC$_{50}$ (nM) | SK-HEP-1 EC$_{50}$ (nM) |
|---|---|---|---|---|
| 36 | B | C | ND | ND |
| 37 | B | B | ND | ND |
| 40 | A | B | ND | ND |
| 41 | A | B | ND | ND |

A: < 100 nM; 100 nM ≤ B < 500 nM; 500 nM ≤ C < 1,000 nM; 1,000 nM < D; ND = no data

Example 74: Pharmacokinetic and Tissue Distribution Study

For mice experiments, the liver and blood pharmacokinetics of compounds were analyzed in CD-1 mice following a single oral administration dose of 5 mg/kg compound suspension.

Liver and blood samples for determination of compound concentration were obtained at 2 hours following administration of compounds (n=3 for each compound). The ratios of compound concentrations in liver versus blood in CD-1 mice following a single oral administration dose of 5 mg/kg compound suspension are summarized in FIG. 1. The data in FIG. 1 show that Compounds 18, 40, and 33 have higher liver/blood ratios than NVP-2, demonstrating that these compounds have improved liver selectivity.

Figure 2:
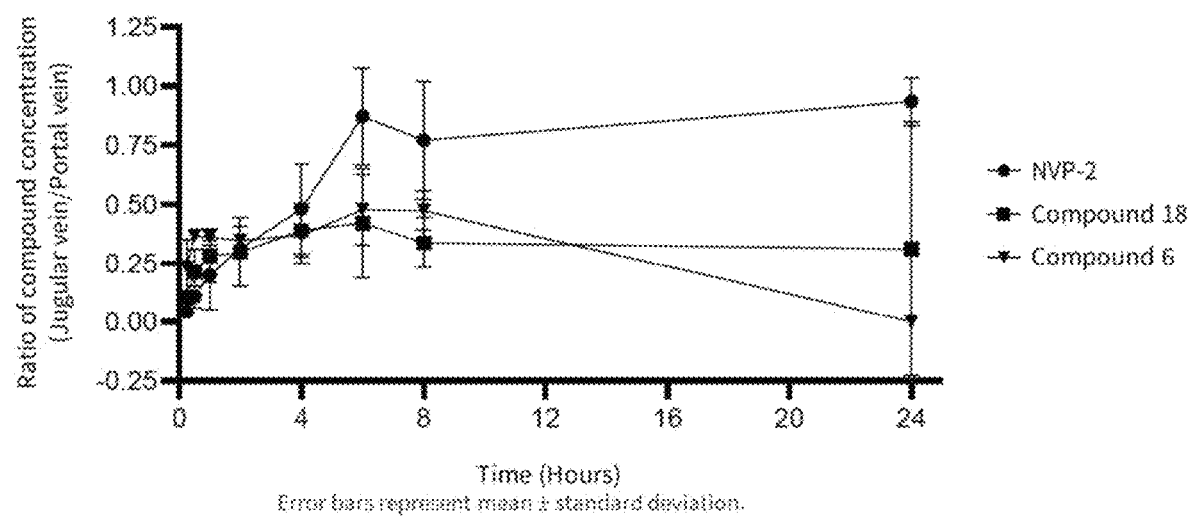
FIG. 2 shows ratios of compound concentrations in blood collected from jugular vein versus portal vein in Sprague-Dawley (SD) rats following a single oral administration dose of 5 mg/kg compound suspension.

For rat experiments, the pharmacokinetics of compounds in blood collected from jugular vein and portal vein were analyzed in Sprague-Dawley (SD) rats following a single oral administration dose of 5 mg/kg compound suspension. Blood samples for determination of compound concentration were obtained from jugular vein and portal vein at 0.25 h, 0.5 h, 1 h, 2 h, 4 h, 6 h, 8 h, and 24 h following administration of compounds (n=3 for each compound). Collected liver and blood samples were analyzed using an LC-MS/MS method to quantify compound concentrations. The ratios of compound concentrations in blood collected from jugular vein versus portal vein in Sprague-Dawley (SD) rats following a single oral administration dose of 5 mg/kg compound suspension are summarized in FIG. 2. The data in FIG. 2 show that Compounds 6 and 18 have a lower liver efflux/influx ratio than NVP-2, demonstrating that these compounds have improved liver selectivity.

Example 75: Tolerability and Safety Assessment Study

Figure 3:
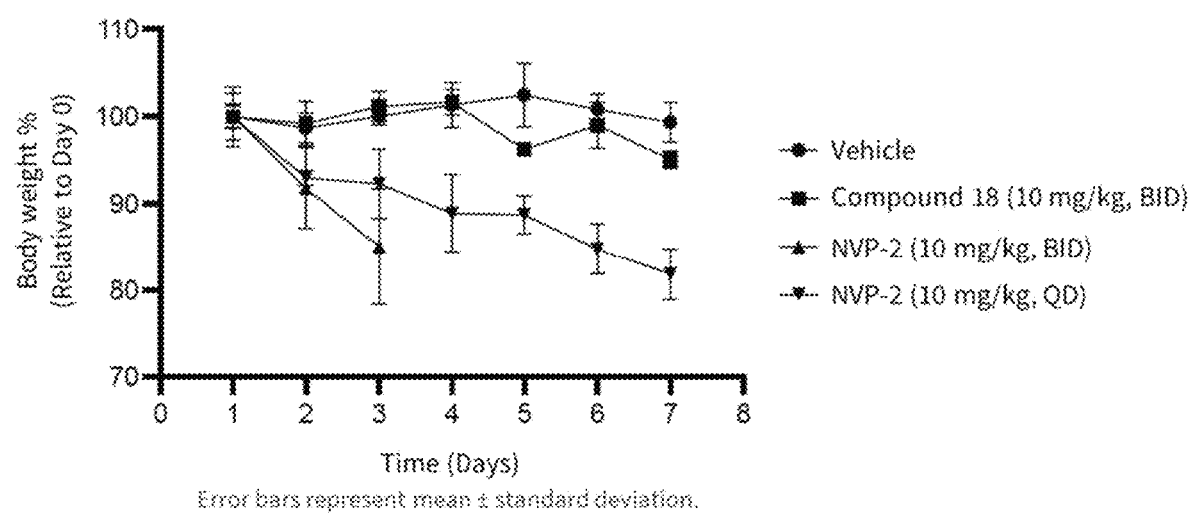
FIG. 3 shows mean weight changes (relative to day 1) of BALB/c nude mice treated with vehicle and compounds.

Based on the body weight, BALB/c nude mice were randomly assigned to respective groups using a computer-generated randomization procedure. Body weights of all animals were measured daily to record weight changes (relative to day 1) of BALB/c nude mice treated with vehicle and compounds. For routine monitoring, all study animals were monitored for behavior such as mobility, food and water consumption, body weight, eye/hair matting and any other abnormal effect. Any mortality and/or abnormal clinical signs were recorded. The animals were euthanized when they lost significant body mass (emaciated, obvious body weight loss >20%). Mean weight changes (relative to day 1) of BALB/c nude mice treated with vehicle and compounds are summarized in FIG. 3. The data in FIG. 3 show that Compound 18 displays lower toxicity than NVP-2.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

It is intended that the following claims define the scope of the invention and that methods and structures within the scope of these claims and their equivalents be covered thereby.

What is claimed is:
1. A compound of Formula (I-A):

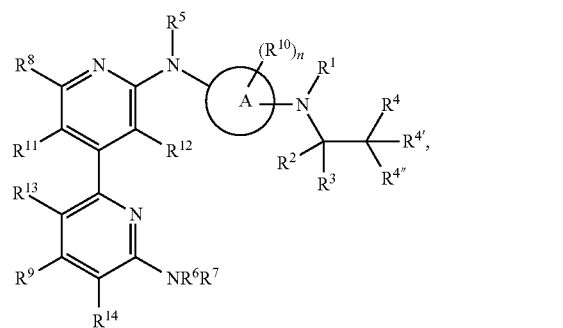

Formula (I-A)

or a pharmaceutically acceptable salt thereof,
wherein:
Ring A is $C_{3-6}$cycloalkyl or $C_{6-10}$aryl;
$R^1$ is selected from H, $C_{1-6}$alkyl, $C_{1-6}$heteroalkyl, $C_{1-6}$halooalkyl, $C_{3-6}$cycloalkyl, 3- to 10-membered heterocycloalkyl, $C_{6-10}$aryl, 6- to 10-membered heteroaryl; wherein each alkyl, cycloalkyl, heterocycloalkyl, aryl, and heteroaryl is independently optionally substituted with one or more substituents selected from oxo, halo, —OR$^{18}$, $C_{1-4}$alkyl, $C_{1-4}$alkoxy, $C_{1-4}$heteroalkyl, $C_{1-4}$haloalkyl, —CN, and —NR$^{20}$R$^{21}$;
$R^2$ is selected from halo, —CN, —OH, —OMe, —OEt, —NH$_2$, —NHMe, —NMe$_2$, Me, Et, n-Pr, i-Pr, —CF$_3$, and cyclopropyl;
$R^3$ is selected from H, halo, —CN, —OR$^{18}$, —SOR$^{15}$, —SO$_2$R$^{15}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —NR$^{19}$C(O)R$^{18}$, —NR$^{19}$C(O)NR$^{16}$R$^{17}$, NR$^{19}$SO$_2$R$^{15}$,—NR$^{19}$SO$_2$NR$^{16}$R$^{17}$, $C_{1-6}$alkyl, $C_{2-6}$alkenyl, $C_{2-6}$alkynyl, $C_{1-6}$heteroalkyl, $C_{1-6}$haloalkyl, $C_{3-6}$cycloalkyl, 3- to 10-membered heterocycloalkyl, $C_{6-10}$aryl, and 6- to 10-membered heteroaryl;
wherein each alkyl, alkenyl, alkynyl, cycloalkyl, heterocycloalkyl, aryl, and heteroaryl is independently optionally substituted with one or more substituents selected from oxo, halo, —OR$^{18}$, $C_{1-4}$alkyl, $C_{1-4}$alkoxy, $C_{1-4}$heteroalkyl, $C_{1-4}$haloalkyl, —CN, and —NR$^{20}$R$^{21}$;
$R^4$ is selected from $C_{1-6}$alkyl, $C_{2-6}$heteroalkyl, $C_{1-6}$haloalkyl, $C_{3-6}$cycloalkyl, 3- to 10-membered heterocycloalkyl, $C_{6-10}$aryl, 6- to 10-membered heteroaryl, —O(C$_{0-4}$alkyl)C$_{3-6}$cycloalkyl, —O(C$_{0-4}$alkyl)(3- to 10-membered heterocycloalkyl), —O(C$_{0-4}$alkyl)C$_{6-10}$aryl, —O(C$_{0-4}$alkyl)(6- to 10-membered heteroaryl), —O(C$_{0-4}$alkyl)C(O)OR$^{18}$, —O(C$_{0-4}$alkyl)

C(O)NR$^{19}$SO$_2$R$^{15}$, —O(C$_{0-4}$alkyl) SO$_2$NR$^{19}$C(O)R$^{18}$, —O(C$_{3-6}$cycloalkyl)C$_{3-6}$cycloalkyl, —O(C$_{3-6}$cycloalkyl)(3- to 10-membered heterocycloalkyl), —O(C$_{3-6}$cycloalkyl)C$_{6-10}$aryl, —O(C$_{3-6}$cycloalkyl) (6- to 10-membered heteroaryl), —O(C$_{3-6}$cycloalkyl)C(O)OR$^{18}$, —(C$_{1-4}$alkyl)C$_{3-6}$cycloalkyl, —(C$_{1-4}$ alkyl)(3- to 10-membered heterocycloalkyl), —(C$_{1-4}$alkyl)C$_{6-10}$aryl, —(C$_{1-4}$alkyl)(6- to 10-membered heteroaryl), and —(C$_{1-4}$alkyl)C(O)OR$^{18}$; wherein each alkyl, heteroalkyl, cycloalkyl, heterocycloalkyl, aryl, and heteroaryl is independently optionally substituted with one or more substituents selected from C$_{1-4}$alkyl, oxo, halo, —OR$^{18}$, —CN, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —(C$_{1-4}$alkyl)OC(O)(C$_{1-4}$alkyl), —(C$_{1-4}$alkyl)OC(O)OR$^{18}$, —NR$^{19}$C(O)R$^{18}$, —NR$_{19}$C(O)NR$^{16}$R$^{17}$, —NR$^{19}$SO$_2$R$^{15}$, and —NR$^{19}$SO$_2$NR$^{16}$R$^{17}$; and R$^{4'}$ and R$^{4''}$ are each independently selected from H, C$_{1-6}$-alkyl, C$_{2-6}$heteroalkyl, C$_{1-6}$haloalkyl, C$_{3-6}$cycloalkyl, 3- to 10-membered heterocycloalkyl, C$_{6-10}$aryl, 6- to 10-membered heteroaryl, —O(C$_{0-4}$alkyl)C$_{3-6}$cycloalkyl, —O(C$_{0-4}$alkyl)(3- to 10-membered heterocycloalkyl), —O(C$_{0-4}$alkyl)C$_{6-10}$aryl, —O(C$_{0-4}$alkyl)(6- to 10-membered heteroaryl), —O(C$_{0-4}$alkyl)C(O)OR$^{18}$, —O(C$_{0-4}$alkyl)C(O)NR$^{19}$SO$_2$R$^{15}$, —O(C$_{0-4}$alkyl)SO$_2$ NR$^{19}$C(O)R$^{18}$, —O(C$_{3-6}$cycloalkyl)C$_{3-6}$cycloalkyl, —O(C$_{3-6}$cycloalkyl)(3- to 10-membered heterocycloalkyl), —O(C$_{3-6}$cycloalkyl)C$_{6-10}$aryl, —O(C$_{3-6}$cycloalkyl) (6- to 10-membered heteroaryl), —O(C$_{3-6}$cycloalkyl)C(O)OR$^{18}$, —(C$_{1-4}$alkyl)C$_{3-6}$cycloalkyl, —(C$_{1-4}$ alkyl)(3- to 10-membered heterocycloalkyl), —(C$_{1-4}$alkyl)C$_{6-10}$aryl, and —(C$_{1-4}$alkyl)(6- to 10-membered heteroaryl); wherein each alkyl, heteroalkyl, cycloalkyl, heterocycloalkyl, aryl, and heteroaryl is independently optionally substituted with one or more substituents selected from oxo, halo, —OR$^{18}$, —CN, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —(C$_{1-4}$alkyl)OC(O)(C$_{1-4}$alkyl), —(C$_{1-4}$alkyl)OC(O)OR$^{18}$, —NR$^{19}$C(O)R$^{18}$, —NR$^{19}$C(O)NR$^{16}$R$^{17}$, NR$^{19}$SO$_2$R$^{15}$, and —NR$^{19}$SO$_2$NR$^{16}$R$^{17}$; or R$^3$ is H; and R$^4$, R$^{4'}$, and R$^{4''}$ are taken together, along with the carbon atom to which they are attached, to form —C(O)R$^{18}$ or 6- to 10-membered heteroaryl;

R$^5$ is selected from H, C$_{1-6}$alkyl, C$_{1-6}$heteroalkyl, C$_{1-6}$haloalkyl, C$_{3-6}$cycloalkyl, 3- to 10-membered heterocycloalkyl, C$_{6-10}$aryl, and 6- to 10-membered heteroaryl; wherein each alkyl, cycloalkyl, heterocycloalkyl, aryl, and heteroaryl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

R$^6$ and R$^7$ are each independently selected from H, C$_{1-6}$alkyl, C$_{1-6}$heteroalkyl, C$_{1-6}$haloalkyl, C$_{3-6}$cycloalkyl, 3- to 10-membered heterocycloalkyl, C$_{6-10}$aryl, 6- to 10-membered heteroaryl, —(C$_{1-4}$alkyl)C$_{3-6}$cycloalkyl, —(C$_{1-4}$alkyl)(3- to 10-membered heterocycloalkyl), —(C$_{1-4}$alkyl)C$_{6-10}$aryl, and —(C$_{1-4}$alkyl)(6- to 10-membered heteroaryl); wherein each alkyl, cycloalkyl, heterocycloalkyl, aryl, and heteroaryl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$haloalkyl, —CN, and —NR$^{20}$R$^{21}$;

R$^8$ and R$^9$ are both H;

each R$^{10}$ is independently selected from halo, —CN, —OR$^{18}$, —NR$^{16}$R$^{17}$, —C(O)NR$^{16}$R$^{17}$, —SO$_2$NR$^{16}$R$^{17}$, —C(O)NR$^{16}$R$^{17}$, —C(O)R$^{18}$, —C(O)OR$^{18}$, —NR$^{19}$C(O)R$^{18}$, C$_{1-6}$alkyl, C$_{1-6}$heteroalkyl, C$_{1-6}$haloalkyl, C$_{3-6}$cycloalkyl, 3- to 10-membered heterocycloalkyl; wherein each alkyl, cycloalkyl, and heterocycloalkyl is independently optionally substituted with one or more substituents selected from oxo, halo, —OR$^{18}$, C$_{1-4}$alkyl, C$_{1-4}$alkoxy, C$_{1-4}$heteroalkyl, C$_{1-4}$halooalkyl, —CN, and —NR$^{20}$R$^{21}$;

R$^{11}$, R$^{12}$, R$^{13}$, and R$^{14}$ are each independently selected from H, halo, —CN, —OR$^{18}$, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —NR$^{19}$C(O)R$^{18}$, C$_{1-6}$alkyl, and C$_{1-6}$haloalkyl;

each R$^{15}$ is independently selected from C$_{1-4}$alkyl, C$_{1-4}$haloalkyl, C$_{3-6}$cycloalkyl, 3- to 10-membered heterocycloalkyl, C$_{6-10}$aryl, and 6- to 10-membered heteroaryl;

each R$^{16}$ and R$^{17}$ is independently selected from H, C$_{1-4}$alkyl, C$_{1-4}$heteroalkyl, C$_{1-4}$haloalkyl, C$_{3-6}$cycloalkyl, 3- to 10-membered heterocycloalkyl, C$_{6-10}$aryl, 6- to 10-membered heteroaryl; or an R$^{16}$ and an R$^{17}$ may be taken together along with the nitrogen atom to which they are attached to form a 3- to 10-membered heterocycloalkyl;

each R$^{18}$ is independently selected from H, C$_{1-4}$alkyl, C$_{1-4}$heteroalkyl, C$_{1-4}$haloalkyl, and C$_{3-6}$cycloalkyl;

each R$^{19}$ is independently selected from H, C$_{1-4}$alkyl, C$_{1-4}$heteroalkyl, C$_{1-4}$haloalkyl, and C$_{3-6}$cycloalkyl; and each R$^{20}$ and R$^{21}$ is independently selected from H, C$_{1-4}$alkyl, C$_{1-4}$heteroalkyl, C$_{1-4}$haloalkyl, C$_{3-6}$cyckloalkyl, 3- to 10-membered heterocycloalkyl, C$_{6-10}$aryl, 6- to 10-membered heteroaryl; or an R$^{20}$ and an R$^{21}$ may be taken together along with the nitrogen atom to which they are attached to form a 3- to 10-membered heterocycloalkyl; and n is 0, 1, 2, 3, or 4.

2. The compound or pharmaceutically acceptable salt of claim 1,
wherein the compound of Formula (I-A) is a compound of Formula (I-B):

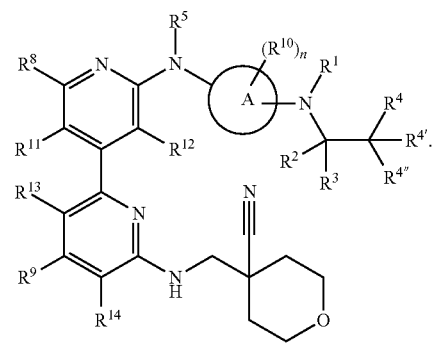

Formula (I-B)

3. The compound or pharmaceutically acceptable salt of claim 1,
wherein Ring A is C$_{3-6}$cycloalkyl.

4. The compound or pharmaceutically acceptable salt of claim 1,
wherein Ring A is selected from the group consisting of:

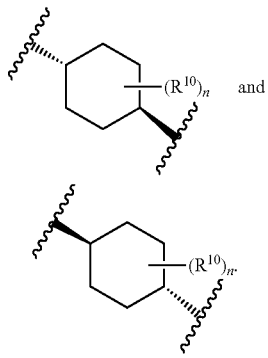

and

5. The compound or pharmaceutically acceptable salt of claim 1,
wherein $R^{11}$, $R^{12}$, $R^{13}$, and $R^{14}$ are each independently selected from H, halo, —CN, —OR$^{18}$, and —NR$^{16}$R$^{17}$.

6. The compound or pharmaceutically acceptable salt of claim 1,
wherein $R^{11}$ is chloro, and $R^{12}$, $R^{13}$, and $R^{14}$ are each H.

7. The compound or pharmaceutically acceptable salt of claim 1,
wherein $R^1$ is selected from H, $C_{1-6}$alkyl, $C_{1-6}$haloalkyl, and $C_{3-6}$ cycloalkyl.

8. The compound or pharmaceutically acceptable salt of claim 1,
wherein $R^1$ is Me.

9. The compound or pharmaceutically acceptable salt of claim 1,
wherein $R^1$ is H.

10. The compound or pharmaceutically acceptable salt of claim 1,
wherein $R^2$ is Me.

11. The compound or pharmaceutically acceptable salt of claim 1,
wherein $R^3$ is selected from H, Me, Et, —CF$_3$, and cyclopropyl.

12. The compound or pharmaceutically acceptable salt of claim 1,
wherein $R^3$ is H.

13. The compound or pharmaceutically acceptable salt of claim 1,
wherein $R^2$ is Me and $R^3$ is H.

14. The compound or pharmaceutically acceptable salt of claim 1,
wherein:
$R^4$ is selected from $C_{1-6}$alkyl, $C_{2-6}$heteroalkyl, $C_{1-6}$haloalkyl, $C_{3-6}$cycloalkyl, 3- to 10-membered heterocycloalkyl, $C_{6-10}$aryl, 6- to 10-membered heteroaryl, —O($C_{0-4}$alkyl)$C_{3-6}$cycloalkyl, —O($C_{0-4}$alkyl)(3- to 10-membered heterocycloalkyl), —O($C_{0-4}$alkyl)$C_{6-10}$aryl, —O($C_{0-4}$alkyl)(6- to 10-membered heteroaryl), —O($C_{0-4}$alkyl)C(O)OR$^{18}$, —O($C_{0-4}$alkyl)C(O)NR$^{19}$SO$_2$R$^{15}$, —O($C_0$-$_4$alkyl)SO$_2$NR$^{19}$C(O)R$^{18}$, —O($C_{3-6}$cycloalkyl)$C_{3-6}$cycloalkyl, —O($C_{3-6}$cycloalkyl)(3- to 10-membered heterocycloalkyl), —O($C_{3-6}$cycloalkyl)$C_{6-10}$aryl, —O($C_{3-6}$cycloalkyl)(6- to 10-membered heteroaryl), —O($C_{3-6}$cycloalkyl)C(O)OR$^{18}$, —($C_{1-4}$-alkyl)$C_{3-6}$cycloalkyl, —($C_{1-4}$-alkyl)(3- to 10-membered heterocycloalkyl), —($C_{1-4}$-alkyl)$C_{6-10}$aryl, —($C_{1-4}$-alkyl)(6- to 10-membered heteroaryl), and —($C_{1-4}$-alkyl)C(O)OR$^{18}$; wherein each alkyl, heteroalkyl, cycloalkyl, heterocycloalkyl, aryl, and heteroaryl is independently optionally substituted with one or more substituents selected from $C_{1-4}$alkyl, oxo, halo, —OR$^{18}$, —CN, —NR$^{16}$R$^{17}$, —C(O)NR$^{16}$R$^{17}$, —SO$_2$NR$^{16}$R$^{17}$, —C(O)R$^{18}$, —C(O)OR$^{18}$, —($C_{1-4}$-alkyl)OC(O)($C_{1-4}$alkyl), —($C_{1-4}$-alkyl)OC(O)OR$^{18}$, —NR$^{19}$C(O)R$^{18}$, —NR$^{19}$C(O)NR$^{16}$R$^{17}$, —NR$^{19}$SO$_2$R$^{15}$, and —NR$^{19}$SO$_2$NR$^{16}$R$^{17}$; and
$R^{4'}$ and $R^{4''}$ are each independently selected from H, $C_{1-6}$-alkyl, $C_{1-6}$haloalkyl, and $C_{3-6}$cycloalkyl; wherein each alkyl and cycloalkyl is independently optionally substituted with one or more substituents selected from halo, —OR$^{18}$, —CN, and —NR$^{16}$R$^{17}$; or
$R^3$ is H; and
$R^4$, $R^{4'}$, and $R^{4''}$ are taken together, along with the carbon atom to which they are attached, to form —C(O)R$^{18}$ or 6- to 10-membered heteroaryl.

15. The compound or pharmaceutically acceptable salt of claim 1,
wherein:
$R^4$ is selected from $C_{2-6}$heteroalkyl, $C_{1-6}$-haloalkyl, 6- to 10-membered heteroaryl, —O($C_{0-4}$alkyl)(3- to 10-membered heterocycloalkyl), —O($C_{0-4}$alkyl)$C_{6-10}$aryl, —O($C_{0-4}$alkyl)(6- to 10-membered heteroaryl), —O($C_{0-4}$alkyl)C(O)OR$^{18}$, —O($C_{0-4}$alkyl)C(O)NR$^{19}$SO$_2$R$^{15}$, —O($C_{0-4}$alkyl)SO$_2$NR$^{19}$C(O)R$^{18}$, —O($C_{3-6}$cycloalkyl)(6- to 10-membered heteroaryl), —O($C_{3-6}$cycloalkyl)C(O)OR$^{18}$, —($C_{1-4}$-alkyl)(6- to 10-membered heteroaryl) and —($C_{1-4}$alkyl)C(O)OR$^{18}$; wherein each alkyl, heteroalkyl, cycloalkyl, heterocycloalkyl, aryl, and heteroaryl is independently optionally substituted with one or more substituents selected from $C_{1-4}$alkyl, oxo, halo, —OR$^{18}$, —CN, —NR$^{16}$R$^{17}$, —C(O)NR$^{16}$R$^{17}$, —SO$_2$NR$^{16}$R$^{17}$, —C(O)OR$^{18}$, —($C_{1-4}$-alkyl)OC(O)($C_{1-4}$alkyl), —($C_{1-4}$alkyl)OC(O)OR$^{18}$, —NR$^{19}$C(O)R$^{18}$, —NR$^{19}$C(O)NR$^{16}$R$^{17}$, —NR$^{19}$SO$_2$R$^{15}$, and —NR$^{19}$SO$_2$NR$^{16}$R$^{17}$; and
$R^{4'}$ and $R^{4''}$ are both H; or
$R^3$ is H; and
$R^4$, $R^{4'}$, and $R^{4''}$ are taken together, along with the carbon atom to which they are attached, to form —C(O)R$^{18}$ or 6- to 10-membered heteroaryl.

16. The compound or pharmaceutically acceptable salt of claim 1,
wherein:
$R^4$ is selected from $C_{2-6}$heteroalkyl, —O($C_{0-4}$alkyl)(6- to 10-membered heteroaryl), —O($C_{0-4}$alkyl)C(O)OR$^{18}$, —O($C_{0-4}$alkyl)C(O)NR$^{19}$SO$_2$R$^{15}$, and ($C_{1-4}$-alkyl)C(O)OR$^{18}$; wherein each alkyl, heteroalkyl, and heteroaryl is independently optionally substituted with one or more substituents selected from $C_{1-4}$-alkyl, oxo, halo, —OR$^{18}$, —CN, —NR$^{16}$R$^{17}$, —C(O)NR$^{16}$R$^{17}$, —SO$_2$NR$^{16}$R$^{17}$, —C(O)R$^{18}$, —($C_{1-4}$-alkyl)OC(O) ($C_{1-4}$alkyl), —($C_{1-4}$-alkyl)OC(O)OR$^{18}$, —NR$^{19}$C(O)R$^{18}$, —NR$^{19}$C(O)NR$^{16}$R$^{17}$, —NR$^{19}$SO$_2$R$^{15}$, and —NR$^{19}$SO$_2$NR$^{16}$R$^{17}$; and
$R^{4'}$ and $R^{4''}$ are both H.

17. The compound or pharmaceutically acceptable salt of claim 16,
wherein $R^4$ is a 3- to 8-membered heteroalkyl comprising one or more O skeletal chain atom, wherein $R^4$ is connected through an O or a carbon in the heteroalkyl.

18. The compound or pharmaceutically acceptable salt of claim 1,
wherein $R^5$ is selected from H, $C_{1-6}$alkyl, $C_{1-6}$haloalkyl, and $C_{3-6}$cycloalkyl.

19. The compound or pharmaceutically acceptable salt of claim 1,
wherein $R^5$ is H.

20. The compound or pharmaceutically acceptable salt of claim 1,
wherein $R^6$ and $R^7$ are each independently selected from H and —($C_{1-4}$alkyl)(3- to 10-membered heterocycloalkyl); wherein each alkyl and heterocycloalkyl is independently optionally substituted with one or more substituents selected from halo, —$OR^{18}$, —CN, and —$NR^{20}R^{21}$.

21. The compound or pharmaceutically acceptable salt of claim 10,
wherein one of $R^6$ and $R^7$ is H and the other is

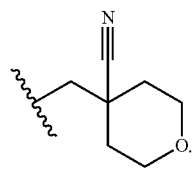 [SMILES: *CC1(C#N)CCOCC1]

22. The compound or pharmaceutically acceptable salt of claim 1,
wherein n is 0.

23. The compound or pharmaceutically acceptable salt of claim 1,
wherein $R^1$ is H, $R^2$ is Me, $R^3$ is H, $R^5$ is H, $R^8$ and $R^9$ are both H, and one of $R^6$ and $R^7$ is
H and the other is

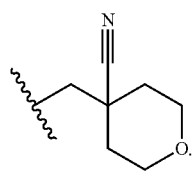 [SMILES: *CC1(C#N)CCOCC1]

24. The compound or pharmaceutically acceptable salt of claim 23,
wherein $R^{11}$ is chloro, and $R^{12}$, $R^{13}$, and $R^{14}$ are each H.

25. The compound or pharmaceutically acceptable salt of claim 1,
wherein the compound of Formula (I) is represented by Formula (I-C), Formula (I-D), Formula (I-E), or Formula (I-F):

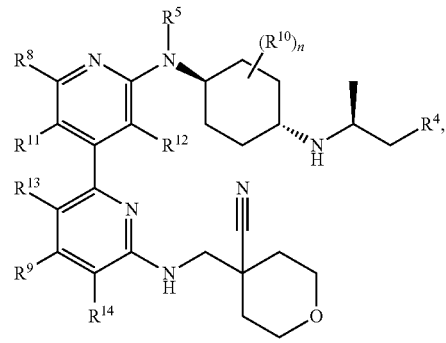

Formula (I-C)

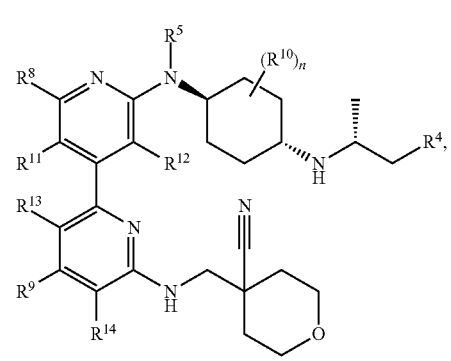

Formula (I-D)

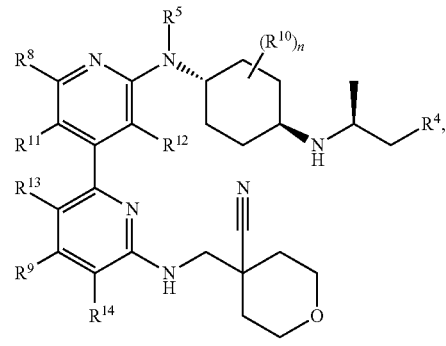

Formula (I-E)

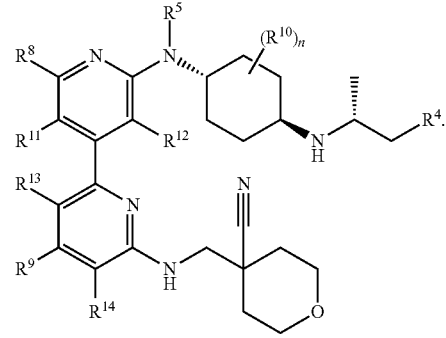

Formula (I-F)

26. The compound or pharmaceutically acceptable salt of claim 1,
wherein the compound is selected from the group consisting of:

259
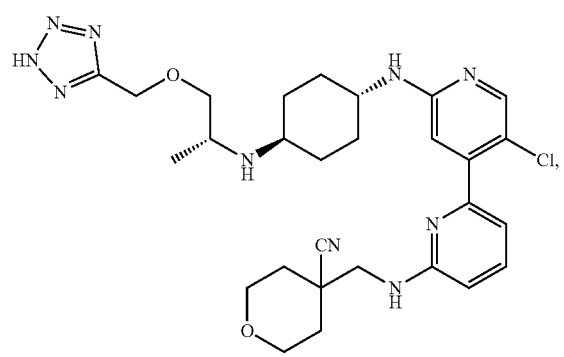
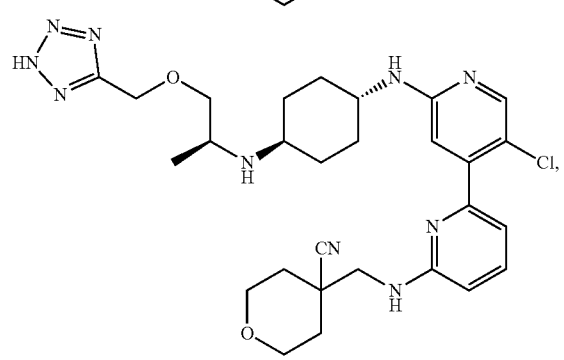
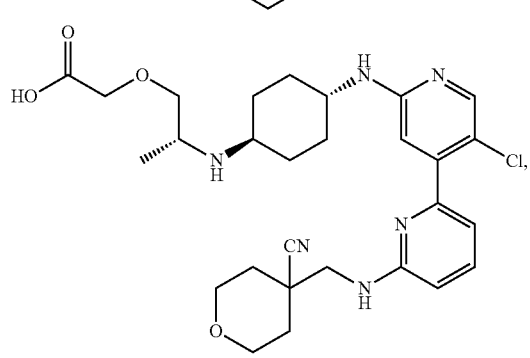
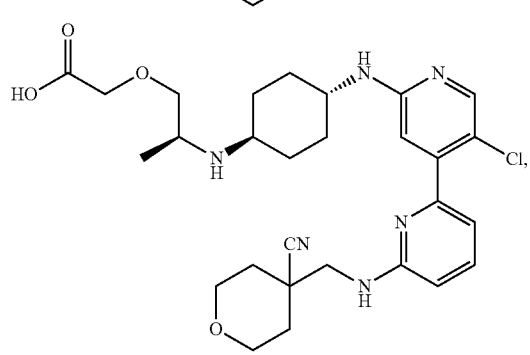
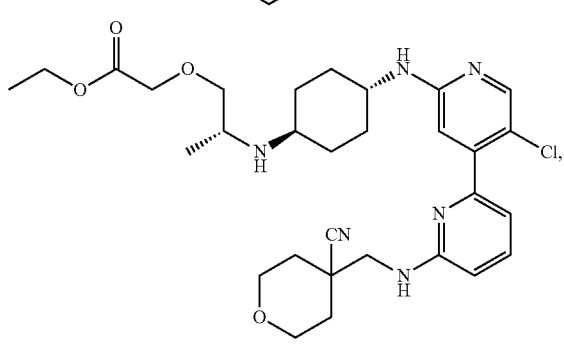
260
-continued
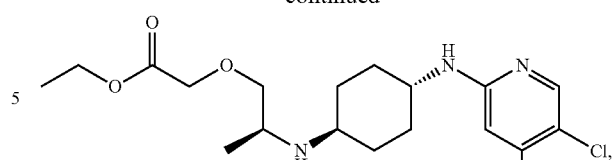
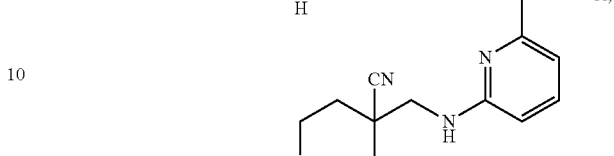
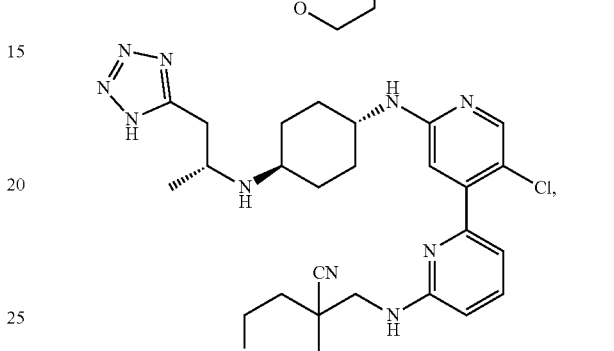
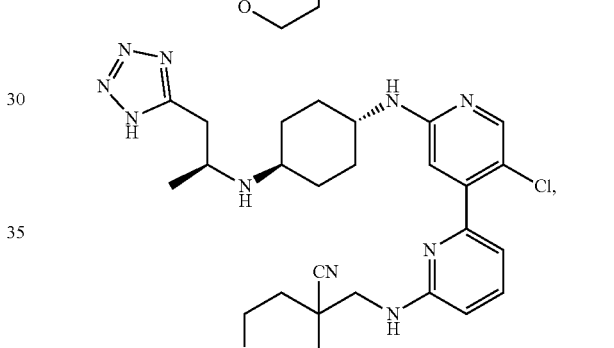
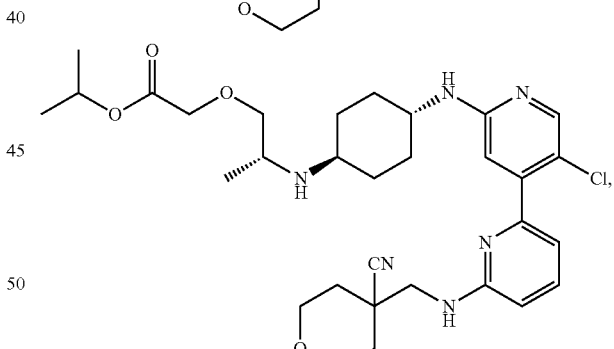
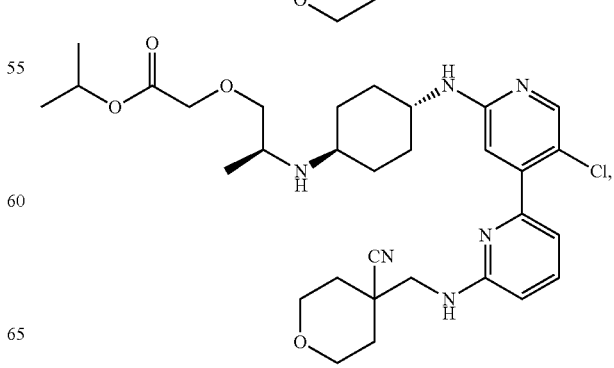

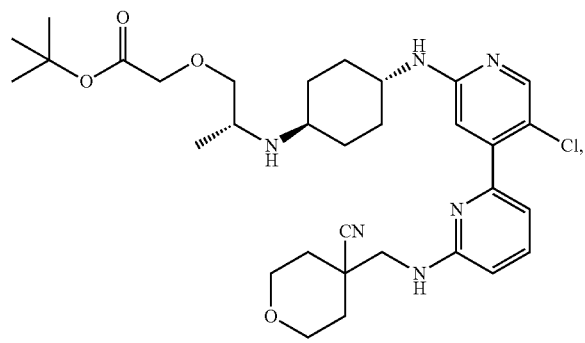
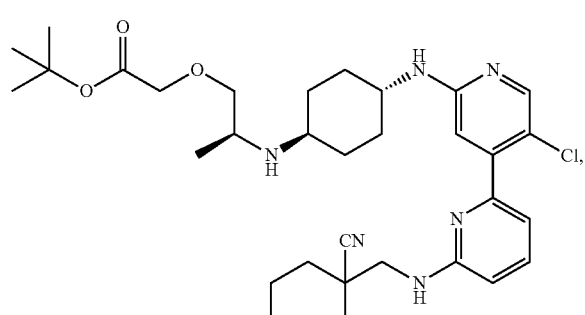
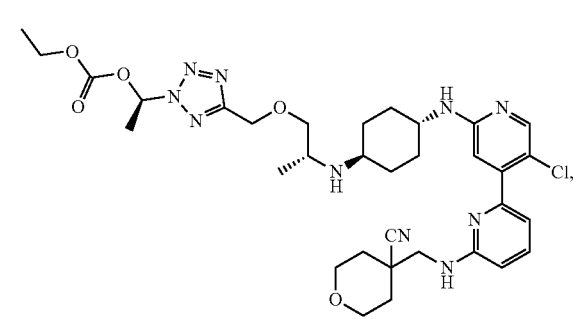
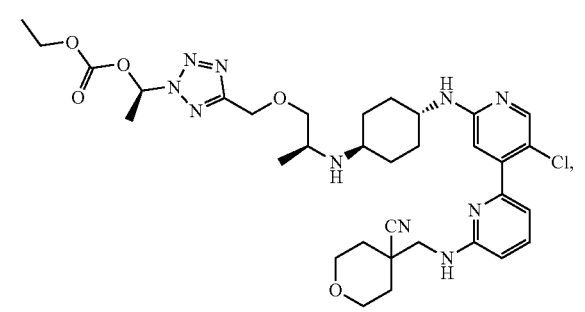
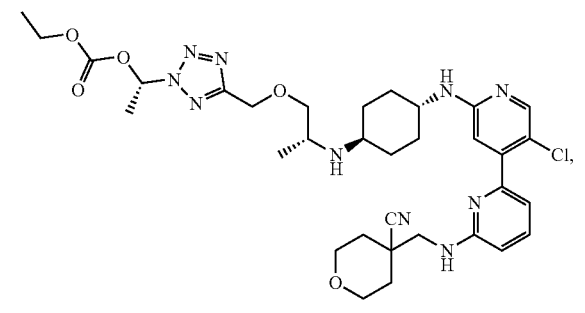
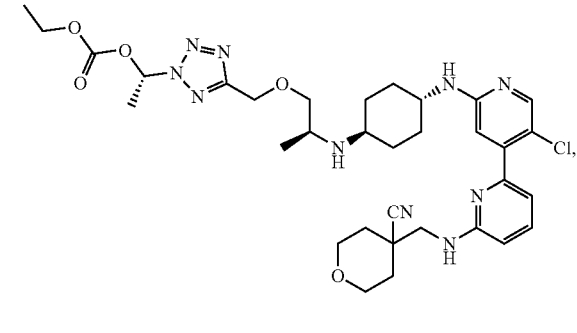
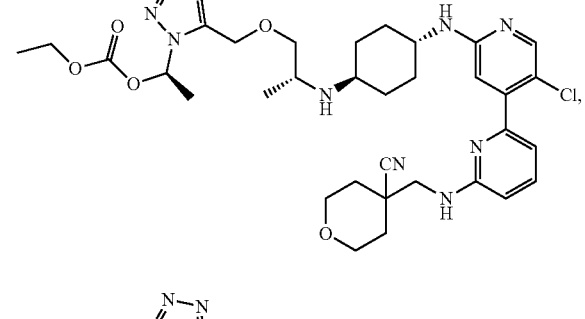
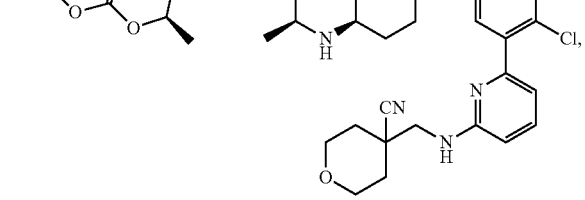
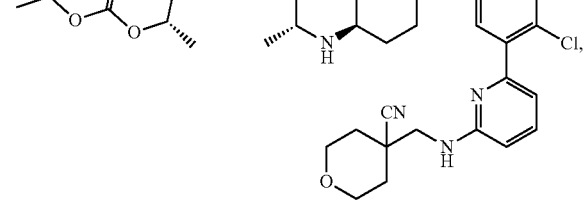
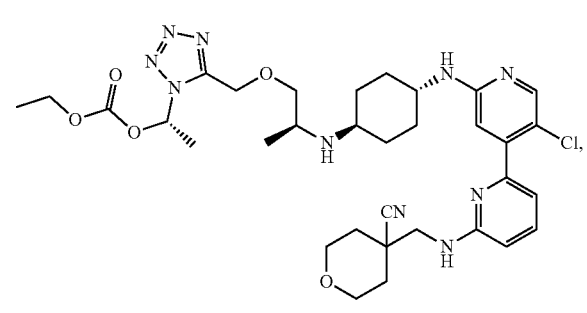

263
-continued
264
-continued
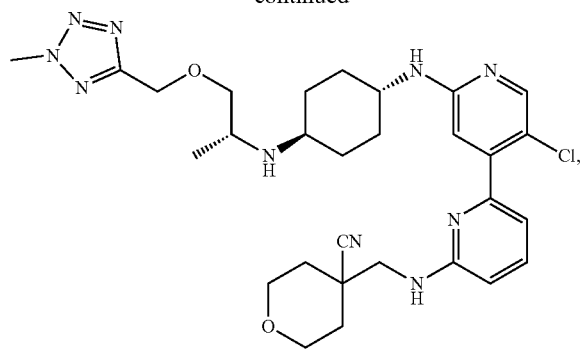
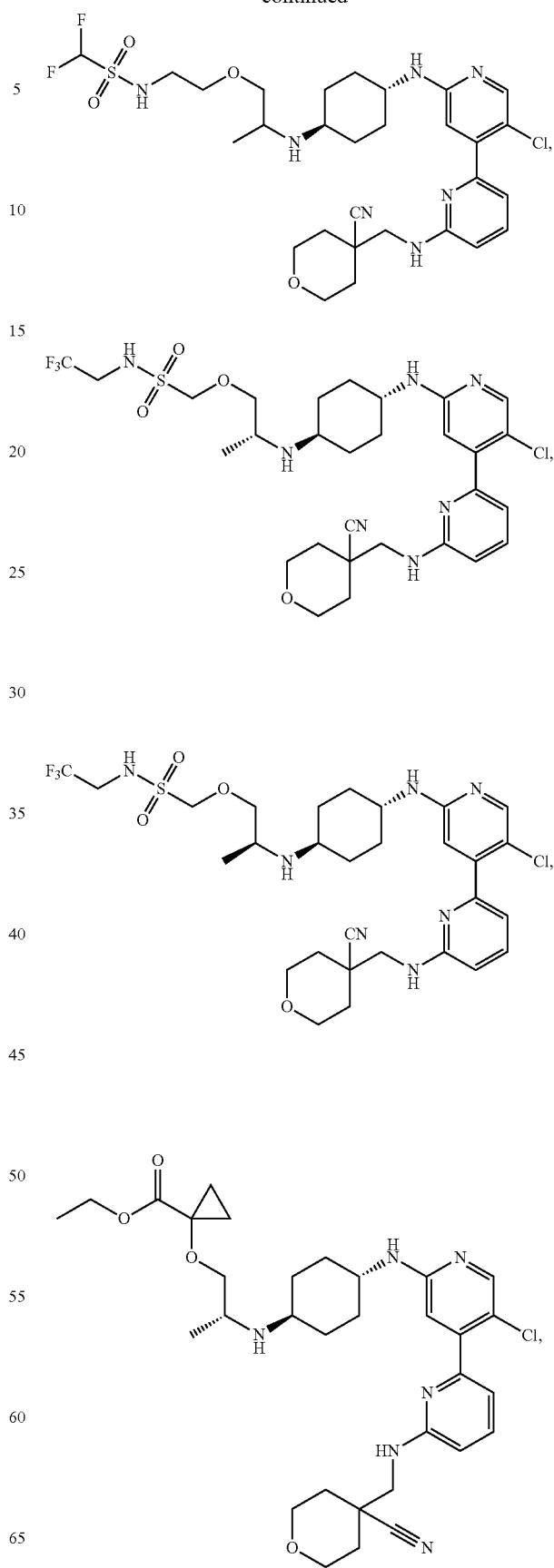

265
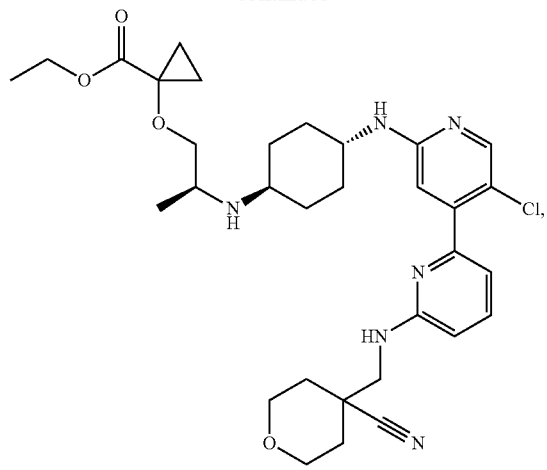
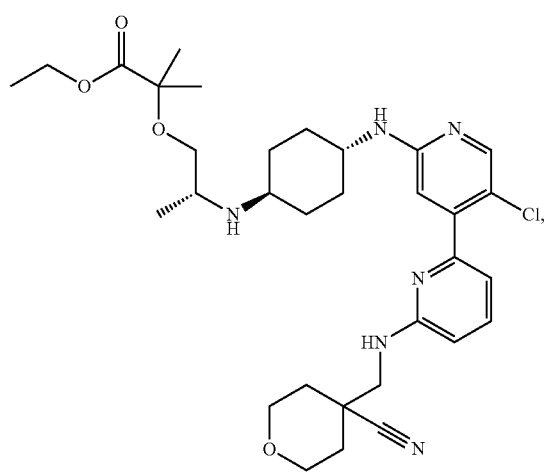
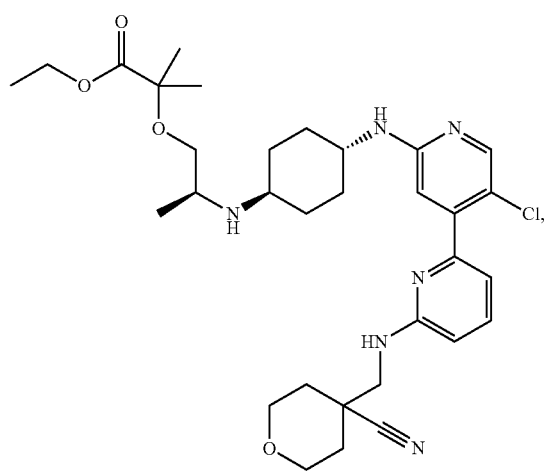
266
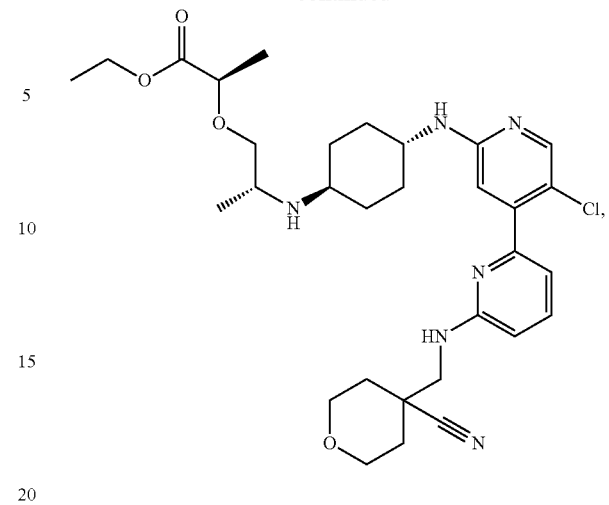
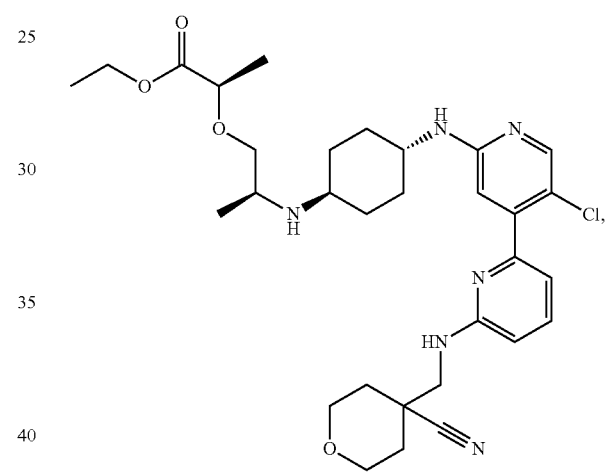
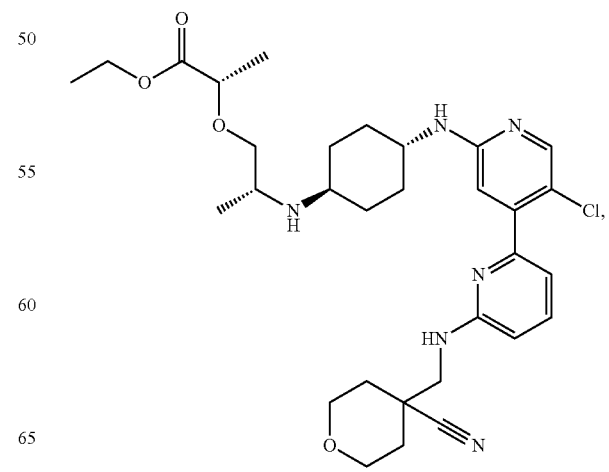

267
-continued
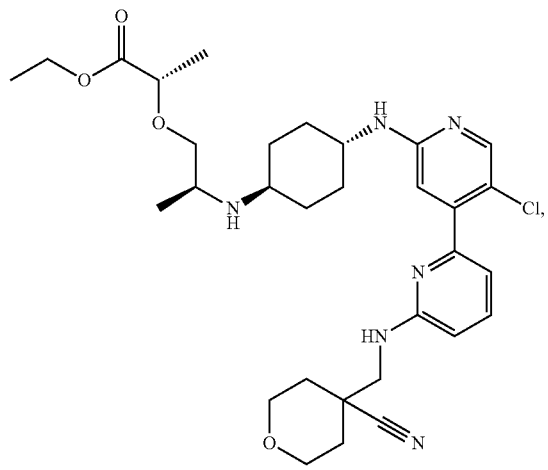
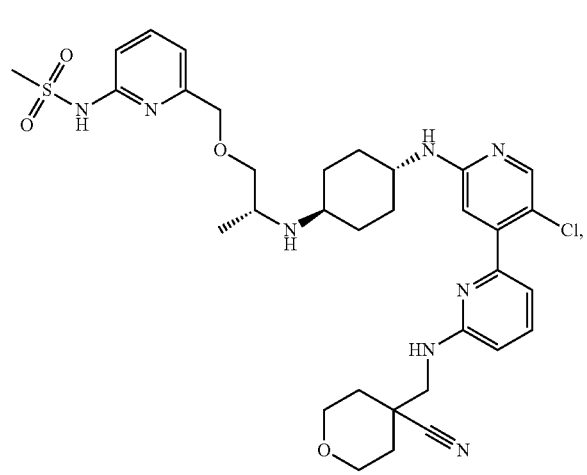
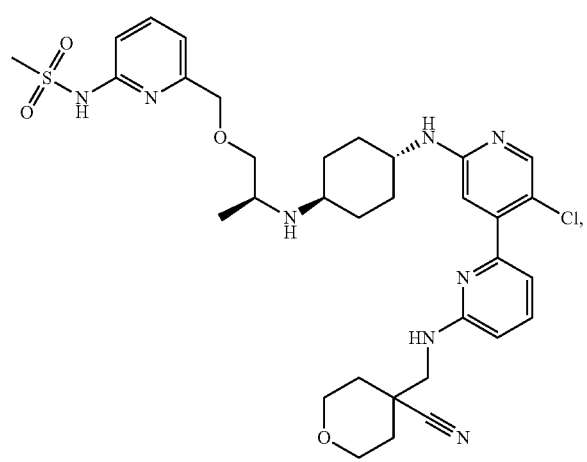
268
-continued
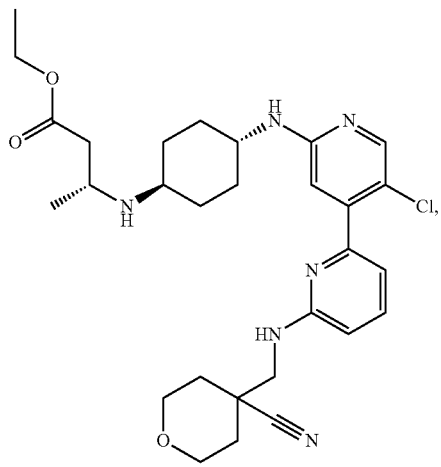
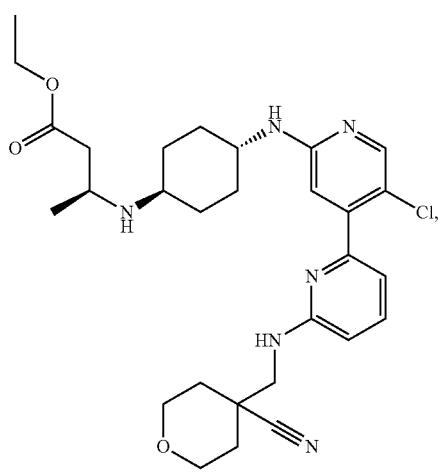
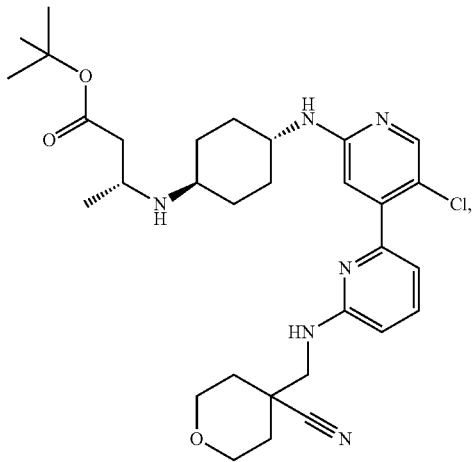

269
-continued
270
-continued
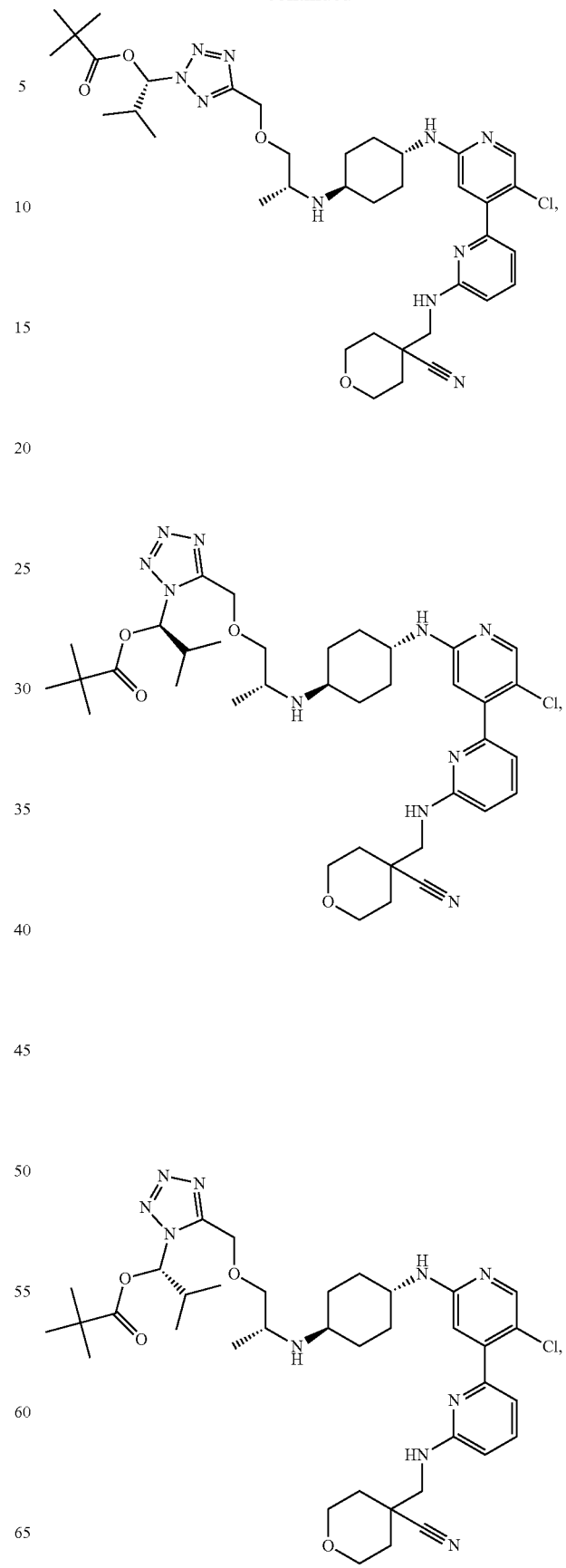

271
-continued
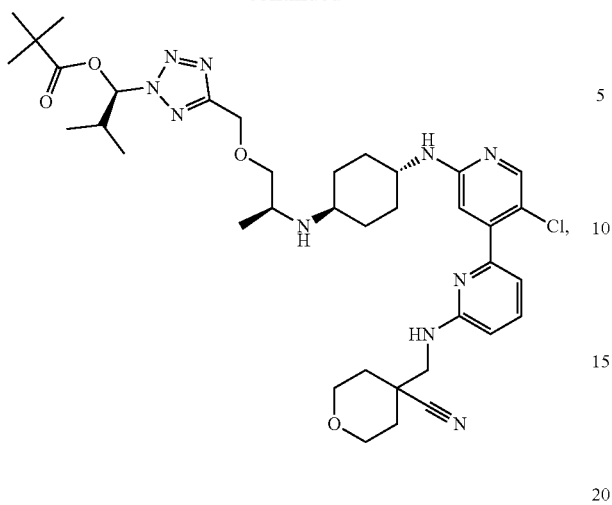
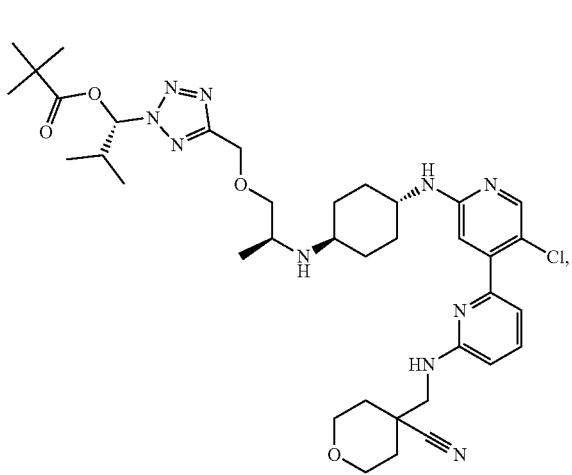
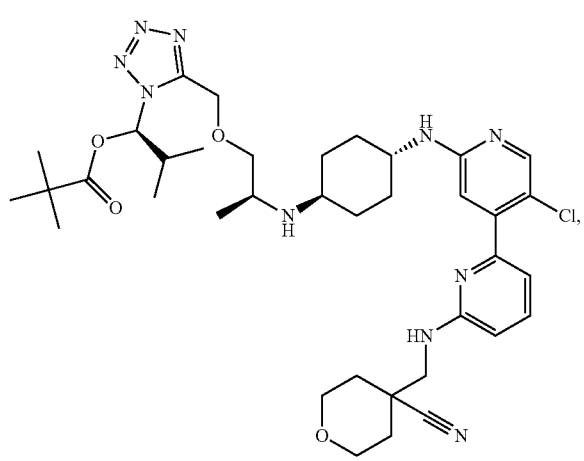
272
-continued
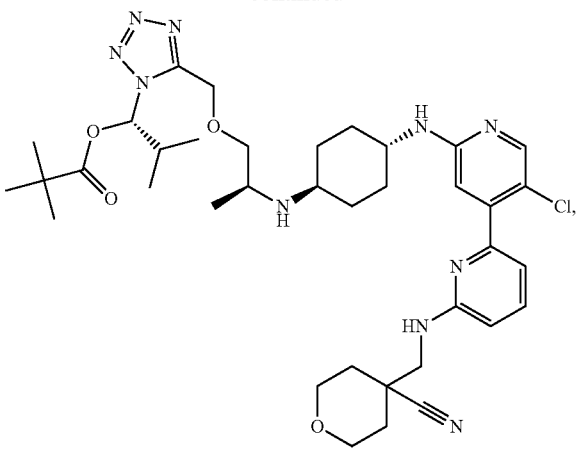
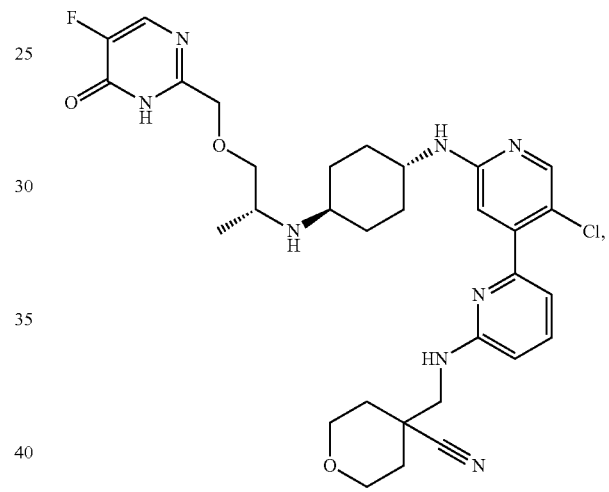
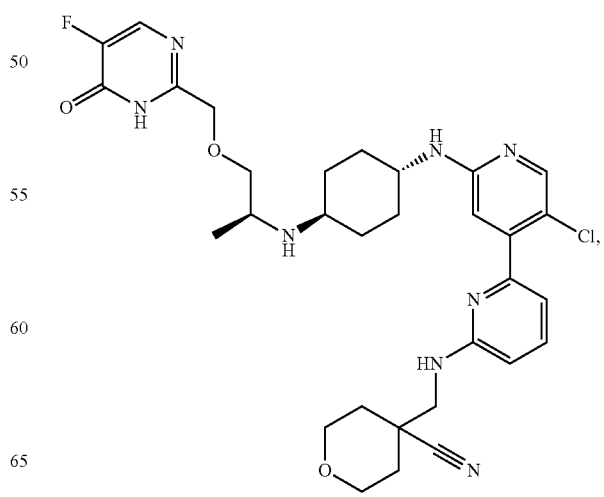

273
-continued
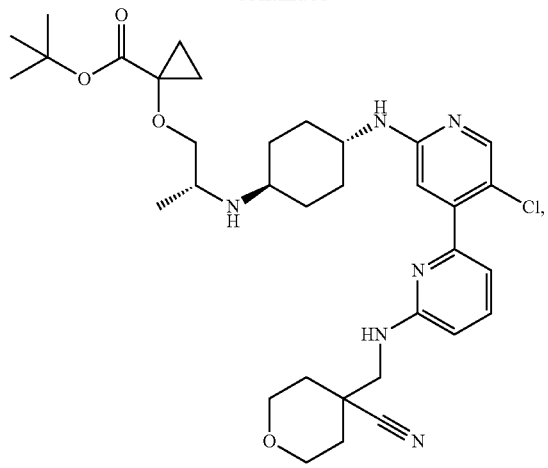
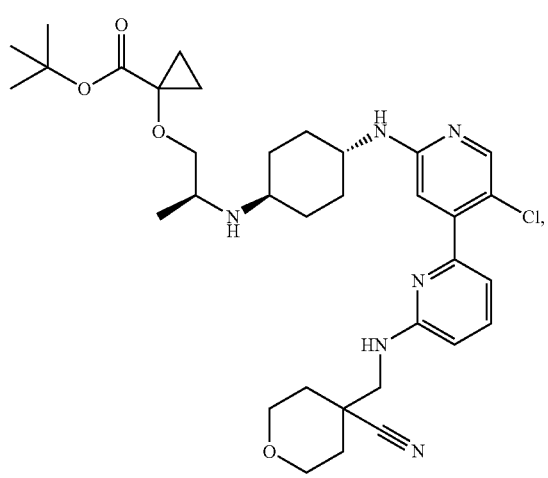
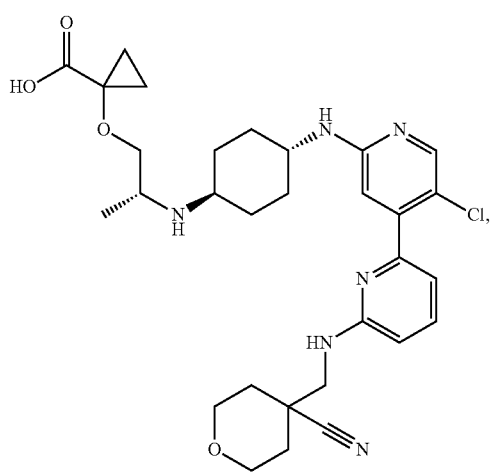
274
-continued
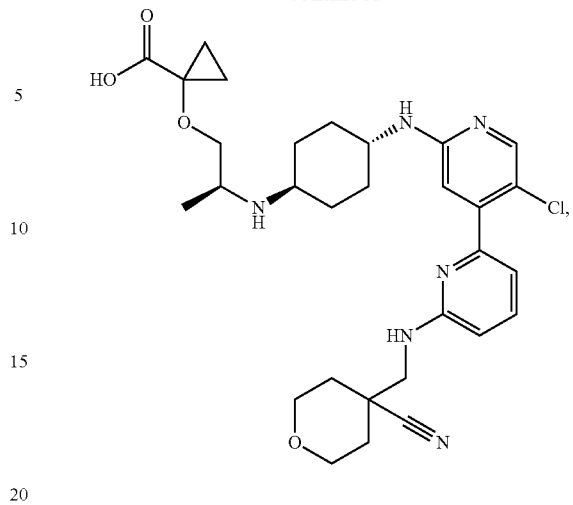
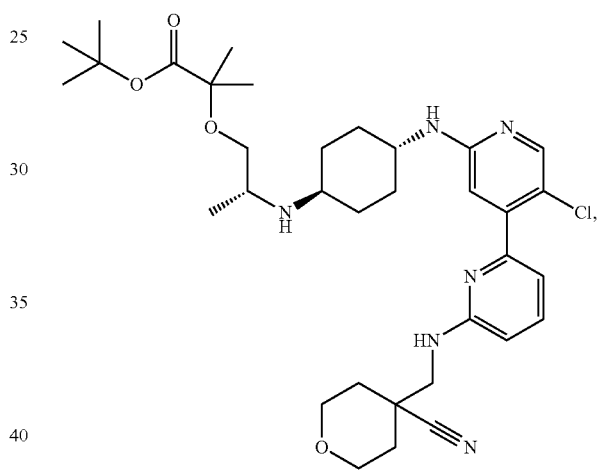
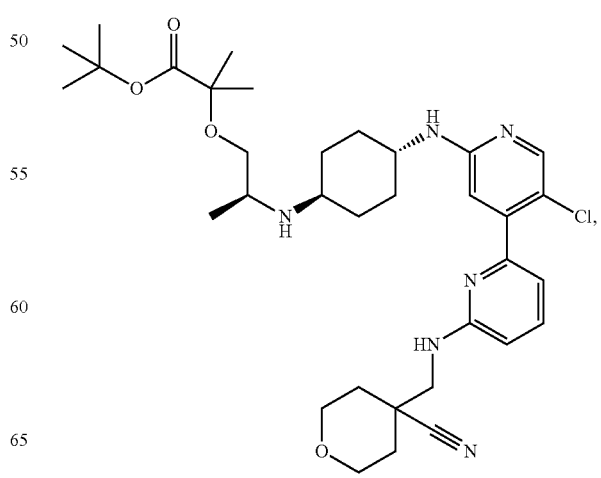

275
-continued
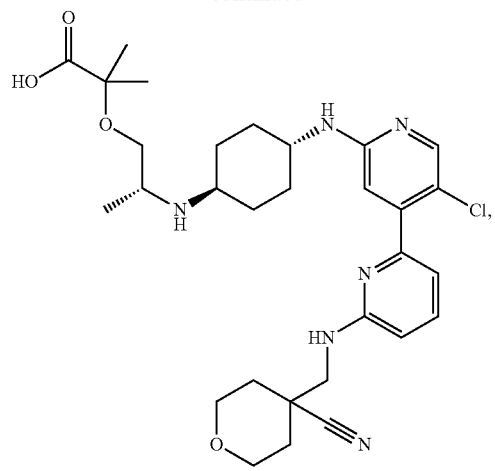
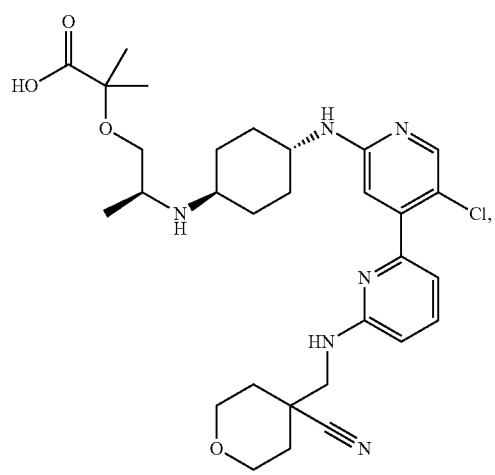
276
-continued
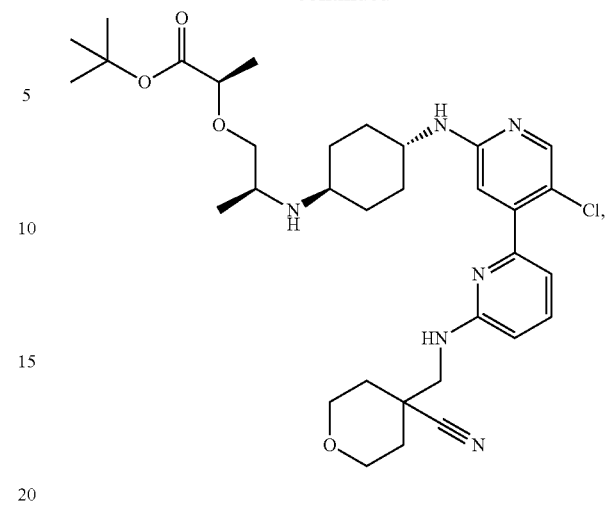
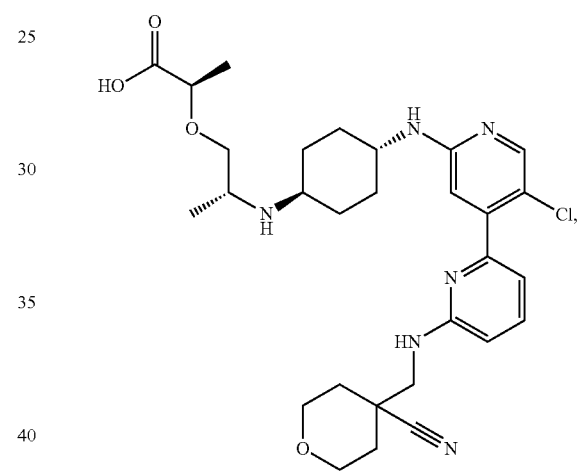
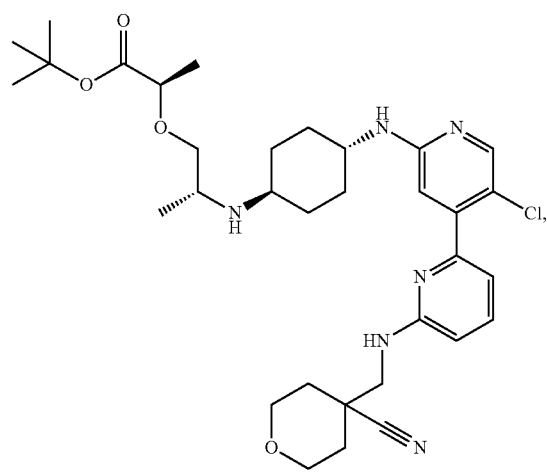
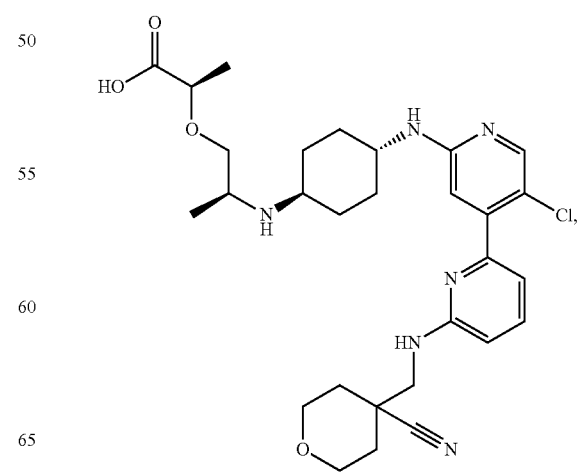

277
-continued
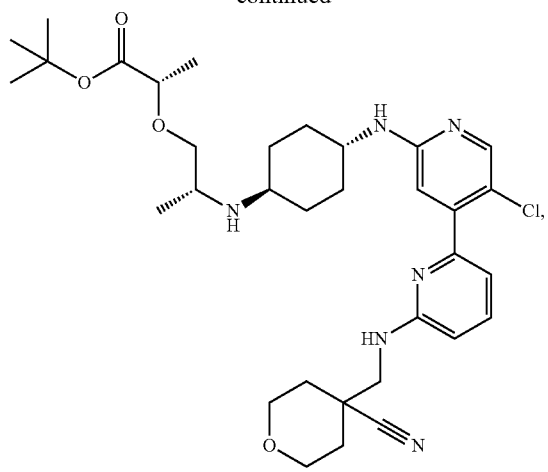
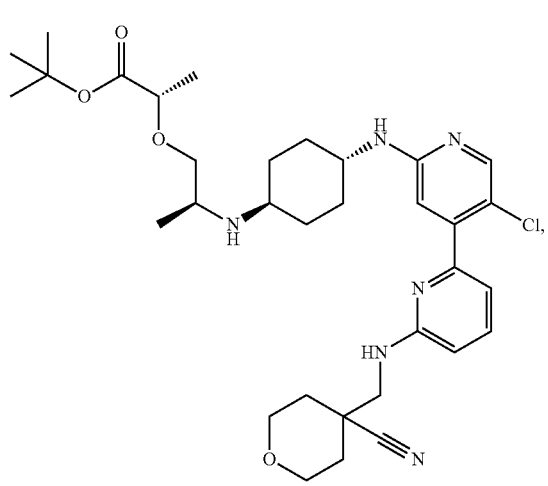
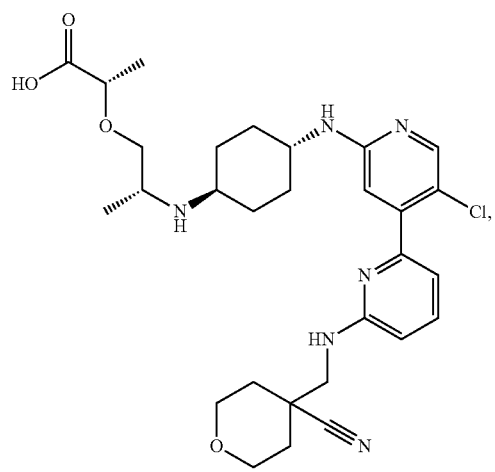
278
-continued
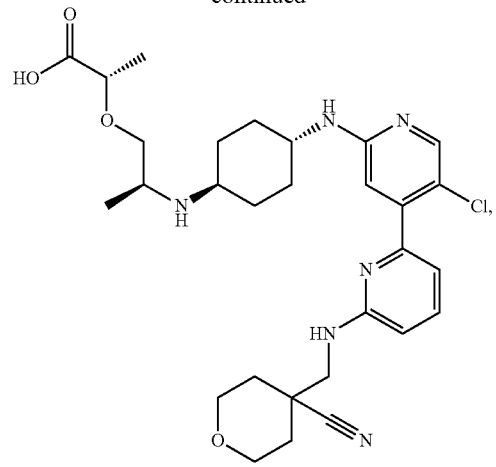
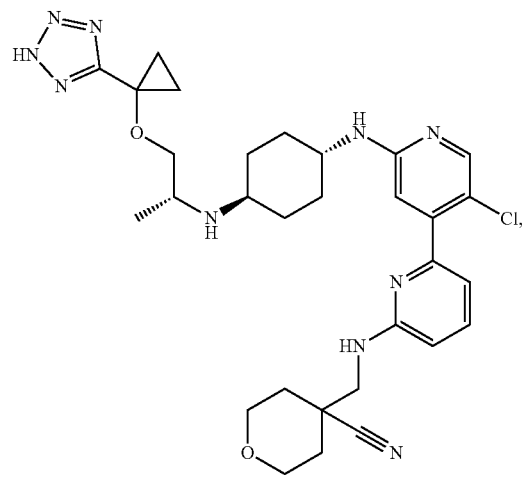
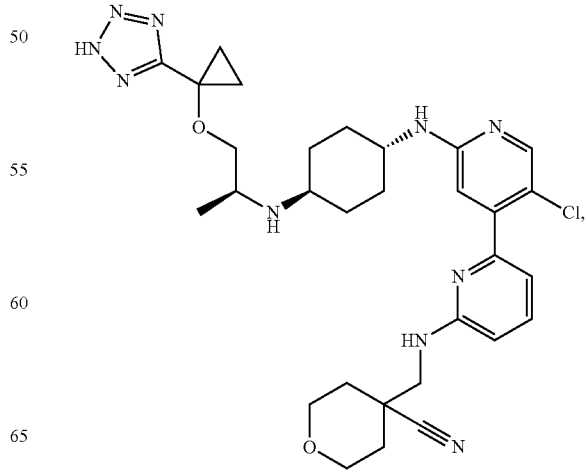

279
-continued
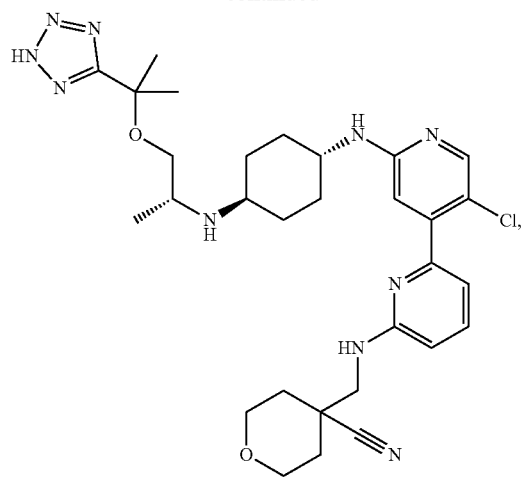
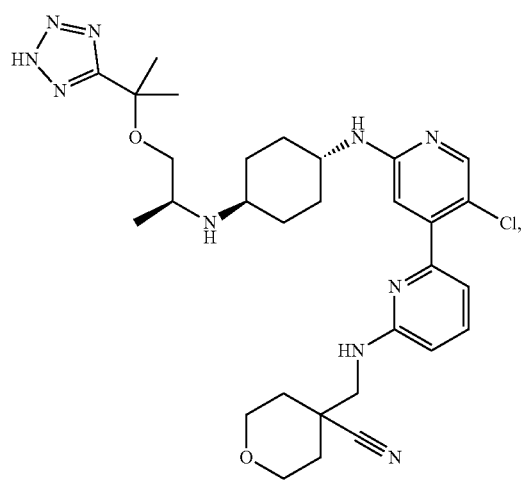
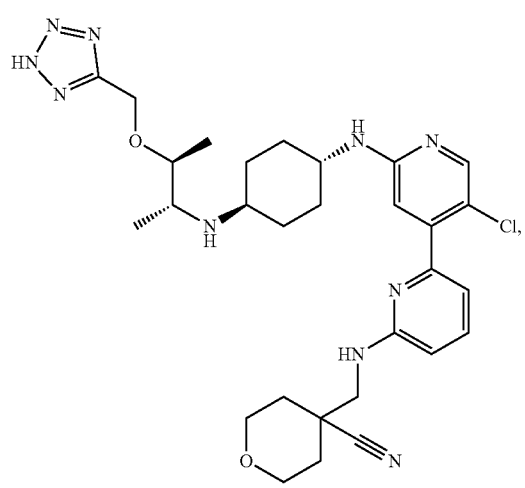
280
-continued
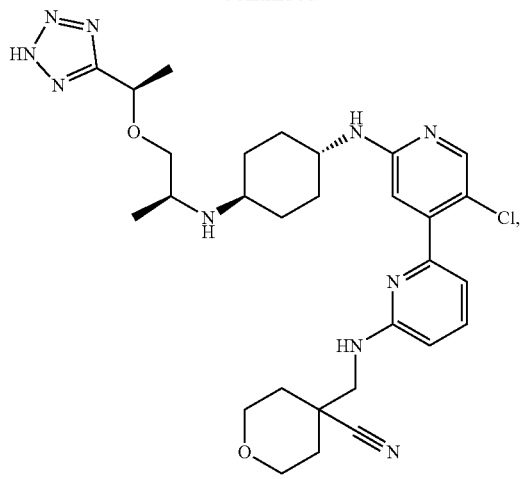
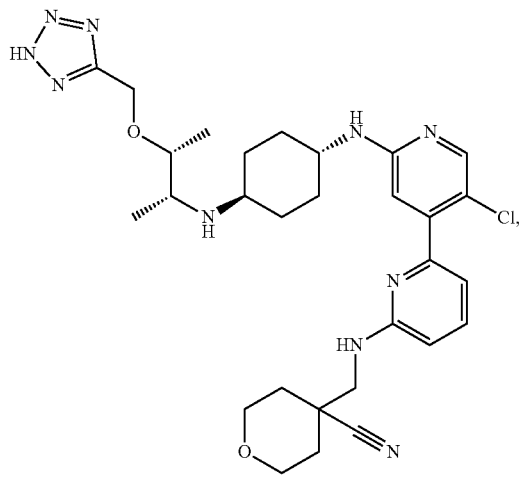
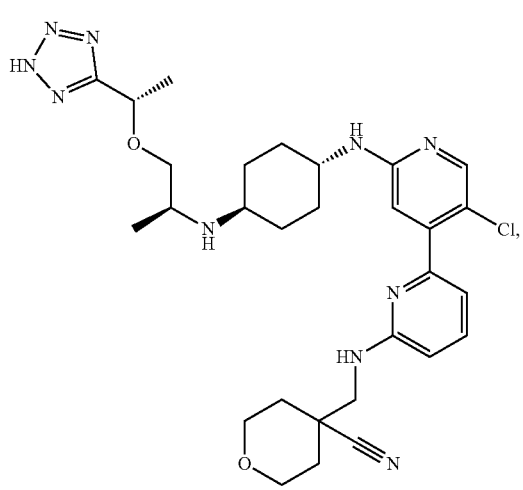

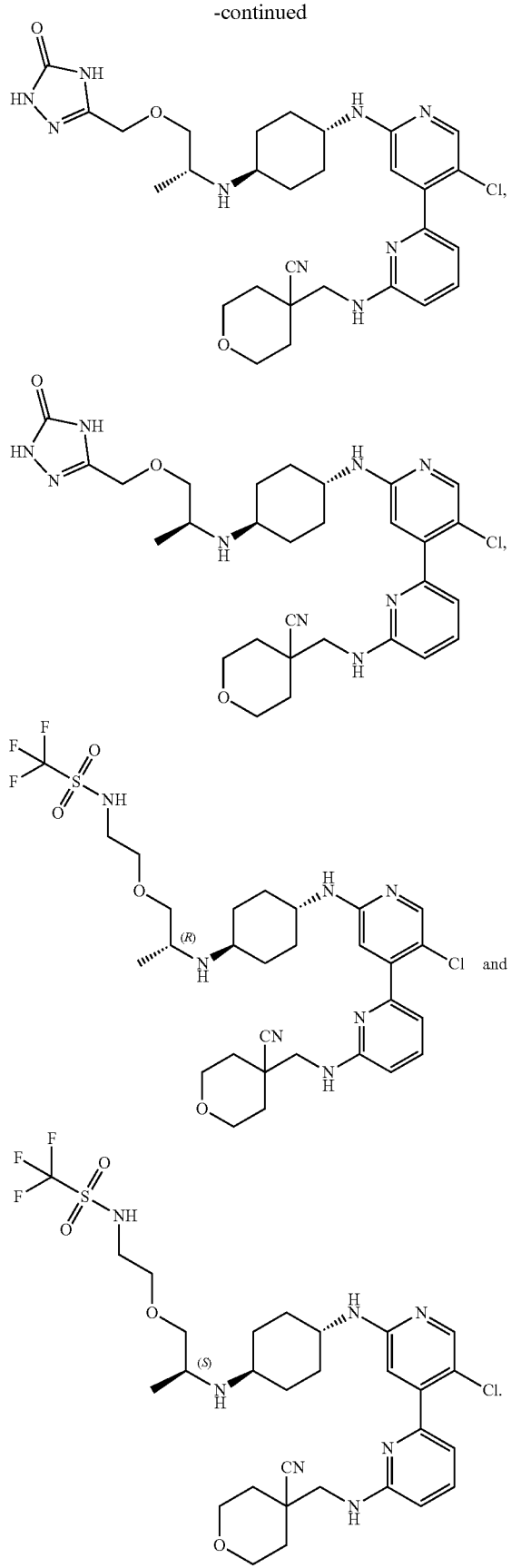
27. The compound or pharmaceutically acceptable salt of claim 1,
wherein the compound is selected from the group consisting of:
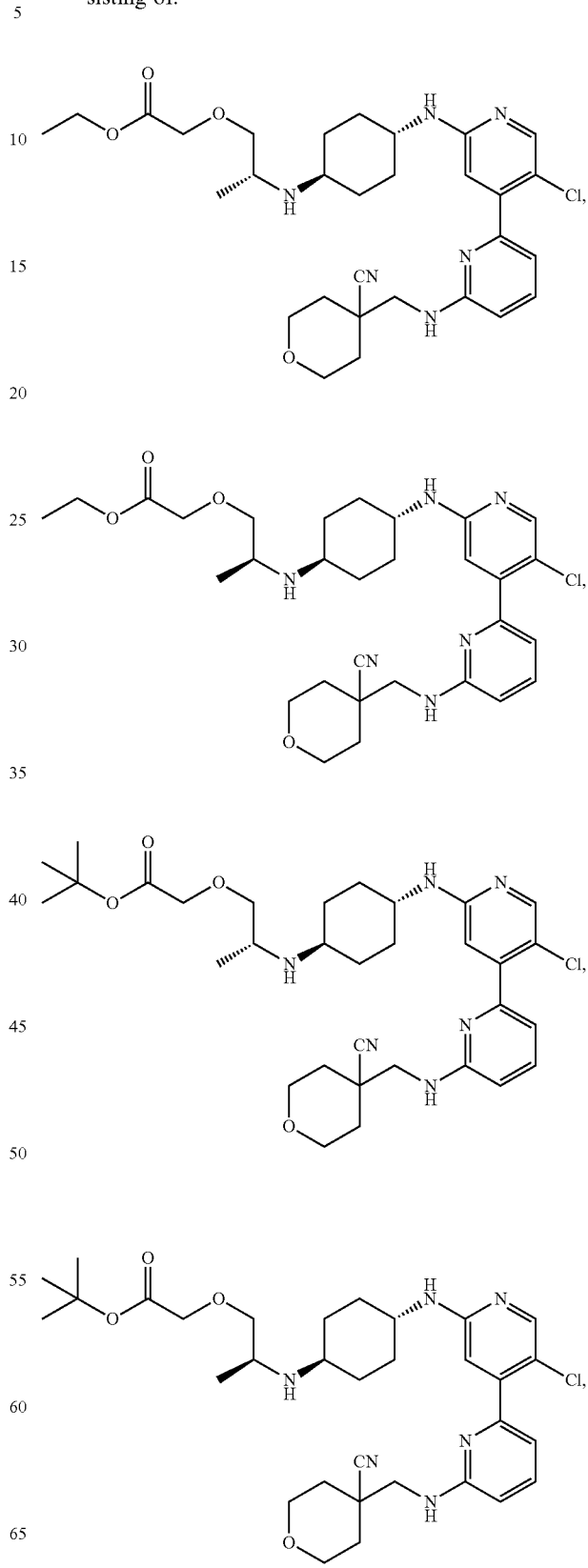

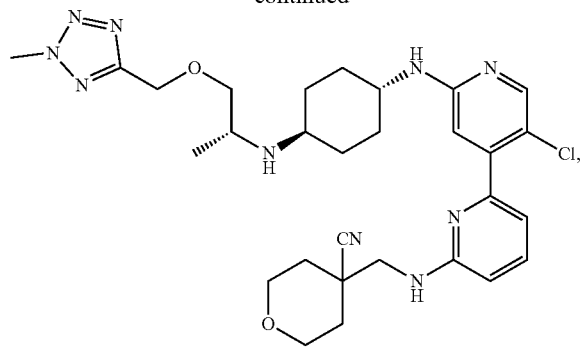
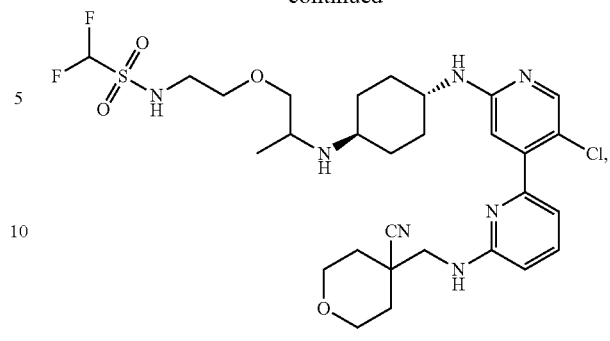

28. The compound or pharmaceutically acceptable salt of claim 1,
wherein the compound is
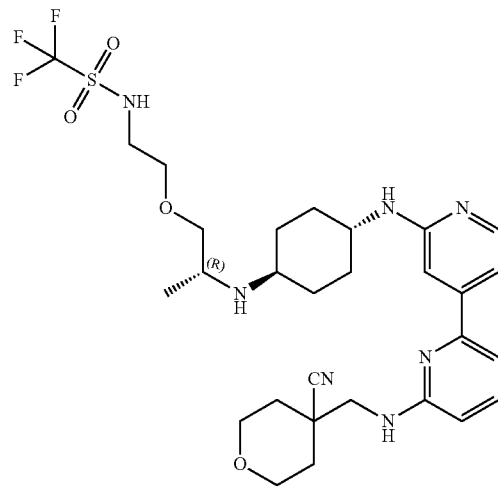
or
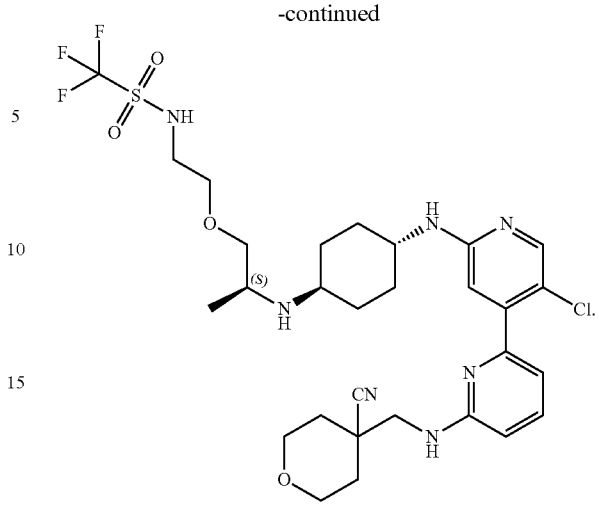
29. A pharmaceutical composition comprising the compound or pharmaceutically acceptable salt of claim 1, and a pharmaceutically acceptable excipient.
* * * * *